US010183917B2

(12) United States Patent
Wang et al.

(10) Patent No.: US 10,183,917 B2
(45) Date of Patent: Jan. 22, 2019

(54) TRICYCLIC COMPOUNDS AND USES THEREOF IN MEDICINE

(71) Applicant: Sunshine Lake Pharma Co., Ltd., Dongguan, Guangdong (CN)

(72) Inventors: Xiaojun Wang, Dongguan (CN); Xinye Yang, Dongguan (CN); Shengqiang Pan, Dongguan (CN); Rui Guo, Dongguan (CN); Junwen Wu, Dongguan (CN); Yingjun Zhang, Dongguan (CN); Changchung Cheng, Guangdong (CN)

(73) Assignee: SUNSHINE LAKE PHARMA CO., LTD., Dongguan, Guangdong (CN)

( * ) Notice: Subject to any disclaimer, the term of this patent is extended or adjusted under 35 U.S.C. 154(b) by 0 days.

(21) Appl. No.: 15/541,018

(22) PCT Filed: Feb. 5, 2016

(86) PCT No.: PCT/CN2016/073617
§ 371 (c)(1),
(2) Date: Jun. 30, 2017

(87) PCT Pub. No.: WO2016/127924
PCT Pub. Date: Aug. 18, 2016

(65) Prior Publication Data
US 2018/0030003 A1 Feb. 1, 2018

(30) Foreign Application Priority Data

Feb. 13, 2015 (CN) .......................... 2015 1 0083621

(51) Int. Cl.
| | | |
|---|---|---|
| *C07D 261/08* | (2006.01) |
| *C07D 249/06* | (2006.01) |
| *A61K 31/42* | (2006.01) |
| *A61K 31/4353* | (2006.01) |
| *A61K 31/4985* | (2006.01) |
| *A61K 31/519* | (2006.01) |
| *C07D 411/12* | (2006.01) |
| *C07D 413/12* | (2006.01) |
| *C07D 471/04* | (2006.01) |
| *C07D 491/044* | (2006.01) |
| *C07D 497/04* | (2006.01) |
| *C07D 498/14* | (2006.01) |
| *C07D 491/052* | (2006.01) |
| *C07D 491/147* | (2006.01) |
| *C07D 498/04* | (2006.01) |

(52) U.S. Cl.
CPC ............ *C07D 261/08* (2013.01); *A61K 31/42* (2013.01); *A61K 31/4353* (2013.01); *A61K 31/4985* (2013.01); *A61K 31/519* (2013.01); *C07D 249/06* (2013.01); *C07D 411/12* (2013.01); *C07D 413/12* (2013.01); *C07D 471/04* (2013.01); *C07D 491/044* (2013.01); *C07D 491/052* (2013.01); *C07D 491/147* (2013.01); *C07D 497/04* (2013.01); *C07D 498/04* (2013.01); *C07D 498/14* (2013.01)

(58) Field of Classification Search
CPC ........................... C07D 261/08; C07D 249/06
See application file for complete search history.

(56) References Cited

U.S. PATENT DOCUMENTS

| | | |
|---|---|---|
| 6,639,078 B1 | 10/2003 | Haffner et al. |
| 7,034,046 B2 | 4/2006 | Bauer et al. |
| 7,319,109 B2 | 1/2008 | Boggs et al. |
| 7,705,028 B2 | 4/2010 | Caldwell et al. |
| 7,846,960 B2 | 12/2010 | Bell et al. |
| 7,863,302 B2 | 1/2011 | Bell et al. |
| 7,960,552 B2 | 6/2011 | Bass, III et al. |
| 8,106,077 B2 | 1/2012 | Bell et al. |
| 8,153,624 B2 | 4/2012 | Genin et al. |
| 8,193,192 B2 | 6/2012 | Kremoser et al. |
| 8,466,143 B2 | 6/2013 | Martin et al. |
| 8,952,042 B2 | 2/2015 | Kremoser et al. |
| 9,139,539 B2 | 9/2015 | Kinzel et al. |
| 9,150,568 B2 | 10/2015 | Tully et al. |
| 2010/0184809 A1 | 7/2010 | Kremoser et al. |
| 2010/0216827 A1 | 8/2010 | Ma et al. |

(Continued)

FOREIGN PATENT DOCUMENTS

| | | |
|---|---|---|
| CN | 104045635 A | 9/2014 |
| CN | 104513213 A | 4/2015 |

(Continued)

OTHER PUBLICATIONS

Prueksaritanont, et al. Toxicology and Applied Pharmacology 217 (2006) 143-152.*
Chinthakindi, et al. European Journal of Medicinal Chemistry 60 (2013) 365-375.*
Cancer and Metastasis Reviews (1998), 17(1), 91-106.*
Science (1999), vol. 286, 531-537.*
Cancer [online], [retrieved on Jul. 6, 2007]. Retrieved from the internet, URL http://www.nlm.nih.gov/medlineplus/cancer.html>.*
ISR of PCT/CN2016/073617, Apr. 22, 2016.
Written Opinion of PCT/CN2016/073617, dated Apr. 29, 2016.
Eng. translation, Eng. translation of the abstract of CN 104513213.
Eng. translation, Eng. translation of the abstract of CN 104045635.

(Continued)

*Primary Examiner* — Shawquia Jackson
(74) *Attorney, Agent, or Firm* — Kam Wah Law

(57) ABSTRACT

The present invention relates to novel tricyclic compounds which can bind to FXR and act as modulators of the FXR, or a stereoisomer, a geometric isomer, a tautomer, an N-oxide, a hydrate, a solvate, a metabolite, a pharmaceutically acceptable salt or a prodrug thereof, and the uses of the compounds for the treatment of diseases and/or conditions mediated by FXR. The invention further provides a pharmaceutical composition containing the compound disclosed herein and a method of treatment of diseases and/or conditions mediated by FXR comprising administering the compound or the pharmaceutical composition.

12 Claims, No Drawings

(56) References Cited

U.S. PATENT DOCUMENTS

| | | |
|---|---|---|
| 2010/0249179 A1 | 9/2010 | Deaton et al. |
| 2011/0034507 A1 | 2/2011 | Akwabi-Ameyaw et al. |
| 2011/0039824 A1 | 2/2011 | Lundquist et al. |
| 2013/0261108 A1 | 10/2013 | Tully et al. |
| 2014/0039007 A1 | 2/2014 | Tully |
| 2016/0340317 A1 | 11/2016 | Chianelli et al. |

FOREIGN PATENT DOCUMENTS

| | | |
|---|---|---|
| EP | 1182200 A1 | 2/2002 |
| WO | WO2009149795 A2 | 12/2009 |
| WO | WO2004026030 A2 | 4/2014 |
| WO | WO2015138986 A1 | 9/2015 |
| WO | WO2016096115 A1 | 6/2016 |
| WO | WO2016096116 A1 | 6/2016 |
| WO | WO2016103037 A1 | 6/2016 |

OTHER PUBLICATIONS

Matthew Lantz Crawley; Farnesoid X receptor modulators: a patent review; Expert Opinion on Therapeutic Patents, 2010, 20(8), 1047-1057.

Lundquist JT etc.; Improvement of physiochemical properties of the tetrahydroazepinoindole series of farnesoid X receptor (FXR) agonists: beneficial modulation of lipids in primates; J Med Chem. Feb. 25, 2010;53(4):1774-87.

Akwabi-Ameyaw A etc.; Conformationally constrained farnesoid X receptor (FXR) agonists: Naphthoic acid-based analogs of GW 4064; Bioorg Med Chem Lett. Aug. 1, 2008;18(15):4339-43.

Extended European Search Report of European Patent Application No. 16 748 725.5.

* cited by examiner

TRICYCLIC COMPOUNDS AND USES THEREOF IN MEDICINE

CROSS-REFERENCE TO RELATED APPLICATION

This is a U.S. national stage application of the International Patent Application No. PCT/CN2016/073617, filed 5 Feb. 2016, which claims priority to Chinese Patent Application No. 201510083621.5, filed 13 Feb. 2015, both of which are incorporated herein by reference in their entireties.

FIELD OF THE INVENTION

The present invention relates to tricyclic compounds which can bind to the FXR and act as FXR modulators, and pharmaceutical compositions thereof, as well as the uses of said compounds and pharmaceutical compositions in the preparation of medicaments for the treatment of diseases and/or conditions mediated by FXR.

BACKGROUND OF THE INVENTION

FXR is a member of the nuclear hormone receptor superfamily, and is mainly expressed in the liver, kidneys and intestines (Seol et al. Mol. Endocrinol (1995), 9:72-85; Forman Cell (1995), 81:687-693). It functions as a heterodimer with the RXR, and regulates gene transcription by binding to the response elements of the target gene promoter. The FXR-RXR heterodimer binds with highest affinity to an inverted repeat −1(IR−1) response element, in which consensus receptor-binding hexamers are separated by a nucleotide. FXR is part of an interrelated process, and FXR is activated by bile acids (cholesterol metabolism end products) (Makishima et al., Science (1999), 284:1362-1365; Parks et al., Science (1999), 284:1365-1368; Wang et al., Mol. Cell. (1999), 3:543-553), and the bile acid is used to inhibit cholesterol catabolism. (Urizar et al., (2000) J. Biol. Chem. 275:39313-393170).

FXR is a critical regulator of cholesterol homeostasis, triglyceride synthesis and adipogenesis (Crawley, Expert Opinion Ther. Patents (2010), 20:1047-1057). In addition to the treatment of dyslipidemia, obesity, vitamin D-related diseases, intestinal diseases, drug-induced side effects as well as hepatitis (Crawley, Expert Opinion Ther. Patents (2010), 20:1047-1057), FXR related indications also include gallbladder disease, chronic hepatitis, nonalcoholic fatty liver disease (NAFLD), nonalcoholic steatohepatitis (NASH), cholestasis, liver fibrosis, cirrhosis of liver, hepatitis B, metabolic diseases, lipid metabolism disorders, carbohydrate metabolic diseases, cardiovascular and metabolic diseases, atherosclerosis, type II diabetes and diabetic complications (Frank G. Schaap et al., Journal of Medicinal Chemistry, (2005), 48:5383-5402).

Small molecule compounds which act as FXR modulators have been disclosed in the following publications: WO 2000/037077, WO 2003/015771, WO 2004/048349, WO 2007/076260, WO 2007/092751, WO 2007/140174, WO 2007/140183, WO 2008/051942, WO 2008/157270, WO 2009/005998, WO 2009/012125, WO 2009/149795, WO 2008/025539, WO 2008/025540, WO 2012/087520, WO 2012/087521, WO 2012/087519, WO2013/007387 and WO 2015/036442. R. C. Buijsman et al. reviewed smaller molecule modulators of FXR (R. C. Buijsman et al., Curr. Med. Chem. 2005, 12, 1017-1075).

SUMMARY OF THE INVENTION

Although the development of FXR modulators has a certain progress, the development space is still enormous. The object of the present invention is to provide novel tricyclic compounds which act as FXR modulators. The biological activity and pharmacokinetic properties of the compounds disclosed herein are superior to these of the known FXR modulators.

The present invention provides a compound, or a pharmaceutical composition thereof, which binds to FXR (or NR1H4 receptor) and act as modulator of FXR (or NR1H4 receptor). The present invention further relates to said compound or the use of said compound in the preparation of a medicament for the treatment of diseases and/or conditions through said compounds binding to the FXR nuclear receptor. The present invention further describes the synthetic method of the compounds. The compounds of the invention exhibit improved biological activity and pharmacokinetic advantages.

Specifically:

In one aspect, provided herein is a compound having formula (I), or a stereoisomer, a geometric isomer, a tautomer, an N-oxide, a hydrate, a solvate, a metabolite, a pharmaceutically acceptable salt or a prodrug thereof,

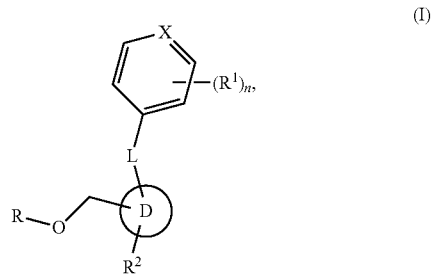

Wherein:

X is N, CH or $^{\oplus}$N—O$^{\ominus}$;

ring D is a five-membered heteroaromatic ring or five-membered heterocycle;

L is a bond, —(CR$^3$R$^4$)$_f$—, —(CR$^3$R$^4$)$_f$—O—, —(CR$^3$R$^4$)$_f$—NH— or —(CR$^3$R$^4$)$_f$—S(=O)$_t$—;

R is fused tricyclyl or fused heterotricyclyl, wherein R is optionally substituted with one, two, three, four or five R$^8$;

each R$^1$ is independently H, deuterium, F, Cl, Br, I, hydroxy, amino, nitro, cyano, alkyl, haloalkyl, haloalkoxy, cycloalkyl, heterocyclyl, alkenyl, alkynyl, alkylamino, alkoxy, aryl or heteroaryl;

R$^2$ is H, deuterium, F, Cl, Br, I, hydroxy, amino, nitro, cyano, alkyl, haloalkyl, haloalkoxy, alkoxyalkyl, cycloalkyl, hydroxyalkyl, heterocyclyl, alkylamino or alkoxy;

each of R$^3$ and R$^4$ is independently H, deuterium, C$_{1-4}$ alkyl, F, Cl, Br, I or C$_{1-4}$ haloalkyl;

each R$^8$ is independently H, deuterium, F, Cl, Br, I, hydroxy, nitro, amino, aminoalkyl, alkylamino, alkyl, hydroxyalkyl, alkoxy, haloalkyl, haloalkoxy, cycloalkyl, cycloalkoxy, alkenyl, alkynyl, aryl, halo-substituted aryl, arylalkyl, oxo (=O), -L$^1$-C(=O)OR$^{15}$, -L$^1$-S(=O)$_t$R$^{16}$, —O-L$^2$-C(=O)OR$^{15}$, —O-L$^2$-S(=O)$_t$R$^{16}$, —C(=O)NR$^{17}$R$^{18}$, —C(=O)N(R$^{17}$)S(=O)$_2$R$^{16}$, —C(=NR$^{17}$)NR$^{17}$R$^{18}$, —C(=O)N(R$^{17}$)-L$^3$-S(=O)$_2$OR$^{15}$, —C(=O)N(R$^{17}$)C(=O)OR$^{15}$, —C(=O)N(R$^{17}$)-L$^3$-C(=O)OR$^{15}$, cyano, heterocyclyl or heteroaryl; or two R$^8$, together with the same C atom to which they are attached, independently and optionally form cycloalkyl or heterocyclyl; or two $R^8$, together with the adjacent C atoms to which they are attached, independently and optionally form cycloalkyl, heterocyclyl, aryl or heteroaryl; wherein $R^8$ is independently and optionally substituted with one or more $R^{19}$;

each $R^{15}$ is independently H, deuterium, alkyl, aminoalkyl, alkenyl, alkynyl, haloalkyl, cycloalkyl, heterocyclyl or aryl;

each $R^{16}$ is independently H, deuterium, hydroxy, amino, alkyl, aminoalkyl, alkenyl, alkynyl, haloalkyl, cycloalkyl, heterocyclyl, aryl or $-NR^{17}R^{18}$;

each of $R^{17}$ and $R^{18}$ is independently H, deuterium, alkyl, aminoalkyl, alkenyl, alkynyl, haloalkyl, cycloalkyl, heterocyclyl or aryl; or $R^{17}$ and $R^{18}$, together with the N atom to which they are attached, independently and optionally form heterocyclyl or heteroaryl;

each $L^1$ is independently a bond, $-C(=O)-$, $C_{1-6}$ alkylene, $C_{2-6}$ alkenylene or $C_{2-6}$ alkynylene;

each $L^2$ is independently $C_{1-6}$ alkylene, $C_{2-6}$ alkenylene or $C_{2-6}$ alkynylene;

each $L^3$ is independently a bond or $C_{1-4}$ alkylene;

n is 0, 1, 2, 3 or 4;

each f is independently 0, 1 or 2;

each t is independently 0, 1, or 2;

wherein each of said hydroxy, amino, alkyl, hydroxyalkyl, aminoalkyl, alkenyl, alkynyl, cycloalkyl, haloalkyl, alkylamino, alkoxy, alkoxyalkyl, cycloalkyloxy, haloalkoxy, heterocyclyl, aryl, heteroaryl, halo-substituted aryl, aryl alkyl, $C_{1-4}$ haloalkyl, $C_{1-6}$ alkylene, $C_{2-6}$ alkenylene, $C_{2-6}$ alkynylene and $C_{1-4}$ alkylene of $R^1$, $R^2$, $R^3$, $R^4$, $R^8$, $R^{15}$, $R^{16}$, $R^{17}$, $R^{18}$, $L^1$, $L^2$ and $L^3$ is independently and optionally substituted with one or more $R^9$; and each of $R^9$ and $R^{19}$ is independently H, deuterium, F, Cl, Br, I, cyano, oxo (=O), hydroxy, alkyl, alkylamino, amino, aryl, heterocyclyl, heteroaryl, alkenyl, alkynyl, cycloalkyl, alkoxy or haloalkyl.

In some embodiments, L is a bond, $-CH_2-$, $-O-$, $-NH-$, $-S-$, $-CH_2-O-$, $-CH_2-NH-$, $-CH_2-S-$ or $-CH_2-S(=O)_2-$.

In some embodiments, each $R^1$ is independently H, deuterium, F, Cl, Br, I, hydroxy, amino, nitro, cyano, $C_{1-6}$ alkyl, $C_{1-6}$ haloalkyl, $C_{1-6}$ haloalkoxy, $C_{3-6}$ cycloalkyl, $C_{2-9}$ heterocyclyl, $C_{2-6}$ alkenyl, $C_{2-6}$ alkynyl, $C_{1-6}$ alkylamino, $C_{1-6}$ alkoxy, $C_{6-10}$ aryl or $C_{1-9}$ heteroaryl;

$R^2$ is H, deuterium, F, Cl, Br, I, hydroxy, amino, nitro, cyano, $C_{1-6}$ alkyl, $C_{1-6}$ haloalkyl, $C_{1-6}$ haloalkoxy, $C_{1-6}$ alkoxy-$C_{1-6}$-alkyl, $C_{3-6}$ cycloalkyl, $C_{1-6}$ hydroxyalkyl, $C_{2-9}$ heterocyclyl, $C_{1-6}$ alkylamino or $C_{1-6}$ alkoxy;

wherein each of said hydroxy, amino, $C_{1-6}$ alkyl, $C_{2-6}$ alkenyl, $C_{2-6}$ alkynyl, $C_{3-6}$ cycloalkyl, $C_{1-6}$ haloalkyl, $C_{1-6}$ alkylamino, $C_{1-6}$ alkoxy, $C_{1-6}$ haloalkoxy, $C_{1-6}$ hydroxyalkyl, $C_{1-6}$ alkoxy-$C_{1-6}$-alkyl, $C_{2-9}$ heterocyclyl, $C_{6-10}$ aryl and $C_{1-9}$ heteroaryl of $R^1$ and $R^2$ is independently and optionally substituted with one or more $R^9$; and wherein $R^9$ is as defined herein.

In other embodiments, each $R^1$ is independently H, deuterium, F, Cl, Br, I, hydroxy, amino, nitro, cyano, $C_{1-3}$ alkyl, $C_{1-3}$ haloalkyl, $C_{1-3}$ haloalkoxy, $C_{3-6}$ cycloalkyl, $C_{2-9}$ heterocyclyl, $C_{2-4}$ alkenyl, $C_{2-4}$ alkynyl, $C_{1-3}$ alkylamino, $C_{1-3}$ alkoxy, $C_{6-10}$ aryl or $C_{1-9}$ heteroaryl;

$R^2$ is H, deuterium, F, Cl, Br, I, hydroxy, amino, nitro, cyano, $C_{1-3}$ alkyl, $C_{1-3}$ haloalkyl, $C_{1-3}$ haloalkoxy, $C_{1-3}$ alkoxy-$C_{1-3}$-alkyl, $C_{3-6}$ cycloalkyl, $C_{1-3}$ hydroxyalkyl, $C_{2-9}$ heterocyclyl, $C_{1-3}$ alkylamino or $C_{1-3}$ alkoxy;

wherein each of said hydroxy, amino, $C_{1-3}$ alkyl, $C_{2-4}$ alkenyl, $C_{2-4}$ alkynyl, $C_{3-6}$ cycloalkyl, $C_{1-3}$ haloalkyl, $C_{1-3}$ alkylamino, $C_{1-3}$ alkoxy, $C_{1-3}$ haloalkoxy, $C_{1-3}$ hydroxyalkyl, $C_{1-3}$ alkoxy-$C_{1-3}$-alkyl, $C_{2-9}$ heterocyclyl, $C_{6-10}$ aryl and $C_{1-9}$ heteroaryl of $R^1$ and $R^2$ is independently and optionally substituted with one or more $R^9$; and wherein $R^9$ is as defined herein.

In some embodiments, each $R^8$ is independently H, deuterium, F, Cl, Br, I, hydroxy, nitro, amino, $C_{1-6}$ aminoalkyl, $C_{1-6}$ alkylamino, $C_{1-6}$ alkyl, $C_{1-4}$ hydroxyalkyl, $C_{1-6}$ alkoxy, $C_{1-6}$ haloalkyl, $C_{1-6}$ haloalkoxy, $C_{3-6}$ cycloalkyl, $C_{3-6}$ cycloalkoxy, $C_{2-6}$ alkenyl, $C_{2-6}$ alkynyl, $C_{6-10}$ aryl, halo-substituted $C_{6-10}$ aryl, $C_{6-10}$ aryl-$C_{1-6}$-alkyl, oxo (=O), $-L^1-C(=O)OR^{15}$, $-L^1-S(=O)_fR^{16}$, $-O-L^2-C(=O)OR^{15}$, $-O-L^2-S(=O)_fR^{16}$, $-C(=O)NR^{17}R^{18}$, $-C(=O)N(R^{17})S(=O)_2R^{16}$, $-C(=NR^{17})NR^{17}R^{18}$, $-C(=O)N(R^{17})-L^3-S(=O)_2OR^{15}$, $-C(=O)N(R^{17})C(=O)OR^{15}$, $-C(=O)N(R^{17})-L^3-C(=O)OR^{15}$, cyano, $C_{2-9}$ heterocyclyl or $C_{1-9}$ heteroaryl; or two $R^8$, together with the same C atom to which they are attached, independently and optionally form $C_{3-6}$ cycloalkyl or $C_{2-9}$ heterocyclyl; or two $R^8$, together with the adjacent C atoms to which they are attached, independently and optionally form $C_{3-6}$ cycloalkyl, $C_{2-9}$ heterocyclyl, $C_{6-10}$ aryl or $C_{1-9}$ heteroaryl; wherein $R^8$ is independently and optionally substituted with one or more $R^{19}$;

each $R^{15}$ is independently H, deuterium, $C_{1-6}$ alkyl, $C_{1-6}$ aminoalkyl, $C_{2-6}$ alkenyl, $C_{2-6}$ alkynyl, $C_{1-6}$ haloalkyl, $C_{3-6}$ cycloalkyl, $C_{2-9}$ heterocyclyl or $C_{6-10}$ aryl;

each $R^{16}$ is independently H, deuterium, hydroxy, amino, $C_{1-6}$ alkyl, $C_{1-6}$ aminoalkyl, $C_{2-6}$ alkenyl, $C_{2-6}$ alkynyl, $C_{1-6}$ haloalkyl, $C_{3-6}$ cycloalkyl, $C_{2-9}$ heterocyclyl, $C_{6-10}$ aryl or $-NR^{17}R^{18}$;

each of $R^{17}$ and $R^{18}$ is independently H, deuterium, $C_{1-6}$ alkyl, $C_{1-6}$ aminoalkyl, $C_{2-6}$ alkenyl, $C_{2-6}$ alkynyl, $C_{1-6}$ haloalkyl, $C_{3-6}$ cycloalkyl, $C_{2-9}$ heterocyclyl or $C_{6-10}$ aryl; or $R^{17}$ and $R^{18}$, together with the N atom to which they are attached, independently and optionally form $C_{2-9}$ heterocyclyl or $C_{1-9}$ heteroaryl;

wherein each of said hydroxy, amino, $C_{1-6}$ alkyl, $C_{1-4}$ hydroxyalkyl, $C_{1-6}$ aminoalkyl, $C_{2-6}$ alkenyl, $C_{2-6}$ alkynyl, $C_{3-6}$ cycloalkyl, $C_{1-6}$ haloalkyl, $C_{1-6}$ alkylamino, $C_{1-6}$ alkoxy, $C_{3-6}$ cycloalkoxy, $C_{1-6}$ haloalkoxy, halo-substituted $C_{6-10}$ aryl, $C_{6-10}$ aryl-$C_{1-6}$-alkyl, $C_{2-9}$ heterocyclyl, $C_{6-10}$ aryl or $C_{1-9}$ heteroaryl of $R^8$, $R^{15}$, $R^{16}$, $R^{17}$ and $R^{18}$ is independently and optionally substituted with one or more $R^9$; and each of $R^9$ and $R^{19}$ is independently H, deuterium, F, Cl, Br, I, cyano, oxo (=O), hydroxy, $C_{1-6}$ alkyl, $C_{1-6}$ alkylamino, amino, $C_{6-10}$ aryl, $C_{2-9}$ heterocyclyl, $C_{1-9}$ heteroaryl, $C_{2-6}$ alkenyl, $C_{2-6}$ alkynyl, $C_{3-6}$ cycloalkyl, $C_{1-6}$ alkoxy or $C_{1-6}$ haloalkyl.

In some embodiments,

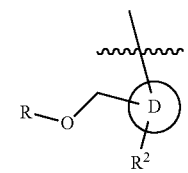

(Ia)

of Formula (I) is:

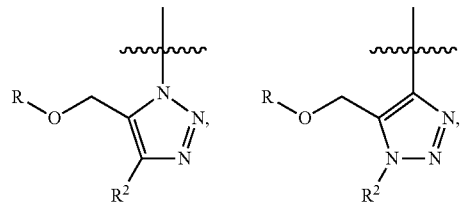

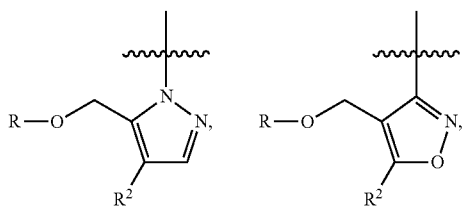

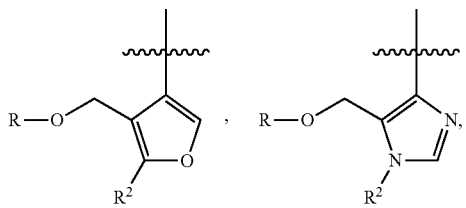

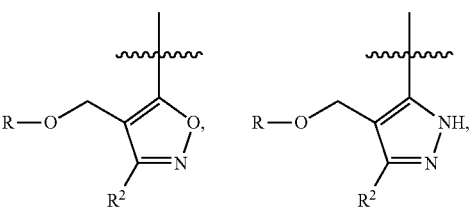

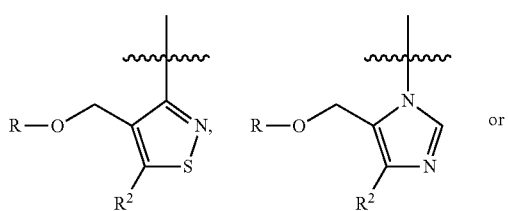

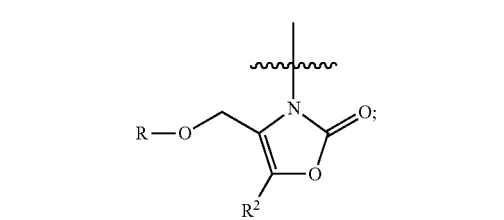

and wherein each of R and $R^2$ is as defined herein.

In some embodiments, provided herein is a compound having Formula (II) or a stereoisomer, a geometric isomer, a tautomer, an N-oxide, a hydrate, a solvate, a metabolite, a pharmaceutically acceptable salt or a prodrug thereof,

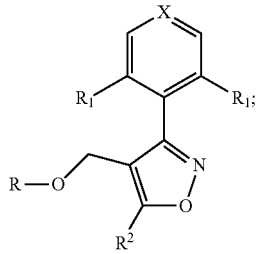

(II)

wherein X, each $R^1$, R and $R^2$ are as defined herein.

In some embodiments, provided herein is a compound having Formula (IV), or a stereoisomer, a geometric isomer, a tautomer, an N-oxide, a hydrate, a solvate, a metabolite, a pharmaceutically acceptable salt or a prodrug thereof,

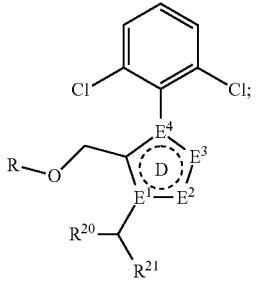

(IV)

wherein ring D is a five-membered heteroaromatic ring;

$E^1$ and $E^4$ are each independently C or N;

$E^2$ and $E^3$ are each independently C, CH, N, NH, O or S;

$R^{20}$ and $R^{21}$ are each independently H, $C_{1-2}$ alkyl, $C_{1-2}$ haloalkyl; or $R^{20}$ and $R^{21}$, together with the C atom to which they are attached, independently and optionally form $C_{3-6}$ cycloalkyl; and wherein R is as defined herein.

In some embodiments, provided herein is a compound having Formula (V), or a stereoisomer, a geometric isomer, a tautomer, an N-oxide, a hydrate, a solvate, a metabolite, a pharmaceutically acceptable salt or a prodrug thereof,

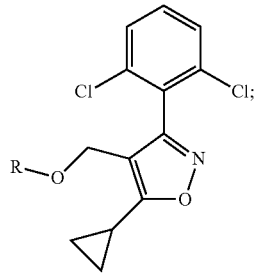

(V)

and wherein R is as defined herein.

In some embodiments, R is:

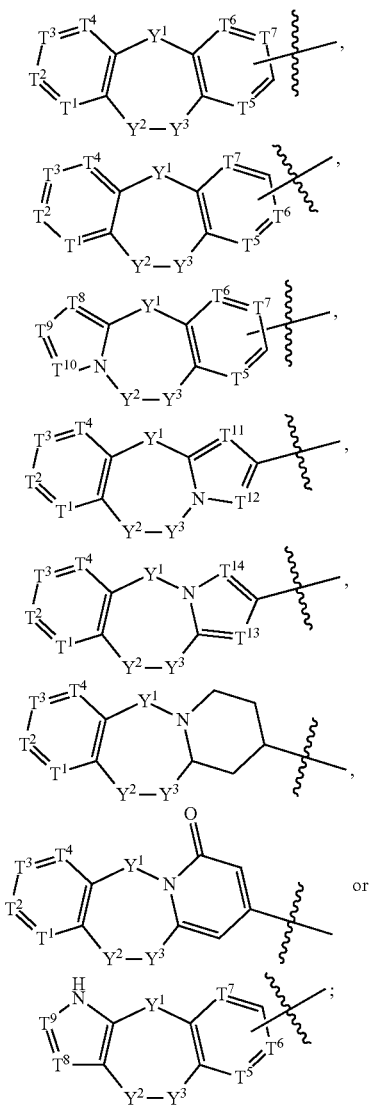

wherein each moiety represented by R is independently and optionally substituted with one, two, three, four or five $R^8$;

each of $T^1$, $T^2$, $T^3$, $T^4$, $T^5$, $T^6$, $T^7$, $T^8$, $T^9$, $T^{10}$, $T^{11}$, $T^{12}$, $T^{13}$ and $T^{14}$ is independently CH, $^\oplus$N—O$^\ominus$ or N;

$Y^1$ is a bond, —O—, —S(=O)$_t$—, —NR$^5$—, —NR$^5$—C(=O)—, —C(=O)—NR$^5$—, —S(=O)$_t$—NR$^5$—, —NR$^5$—S(=O)$_t$—, —(CR$^6$R$^7$)$_y$— or —C(=O)—;

each of $Y^2$ and $Y^3$ is independently a bond, —O—, —S(=O)$_t$—, —NR$^5$—, —CR$^6$R$^7$—, —(CR$^6$R$^7$)$_y$— or —C(=O)—, or $Y^2$ is connected with $Y^3$ to form —CR$^6$=CR$^7$—;

wherein CR$^6$R$^7$ of —(CR$^6$R$^7$)$_y$— is independently and optionally replaced with —O—, —S(=O)$_t$— or —NR$^5$—;

y is 0, 1, 2, 3 or 4;

each $R^5$ is independently H, deuterium, alkyl, aminoalkyl, haloalkyl, cycloalkyl, heterocyclyl, aryl, halo-substituted aryl or arylalkyl; and each of $R^6$ and $R^7$ is independently H, deuterium, F, Cl, Br, I, cyano, hydroxy, hydroxyalkyl, alkyl, alkylamino, aminoalkyl, alkenyl, alkynyl, cycloalkyl, haloalkyl, aryl, halo-substituted aryl or arylalkyl; or $R^6$ and $R^7$, together with the C atom to which they are attached, independently and optionally form cycloalkyl or heterocyclyl; and wherein each of $R^8$ and t is as defined herein.

In other embodiments, each $R^5$ is independently H, deuterium, $C_{1-6}$ alkyl, $C_{1-6}$ aminoalkyl, $C_{1-6}$ haloalkyl, $C_{3-6}$ cycloalkyl, $C_{2-9}$ heterocyclyl, $C_{6-10}$ aryl, halo-substituted $C_{6-10}$ aryl or $C_{6-10}$ aryl-$C_{1-6}$-alkyl; and each of $R^6$ and $R^7$ is independently H, deuterium, F, Cl, Br, I, cyano, hydroxy, $C_{1-6}$ hydroxyalkyl, $C_{1-6}$ alkyl, $C_{1-6}$ alkylamino, $C_{1-6}$ aminoalkyl, $C_{2-6}$ alkenyl, $C_{2-6}$ alkynyl, $C_{3-6}$ cycloalkyl, $C_{1-6}$ haloalkyl, $C_{6-10}$ aryl, halo-substituted $C_{6-10}$ aryl or $C_{6-10}$ aryl-$C_{1-6}$-alkyl; or $R^6$ and $R^7$, together with the C atom to which they are attached, independently and optionally form $C_{3-6}$ cycloalkyl or $C_{2-9}$ heterocyclyl.

In other embodiments, each $R^5$ is independently H, deuterium, $C_{1-3}$ alkyl, $C_{1-3}$ aminoalkyl, $C_{1-3}$ haloalkyl, $C_{3-6}$ cycloalkyl, $C_{2-6}$ heterocyclyl, phenyl or benzyl; and each of $R^6$ and $R^7$ is independently H, deuterium, F, Cl, Br, I, cyano, hydroxy, $C_{1-3}$ alkyl, $C_{1-4}$ hydroxyalkyl, $C_{1-3}$ alkylamino, $C_{1-3}$ aminoalkyl, $C_{2-4}$ alkenyl, $C_{2-4}$ alkynyl, $C_{3-6}$ cycloalkyl, $C_{1-3}$ haloalkyl, phenyl or benzyl; or $R^6$ and $R^7$, together with the C atom to which they are attached, independently and optionally form $C_{3-6}$ cycloalkyl or $C_{2-6}$ heterocyclyl.

In other embodiments, R is:

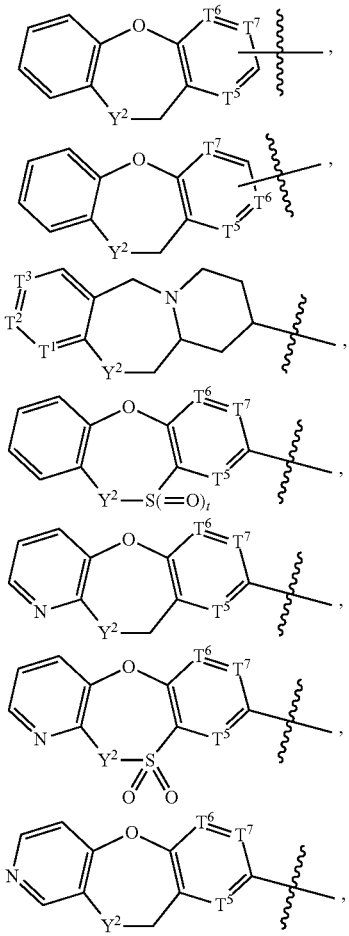

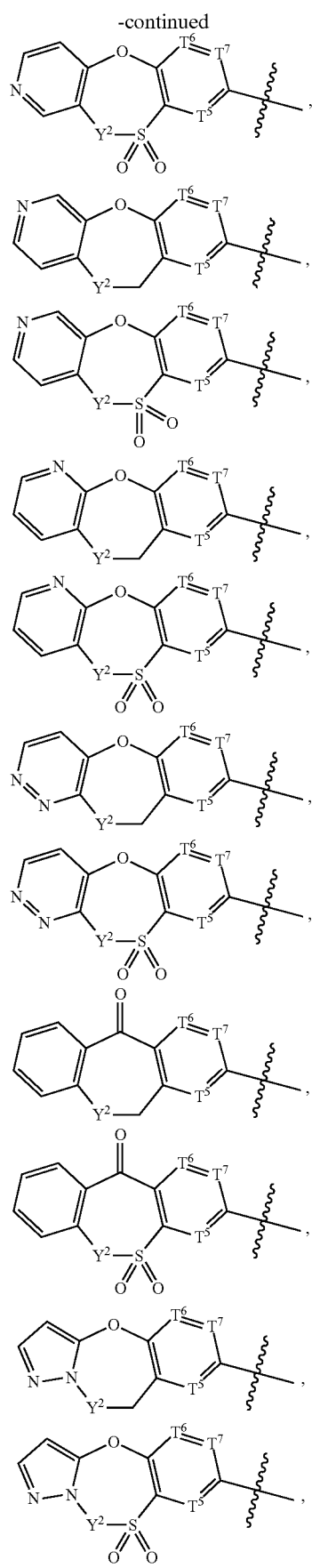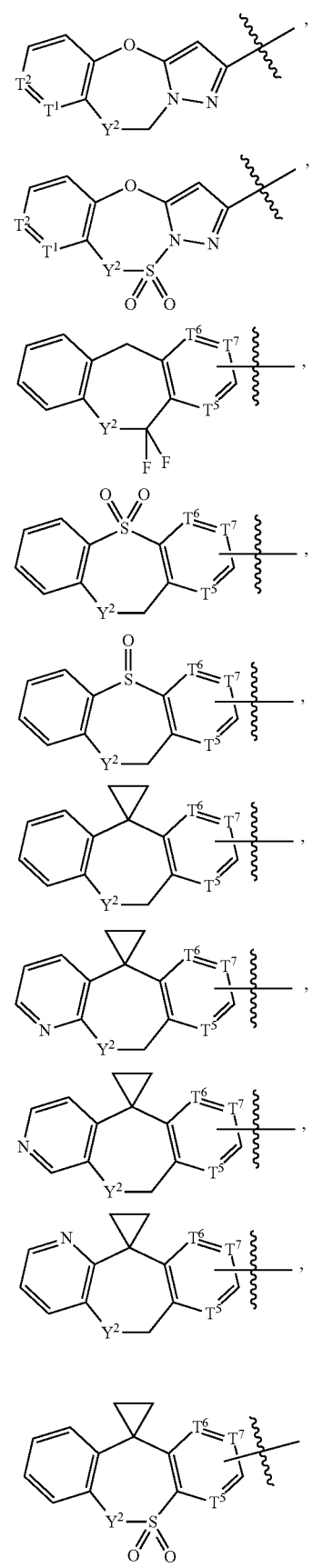

-continued
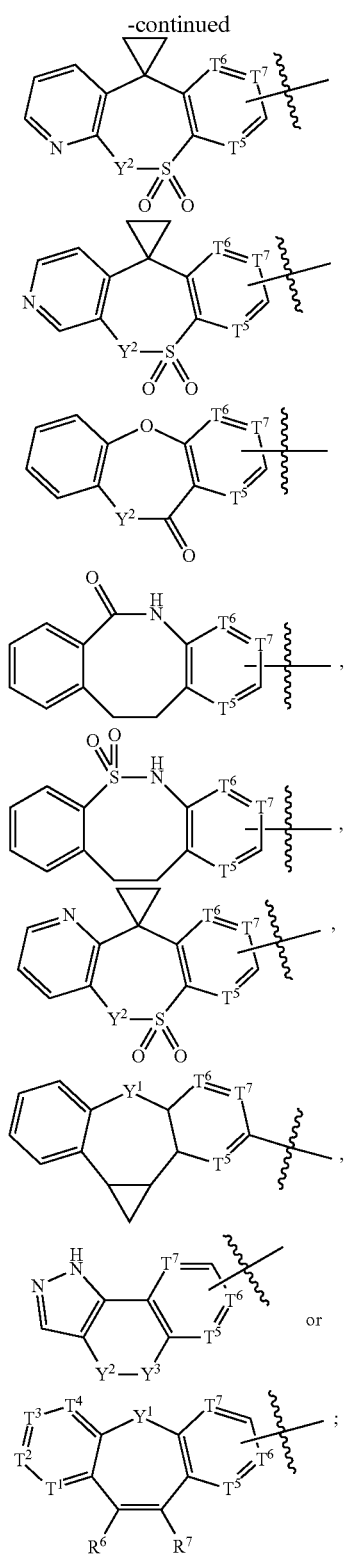
wherein each moiety represented by R is independently and optionally substituted with one, two, three, four or five $R^8$;
each of $T^1$, $T^2$, $T^5$, $T^6$ and $T^7$ is independently CH, $^{\oplus}$N—O$^{\ominus}$ or N; and
each of $R^8$, t, $Y^1$, $Y^2$, $Y^3$, $R^6$ and $R^7$ is as defined herein.
In other embodiments, R is:
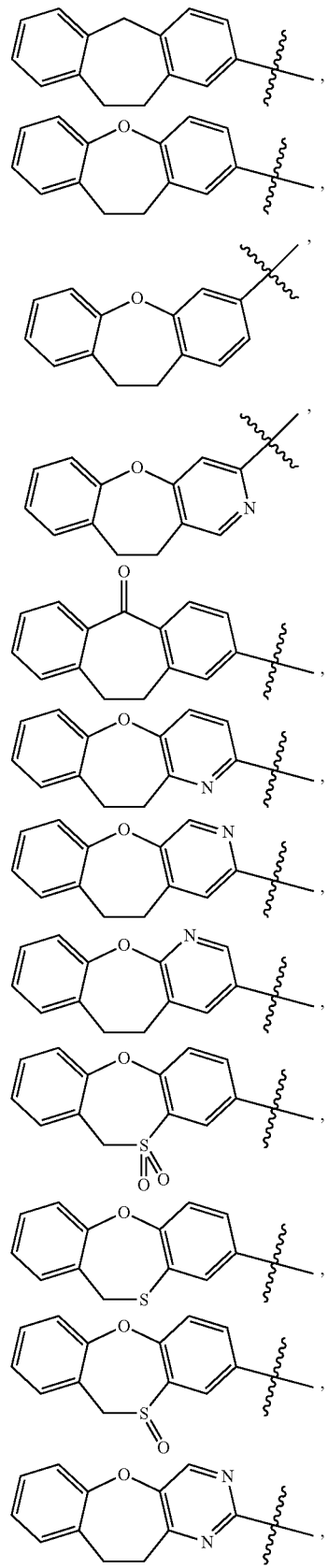

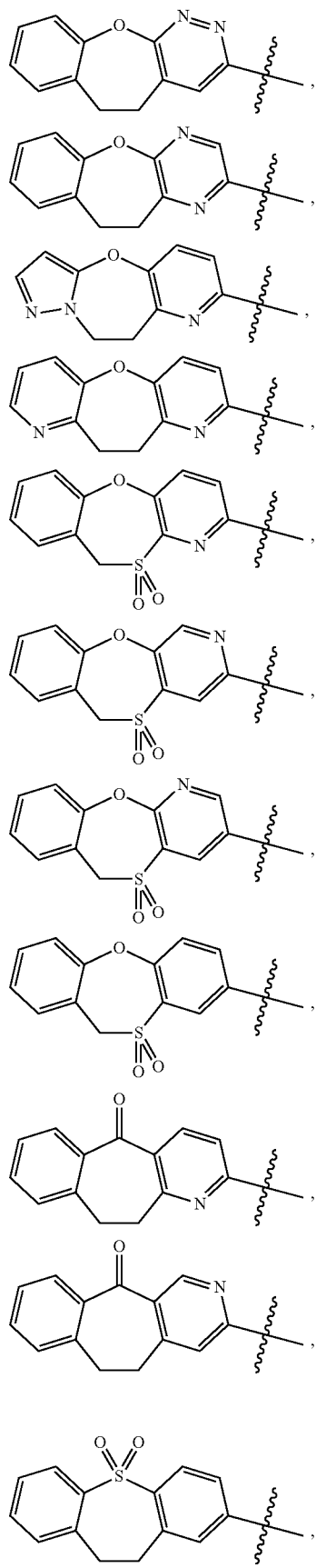
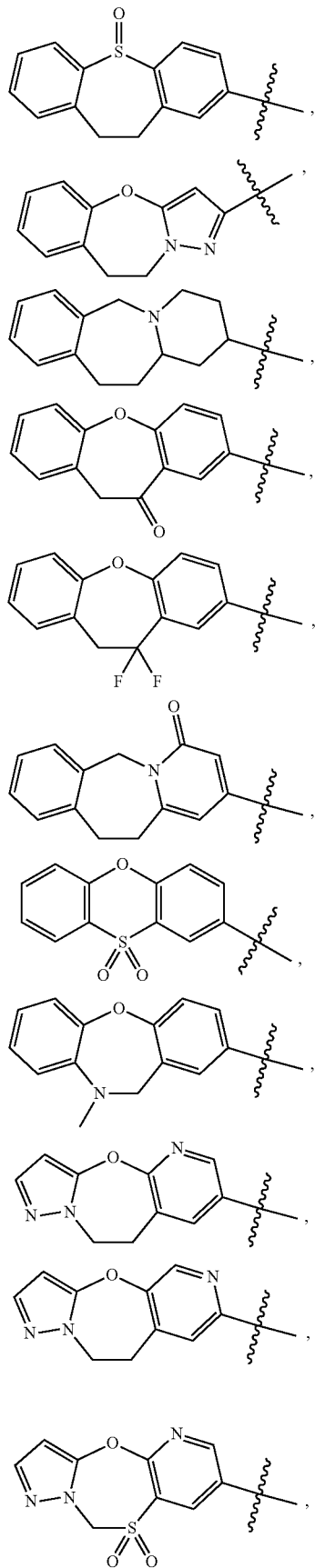

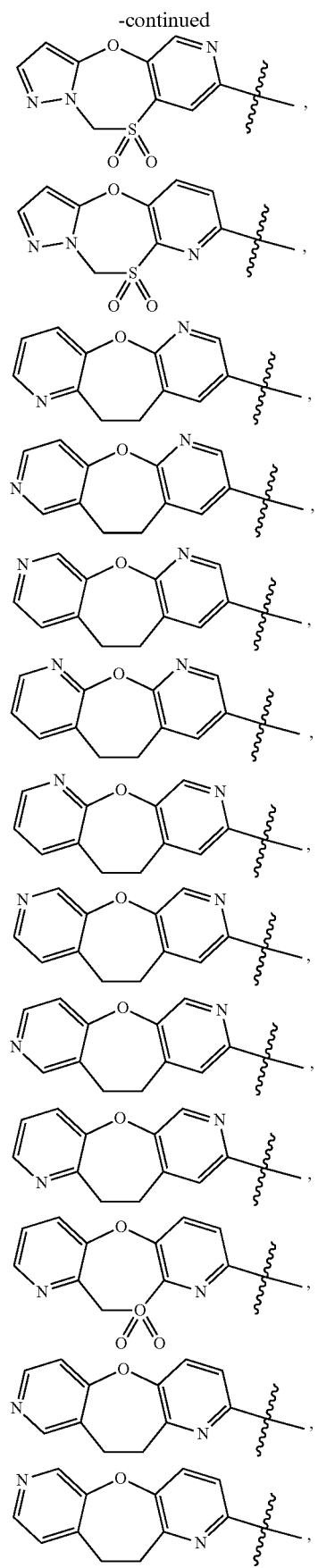
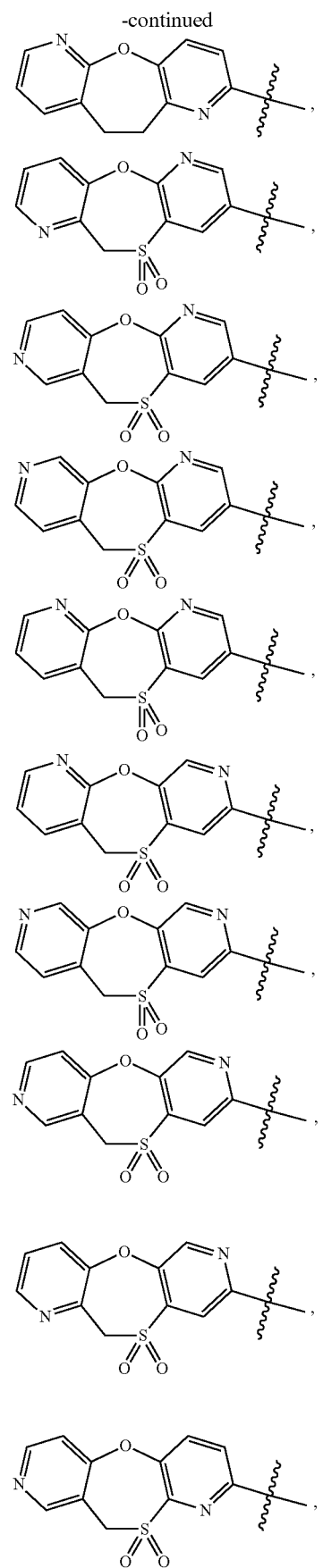

-continued

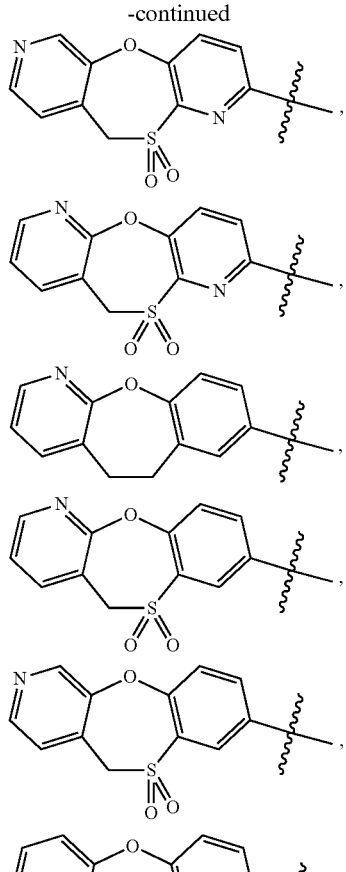

-continued

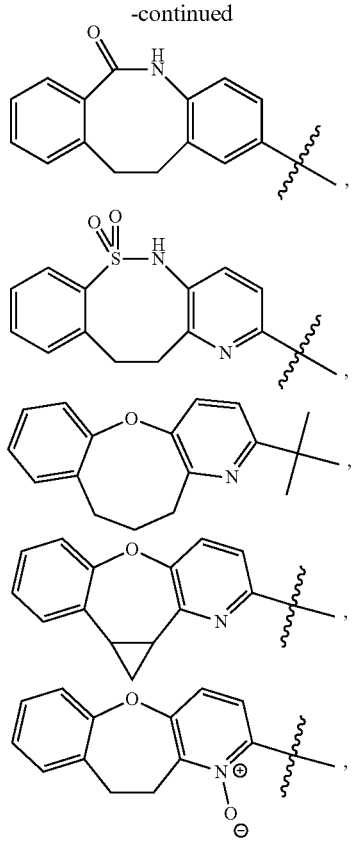

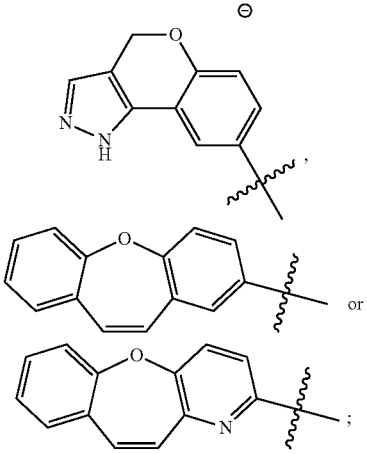

wherein each moiety represented by R is independently and optionally substituted with one, two, three, four or five $R^8$; and each said $R^8$ is as defined herein.

In other embodiments, each $R^8$ is independently H, deuterium, F, Cl, Br, I, hydroxy, nitro, amino, $C_{1-3}$ aminoalkyl, $C_{1-3}$ alkylamino, $C_{1-3}$ alkyl, $C_{1-4}$ hydroxyalkyl, $C_{1-3}$ alkoxy, $C_{1-3}$ haloalkyl, $C_{1-3}$ haloalkoxy, $C_{3-6}$ cycloalkyl, $C_{3-6}$ cycloalkyloxy, $C_{2-4}$ alkenyl, $C_{2-4}$ alkynyl, $C_{6-10}$ aryl, halo-substituted $C_{6-10}$ aryl, $C_{6-10}$ aryl-$C_{1-4}$alkyl, oxo (=O), —C(=O)OR$^{15}$, —S(=O)$_t$R$^{16}$, —C(=O)NR$^{17}$R$^{18}$, —C(=O)N(R$^{17}$)S(=O)$_2$R$^{16}$, —C(=O)NH—C$_{1-4}$ alkylene —S(=O)$_2$OR$^{15}$, —C(=O)NH—C$_{1-4}$ alkylene —C(=O)OR$^{15}$, cyano, triazolyl or tetrazolyl; or two $R^8$, together with the same C atom to which they are attached, independently and optionally form $C_{3-6}$ cycloalkyl or $C_{2-9}$ heterocyclyl; or two $R^8$, together with the adjacent C atoms to which they are attached, independently and optionally form $C_{3-6}$ cycloalkyl, $C_{2-9}$ heterocyclyl, $C_{6-10}$ aryl or $C_{1-9}$ heteroaryl; wherein each $R^8$ is optionally and independently substituted with one or more $R^{19}$;

each $R^{15}$ is H, deuterium, $C_{1-4}$ alkyl, $C_{1-4}$ aminoalkyl, $C_{2-4}$ alkenyl, $C_{2-4}$ alkynyl, $C_{1-4}$ haloalkyl, $C_{3-6}$ cycloalkyl, $C_{1-6}$ heterocyclyl or $C_{6-10}$ aryl;

each $R^{16}$ is H, deuterium, hydroxy, amino, $C_{1-4}$ alkyl, $C_{1-4}$ aminoalkyl, $C_{2-4}$ alkenyl, $C_{2-4}$ alkynyl, $C_{1-4}$ haloalkyl, $C_{3-6}$ cycloalkyl, $C_{2-6}$ heterocyclyl, $C_{6-10}$ aryl or —NR$^{17}$R$^{18}$;

each of $R^{17}$ and $R^{18}$ is independently H, deuterium, $C_{1-4}$ alkyl, $C_{1-4}$ aminoalkyl, $C_{2-4}$ alkenyl, $C_{2-4}$ alkynyl, $C_{1-3}$ haloalkyl, $C_{3-6}$ cycloalkyl, $C_{2-6}$ heterocyclyl or $C_{6-10}$ aryl; and each $R^{19}$ is as defined herein.

In some embodiments, each $R^1$ is independently H, deuterium, F, Cl, Br, I, hydroxy, amino, nitro, cyano, methyl, ethyl, n-propyl, isopropyl, t-butyl, dimethylamino, difluoromethyl, trifluoromethyl, tert-butyloxy, difluoromethyloxy, trifluoromethyloxy, cyclopropyl, oxiranyl, phenyl, naphthyl, oxazolyl, pyrazolyl or thiazolyl; and each $R^2$ is independently H, deuterium, F, Cl, Br, I, hydroxy, amino, nitro, cyano, methyl, ethyl, n-propyl, isopropyl, t-butyl, dimethylamino, difluoromethyl, trifluoromethyl, tert-butyloxy, difluoromethyloxy, trifluoromethyloxy, methoxymethyl, isopropoxymethyl, tert-butoxymethyl, cyclopropyl, cycobutyl, oxiranyl or pyrrolidinyl.

In other embodiments, each $R^8$ is independently H, deuterium, F, Cl, Br, I, hydroxy, nitro, amino, oxo (=O), $C_{1-3}$ alkyl, $C_{1-3}$ haloalkyl, —COOH, —C(=O)O—$C_{1-4}$ alkyl, —C(=O)NHS(=O)$_2$—$C_{1-4}$ alkyl, —C(=O)NHS(=O)$_2$-phenyl, —C(=O)NH—$C_{1-4}$ alkylene —S(=O)$_2$OH, —C(=O)NH—$C_{1-4}$ alkylene —C(=O)OH, —S(=O)$_2$NH$_2$, —S(=O)$_2$OH, —S(=O)$_2$—$C_{1-2}$ alkyl, —C(=O)NH$_2$, —C(=O)N(CH$_3$)$_2$, cyano, triazolyl or tetrazolyl.

In one aspect, provided herein is a pharmaceutical composition comprising a compound of Formula (I), Formula (II), Formula (IV) or Formula (V) disclosed herein, or a stereoisomer, a geometric isomer, a tautomer, an N-oxide, a hydrate, a solvate, a metabolite, a pharmaceutically acceptable salt or a prodrug thereof, and a pharmaceutically acceptable carrier, excipient, diluent, adjuvant, vehicle or a combination thereof.

In one aspect, provided herein is use of the compound of Formula (I), Formula (II), Formula (IV) or Formula (V) disclosed herein or the pharmaceutical composition thereof in the manufacture of a medicament for preventing, managing, treating or lessening a disease mediated by FXR.

In some embodiments, the disease mediated by FXR is a cardiovascular and cerebrovascular disease, a disease related to dyslipidemia, obesity, metabolic syndrome, a hyperproliferative disease, fibrosis, an inflammatory disease or a disease related to liver and gallbladder.

In some embodiments, the cardiovascular and cerebrovascular disease comprises atherosclerosis, acute myocardial infarction, veno-occlusive disease, portal hypertension, pulmonary hypertension, heart failure, peripheral arterial occlusive disease (PAOD), sexual dysfunction, stroke or thrombosis.

In some embodiments, the obesity and metabolic syndrome comprise insulin resistance, hyperglycemia, hyperinsulinemia, elevated blood level of fatty acids or glycerol, hyperlipidemia, obesity, hypertriglyceridemia, hypercholesterolemia, X syndrome, diabetic complications, atherosclerosis, hypertension, acute anemia, neutropenia, dyslipidemia, type II diabetes, diabetic nephropathy, diabetic neuropathy, diabetic retinopathy or the merger disorders of diabetes and abnormally high BMI.

In some embodiments, the hyperproliferative disease comprises hepatocellular carcinoma, adenomatous, polyposis, colon cancer, breast cancer, membrane cancer, Barrett's esophageal cancer and other forms of gastrointestinal tract disease or liver tumor.

In some embodiments, the fibrosis, inflammatory disease and disease related to liver and gallbladder comprise non-alcoholic fatty liver disease (NAFLD), nonalcoholic steatohepatitis (NASH), cholestasis, liver fibrosis, primary biliary cirrhosis (PBC), primary sclerosing cholangitis (PSC), progressive familial intrahepatic cholestasis (PFIC), cystic fibrosis, drug-induced bile duct injury, cirrhosis of the liver, hepatitis B, sebaceous disease, cirrhosis of the liver caused by alcohol, biliary obstruction, cholelithiasis, colitis, newborn yellow disease, riboflavin disease prevention or intestinal bacterial overgrowth.

In other aspect, provided herein is a method of preventing, managing, treating or lessening a disease mediated by FXR comprising administering to the patient a therapeutic effective amount of the compound or the pharmaceutical composition disclosed herein.

In other aspect, provided herein is the compound or the pharmaceutical composition disclosed herein for use in preventing, managing, treating or lessening a disease mediated by FXR in a patient.

In other aspect, provided herein is a method of preparing, separating or purifying the compound of Formula (I), Formula (II), Formula (IV) or Formula (V).

The foregoing merely summarizes certain aspects disclosed herein and is not intended to be limiting in nature. These aspects and other aspects and embodiments are described more fully below.

DETAILED DESCRIPTION OF THE INVENTION

Definitions and General Terminology

Reference will now be made in detail to certain embodiments disclosed herein, examples of which are illustrated in the accompanying structures and formulas. The present invention is expected to cover all alternatives, variants and equivalents, which may be included within the scope of the invention as defined in claim. Those skilled in the art will recognize many methods and materials similar or equivalent to those described herein, which may be applied to the practice of the present invention. The present invention is by no means limited to the methods and materials described herein. There are a lot of literature and similar substances distinguished or inconsistent with the present invention, including but not limited to the definitions of terms, the use of terminology, described techniques, or the like, this application controls.

The present invention will apply the following definitions unless otherwise specified. For purposes of this invention, the chemical elements are defined according to the Periodic Table, CAS version and chemical manuals, 75, th Ed, 1994. Additionally, general principles of organic chemistry are described in "Organic Chemistry", Thomas Sorrell, University Science Books, Sausalito: 1999, and Smith et al., and "March's Advanced Organic Chemistry", John Wiley & Sons, New York: 2007, all of which are incorporated herein by reference in their entireties.

The term "comprise" is an open expression, it includes the contents disclosed herein, but don't exclude other contents.

As described herein, compounds disclosed herein may optionally be substituted with one or more substituents, such as are illustrated generally formula in the invention, or as exemplified by particular classes, subclasses, and species of the invention. It will be appreciated that the phrase "optionally substituted" is used interchangeably with the phrase "substituted or unsubstituted". In general, the term "optionally" whether or not located before the term "substituted" refers to the replacement of one or more hydrogen radicals in a given structure with the radical of a specified substituent. Unless otherwise indicated, an optionally substituted group may have a substituent at each substitutable position of the group. When more than one position in a given structure can be substituted with more than one substituent selected from a specified group, the substituent may be either the same or different at each position. Wherein the substituents may be, but are not limited to H, F, Cl, Br, I, nitro, cyano, oxo (=O), hydroxy, alkyl, hydroxyalkyl, alkylamino, aminoalkyl, haloalkoxy, cycloalkyl, amino, aryl, heterocyclyl, heteroaryl, alkenyl, alkynyl, cycloalkyloxy, alkoxy, alkoxyalkyl haloalkyl, —COOH, -alkylene —C(=O)O-alkyl, -alkylene-S(=O)$_2$-alkyl, -alkylene-S(=O)$_2$-amino, —S(=O)$_2$-alkyl, —S(=O)$_2$-amino, —S(=O)$_2$OH, —O-alkylene-C(=O)O-alkyl, —O-alkylene-S(=O)$_2$-alkyl, —O-alkylene-S(=O)$_2$-amino, —O-alkylene-S(=O)$_2$OH, —C(=O)NH$_2$, —C(=O)NH-alkyl, —C(=O)N(alkyl)-alkyl, —C(=O)NHS(=O)$_2$-alkyl, —C(=O)NHS(=O)$_2$-amino, —C(=O)NHS(=O)$_2$OH, —N(R$^{17}$)C(=O)NR$^{17}$R$^{18}$, —OC(=O)R$^{16}$, —N(haloalkyl)-alkyl, —N(alkyl)-S(=O)$_2$-alkyl, —NHS(=O)$_2$-alkyl, —NHS(=O)$_2$-haloalkyl, —N(alkyl)S(=O)$_2$-haloalkyl, —N(alkyl)S(=O)$_2$-alkylamino, —NHC(=O)-alkyl, —NHC(=O)-haloalkyl, —N(alkyl)C(=O)-haloalkyl, —N(alkyl)C(=O)-alkylamino, —N(alkyl)C(=O)O-alkyl, —NHC(=O)O-alkyl, —NHC(=O)O-haloalkyl, —N(alkyl)C(=O)O-haloalkyl, —N(alkyl)C(=O)O-aminoalkyl, —NHC(=O)—NH$_2$, —NHC(=O)NH-(alkyl), —NHC(=O)NH(haloalkyl), —NHC(=O)N(alkyl)-alkyl, —OC(=O)-alkyl, —OC(=O)-amino, —OC(=O)-alkylamino, —OC(=O)-aminoalkyl, —OC(=O)-alkoxy, —C(=O)N(alkyl)S(=O)$_2$-alkyl, —C(=O)N(alkyl)S(=O)$_2$-amino, —C(=O)NH—S(=O)$_2$OH, —C(=NH)NH$_2$, —C(=NH)NH-alkyl, —C(=NH)N(alkyl)-alkyl, —C(=N-alkyl)-NH$_2$, —C(=O)NH-alkylene-S(=O)$_2$OH, —C(=O)NHC(=O)OH, —C(=O)NHC(=O)O-alkyl, —C(=O)N(alkyl)C(=O)O-alkyl, —C(=O)NH-alkylene-C(=O)OH and —C(=O)NH-alkylene-C(=O)O-alkyl, and the like, and wherein R$^{16}$, R$^{17}$ and R$^{18}$ are as defined herein.

The term "alkyl" refers to a saturated linear or branched-chain monovalent hydrocarbon radical of 1 to 20 carbon atoms, or 1 to 10 carbon atoms, or 1 to 6 carbon atoms, or 1 to 4 carbon atoms, or 1 to 3 carbon atoms, or 1 to 2 carbon atoms, wherein the alkyl radical may be optionally and independently substituted with one or more substituents described herein. Some non-limiting examples of the alkyl group include, methyl (Me, —CH$_3$), ethyl (Et, —CH$_2$CH$_3$), n-propyl (n-Pr, —CH$_2$CH$_2$CH$_3$), isopropyl (i-Pr, —CH(CH$_3$)$_2$), n-butyl (n-Bu, —CH$_2$CH$_2$CH$_2$CH$_3$), isobutyl (i-Bu, —CH$_2$CH(CH$_3$)$_2$), sec-butyl (s-Bu, —CH(CH$_3$)CH$_2$CH$_3$), tert-butyl (t-Bu, —C(CH$_3$)$_3$), n-pentyl (—CH$_2$CH$_2$CH$_2$CH$_2$CH$_3$), 2-pentyl (—CH(CH$_3$)CH$_2$CH$_2$CH$_3$), 3-pentyl (—CH(CH$_2$CH$_3$)$_2$), 2-methyl-2-butyl (—C(CH$_3$)$_2$CH$_2$CH$_3$), 3-methyl-2-butyl (—CH(CH$_3$)CH(CH$_3$)$_2$), 3-methyl-1-butyl (—CH$_2$CH$_2$CH(CH$_3$)$_2$), 2-methyl-1-butyl (—CH$_2$CH(CH$_3$)CH$_2$CH$_3$), n-hexyl (—CH$_2$CH$_2$CH$_2$CH$_2$CH$_2$CH$_3$), 2-hexyl (—CH(CH$_3$)CH$_2$CH$_2$CH$_2$CH$_3$), 3-hexyl (—CH(CH$_2$CH$_3$)(CH$_2$CH$_2$CH$_3$)), 2-methyl-2-pentyl (—C(CH$_3$)$_2$CH$_2$CH$_2$CH$_3$), 3-methyl-2-pentyl (—CH(CH$_3$)CH(CH$_3$)CH$_2$CH$_3$), 4-methyl-2-pentyl (—CH(CH$_3$)CH$_2$CH(CH$_3$)$_2$), 3-methyl-3-pentyl (—C(CH$_3$)(CH$_2$CH$_3$)$_2$), 2-methyl-3-pentyl (—CH(CH$_2$CH$_3$)CH(CH$_3$)$_2$), 2,3-dimethyl-2-butyl (—C(CH$_3$)$_2$CH(CH$_3$)$_2$), 3,3-dimethyl-2-butyl (—CH(CH$_3$)C(CH$_3$)$_3$), n-heptyl and n-octyl, etc. The term "alkyl" or the prefix "alk-" is inclusive of both straight chain and branched saturated carbon chain. The term "alkylene" used herein refers to a saturated divalent hydrocarbon group derived from a straight or branched chain saturated hydrocarbon by the removal of two hydrogen atoms, such exaples include, but are not limited to methylene, ethylidene and isopropylidene, and the like.

The term "alkenyl" refers to a linear or branched chain monovalent hydrocarbon radical of 2 to 12 carbon atoms, or 2 to 8 carbon atoms, or 2 to 6 carbon atoms, or 2 to 4 carbon atoms, with at least one site of unsaturation, i.e., a carbon-carbon, sp$^2$ double bond, wherein the alkenyl radical may be independently and optionally substituted with one or more substituents described herein, and includes radicals having "cis" and "trans" orientations, or alternatively, "E" and "Z" orientations. Examples include, but are not limited to, ethenyl or vinyl (—CH=CH$_2$), allyl (—CH$_2$CH=CH$_2$), butenyl (—CH$_2$CH$_2$CH=CH$_2$), and the like.

The term "alkynyl" refers to a linear or branched chain monovalent hydrocarbon radical of 2 to 12 carbon atoms, or 2 to 8 carbon atoms, or 2 to 6 carbon atoms, or 2 to 4 carbon atoms, with at least one site of unsaturation, i.e., a carbon-carbon, sp triple bond, wherein the alkynyl radical is independently and optionally substituted with one or more substituents described herein. Examples include, but are not limited to, ethynyl (—C≡CH), propargyl (—CH$_2$C≡CH), and the like.

The term "heteroatom" refers to one or more of O, S, N, P and Si, including any oxidized form of C, N, S, or P; the quaternized form of any basic N; or a substitutable nitrogen of a heterocyclic ring, for example, N (as in 3,4-dihydro-2H-pyrrolyl), NH (as in pyrrolidinyl) or NR (as in N-substituted pyrrolidinyl); or —CH$_2$— of a heterocyclic ring is oxidized to form —C(=O)— form.

The term "halogen" or "halo" refers to fluoro (F), chloro (Cl), bromo (Br), or iodo (I).

The term "unsaturated" refers to a moiety having one or more units of unsaturation.

The term "alkoxy" refers to an alkyl group, as defined herein, attached to the principal carbon chain through an oxygen atom. In some embodiments, alkoxy is C$_{1-4}$ alkoxy. Examples include, but are not limited to, methoxy, ethoxy, propoxy, butoxy, and the like. The alkoxy group may be optionally substituted with one or more substituents disclosed herein.

The term "alkoxyalkyl" refers to an alkyl group substituted with one or more alkoxy, and alkoxy and alkyl are as defined herein. In some embodiments, alkoxyalkyl is C$_{1-6}$ alkoxy C$_{1-6}$ alkyl. In other embodiments, alkoxyalkyl is C$_{1-3}$ alkoxy C$_{1-3}$ alkyl. And each said alkoxyalkyl can be independently and optionally substituted with one or more substituents described herein. The terms "haloalkyl", "haloalkenyl" or "haloalkoxy" refer to alkyl, alkenyl, or alkoxy, as the case may be, substituted with one or more halogen atoms. In some embodiments, haloalkyl is C$_{1-6}$ haloalkyl. In other embodiments, haloalkyl is C$_{1-3}$ haloalkyl. In some embodiments, haloalkoxy is C$_{1-6}$ haloalkoxy. In other embodiments, haloalkoxy is C$_{1-3}$ haloalkoxy. Some non-limiting examples of "haloalkyl", "haloalkenyl" or "haloalkoxy" groups include trifluoromethyl, 2-chloro-vinyl, 2,2-difluoroethyl, trifluoromethoxy, and the like. And wherein optionally each of the haloalkyl, haloalkenyl or haloalkoxy may be optionally substituted with one or more substituents described herein.

The term "alkylamino" refers to "N-alkylamino" and "N,N-dialkylamino", wherein amino groups are independently substituted with one alkyl radical or two alkyl radicals, respectively. In some embodiments, the alkylamino group is $C_{1-6}$ alkylamino or a ($C_{1-6}$ alkyl) amino group. In other embodiments, the alkylamino group is $C_{1-3}$ alkylamino or a ($C_{1-3}$ alkyl) amino group. Some non-limiting examples of the alkylamino group include monoalkylamino and dialkylamino, such as N-methylamino, N-ethylamino, N,N-dimethylamino, N,N-diethylamino, and the like. And wherein the alkylamino radical is optionally substituted with one or more substituents described herein.

The term "cycloalkyl" refers to a monovalent or multivalent saturated ring having 3 to 12 carbon atoms as a monocyclic, bicyclic, or tricyclic carbon ring system, but not an aromatic ring. In some embodiments, the cycloalkyl group contains 3 to 12 carbon atoms. In other embodiments, the cycloalkyl group contains 3 to 8 carbon atoms. In still other embodiments, the cycloalkyl group contains 3 to 6 carbon atoms. Examples include, but are not limited to, cyclopropyl, cyclobutyl, cyclopentyl, cyclohexyl, and the like. The cycloalkyl group may be optionally substituted with one or more substituents disclosed herein.

The term "cycloalkyloxy" refers to a cycloalkyl attached to the principal carbon chain through an oxygen atom, and cycloalkyl is as defined herein.

The term "heterocycle", "heterocyclyl", or "heterocyclic ring" as used interchangeably herein refers to a saturated or partially unsaturated monocyclic, bicyclic or tricyclic ring containing 3-12 ring atoms, but not an aromatic ring, of which at least one ring atom is a heteroatom. Unless otherwise specified, the heterocyclyl group may be carbon or nitrogen linked, and the heteroatom is as defined herein. Some non-limiting examples of the heterocyclyl group include oxiranyl, azetidinyl, oxetanyl, thietanyl, pyrrolidinyl, 2-pyrrolinyl, 3-pyrrolinyl, pyrazolinyl, pyrazolidinyl, imidazolinyl, imidazolidinyl, tetrahydrofuranyl, dihydrofuranyl, tetrahydrothienyl, dihydrothienyl, 1,3-dioxolanyl, dithiolanyl, tetrahydropyranyl, dihydropyranyl, 2H-pyranyl, 4H-pyranyl, tetrahydrothiopyranyl, piperidinyl, morpholinyl, thiomorpholinyl, piperazinyl, dioxanyl, dithianyl, thioxanyl, homopiperazinyl, homopiperidinyl, oxepanyl, thiepanyl, oxazepinyl, diazepinyl, thiazepinyl and 2-oxa-5-azabicyclo[2.2.1]hept-5-yl. Some non-limiting examples of heterocyclyl wherein —$CH_2$— group is replaced by —C(=O)-moiety include 2-oxopyrrolidinyl, oxo-1,3-thiazolidinyl, 2-piperidinonyl, 3,5-dioxopiperidinyl and pyrimidinedionyl. Some non-limited examples of heterocyclyl wherein the ring sulfur atom is oxidized include sulfolanyl, 1,1-dioxo-thiomorpholinyl. The heterocyclyl group may be optionally substituted with one or more substituents disclosed herein.

In one embodiment, heterocyclyl may be 4-7 membered heterocyclyl. Examples include, but are not limited to, azetidinyl, oxetanyl, thietanyl, pyrrolidinyl, 2-pyrrolinyl, 3-pyrrolinyl, pyrazolinyl, pyrazolidinyl, imidazolinyl, imidazolidinyl, tetrahydrofuranyl, dihydrofuranyl, tetrahydrothienyl, dihydrothienyl, 1,3-dioxolanyl, dithiolanyl, tetrahydropyranyl, dihydropyranyl, 2H-pyranyl, 4H-pyranyl, tetrahydrothiopyranyl, piperidinyl, morpholinyl, thiomorpholinyl, piperazinyl, dioxanyl, dithianyl, thioxanyl, homopiperazinyl, homopiperidinyl, oxepanyl, thiepanyl, oxazepinyl, diazepinyl and thiazepinyl. Some non-limiting examples of heterocyclyl wherein —$CH_2$— group is replaced by —C(=O)— moiety include 2-oxopyrrolidinyl, oxo-1,3-thiazolidinyl, 2-piperidinonyl, pyridine-2(1H)-one-yl, 3,5-dioxopiperidinyl and pyrimidinedionyl. Some non-limited examples of heterocyclyl wherein the ring sulfur atom is oxidized include sulfolanyl and 1,1-dioxo-thiomorpholinyl. The heterocyclyl group containing 4-7 ring atoms may be optionally substituted with one or more substituents disclosed herein.

In other embodiment, heterocyclyl may be 4 membered heterocyclyl. Examples include, but are not limited to, azetidinyl, oxetanyl and thietanyl. The heterocyclyl group containing 4 ring atoms may be optionally substituted with one or more substituents disclosed herein.

In other embodiment, heterocyclyl may be 5 membered heterocyclyl. Examples include, but are not limited to, pyrrolidinyl, 2-pyrrolinyl, 3-pyrrolinyl, pyrazolidinyl, pyrazolidinyl, imidazolinyl, imidazolidinyl, tetrahydrofuranyl, dihydrofuranyl, tetrahydrothienyl, dihydrothienyl, 1,3-dioxolanyl and dithiolanyl. Some non-limiting examples of heterocyclyl wherein —$CH_2$— group is replaced by —C(=O)— moiety include 2-oxopyrrolidinyl and oxo-1,3-thiazolidinyl. Some non-limited examples of heterocyclyl wherein the ring sulfur atom is oxidized include sulfolanyl. The heterocyclyl group containing 5 ring atoms may be optionally substituted with one or more substituents disclosed herein.

In other embodiment, heterocyclyl may be 6 membered heterocyclyl. Examples include, but are not limited to, tetrahydropyranyl, dihydropyranyl, 2H-pyranyl, 4H-pyranyl, tetrahydrothiopyranyl, piperidinyl, morpholinyl, thiomorpholinyl, piperazinyl, dioxanyl, dithianyl and thioxanyl. Some non-limiting examples of heterocyclyl wherein —$CH_2$— group is replaced by —C(=O)— moiety include 2-piperidinonyl, 3,5-dioxopiperidinyl and pyrimidinedionyl. Some non-limited examples of heterocyclyl wherein the ring sulfur atom is oxidized is 1,1-dioxo-thiomorpholinyl. The heterocyclyl group containing 6 ring atoms may be optionally substituted with one or more substituents disclosed herein.

In still other embodiment, heterocyclyl may be 7-12 membered heterocyclyl. Examples include, but are not limited to, 2-oxa-5-azabicyclo[2.2.1]hept-5-yl. The heterocyclyl group containing 7-12 ring atoms may be optionally substituted with one or more substituents disclosed herein.

The term "aryl" refers to monocyclic, bicyclic and tricyclic carbocyclic ring systems having a total of six to fourteen ring members, or six to twelve ring members, or six to ten ring members, wherein at least one ring in the system is aromatic, wherein each ring in the system contains 3 to 7 ring members, and that has a single point or multipoint of attachment to the rest of the molecule. The term "aryl" and "aromatic ring" can be used interchangeably herein. Examples of aryl ring may include phenyl, naphthyl and anthracene. The aryl group may be optionally and independently substituted with one or more substituents disclosed herein.

The term "arylalkyl" refers to an alkyl group subustituted with one or more aryl groups, wherein the alkyl group and aryl group are as defined herein. Some non-limiting examples of the arylalkyl group include phenylmethyl, phenylethyl, and the like.

The term "heteroaryl" refers to monocyclic, bicyclic and tricyclic carbocyclic ring systems having a total of five to twelve ring members, or five to ten ring members, or five to six ring members, wherein at least one ring system is an aromatic ring, and at least one ring system contains one or more hetero atoms, and in which at least one aromatic ring member is selected from heteroatom, and wherein each ring in the system contains 5 to 7 ring members and that has a single point or multipoint of attachment to the rest of the molecule. The term "hetreroaryl" and "heteroaromatic ring" or "heteroaromatic compound" can be used interchangeably herein. The heteroaryl group is optionally substituted with one or more substituents disclosed herein. In one embodiment, a 5-10 membered heteroaryl group comprises 1, 2, 3 or 4 heteroatoms independently selected from O, S and N, wherein the nitrogen atom can be further oxidized.

Some non-limiting examples of heteroaryl rings include furanyl, imidazolyl (e.g., N-imidazolyl, 2-imidazolyl, 4-imidazolyl, 5-imidazolyl), isoxazolyl, oxazolyl (e.g. 2-oxazolyl, 4-oxazolyl, 5-oxazolyl), pyrrolyl (e.g., N-pyrrolyl, 2-pyrrolyl, 3-pyrrolyl), pyridyl, pyrimidinyl (e.g. 2-pyrimidinyl, 4-pyrimidinyl, 5-pyrimidinyl), pyridazinyl, thiazolyl (e.g., 2-thiazolyl, 4-thiazolyl, 5-thiazolyl), tetrazolyl (e.g., 5-tetrazolyl), triazolyl, thienyl (e.g., 2-thienyl, 3-thienyl), pyrazolyl isothiazolyl, 1,2,3-oxadiazolyl, 1,2,5-oxadiazolyl, 1,2,4-oxadiazolyl, 1,2,3-triazolyl, 1,2,3-thiadiazolyl, 1,3,4-thiadiazolyl, 1,2,5-thiadiazolyl, pyrazinyl, 1,3,5-triazinyl, and the following bicycles: benzimidazolyl, benzofuryl, benzothiophenyl, indolyl (e.g., 2-indolyl), purinyl, quinolinyl (e.g., 2-quinolinyl, 3-quinolinyl, 4-quinolinyl), 1,2,3,4-tetrahydroisoquinolinyl, 1,3-benzodioxolyl, indolinyl, isoquinolinyl (e.g., 1-isoquinolinyl, 3-isoquinolinyl or 4-isoquinolinyl), imidazo[1,2-a]pyridyl, pyrazolo[1,5-a]pyridyl, pyrazolo[1,5-a]pyrimidyl, imidazo[1,2-b]pyridazinyl, [1,2,4]triazolo[4,3-b]pyridazinyl, [1,2,4]triazolo[1,5-a]pyrimidinyl, and [1,2,4]triazolo[1,5-a]pyridyl, and the like.

The term "aminoalkyl" refers to a $C_{1-10}$ linear or branched-chain alkyl group substituted with one or more amino groups. In some embodiments, the aminoalkyl is an aminoalkyl group having one to six carbon atoms and one or more amino groups. Some non-limiting examples of the aminoalkyl group include aminomethyl, aminoethyl, aminopropyl, aminobutyl and aminohexyl. The aminoalkyl group is optionally substituted with one or more substituents described herein.

The term "hydroxyalkyl" refers to an alkyl group substituted with one or more hydroxy groups, wherein the alkyl group is as defined herein. Some non-limiting examples of the hydroxyalkyl group include hydroxymethyl, hydroxyethyl, and 1,2-dihydroxy-ethyl, and the like.

The term "halo-substituted aryl" refers to an aryl group substituted with one or more identical or different halogen atoms, wherein halogen and aryl are as described herein. Such examples include, but are not limited to, fluorophenyl, difluorophenyl, trifluorophenyl, chlorophenyl, dichlorophenyl, trichlorophenyl, bromophenyl, tribromophenyl, dibromophenyl, chlorofluorophenyl, fluorobromophenyl, chlorobromophenyl, and the like. The halogen-substituted aryl group is optionally substituted with one or more substituents disclosed herein.

The term "alkylene" refers to a saturated divalent hydrocarbon group derived from a straight or branched chain saturated hydrocarbon by the removal of two hydrogen atoms. Unless otherwise specified, the alkylene group contains 1-12 carbon atoms. Wherein the alkylene group is optionally substituted with one or more substituents described herein. In some embodiments, the alkylene group contains 1-6 carbon atoms. In other embodiments, the alkylene group contains 1-4 carbon atoms. In still other embodiments, the alkylene group contains 1-3 carbon atoms. In yet other embodiments, the alkylene group contains 1-2 carbon atoms. And alkylene group is exemplified by methylene ($-CH_2-$), ethylene ($-CH_2CH_2-$), isopropylene ($-CH(CH_3)CH_2-$), and the like.

The term "alkenylene" refers to an unsaturated divalent hydrocarbon group derived from an alkylene group by the removal of two hydrogen atoms. Unless otherwise specified, the alkenylene group contains 1-12 carbon atoms. Wherein the alkenylene group is optionally substituted with one or more substituents described herein. In some embodiments, the alkenylene group contains 1-6 carbon atoms. In other embodiments, the alkenylene group contains 1-4 carbon atoms. In still other embodiments, the alkenylene group contains 1-3 carbon atoms. In yet other embodiments, the alkenylene group contains 1-2 carbon atoms. Some non-limiting examples of the alkenylene group include ethenylene ($-CH=CH-$), propenylene ($-CH_2CH=CH-$), and the like.

The term "alkylene" refers to a linear or branched divalent hydrocarbon radical of 2 to 12 carbon atoms with at least one site of unsaturation, i.e., a carbon-carbon, sp triple bond, wherein the alkynylene radical may be optionally substituted with one or more substituents described herein. In some embodiments, the alkinylenyl contains 2 to 8 carbon atoms. In other embodiments, the alkynylene contains 2 to 6 carbon atoms. In still other embodiments, the alkynylene contains 2 to 4 carbon atoms. Examples of such groups include, but are not limited to, ethynylene ($-C\equiv C-$), and the like.

The term "fused tricyclic", "fused tricyclyl", refers to a monovalent or multivalent tricyclic system, such as the formula (a), the ring A and ring B share a single bond or a double bond, ring B and ring C share a single bond or a double bond. Each ring of the fused tricyclic system may independently comprises five, six, seven, eight, nine or ten atoms. Fused tricyclic system is aromatic or not aromatic, and such system may comprise isolated or conjugated unsaturation, wherein each ring of the fused tricyclic system is independently saturated or partially saturated non-aromatic carbocyclic ring, or an aromatic ring. Some non-limiting examples of the fused tricyclic group include 10,11-dihydro-5H-dibenzo[a,d][7]annulene, and the like. And the fused tricyclic group is optionally substituted with one or more substituents disclosed herein.

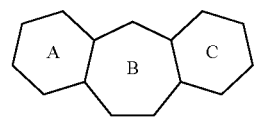

Formula (a)

The term "fused heterotricyclyl" or "fused heterotriciclic" refers to a monovalent or multivalent fused tricyclic system, wherein at least one n is a heteroatom, which is selected from O, S, N, P and Si, including any oxidized form of C, N, S, or P; the quaternized form of any basic N; or a substitutable nitrogen of a heterocyclic ring; or $-CH_2-$ of a heterocyclic ring is oxidized to form $-C(=O)-$ form. Unless otherwise specified, the fused heterotricyclic group may be carbon or nitrogen linked. Fused heterotricyclic is aromatic or not aromatic, wherein each ring of the fused heterotricyclic system is independently saturated or partially saturated non-aromatic ring. The fused heterotricyclic system may be a tricyclic system having 10 to 16 ring atoms, or may be a [5,5,6], [5,6,6], [6,5,6], [6,6,6], [6,7,6], [6,7,5], [5,7,6], or [6,8,6]tricyclic system. Some non-limiting examples of the fused heterotricyclyl group include 10,11- dihydrodibenzo[b,f]oxepin, 10,11-dihydrobenzo[6,7]oxepino[3,2-b]pyridine, 10,11-dihydrobenzo[6,7]oxepino[2,3-c]pyridine, 10,11-dihydrobenzo[6,7]oxepino[2,3-b]pyridine, 11H-dibenzo[b,f][1,4]oxathiepine-10,10-dioxide, 11H-dibenzo[b,f][1,4]oxathiepine, 11H-dibenzo[b,f][1,4]oxathiepine-10-oxide, 10,11-dihydrobenzo[6,7]oxepino[2,3-d]pyrimidine, 5,6-dihydrobenzo[6,7]oxepino[2,3-c]pyridazine, 10,11-dihydrobenzo[6,7]oxepino[2,3-b]pyrazine, 9,10-dihydropyrazolo[5,1-b]pyrido[2,3-j][1,3]oxazepine, 10,11-dihydrooxepino [3,2-b:6,7-b']bipyridine, 10H-benzo[6,7][1,4]oxathiepino[3,2-b]pyridine-11,11-dioxide, 6H-benzo[6,7][1,4]oxathiepino[3,2-c]pyridine-5,5-dioxide, 6H-benzo[6,7][1,4]oxathiepino [3,2-b]pyridine-5,5-dioxide, 10,11-dihydrodibenzo[b,f]thiepine-5,5-dioxide, 9,10-dihydrobenzo [f]pyrazolo[5,1-b][1,3]oxazepine, 1,2,3,4,6,11,12,12a-octahydrobenzo[e]pyrido[1,2-a]azepine, phenoxathiine-10,10-dioxide, 10,11-dihydrodibenzo[b,f][1,4]oxazepine, 6,11-dihydrodibenzo [b,e]thiepine-5,5-dioxide, 10,11-dihydro-5H-benzo[4,5]cyclohepta[1,2-b]pyridine, 6,7-dihydro-5H-benzo[7,8]oxocino[3,2-b]pyridine, 10,11-dihydrooxepino[3,2-b:7,6-c']dipyridine, 10,11-dihydrobenzo[6,7]oxepin[3,2-c]pyridine, 10,11-dihydrodibenzo[b,f]thiepine-5-oxide, 1,4-dihydrobenzopyran[4,3-c]pyrazole, dibenzo[b,f]oxepine, benzo[6,7]oxepino[3,2-b]pyridine. Some non-limiting examples of —CH$_2$— groups in the fused heterotricyclic ring replaced with —C(=O)— group include 11,12-dihydrobenzo[e]pyrido[1,2-a]azepine-4(6H)-one, dibenzo[b,f]oxepin-10(11H)-one, 5H-benzo[5,6]cyclohepta[1,2-c]pyridin-11 (6H)-one, 10,11-dihydro-5H-benzo[4,5]cyclohepta [1,2-b]pyridin-5-one, dibenzo[b,e]thiepine-11(6H)-one-5,5-dioxide, 10,11-dihydro-5H-dibenzo[a,d][7]annulen-5-one, benzo[6,7]oxepino[3,2b]pyridine-11(10H)-one, and the like. And the fused heterotricyclyl group is optionally substituted with one or more substituents disclosed herein.

As described herein, a bond connected to the center position of the ring represents that the bond can connect to any reasonable and connectable position of the ring. For example, Formula (b), a bond connected to the center position of the ring G represents that the bond can connect to any reasonable and connectable position of the ring G, such as Formula (c), Formula (d) and Formula (e).

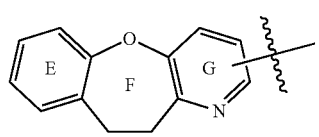

Formula (b)

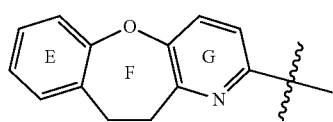

Formula (c)

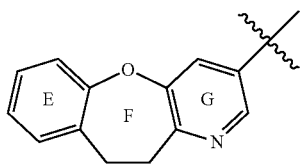

Formula (d)

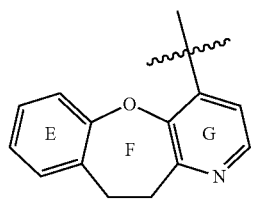

Formula (e)

Furthermore, unless otherwise stated, the phrase "each . . . is independently" is used interchangeably with the phrase "each (of) . . . and . . . is independently". It should be understood broadly that the specific options expressed by the same symbol are independent of each other in different radicals; or the specific options expressed by the same symbol are independent of each other in same radicals. For example, the specific options expressed by T$^1$ of the formula (f) and the formula (g) are independent of each other; Meanwhile, in the same formula, such as formula (h), the specific options of multi-R$^1$ are independent of each other; the specific options of multi-n are independent of each other.

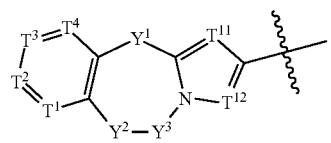

Formula (f)

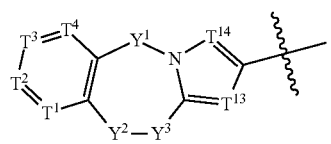

Formula (g)

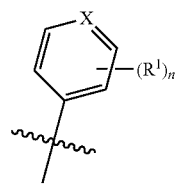

Formula (h)

Unless otherwise stated, structures depicted herein are also meant to include all isomeric (e.g., enantiomeric, diastereomeric, geometric or conformational) forms of the structure; for example, the R and S configurations for each asymmetric center, (Z) and (E) double bond isomers, and (Z) and (E) conformational isomers. Therefore, single stereochemical isomers as well as enantiomeric, diastereomeric, geometric, or conformational mixtures of the present compounds are within the scope disclosed herein.

Unless otherwise stated, structures and compounds depicted herein are also meant to include all isomeric (e.g., enantiomeric, diastereomeric, geometric or conformational) forms, N-oxide, hydrate, solvate, metabolite, pharmaceutically acceptable salt or a prodrug thereof. Therefore, single stereochemical isomers as well as enantiomer, diastereomer, geometric isomer, conformer, N-oxide, anhydrate, solvate, metabolite, pharmaceutically acceptable salt or prodrug of the compounds disclosed herein are within the scope of the present invention. Additionally, unless otherwise stated, structures depicted herein are also meant to include compounds that differ only in the presence of one or more isotopically enriched atoms.

A "metabolite" refers to a product produced through metabolism in the body of a specified compound, a pharmaceutically acceptable salt, analog or derivative, which exhibits similar activity of the compound of Formula (I), (II), (III) or (IV) in vivo or in vitro. The metabolites of a compound may be identified using routine techniques known in the art and their activities can be determined using tests such as those described herein. Such products may result for example from oxidation, reduction, hydrolysis, amidation, deamidation, esterification, deesterification, or enzyme cleavage, and the like, of the administered compound. Accordingly, the invention includes metabolites of the compounds disclosed herein, including metabolites produced by contacting a compound disclosed herein with a mammal for a sufficient time period.

Stereochemical definitions and conventions used herein generally follow S. P. Parker, Ed., McGraw-Hill Dictionary of Chemical Terms (1984) McGraw-Hill Book Company, New York; and Eliel, E. and Wilen, S., "Stereochemistry of Organic Compounds", John Wiley & Sons, Inc., New York, 1994. The compounds disclosed herein may contain asymmetric or chiral centers, and therefore exist in different stereoisomeric forms. It is intended that all stereoisomeric forms of the compounds disclosed herein, including, but not limited to, diastereomers, enantiomers and atropisomers, as well as mixtures thereof such as racemic mixtures, form part of the present invention. Many organic compounds exist in optically active forms, i.e., they have the ability to rotate the plane of plane-polarized light. In describing an optically active compound, the prefixes D and L, or R and S, are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The term "racemic mixture" or "racemate" refers to an equimolar mixture of two enantiomeric species, devoid of optical activity.

The term "tautomer" or "tautomeric form" refers to structural isomers of different energies which are interconvertible via a low energy barrier. Some non-limiting examples of proton tautomers (also known as prototropic tautomers) include interconversions via migration of a proton, such as keto-enol and imine-enamine isomerizations. Valence tautomers include interconversions by reorganization of some of the bonding electrons.

A "pharmaceutically acceptable salts" refers to organic or inorganic salts of a compound disclosed herein. Pharmaceutically acceptable salts are well known in the art. For example, Berge et al., describe pharmaceutically acceptable salts in detail in J. Pharmacol Sci, 1977, 66:1-19, which is incorporated herein by reference. Some non-limiting examples of pharmaceutically acceptable and nontoxic salts include salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid and malonic acid or by using other methods used in the art such as ion exchange. Other pharmaceutically acceptable salts include adipate, malate, 2-hydroxy propionate, alginate, ascorbate, aspartate, benzenesulfonate, benzoate, bisulfate, borate, butyrate, camphorate, camphorsulfonate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, laurylsulfate, malate, malonate, methanesulfonate, 2-naphthalenesulfonate, nicotinate, nitrate, oleate, palmitate, pamoate, pectinate, persulfate, 3-phenylpropionate, picrate, pivalate, propionate, stearate, thiocyanate, p-toluenesulfonate, undecanoate, valerate salts, and the like. Salts derived from appropriate bases include alkali metal, alkaline earth metal, ammonium and $N^+(C_{1-4}$ alkyl$)_4$ salts. This invention also envisions the quaternization of any basic nitrogen-containing groups of the compounds disclosed herein. Water or oil soluble or dispersable products may be obtained by such quaternization. Representative alkali or alkaline earth metal (formed) salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, $C_{1-8}$ sulfonate or aryl sulfonate.

The term "hydrate" refers to the complex where the solvent molecule is water.

The term "solvate" refers to an association or complex of one or more solvent molecules and a compound disclosed herein. Some non-limiting examples of the solvent that form solvates include water, isopropanol, ethanol, methanol, dimethylsulfoxide (DMSO), ethyl acetate, acetic acid and ethanolamine.

An "ester" refers to an in vivo hydrolysable ester of a compound of the Formula (I), (II), (III) or (IV) containing hydroxy group, for example, a pharmaceutically acceptable ester which is hydrolysed in the human or animal body to produce the parent alcohol. Some non-limiting examples of in vivo (of a compound of the Formula (I), (II), (III) or (IV) hydrolysable ester forming groups for hydroxy include phosphate, acetoxymethoxy, 2,2-dimethylpropionyloxymethoxy, alkanoyl, benzoyl, phenylacetyl, alkoxycarbonyl, dialkylcarbamoyl, N-(dialkylaminoethyl)-N-alkylcarbamoyl, and the like.

An "N-oxide" refers to one or more than one nitrogen atoms oxidised to form N-oxides, where a compound contains several amine functions. Particular examples of N-oxides are the N-oxides of a tertiary amine or a nitrogen atom of a nitrogen-containing heterocycle. N-oxides can be formed by treatment of the corresponding amine with an oxidizing agent such as hydrogen peroxide or a per-acid (e.g. a peroxycarboxylic acid) (See, Advanced Organic Chemistiy, by Jerry March, 4th Edition, Wiley Interscience, pages). More particularly, N-oxides can be made by the procedure of L. W. Deady (Syn. Comm. 1977, 7, 509-514), in which the amine compound is reacted with m-chloroperoxybenzoic acid (MCPBA), for example, in an inert solvent such as dichloromethane.

The term "prodrug" refers to a compound that is transformed in vivo into a compound of Formula (I), (II), (III) or (IV). Such a transformation can be affected, for example, by hydrolysis of the prodrug form in blood or enzymatic transformation to the parent form in blood or tissue. Prodrugs of the compounds disclosed herein may be, for example, esters. Some common esters which have been utilized as prodrugs are phenyl esters, aliphatic ($C_1$-$C_{24}$) esters, acyloxymethyl esters, carbonates, carbamates and amino acid esters. For example, a compound disclosed herein that contains a hydroxy group may be acylated at this position in its prodrug form. Other prodrug forms include phosphates, such as, those phosphate compounds derived from the phosphonation of a hydroxy group on the parent compound. A thorough discussion of prodrugs is provided in T. Higuchi and V. Stella, Pro-drugs as Novel Delivery Systems, Vol. 14 of the A.C.S. Symposium Series, Edward B. Roche, ed., Bioreversible Carriers in Drug Design, American Pharmaceutical Association and Pergamon Press, 1987, J. Rautio et al., Prodrugs: Design and Clinical Applications, *Nature Review Drug Discovery*, 2008, 7, 255-270, and S. J. Hecker et al, Prodrugs of Phosphates and Phosphonates, *Journal of Medicinal Chemistry*, 2008, 51, 2328-2345.

The term "protecting group" or "Pg" refers to a substituent that is commonly employed to block or protect a particular functionality while reacting with other functional groups on the compound. For example, an "amino-protecting group" is a substituent attached to an amino group that blocks or protects the amino functionality in the compound. Suitable amino-protecting groups include acetyl, trifluoroacetyl, t-butoxy-carbonyl (BOC), benzyloxycarbonyl (CBZ) and 9-fluorenylmethylenoxy-carbonyl (Fmoc), and the like. Similarly, a "hydroxy-protecting group" refers to a substituent of a hydroxy group that blocks or protects the hydroxy functionality. Suitable protecting groups include Methyl, methoxymethyl, acetyl and silyl, and the like. A "carboxy-protecting group" refers to a substituent of the carboxy group that blocks or protects the carboxy functionality. Common carboxy-protecting groups include —CH$_2$CH$_2$SO$_2$Ph, cyanoethyl, 2-(trimethylsilyl)ethyl, 2-(trimethylsilyl)ethoxy-methyl, 2-(p-toluenesulfonyl)ethyl, 2-(p-nitrophenylsulfonyl)ethyl, 2-(diphenylphosphino) ethyl, nitroethyl, and the like. For a general description of protecting groups and their use, see: T W. Greene, Protective Groups in Organic Synthesis, John Wiley & Sons, New York, 1991; and P. J. Kocienski, Protecting Groups, Thieme, Stuttgart, 2005.

As used herein, the term "therapeutically effective amount" refers to an amount of a compound of the Formula (I), (II), (III) or (IV) which is sufficient to obtain the desired therapeutic effect. Thus, a therapeutically effective amount of a compound of the Formula (I), (II), (III) or (IV) for the treatment of conditions mediated by FXR is sufficient to treat conditions mediated by FXR.

As used herein, the term "dyslipidemia" refers to an abnormality of lipids and lipoproteins, or abnormal amounts of lipids and lipoproteins in the blood, as well as these diseases generated, caused, exacerbated or accompanied by such abnormalities (See Dorland's Illutrated Medical Dictionary, 29th edition, W. B. Saunders Publishing Company, New York, N.Y.). These diseases encompassed within the definition of dyslipidemia include hyperlipidemia, hypertriglyceridemia, low plasma HDL, high plasma LDL, high plasma VLDL, liver cholestasis, and hypercholesterolemia.

As used herein, the term "diseases related to dyslipidemia" include, but are not limited to, atherosclerosis, thrombosis, coronary artery disease, stroke and hypertension disease. And diseases related to dyslipidemia also include metabolic diseases such as obesity, diabetes, insulin resistance and complications thereof. The term "cholestasis" refers to any condition caused by that the flow of bile from the liver is blocked, which may be intrahepatic (i.e., occurring inside the liver) or extrahepatic (i.e., occurring outside the liver).

As used herein, the term "liver fibrosis" includes liver fibrosis caused by any reason, including but not limited to virus-induced liver fibrosis, such as liver fibrosis caused by the hepatitis B and hepatitis C; liver fibrosis caused by contacting with alcohol (alcoholic liver disease), pharmaceutical compounds, oxidative stress, cancer radiation or industrial chemicals; and liver fibrosis caused by primary biliary cirrhosis, fatty liver, obesity, non-alcoholic steatohepatitis, cystic fibrosis, hemochromatosis, and autoimmune hepatitis and other diseases.

As used herein, the term "non-alcoholic fatty liver disease (NAFLD)" refers to a metabolic disease associated with insulin resistance, including simple fatty liver (SFL), non-alcoholic steatohepatitis (NASH), steatohepatic fibrosis and liver cirrhosis.

As used herein, "FXR modulators" refers to a substance that directly binds to the FXR and regulates activity of the FXR, including FXR agonists, FXR partial agonists and FXR antagonists.

As used herein, the term "FXR agonist" refers to a substance that directly binds to the FXR and upregulates activity of the FXR.

Unless otherwise indicated herein or clearly contradicted by the context, the terms "a", "an", "the" and similar terms used in the context of the present invention (particularly in the context of the claims) are to be construed to cover both the singular and the plural.

DESCRIPTION OF COMPOUNDS OF THE INVENTION

The present invention relates to compounds, or pharmaceutical compositions thereof, which bind to FXR (or NR1H4 receptor) and act as modulators of the FXR (or NR1H4 receptor). The present invention further relates to said compounds or the use thereof in the manufacture of a medicament for the treatment of diseases and/or conditions through said compounds binding to the FXR nuclear receptor disclosed herein. The present invention further describes a method for the synthesis of the compounds. The compounds of the invention exhibit improved biological activity and pharmacokinetic advantages.

The invention relates to a compound having formula (I), or a stereoisomer, a geometric isomer, a tautomer, an N-oxide, a hydrate, a solvate, a metabolite, a pharmaceutically acceptable salt or a prodrug thereof,

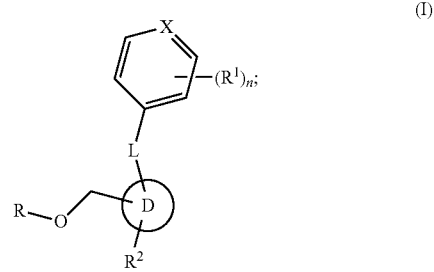

and
wherein each $R^1$, n, X, D, L, $R^2$ and R are as defined herein.

In some embodiments, X is N, CH or $^{\oplus}$N—O$^{\ominus}$.

In some embodiments, ring D is a five-membered heteroaromatic ring or five-membered heterocycle.

In some embodiments, L is a bond, $-(CR^3R^4)_f-$, $-(CR^3R^4)_f-O-$, $-(CR^3R^4)_f-NH-$ or $-(CR^3R^4)_f-S(=O)_t-$; and $R^3$, $R^4$, t and f are as defined herein.

In some embodiments, R is fused tricyclyl or fused heterotricyclyl, wherein R is optionally substituted with one, two, three, four or five $R^8$; and each $R^8$ is as defined herein.

In some embodiments, each $R^1$ is independently H, deuterium, F, Cl, Br, I, hydroxy, amino, nitro, cyano, alkyl, haloalkyl, haloalkoxy, cycloalkyl, heterocyclyl, alkenyl, alkynyl, alkylamino, alkoxy, aryl or heteroaryl; wherein $R^1$ is optionally substituted with one, two, three, four or five $R^9$; and each $R^9$ is as defined herein.

In some embodiments, $R^2$ is H, deuterium, F, Cl, Br, I, hydroxy, amino, nitro, cyano, alkyl, haloalkyl, haloalkoxy, alkoxyalkyl, cycloalkyl, hydroxyalkyl, heterocyclyl, alkylamino or alkoxy; wherein $R^2$ is optionally substituted with one, two, three, four or five $R^9$; and each $R^9$ is as defined herein.

In some embodiments, each of $R^3$ and $R^4$ is independently H, deuterium, $C_{1-4}$ alkyl, F, Cl, Br, I or $C_{1-4}$ haloalkyl; wherein each of $R^3$ and $R^4$ is optionally substituted with one, two, three, four or five $R^9$; and each $R^9$ is as defined herein.

In some embodiments, each $R^8$ is independently H, deuterium, F, Cl, Br, I, hydroxy, nitro, amino, aminoalkyl, alkylamino, alkyl, hydroxyalkyl, alkoxy, haloalkyl, haloalkoxy, cycloalkyl, cycloalkoxy, alkenyl, alkynyl, aryl, halo-substituted aryl, arylalkyl, oxo (=O), -L$^1$-C(=O)OR$^{15}$, -L$^1$-S(=O)$_r$R$^{16}$, $-$O-L$^2$-C(=O)OR$^{15}$, $-$O-L$^2$-S(=O)$_r$R$^{16}$, $-$C(=O)NR$^{17}$R$^{18}$, $-$C(=O)N(R$^{17}$)S(=O)$_2$R$^{16}$, $-$C(=NR$^{17}$)NR$^{17}$R$^{18}$, $-$C(=O)N(R$^{17}$)-L$^3$-S(=O)$_2$OR$^{15}$, $-$C(=O)N(R$^{17}$)C(=O)OR$^{15}$, $-$C(=O)N(R$^{17}$)-L$^3$-C(=O)OR$^{15}$, cyano, heterocyclyl or heteroaryl; or two $R^8$, together with the same C atom to which they are attached, independently and optionally form cycloalkyl or heterocyclyl; or two $R^8$, together with the adjacent C atoms to which they are attached, independently and optionally form cycloalkyl, heterocyclyl, aryl or heteroaryl; wherein $R^8$ is independently and optionally substituted with one or more $R^{19}$;

each $R^{15}$ is independently H, deuterium, alkyl, aminoalkyl, alkenyl, alkynyl, haloalkyl, cycloalkyl, heterocyclyl or aryl;

each $R^{16}$ is independently H, deuterium, hydroxy, amino, alkyl, aminoalkyl, alkenyl, alkynyl, haloalkyl, cycloalkyl, heterocyclyl, aryl or $-$NR$^{17}$R$^{18}$;

each of $R^{17}$ and $R^{18}$ is independently H, deuterium, alkyl, aminoalkyl, alkenyl, alkynyl, haloalkyl, cycloalkyl, heterocyclyl or aryl; or $R^{17}$ and $R^{18}$, together with the N atom to which they are attached, independently and optionally form heterocyclyl or heteroaryl;

each $L^1$ is independently a bond, $-$C(=O)$-$, $C_{1-6}$ alkylene, $C_{2-6}$ alkenylene or $C_{2-6}$ alkynylene;

each $L^2$ is independently $C_{1-6}$ alkylene, $C_{2-6}$ alkenylene or $C_{2-6}$ alkynylene;

each $L^3$ is independently a bond or $C_{1-4}$ alkylene;

$R^8$, $R^{15}$, $R^{16}$, $R^{17}$, $R^{18}$, $L^1$, $L^2$ and $L^3$ are independently and optionally substituted with one or more $R^9$; and each of $R^9$ and $R^{19}$ is as defined herein.

In some embodiments, n is 0, 1, 2, 3 or 4.

In some embodiments, each f is independently 0, 1 or 2.

In some embodiments, each t is independently 0, 1 or 2.

In some embodiments, each $R^9$ is independently H, deuterium, F, Cl, Br, I, cyano, oxo (=O), hydroxy, alkyl, alkylamino, amino, aryl, heterocyclyl, heteroaryl, alkenyl, alkynyl, cycloalkyl, alkoxy or haloalkyl.

In some embodiments, each $R^{19}$ is independently H, deuterium, F, Cl, Br, I, cyano, oxo (=O), hydroxy, alkyl, alkylamino, amino, aryl, heterocyclyl, heteroaryl, alkenyl, alkynyl, cycloalkyl, alkoxy or haloalkyl.

In some embodiments, L is a bond, $-$CH$_2-$, $-$O$-$, $-$NH$-$, $-$S$-$, $-$CH$_2-$O$-$, $-$CH$_2-$NH$-$, $-$CH$_2-$S$-$ or $-$CH$_2-$S(=O)$_2-$.

In some embodiments, each $R^1$ is independently H, deuterium, F, Cl, Br, I, hydroxy, amino, nitro, cyano, $C_{1-6}$ alkyl, $C_{1-6}$ haloalkyl, $C_{1-6}$ haloalkoxy, $C_{3-6}$ cycloalkyl, $C_{2-9}$ heterocyclyl, $C_{2-6}$ alkenyl, $C_{2-6}$ alkynyl, $C_{1-6}$ alkylamino, $C_{1-6}$ alkoxy, $C_{6-10}$ aryl or $C_{1-9}$ heteroaryl;

$R^2$ is H, deuterium, F, Cl, Br, I, hydroxy, amino, nitro, cyano, $C_{1-6}$ alkyl, $C_{1-6}$ haloalkyl, $C_{1-6}$ haloalkoxy, $C_{1-6}$ alkoxy-$C_{1-6}$-alkyl, $C_{3-6}$ cycloalkyl, $C_{1-6}$ hydroxyalkyl, $C_{2-9}$ heterocyclyl, $C_{1-6}$ alkylamino or $C_{1-6}$ alkoxy;

Wherein each of said hydroxy, amino, $C_{1-6}$ alkyl, $C_{2-6}$ alkenyl, $C_{2-6}$ alkynyl, $C_{3-6}$ cycloalkyl, $C_{1-6}$ haloalkyl, $C_{1-6}$ alkylamino, $C_{1-6}$ alkoxy, $C_{1-6}$ haloalkoxy, $C_{1-6}$ hydroxyalkyl, $C_{1-6}$ alkoxy-$C_{1-6}$-alkyl, $C_{2-9}$ heterocyclyl, $C_{6-10}$ aryl and $C_{1-9}$ heteroaryl of $R^1$ and $R^2$ is independently and optionally substituted with one or more $R^9$; and each $R^9$ is as defined herein.

In other embodiments, each $R^1$ is independently H, deuterium, F, Cl, Br, I, hydroxy, amino, nitro, cyano, $C_{1-3}$ alkyl, $C_{1-3}$ haloalkyl, $C_{1-3}$ haloalkoxy, $C_{3-6}$ cycloalkyl, $C_{2-9}$ heterocyclyl, $C_{2-4}$ alkenyl, $C_{2-4}$ alkynyl, $C_{1-3}$ alkylamino, $C_{1-3}$ alkoxy, $C_{6-10}$ aryl or $C_{1-9}$ heteroaryl;

$R^2$ is H, deuterium, F, Cl, Br, I, hydroxy, amino, nitro, cyano, $C_{1-3}$ alkyl, $C_{1-3}$ haloalkyl, $C_{1-3}$ haloalkoxy, $C_{1-3}$ alkoxy-$C_{1-3}$-alkyl, $C_{3-6}$ cycloalkyl, $C_{1-3}$ hydroxyalkyl, $C_{2-9}$ heterocyclyl, $C_{1-3}$ alkylamino or $C_{1-3}$ alkoxy; and Wherein each of said hydroxy, amino, $C_{1-3}$ alkyl, $C_{2-4}$ alkenyl, $C_{2-4}$ alkynyl, $C_{3-6}$ cycloalkyl, $C_{1-3}$ haloalkyl, $C_{1-3}$ alkylamino, $C_{1-3}$ alkoxy, $C_{1-3}$ haloalkoxy, $C_{1-3}$ hydroxyalkyl, $C_{1-3}$ alkoxy-$C_{1-3}$-alkyl, $C_{2-9}$ heterocyclyl, $C_{6-10}$ aryl and $C_{1-9}$ heteroaryl of $R^1$ and $R^2$ is independently and optionally substituted with one or more $R^9$; and each $R^9$ is as defined herein.

In some embodiments, each $R^8$ is independently H, deuterium, F, Cl, Br, I, hydroxy, nitro, amino, $C_{1-6}$ aminoalkyl, $C_{1-6}$ alkylamino, $C_{1-6}$ alkyl, $C_{1-4}$ hydroxyalkyl, $C_{1-6}$ alkoxy, $C_{1-6}$ haloalkyl, $C_{1-6}$ haloalkoxy, $C_{3-6}$ cycloalkyl, $C_{3-6}$ cycloalkoxy, $C_{2-6}$ alkenyl, $C_{2-6}$ alkynyl, $C_{6-10}$ aryl, halo-substituted $C_{6-10}$ aryl, $C_{6-10}$ oxo (=O), -L$^1$-C(=O)OR$^{15}$, -L$^1$-S(=O)$_r$R$^{16}$, $-$O-L$^2$-C(=O)OR$^{15}$, $-$O-L$^2$-S(=O)$_r$R$^{16}$, $-$C(=O)NR$^{17}$R$^{18}$, $-$C(=O)N(R$^{17}$)S(=O)$_2$R$^{16}$, $-$C(=NR$^{17}$)NR$^{17}$R$^{18}$, $-$C(=O)N(R$^{17}$)-L$^3$-S(=O)$_2$OR$^{15}$, $-$C(=O)N(R$^{17}$)C(=O)OR$^{15}$, $-$C(=O)N(R$^{17}$)-L$^3$-C(=O)OR$^{15}$, cyano, $C_{2-9}$ heterocyclyl or $C_{1-9}$ heteroaryl; or two $R^8$, together with the same C atom to which they are attached, independently and optionally form $C_{3-6}$ cycloalkyl or $C_{2-9}$ heterocyclyl; or two $R^8$, together with the adjacent C atoms to which they are attached, independently and optionally form $C_{3-6}$ cycloalkyl, $C_{2-9}$ heterocyclyl, $C_{6-10}$ aryl or $C_{1-9}$ heteroaryl; wherein $R^8$ is independently and optionally substituted with one or more $R^{19}$;

each $R^{15}$ is independently H, deuterium, $C_{1-6}$ alkyl, $C_{1-6}$ aminoalkyl, $C_{2-6}$ alkenyl, $C_{2-6}$ alkynyl, $C_{1-6}$ haloalkyl, $C_{3-6}$ cycloalkyl, $C_{2-9}$ heterocyclyl or $C_{6-10}$ aryl;

each $R^{16}$ is independently H, deuterium, hydroxy, amino, $C_{1-6}$ alkyl, $C_{1-6}$ aminoalkyl, $C_{2-6}$ alkenyl, $C_{2-6}$ alkynyl, $C_{1-6}$ haloalkyl, $C_{3-6}$ cycloalkyl, $C_{2-9}$ heterocyclyl, $C_{6-10}$ aryl or $-$NR$^{17}$R$^{18}$;

each of $R^{17}$ and $R^{18}$ is independently H, deuterium, $C_{1-6}$ alkyl, $C_{1-6}$ aminoalkyl, $C_{2-6}$ alkenyl, $C_{2-6}$ alkynyl, $C_{1-6}$ haloalkyl, $C_{3-6}$ cycloalkyl, $C_{2-9}$ heterocyclyl or $C_{6-10}$ aryl; or $R^{17}$ and $R^{18}$, together with the N atom to which they are attached, independently and optionally form $C_{2-9}$ heterocyclyl or $C_{1-9}$ heteroaryl;

wherein each of said hydroxy, amino, $C_{1-6}$ alkyl, $C_{1-4}$ hydroxyalkyl, $C_{1-6}$ aminoalkyl, $C_{2-6}$ alkenyl, $C_{2-6}$ alkynyl, $C_{3-6}$ cycloalkyl, $C_{1-6}$ haloalkyl, $C_{1-6}$ alkylamino, $C_{1-6}$ alkoxy, $C_{3-6}$ cycloalkoxy, $C_{1-6}$ haloalkoxy, halo-substituted $C_{6-10}$ aryl, $C_{6-10}$ aryl-$C_{1-6}$-alkyl, $C_{2-9}$ heterocyclyl, $C_{6-10}$ aryl or $C_{1-9}$ heteroaryl of $R^8$, $R^{15}$, $R^{16}$, $R^{17}$ and $R^{18}$ is independently and optionally substituted with one or more $R^9$; and each of $R^9$ and $R^{19}$ is as defined herein.

In some embodiments, each $R^9$ is independently H, deuterium, F, Cl, Br, I, cyano, oxo (=O), hydroxy, $C_{1-6}$ alkyl, $C_{1-6}$ alkylamino, amino, $C_{6-10}$ aryl, $C_{2-9}$ heterocyclyl, $C_{1-9}$ heteroaryl, $C_{2-6}$ alkenyl, $C_{2-6}$ alkynyl, $C_{3-6}$ cycloalkyl, $C_{1-6}$ alkoxy or $C_{1-6}$ haloalkyl.

In some embodiments, each $R^{19}$ is independently H, deuterium, F, Cl, Br, I, cyano, oxo (=O), hydroxy, $C_{1-6}$ alkyl, $C_{1-6}$ alkylamino, amino, $C_{6-10}$ aryl, $C_{2-9}$ heterocyclyl, $C_{1-9}$ heteroaryl, $C_{2-6}$ alkenyl, $C_{2-6}$ alkynyl, $C_{3-6}$ cycloalkyl, $C_{1-6}$ alkoxy or $C_{1-6}$ haloalkyl.

In some embodiments, (Ia)

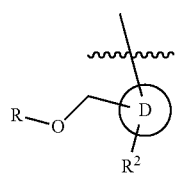

of Formula (I) is:

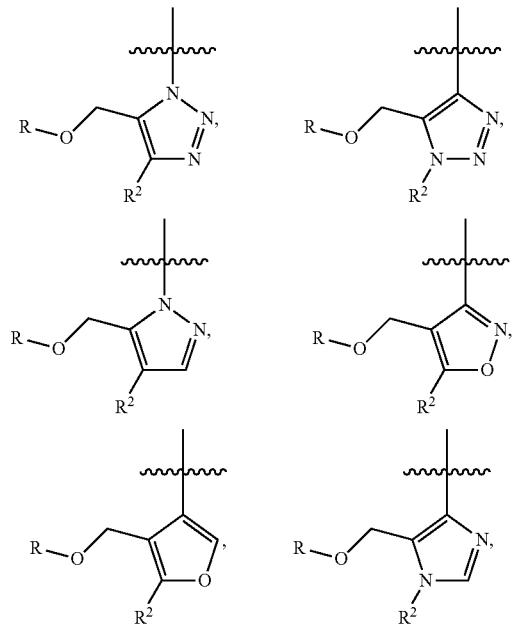

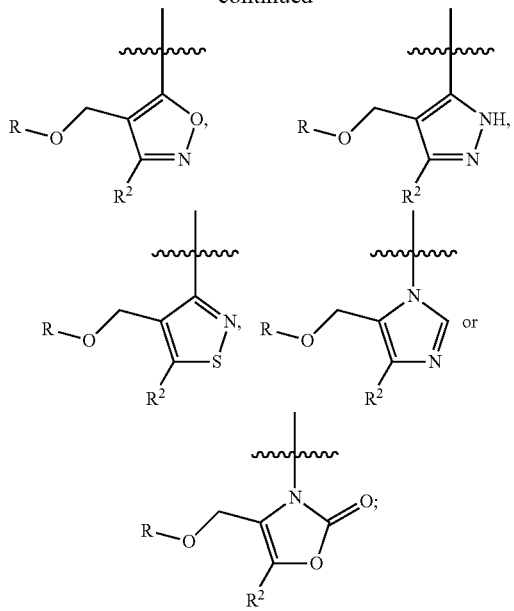

and
wherein R and $R^2$ are as defined herein.

In some embodiments, provided herein is a compound having Formula (III), or a stereoisomer, a geometric isomer, a tautomer, an N-oxide, a hydrate, a solvate, a metabolite, a pharmaceutically acceptable salt or a prodrug thereof, (III)

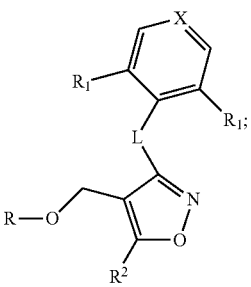

and
wherein each $R^1$, $R^2$, R, L and X are as defined herein.

In some embodiments, provided herein is a compound having Formula (II) or a stereoisomer, a geometric isomer, a tautomer, an N-oxide, a hydrate, a solvate, a metabolite, a pharmaceutically acceptable salt or a prodrug thereof, (II)

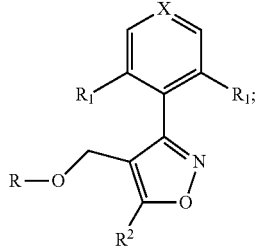

and
wherein each $R^1$, $R^2$, R and X are as defined herein.

In some embodiments, provided herein is a compound having Formula (IIIa), or a stereoisomer, a geometric isomer, a tautomer, an N-oxide, a hydrate, a solvate, a metabolite, a pharmaceutically acceptable salt or a prodrug thereof,

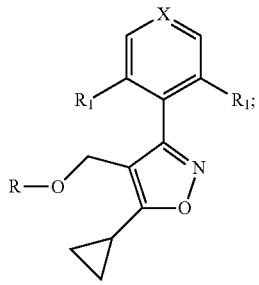

(IIIa)

and wherein each $R^1$, R and X are as defined herein.

In some embodiments, provided herein is a compound having Formula (IIIb), or a stereoisomer, a geometric isomer, a tautomer, an N-oxide, a hydrate, a solvate, a metabolite, a pharmaceutically acceptable salt or a prodrug thereof,

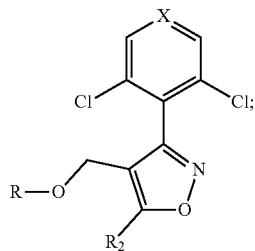

(IIIb)

and wherein $R^2$, R and X are as defined herein.

In some embodiments, provided herein is a compound having Formula (IIIc), or a stereoisomer, a geometric isomer, a tautomer, an N-oxide, a hydrate, a solvate, a metabolite, a pharmaceutically acceptable salt or a prodrug thereof,

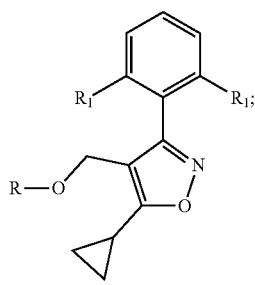

(IIIc)

and

Wherein each $R^1$ and R are as defined herein.

In some embodiments, provided herein is a compound having Formula (IIId), or a stereoisomer, a geometric isomer, a tautomer, an N-oxide, a hydrate, a solvate, a metabolite, a pharmaceutically acceptable salt or a prodrug thereof,

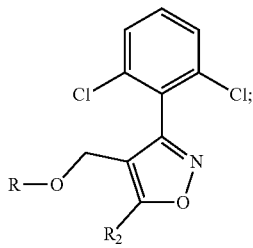

(IIId)

and wherein $R^2$ and R are as defined herein.

In some embodiments, provided herein is a compound having Formula (IV), or a stereoisomer, a geometric isomer, a tautomer, an N-oxide, a hydrate, a solvate, a metabolite, a pharmaceutically acceptable salt or a prodrug thereof,

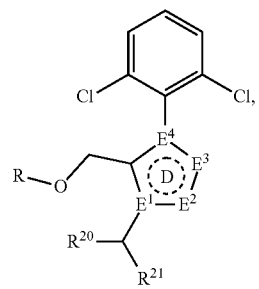

(IV)

wherein ring D is a five-membered heteroaromatic ring;

$E^1$ and $E^4$ are each independently C or N;

$E^2$ and $E^3$ are each independently C, CH, N, NH, O or S; and $R^{20}$ and $R^{21}$ are each independently H, $C_{1-2}$ alkyl, $C_{1-2}$ haloalkyl; or $R^{20}$ and $R^{21}$, together with the C atom to which they are attached, independently and optionally form $C_{3-6}$ cycloalkyl; and R is as defined hererin.

In some embodiments, provided herein is a compound having Formula (V), or a stereoisomer, a geometric isomer, a tautomer, an N-oxide, a hydrate, a solvate, a metabolite, a pharmaceutically acceptable salt or a prodrug thereof,

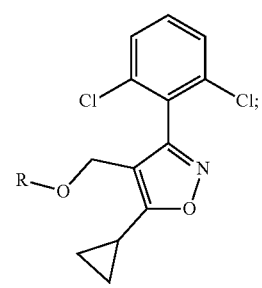

(V)

and

R is as defined hererin.

In some embodiments, R is:

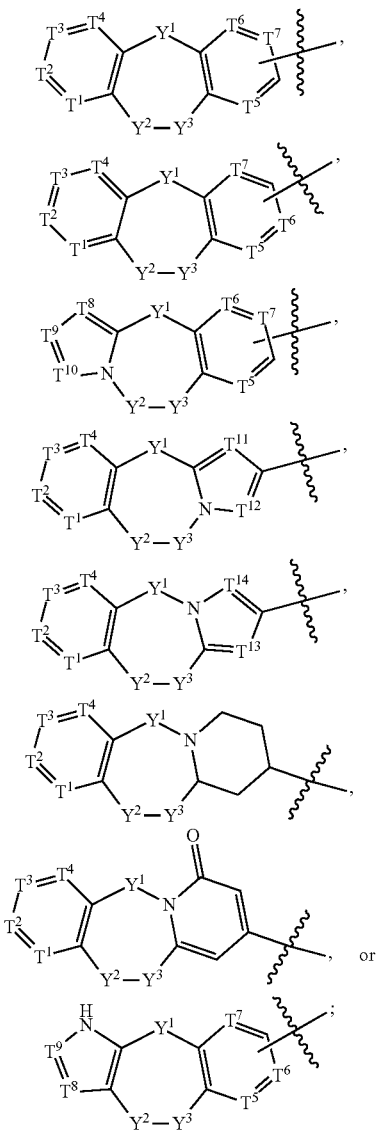

wherein each moiety represented by R is independently and optionally substituted with one, two, three, four or five $R^8$;

each of $T^1$, $T^2$, $T^3$, $T^4$, $T^5$, $T^6$, $T^7$, $T^8$, $T^9$, $T^{10}$, $T^{11}$, $T^{12}$, $T^{13}$ and $T^{14}$ is independently CH, $^{\oplus}$N—O$^{\ominus}$ or N;

$Y^1$ is a bond, —O—, —S(=O)$_t$—, —NR$^5$—, —NR$^5$—C(=O)—, —C(=O)—NR$^5$—, —S(=O)$_t$—NR$^5$—, —NR$^5$—S(=O)$_t$—, —(CR$^6$R$^7$)$_y$— or —C(=O)—;

each of $Y^2$ and $Y^3$ is independently a bond, —O—, —S(=O)$_t$—, —NR$^5$—, —CR$^6$R$^7$—, —(CR$^6$R$^7$)$_y$— or —C(=O)—, or $Y^2$ is connected with $Y^3$ to form —CR$^6$=CR$^7$—;

wherein CR$^6$R$^7$ of —(CR$^6$R$^7$)$_y$— is independently and optionally replaced with —O—, —S(=O)$_t$— or —NR$^5$—;

y is 0, 1, 2, 3 or 4;

each $R^5$ is independently H, deuterium, alkyl, aminoalkyl, haloalkyl, cycloalkyl, heterocyclyl, aryl, halo-substituted aryl or arylalkyl;

each of $R^6$ and $R^7$ is independently H, deuterium, F, Cl, Br, I, cyano, hydroxy, hydroxyalkyl, alkyl, alkylamino, aminoalkyl, alkenyl, alkynyl, cycloalkyl, haloalkyl, aryl, halo-substituted aryl or arylalkyl; or $R^6$ and $R^7$, together with the C atom to which they are attached, independently and optionally form cycloalkyl or heterocyclyl; and $R^8$ and t are as defined herein.

In other embodiments, each $R^5$ is independently H, deuterium, $C_{1-6}$ alkyl, $C_{1-6}$ aminoalkyl, $C_{1-6}$ haloalkyl, $C_{3-6}$ cycloalkyl, $C_{2-9}$ heterocyclyl, $C_{6-10}$ aryl, halo-substituted $C_{6-10}$ aryl or $C_{6-10}$ aryl-$C_{1-6}$-alkyl; and each of $R^6$ and $R^7$ is independently H, deuterium, F, Cl, Br, I, cyano, hydroxy, $C_{1-6}$ hydroxyalkyl, $C_{1-6}$ alkyl, $C_{1-6}$ alkylamino, $C_{1-6}$ aminoalkyl, $C_{2-6}$ alkenyl, $C_{2-6}$ alkynyl, $C_{3-6}$ cycloalkyl, $C_{1-6}$ haloalkyl, $C_{6-10}$ aryl, halo-substituted $C_{6-10}$ aryl or $C_{6-10}$ aryl-$C_{1-6}$-alkyl; or $R^6$ and $R^7$, together with the C atom to which they are attached, independently and optionally form $C_{3-6}$ cycloalkyl or $C_{2-9}$ heterocyclyl.

In still other embodiments, each $R^5$ is independently H, deuterium, $C_{1-3}$ alkyl, $C_{1-3}$ aminoalkyl, $C_{1-3}$ haloalkyl, $C_{3-6}$ cycloalkyl, $C_{2-6}$ heterocyclyl, phenyl or benzyl; and each of $R^6$ and $R^7$ is independently H, deuterium, F, Cl, Br, I, cyano, hydroxy, $C_{1-3}$ alkyl, $C_{1-4}$ hydroxyalkyl, $C_{1-3}$ alkylamino, $C_{1-3}$ aminoalkyl, $C_{2-4}$ alkenyl, $C_{2-4}$ alkynyl, $C_{3-6}$ cycloalkyl, $C_{1-3}$ haloalkyl, phenyl or benzyl; or $R^6$ and $R^7$, together with the C atom to which they are attached, independently and optionally form $C_{3-6}$ cycloalkyl or $C_{2-6}$ heterocyclyl.

In some embodiments, R is:

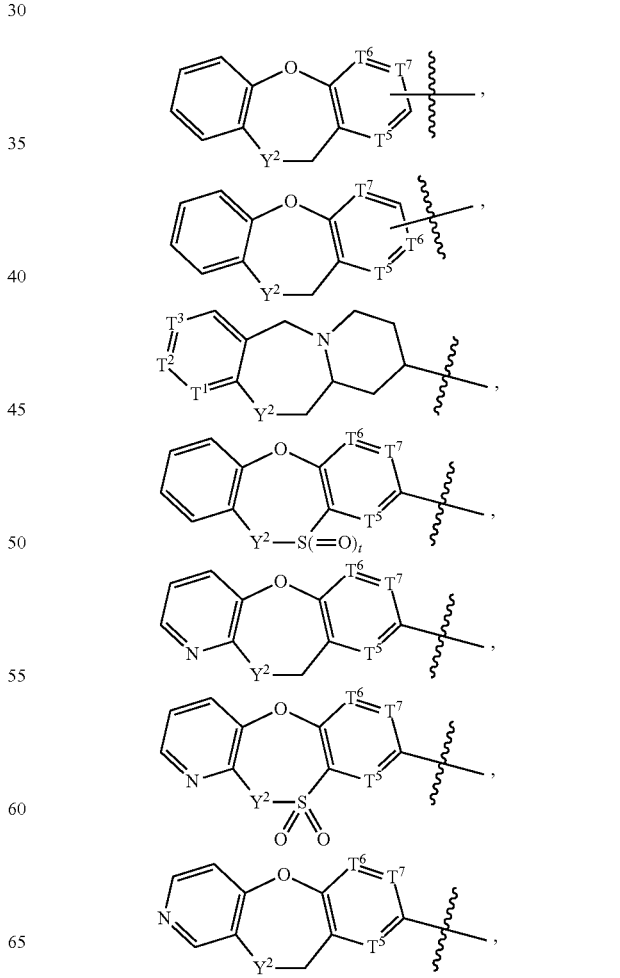

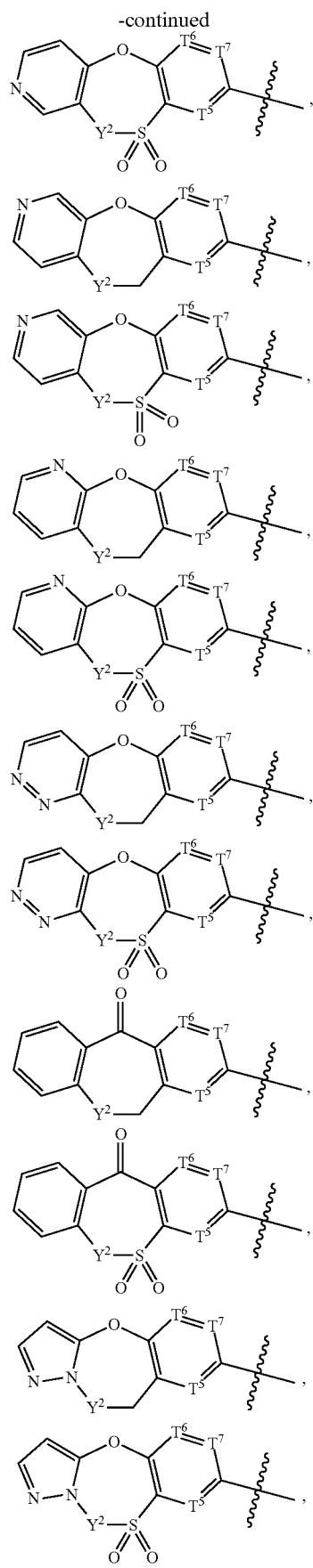
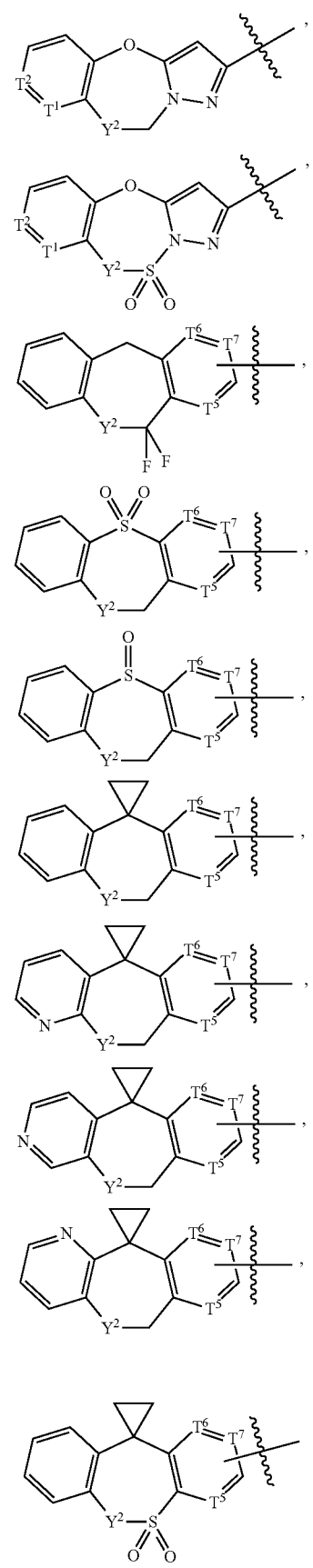

-continued
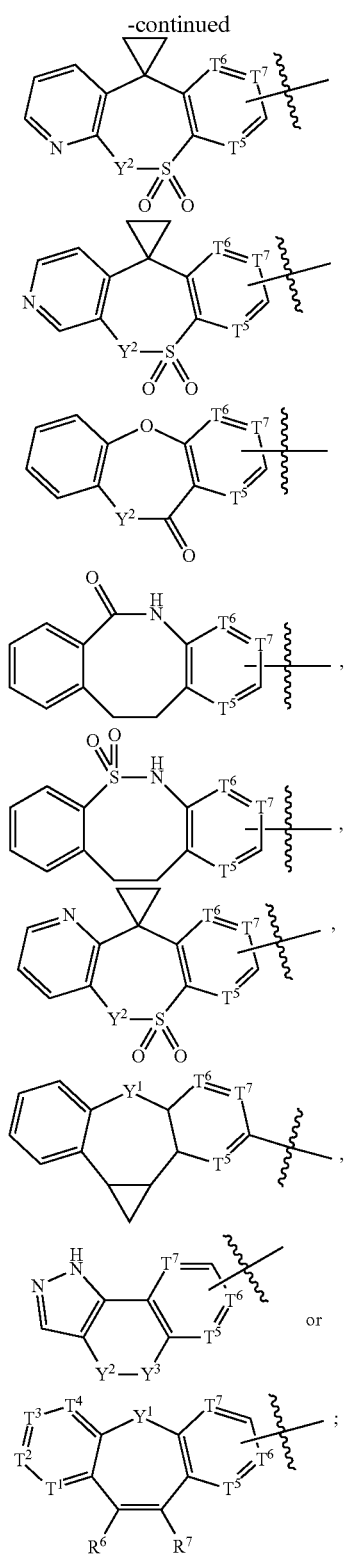
wherein each moiety represented by R is independently and optionally substituted with one, two, three, four or five $R^8$;
each of $T^1$, $T^2$, $T^5$, $T^6$ and $T^7$ is independently CH, $^{\oplus}$N—O$^{\ominus}$ or N; and
each of $R^8$, t, $Y^1$, $Y^2$, $Y^3$, $R^6$ and $R^7$ is as defined herein.
In some embodiments, R is:
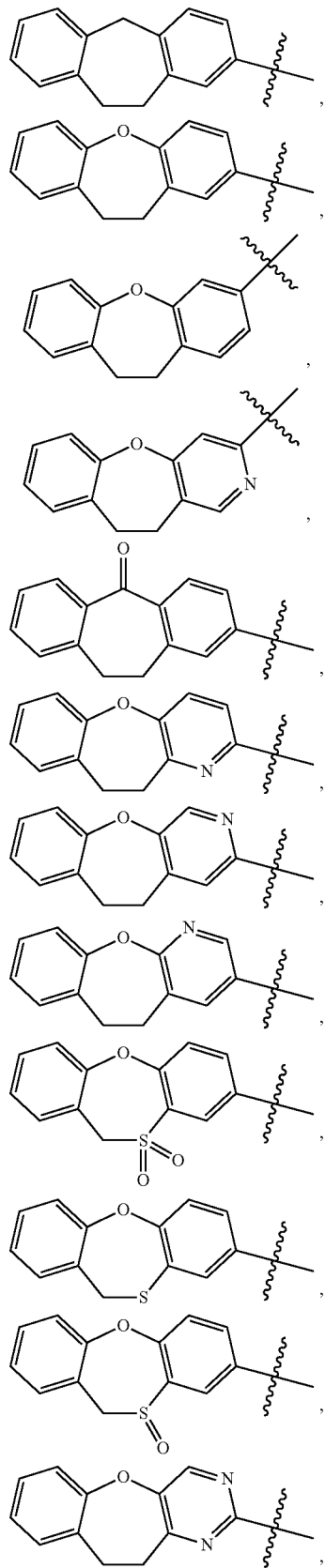

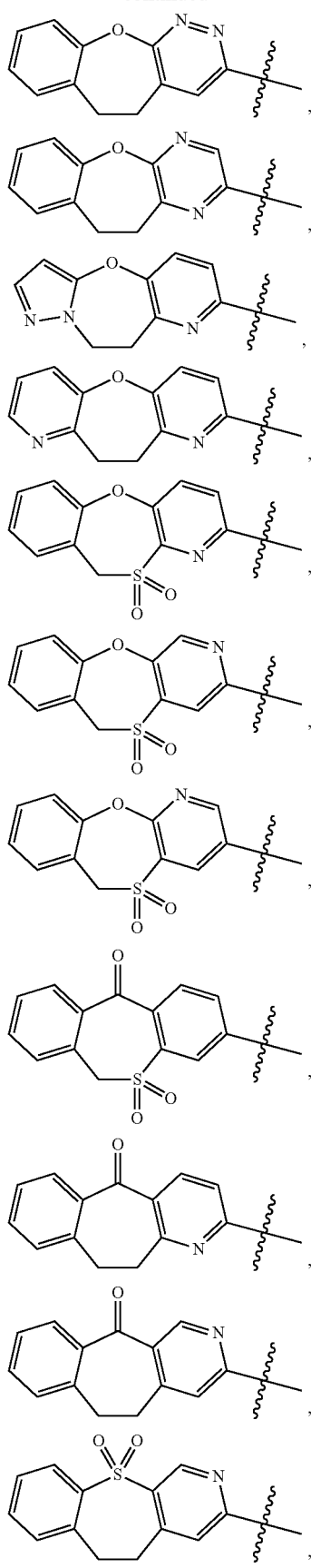
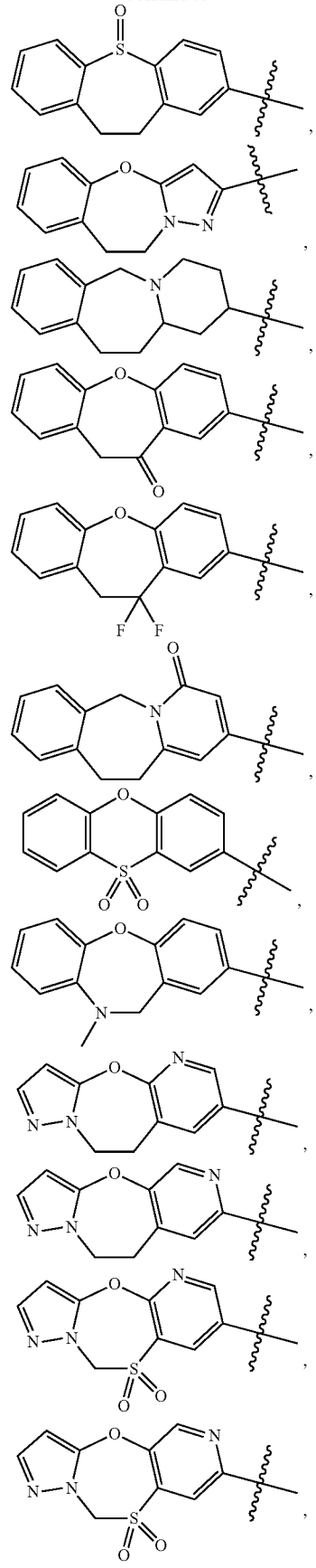

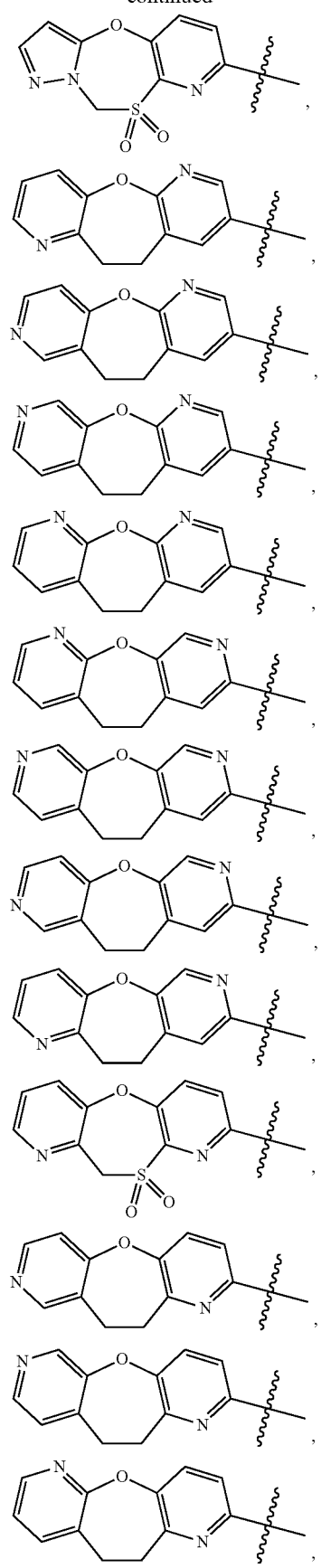
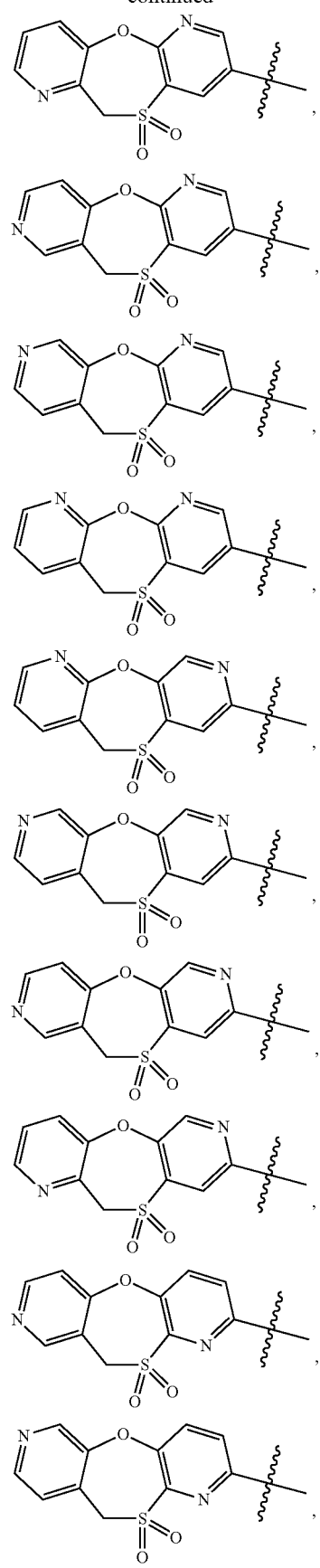

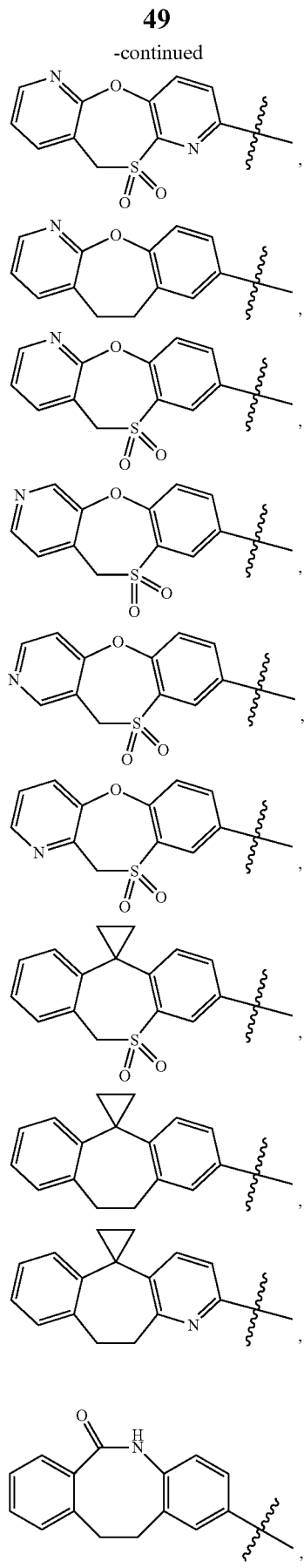

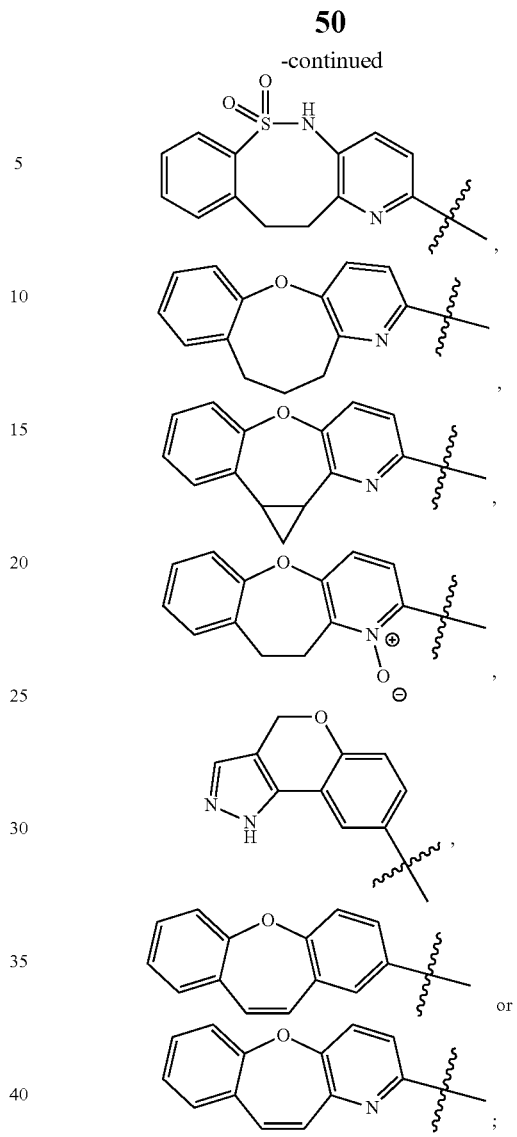

wherein each moiety represented by R is independently and optionally substituted with one, two, three, four or five $R^8$; and $R^8$ is as defined herein.

In some embodiments, each $R^8$ is independently H, deuterium, F, Cl, Br, I, hydroxy, nitro, amino, $C_{1-3}$ aminoalkyl, $C_{1-3}$ alkylamino, $C_{1-3}$ alkyl, $C_{1-4}$ hydroxyalkyl, $C_{1-3}$ alkoxy, $C_{1-3}$ haloalkyl, $C_{1-3}$ haloalkoxy, $C_{3-6}$ cycloalkyl, $C_{3-6}$ cycloalkyloxy, $C_{2-4}$ alkenyl, $C_{2-4}$ alkynyl, $C_{6-10}$ aryl, halo-substituted $C_{6-10}$ aryl, $C_{6-10}$ aryl-$C_{1-4}$-alkyl, oxo (=O), —C(=O)OR$^{15}$, —S(=O)R$^{16}$, —C(=O)NR$^{17}$R$^{18}$, —C(=O)N(R$^{17}$)S(=O)$_2$R$^{16}$, —C(=O)NH—C$_{1-4}$ alkylene —S(=O)$_2$OR$^{15}$, —C(=O)NH—C$_{1-4}$ alkylene —C(=O)OR$^{15}$, cyano, triazolyl or tetrazolyl; or two $R^8$, together with the same C atom to which they are attached, independently and optionally form $C_{3-6}$ cycloalkyl or $C_{2-9}$ heterocyclyl; or two $R^8$, together with the adjacent C atoms to which they are attached, independently and optionally form $C_{3-6}$ cycloalkyl, $C_{2-9}$ heterocyclyl, $C_{6-10}$ aryl or $C_{1-9}$ heteroaryl; wherein each $R^8$ is optionally and independently substituted with one or more $R^{19}$;

each $R^{15}$ is H, deuterium, $C_{1-4}$ alkyl, $C_{1-4}$ aminoalkyl, $C_{2-4}$ alkenyl, $C_{2-4}$ alkynyl, $C_{1-4}$ haloalkyl, $C_{3-6}$ cycloalkyl, $C_{1-6}$ heterocyclyl or $C_{6-10}$ aryl;

each $R^{16}$ is H, deuterium, hydroxy, amino, $C_{1-4}$ alkyl, $C_{1-4}$ aminoalkyl, $C_{2-4}$ alkenyl, $C_{2-4}$ alkynyl, $C_{1-4}$ haloalkyl, $C_{3-6}$ cycloalkyl, $C_{2-6}$ heterocyclyl, $C_{6-10}$ aryl or —$NR^{17}R^{18}$;

each of $R^{17}$ and $R^{18}$ is independently H, deuterium, $C_{1-4}$ alkyl, $C_{1-4}$ aminoalkyl, $C_{2-4}$ alkenyl, $C_{2-4}$ alkynyl, $C_{1-3}$ haloalkyl, $C_{3-6}$ cycloalkyl, $C_{2-6}$ heterocyclyl or $C_{6-10}$ aryl; and wherein each of said $R^{19}$ and t is as defined herein.

In some embodiments, each $R^1$ is independently H, deuterium, F, Cl, Br, I, hydroxy, amino, nitro, cyano, methyl, ethyl, n-propyl, isopropyl, t-butyl, dimethylamino, difluoromethyl, trifluoromethyl, tert-butyloxy, difluoromethyloxy, trifluoromethyloxy, cyclopropyl, oxiranyl, phenyl, naphthyl, oxazolyl, pyrazolyl or thiazolyl, and $R^2$ is independently H, deuterium, F, Cl, Br, I, hydroxy, amino, nitro, cyano, methyl, ethyl, n-propyl, isopropyl, t-butyl, dimethylamino, difluoromethyl, trifluoromethyl, tert-butyloxy, difluoromethyloxy, trifluoromethyloxy, methoxymethyl, isopropoxymethyl, tert-butoxymethyl, cyclopropyl, cycobutyl, oxiranyl or pyrrolidinyl.

In some embodiments, $R^8$ is H, deuterium, F, Cl, Br, I, hydroxy, nitro, amino, oxo (=O), $C_{1-3}$ alkyl, $C_{1-3}$ haloalkyl, —COOH, —C(=O)O—$C_{1-4}$ alkyl, —C(=O)NHS(=O)$_2$—$C_{1-4}$ alkyl, —C(=O)NHS(=O)$_2$-phenyl, —C(=O)NH—$C_{1-4}$ alkylene-S(=O)$_2$OH, —C(=O)NH—$C_{1-4}$ alkylene —C(=O)OH, —S(=O)$_2$NH$_2$, —S(=O)$_2$OH, —S(=O)$_2$—$C_{1-2}$ alkyl, —C(=O)NH$_2$, —C(=O)N(CH$_3$)$_2$, cyano, triazolyl or tetrazolyl.

In some embodiments, provided herein is the compound having one of the following structures, or a stereoisomer, a geometric isomer, a tautomer, an N-oxide, a solvate, a hydrate, a metabolite, ester, a pharmaceutically acceptable salt or a prodrug thereof, but are not limited to:

(1)

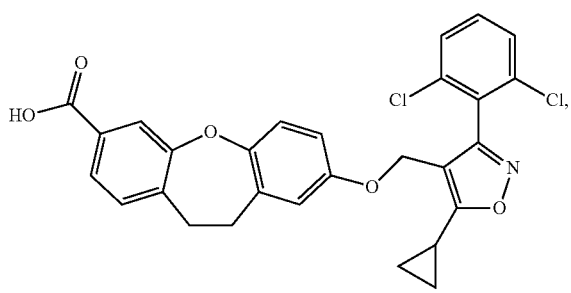

(2)

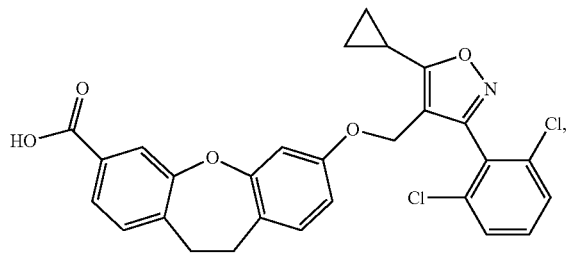

(3)

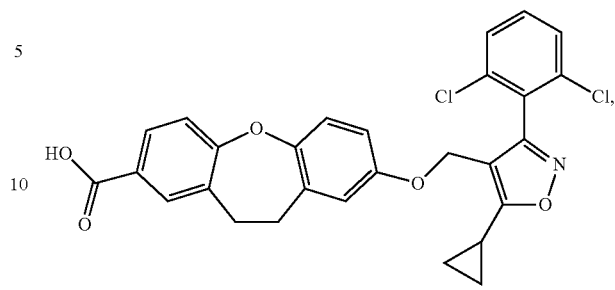

(4)

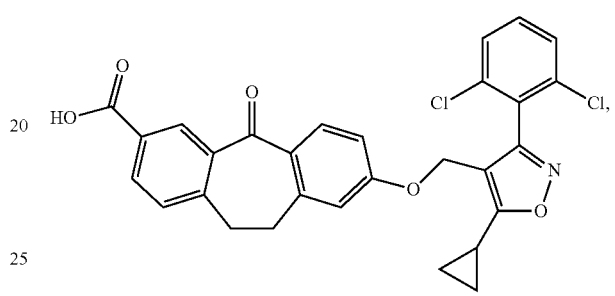

(5)

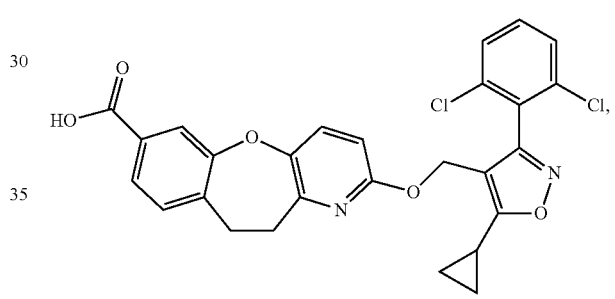

(6)

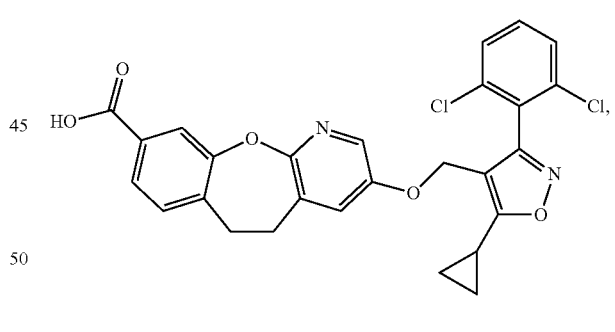

(7)

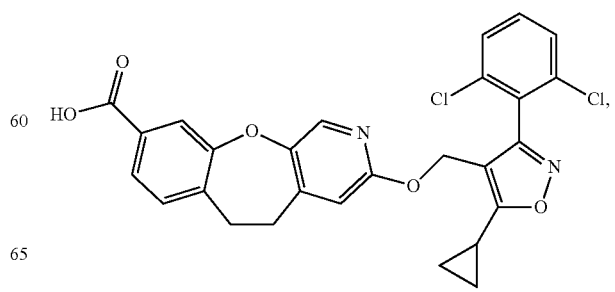

-continued
(8)
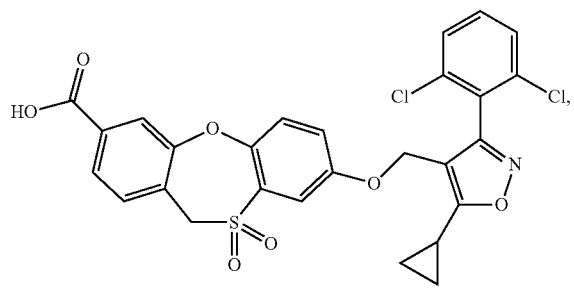
(9)
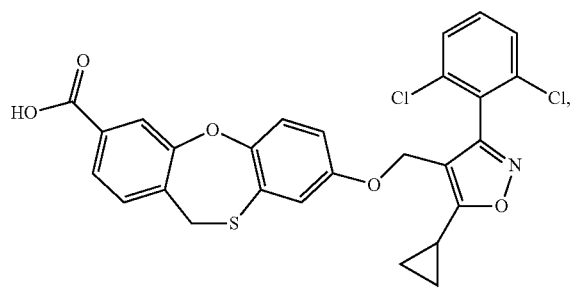
(10)
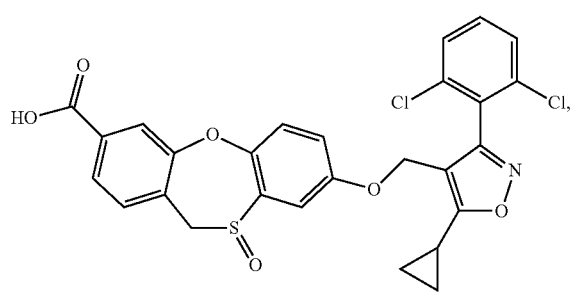
(11)
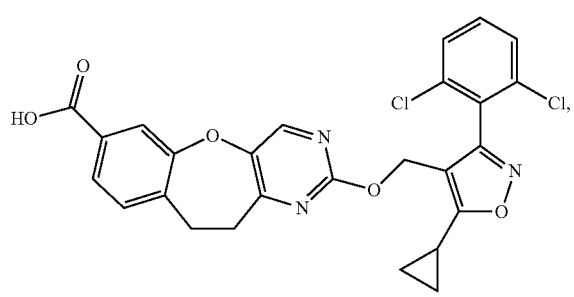
(12)
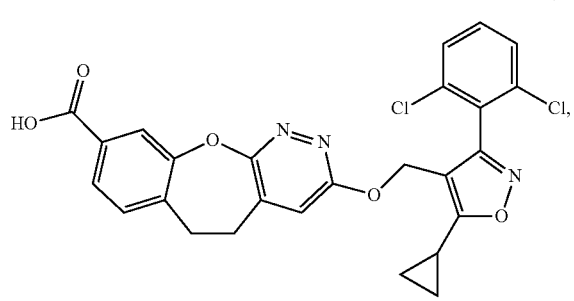
-continued
(13)
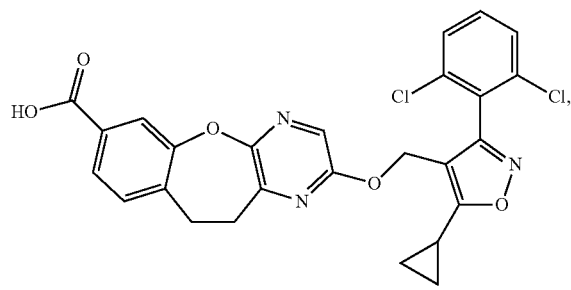
(14)
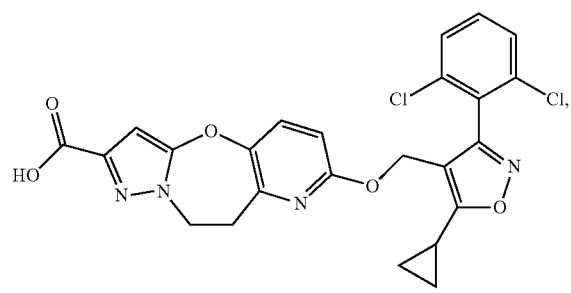
(15)
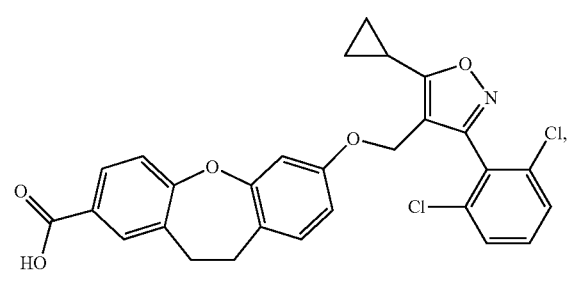
(16)
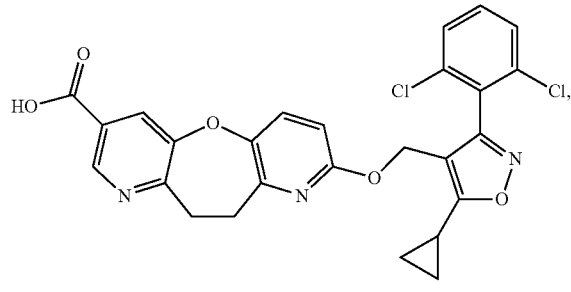
(17)
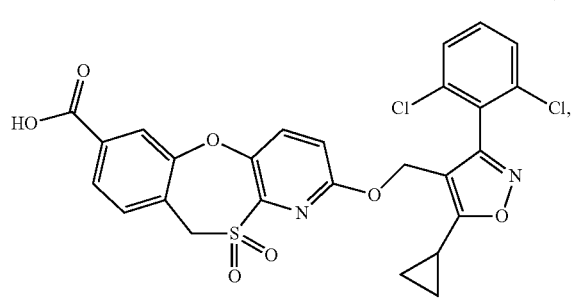

(18)
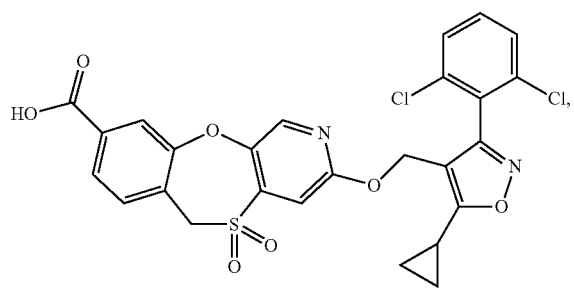 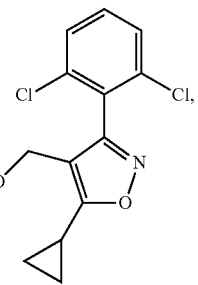
(19)
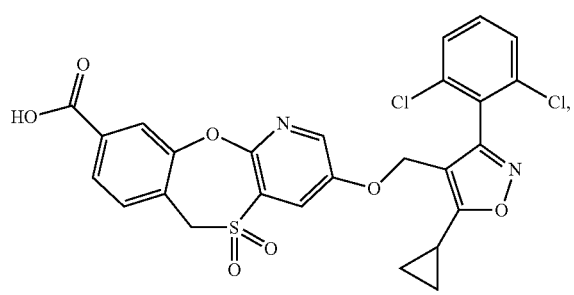 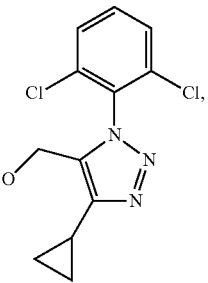
(20)
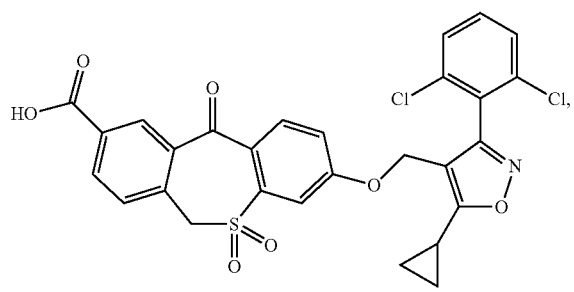 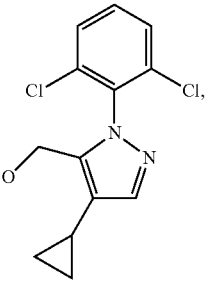
(21)
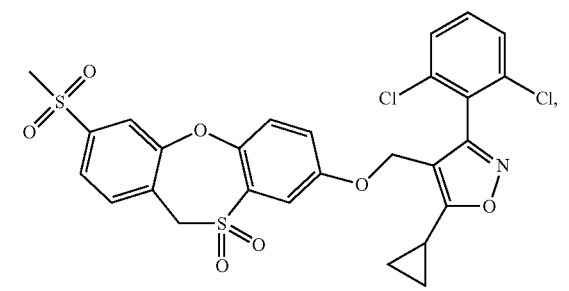 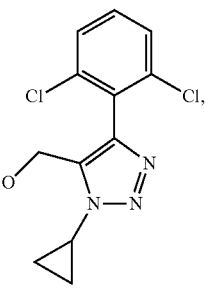
(22)
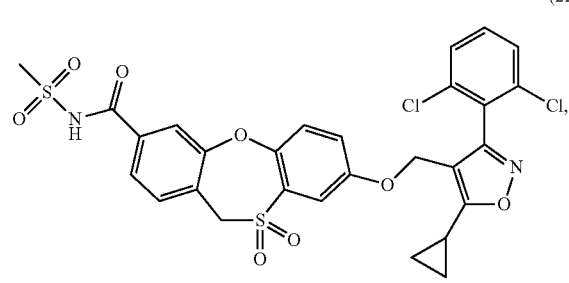 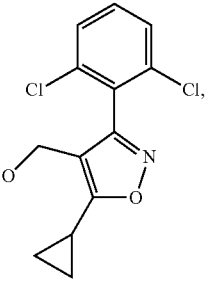

(28) 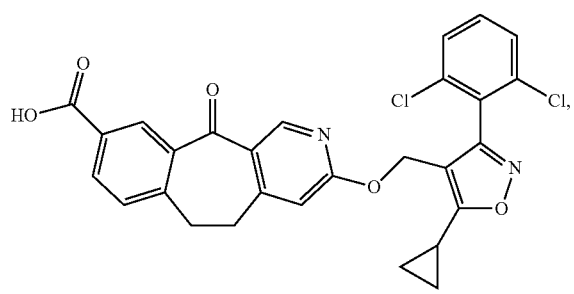
(29) 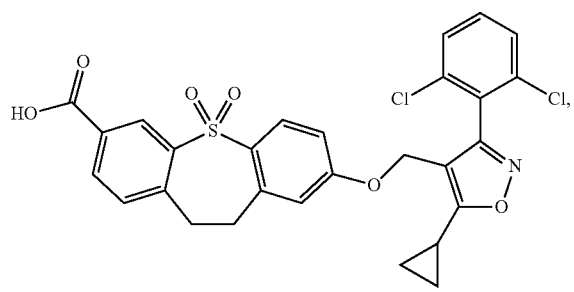
(30) 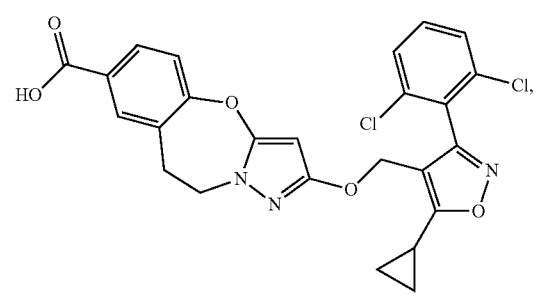
(31) 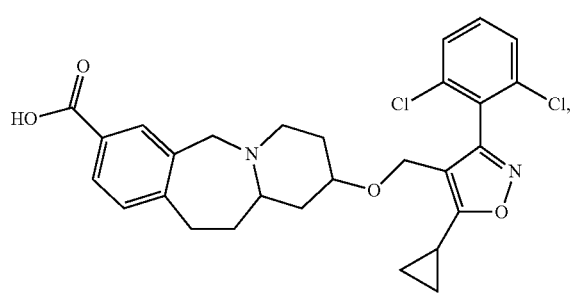
(32)
(33) 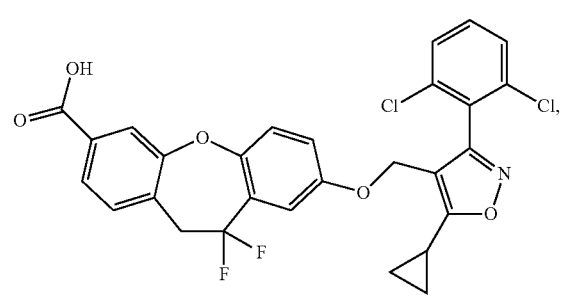
(34) 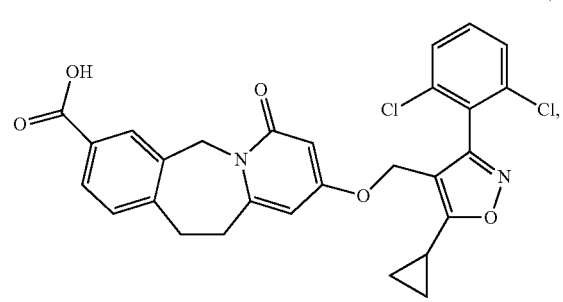
(35) 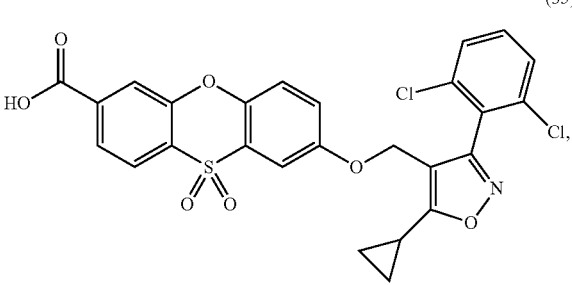
(36) 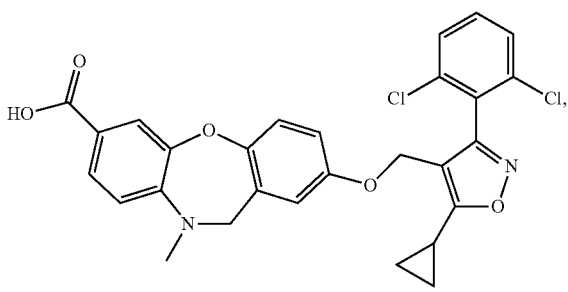
(37) 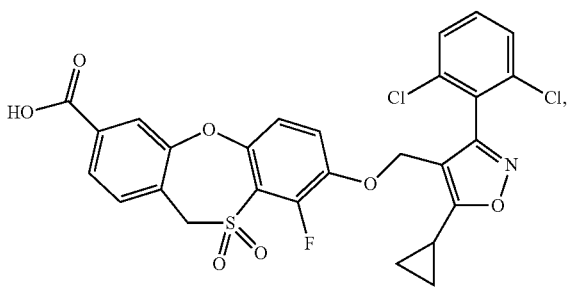

(38)
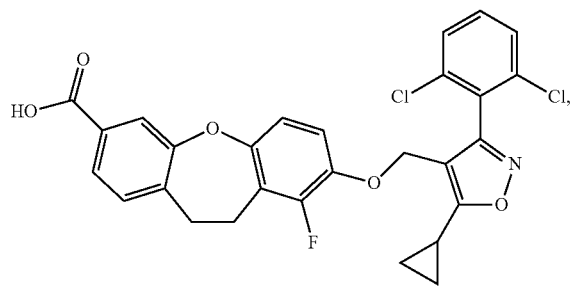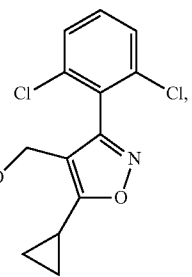
(39)
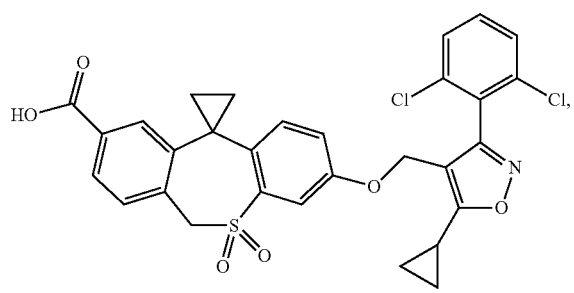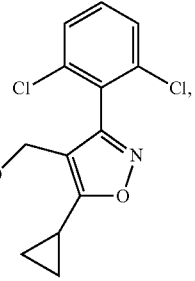
(40)
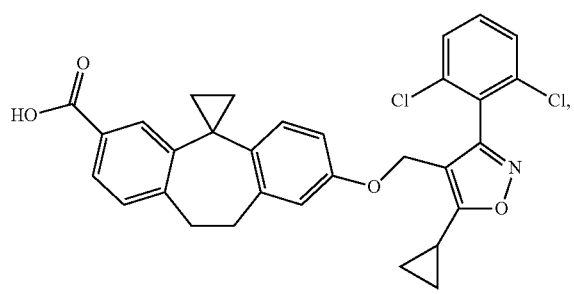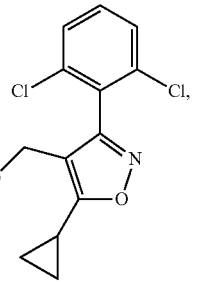
(41)
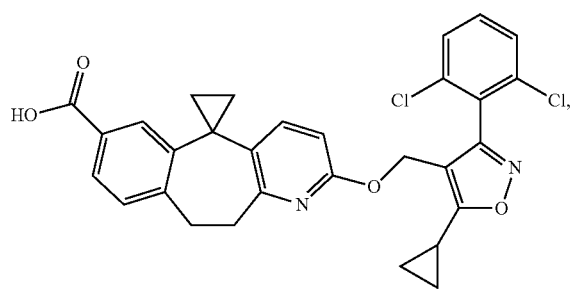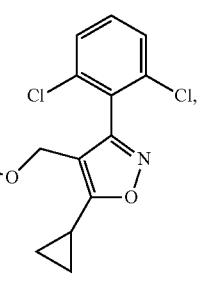
(42)
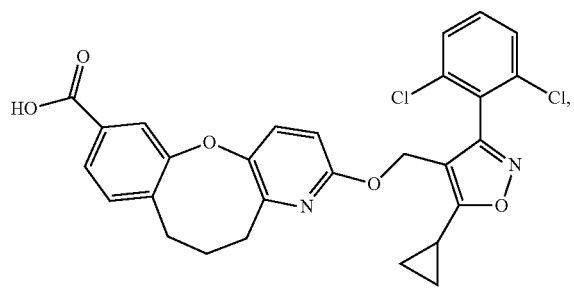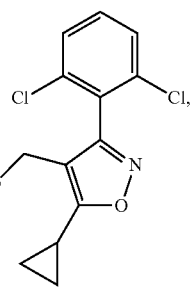
(43)
(44)
(45)
(46)
(47)

-continued
(48)
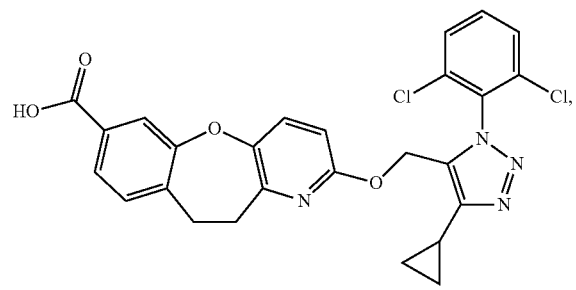
(49)
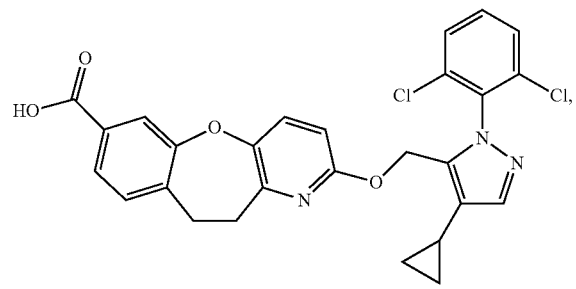
(50)
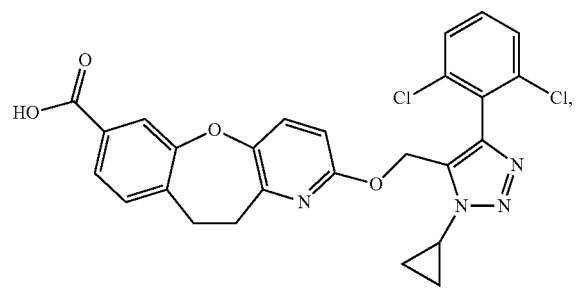
(51)
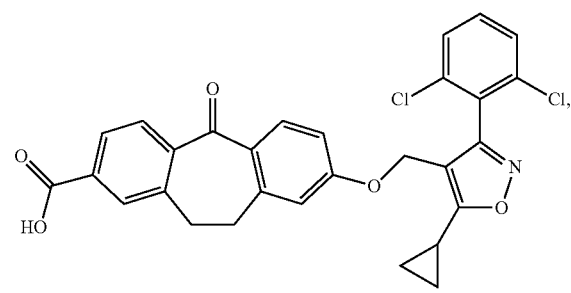
(52)
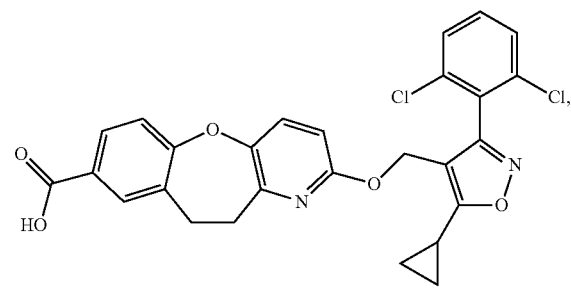
-continued
(53)
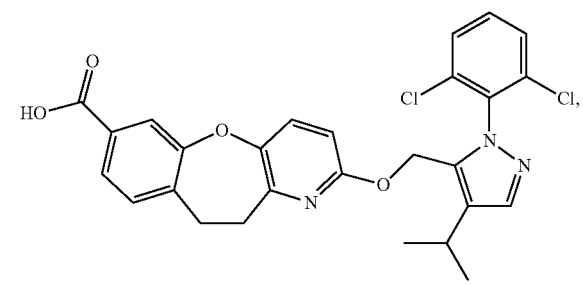
(54)
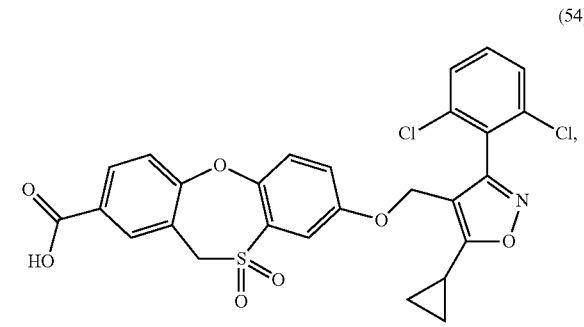
(55)
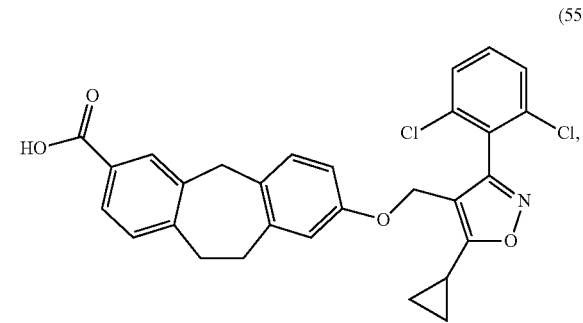
(56)
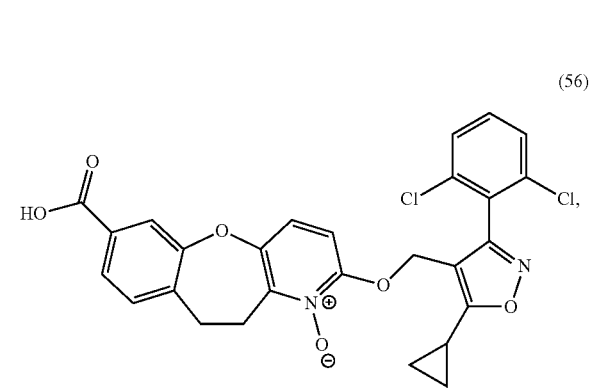
(57)
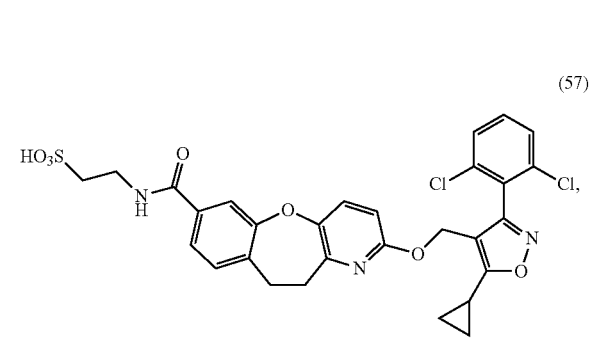

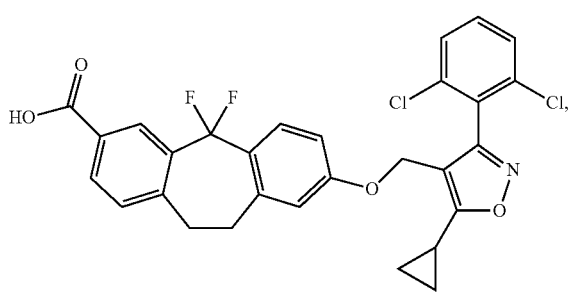

(58)

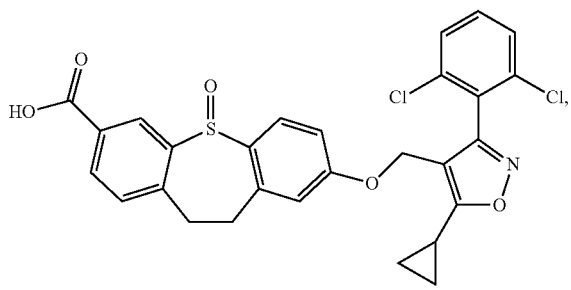

(59)

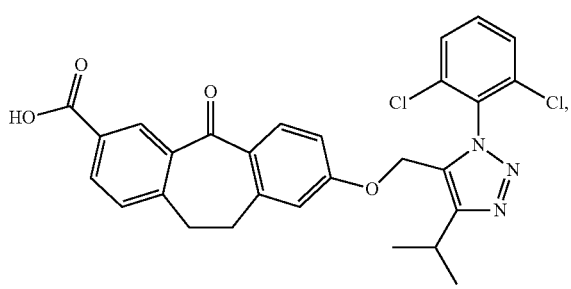

(60)

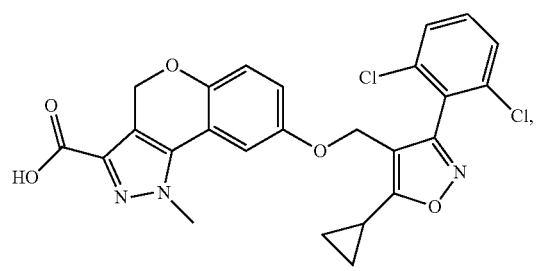

(61)

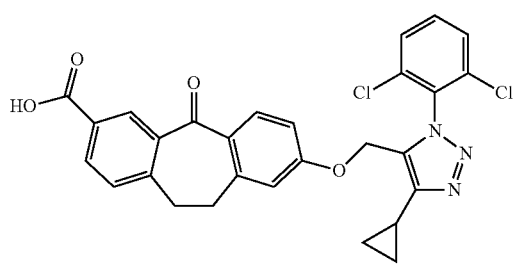

(62)

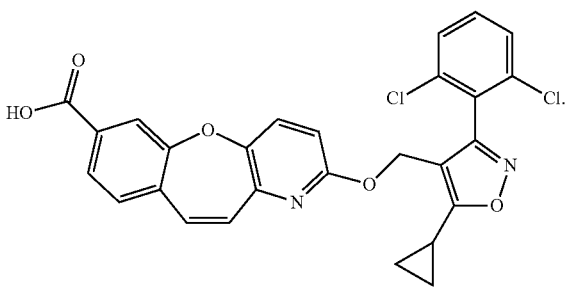

(63)

In one aspect, provided herein is a pharmaceutical composition comprising a compound of Formula (I), (II), (III), (IIIa), (IIIb), (IIIc), (IIId), (IV) or (V) disclosed herein, or a stereoisomer, a geometric isomer, a tautomer, an N-oxide, a hydrate, a solvate, a metabolite, a pharmaceutically acceptable salt or a prodrug thereof, and a pharmaceutically acceptable carrier, excipient, diluent, adjuvant, vehicle or a combination thereof.

In one aspect, provided herein is use of the compound of Formula (I), (II), (III), (IIIa), (IIIb), (IIIc), (IIId), (IV) or (V) disclosed herein or the pharmaceutical composition thereof in the manufacture of a medicament for preventing, managing, treating or lessening a disease mediated by FXR.

In some embodiments, the disease mediated by FXR is a cardiovascular and cerebrovascular disease, a disease related to dyslipidemia, obesity, metabolic syndrome, a hyperproliferative disease, fibrosis, an inflammatory disease or a hepatobiliary related disease.

In some embodiments, the cardiovascular and cerebrovascular disease comprises atherosclerosis, acute myocardial infarction, veno-occlusive disease, portal hypertension, pulmonary hypertension, heart failure, peripheral arterial occlusive disease (PAOD), sexual dysfunction, stroke or thrombosis.

In some embodiments, the obesity and metabolic syndrome comprise insulin resistance, hyperglycemia, hyperinsulinemia, elevated blood level of fatty acids or glycerol, hyperlipidemia, obesity, hypertriglyceridemia, hypercholesterolemia, X syndrome, diabetic complications, atherosclerosis, hypertension, acute anemia, neutropenia, dyslipidemia, type II diabetes, diabetic nephropathy, diabetic neuropathy, diabetic retinopathy or the merger disorders of diabetes and abnormally high BMI.

In some embodiments, the hyperproliferative disease comprises hepatocellular carcinoma, adenomatous, polyposis, colon cancer, breast cancer, membrane cancer, Barrett's esophageal cancer and other forms of gastrointestinal tract disease or liver tumor.

In some embodiments, the fibrosis, inflammatory disease and hepatobiliary related disease comprise nonalcoholic fatty liver disease (NAFLD), nonalcoholic steatohepatitis (NASH), cholestasis, liver fibrosis, primary biliary cirrhosis (PBC), primary sclerosing cholangitis (PSC), progressive familial intrahepatic cholestasis (PFIC), cystic fibrosis, drug-induced bile duct injury, cirrhosis of the liver, hepatitis B, sebaceous disease, cirrhosis of the liver caused by alcohol, biliary obstruction, cholelithiasis, colitis, newborn yellow disease, riboflavin disease prevention or intestinal bacterial overgrowth.

In one aspect, provided herein is a method of preventing, managing, treating or lessening the tissue or organ fibrotic disease mediated by FXR comprising administering a therapeutic effective amount of the compound or the pharmaceutical composition of the present invention to the patient.

In one aspect, provided herein is a method of preventing, managing, treating or lessening a disease mediated by FXR comprising administering a pharmaceutically acceptable effective dosage of the compounds of the the present invention to the patient.

In other aspect, provided herein is use of the pharmaceutical composition the compound of Formula (I), (II), (III), (IIIa), (IIIb), (IIIc), (IIId), (IV) or (V) disclosed herein in the manufacture of a medicament for preventing, managing, treating or lessening a disease mediated by FXR in a patient.

In other aspect, provided herein is use of the compound of Formula (I), (II), (III), (IIIa), (IIIb), (IIIc), (IIId), (IV) or (V) disclosed herein or the pharmaceutical composition thereof in preventing or treating human or animal disease mediated by FXR comprising administering a pharmaceutically acceptable therapeutic effective amount of the compounds or the pharmaceutical composition to the human or animal.

In other aspect, provided herein is a method of preparing, separating or purifying the compound of Formula (I), (II), (III), (IIIa), (IIIb), (IIIc), (IIId), (IV) or (V).

Pharmaceutical Compositions, Preparations, Administration, and Uses of the Compounds and Pharmaceutical Compositions In other aspect, the characteristics of the pharmaceutical compositions of the present invention include compounds of formula (I), (II), (III), (IIIa), (IIIb), (IIIc), (IIId), (IV) or (V) compounds listed in the present invention, or compounds of embodiments 1-35, and a pharmaceutically acceptable carrier, adjuvant or vehicle. The amount of the compound in the composition of the present invention is effective and detectable for treating or lessening disease mediated by FXR in the patients.

It will also be appreciated that the compounds disclosed herein can exist in free form, or where appropriate, as a pharmaceutically acceptable derivative thereof. Some non-limiting examples of the pharmaceutically acceptable derivative include pharmaceutically acceptable prodrugs, salts, esters, salts of such esters, or any other adducts or derivatives which upon administration to a patient in need is capable of providing, directly or indirectly, a compound as otherwise described herein, or a metabolite or residue thereof.

As described above, the pharmaceutically acceptable compositions disclosed herein further comprise a pharmaceutically acceptable carrier, an adjuvant, or a vehicle, which, as used herein, includes any and all solvents, diluents, or other liquid vehicle, dispersion or suspension aids, surface active agents, isotonic agents, thickening or emulsifying agents, preservatives, solid binders, lubricants, and the like, as suited to the particular dosage form desired. As described in the following references: In Remington: The Science and Practice of Pharmacy, 21st ed., 2005, ed. D. B. Troy, Lippincott Williams & Wilkins, Philadelphia, and Encyclopedia of Pharmaceutical Technology, eds. J. Swarbrick and J. C. Boylan, 1988-1999, Marcel Dekker, New York, both of which are herein incorporated by reference in their entireties, and discloses various carriers used in formulating pharmaceutically acceptable compositions and known techniques for the preparation thereof. Except insofar as any conventional carrier medium incompatible with the compounds disclosed herein, such as by producing any undesirable biological effect or otherwise interacting in a deleterious manner with any other components of the pharmaceutically acceptable composition, its use is contemplated to be within the scope of this invention.

The compound of the present invention can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). In preparing the compositions for oral dosage form, any of the usual pharmaceutical media may be employed, such as, for example, water, glycol, oils, alcohols, fragrances, corrosion agents, coloring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case of oral solid preparations, such as, for example, powders, hard capsules and soft capsules and tablets, with the solid oral preparations being preferred over the liquid preparations.

Because of their ease of administration, tablets and capsules represent the most advantageous oral dosage unit form in which case solid pharmaceutical carriers are obviously employed. If desired, tablets may be coated by standard aqueous or nonaqueous techniques. Such compositions and preparations should contain at least 0.1 percent of active compound. The percentage of active compound in these compositions may, of course, be varied and may conveniently be between about 2 percent to about 60 percent of the weight of the unit. The amount of active compound in such therapeutically useful compositions is such that an effective dose will be obtained. The active compounds can also be administered intranasally as, for example, liquid drops or spray.

The tablets, pills, capsules and the like may also contain a binder (such as gum tragacanth, acacia, corn starch or gelatin); excipients (such as dicalcium phosphate); a disintegrant agent (such as corn starch, potato starch, alginic acid); a lubricant (such as magnesium stearate); and a sweetening agent (such as sucrose, lactose or saccharin). When a dosage unit form is a capsule, it may contain, in addition to materials of the above type, a liquid carrier (such as a fatty oil).

Various other materials may be present as coatings or to modify the physical form of the dosage unit. For instance, tablets may be coated with shellac, sugar or both. A syrup or elixir may contain, in addition to the active ingredient, sucrose as a sweetening agent, methyl or propylparaben as preservatives, a dye and a flavoring (such as cherry or orange flavor).

Ophthalmic formulations, eye ointments, powders, solutions and the like, are also contemplated as being within the scope of this invention.

The compounds of the present invention may also be administered parenterally. Solutions or suspensions of these active compounds can be prepared suitably mixed with a surfactant (e.g., hydroxyl-propylcellulose) in water. Dispersions can also be prepared in glycerol, liquid polyethylene glycols and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation. In all cases, the form must be sterile and must be fluid to the extent easy syringability exsists. It must be stable under the conditions of manufacture and storage and must be preserved against the contaminating action of microorganisms such as bacteria and fungi. The carrier can be a solvent or dispersion medium containing, for example, water, ethanol, polyol (e.g. glycerol, propylene glycol and liquid polyethylene glycol), suitable mixtures thereof, and vegetable oils.

Any suitable route of administration may be employed for providing a mammal, especially a human, with an effective dose of a compound of the present invention. For example, oral, rectal, topical, parenteral, ocular, pulmonary, nasal, and the like may be employed. Dosage forms include tablets, troches, dispersions, suspensions, solutions, capsules, creams, ointments, aerosols and the like. Preferably compounds of the present invention are administered orally.

The therapeutically effective dosage of a compound, the pharmaceutical composition, or the combinations thereof, is dependent on the species of the subject, the body weight, age and individual condition, the disorder or disease or the severity thereof being treated. A physician, clinician or veterinarian of ordinary skill can readily determine the effective amount of each of the active ingredients necessary to prevent, treat or inhibit the progress of the disorder or disease.

When treating or preventing of conditions mediated by FXR for which compounds of the present invention are indicated, generally satisfactory results are obtained when the compounds of the present invention are administered at a daily dose of from about 0.1 milligrams to about 100 milligrams per kilogram of animal body weight, preferably given as a single daily dose or in divided doses two to six times a day, or in sustained release form. For most large mammals, the total daily dose is from about 1.0 milligrams to about 1000 milligrams, preferably from about 1.0 milligrams to about 50 milligrams. In the case of a 70 kg human, the total daily dose will generally from about 7.0 milligrams to about 350 milligrams. This dosage regimen may be adjusted to provide the optimal therapeutic response.

The present invention relates to compounds, compositions, or a pharmaceutically acceptable salt or hydrate thereof for effective use in preventing, managing, treating or alleviating a disease mediated by the FXR, particularly effective in the treatment of non-alcoholic fatty liver (NAFLD), Nonalcoholic steatohepatitis (NASH), obesity, hypertriglyceridemia, atherosclerosis, chronic intrahepatic cholestasis, primary biliary cirrhosis (PBC), primary sclerosing cholangitis (PSC), progressive familial intrahepatic cholestasis (PFIC), drug-induced bile duct injury, gallstones, cirrhosis, hepatitis B, steatosis, cirrhosis of the liver caused by alcohol, cystic fibrosis, biliary obstruction, gallstone disease, liver fibrosis, dyslipidemia, atherosclerosis, type II diabetes, diabetic nephropathy, diabetic neuropathy, diabetic retinopathy, peripheral arterial occlusive disease (PAOD), colitis, newborn yellow disease, riboflavin disease prevention, vein occlusive disease, portal hypertension, metabolic syndrome, acute myocardial infarction, acute stroke, thrombosis, hypercholesterolemia, intestinal bacterial overgrowth, erectile dysfunction, gastrointestinal tumor and liver tumor.

General Synthetic Procedures

Generally, the compounds disclosed herein may be prepared by methods described herein, wherein the substituents are as defined for Formula (I), (II), (III), (IIIa), (IIIb), (IIIc), (IIId), (IV) or (V) above, except where further noted. The following non-limiting schemes and examples are presented to further exemplify the invention.

Persons skilled in the art will recognize that the chemical reactions described may be readily adapted to prepare a number of other compounds disclosed herein, and alternative methods for preparing the compounds disclosed herein are deemed to be within the scope disclosed herein. For example, the synthesis of non-exemplified compounds according to the invention may be successfully performed by modifications apparent to those skilled in the art, e.g., by appropriately protecting interfering groups, by utilizing other suitable reagents known in the art other than those described, and/or by making routine modifications of reaction conditions. Alternatively, the known reaction conditions or the reaction disclosed in the present invention will be recognized as having applicability for preparing other compounds disclosed herein.

In the examples described below, unless otherwise indicated all temperatures are set forth in degrees Celsius. Reagents were purchased from commercial suppliers such as Aldrich Chemical Company, Arco Chemical Company and Alfa Chemical Company, and were used without further purification unless otherwise indicated. Common solvents were purchased from commercial suppliers such as Shantou XiLong Chemical Factory, Guangdong Guanghua Reagent Chemical Factory Co. Ltd., Guangzhou Reagent Chemical Factory, Tianjin YuYu Fine Chemical Ltd., Qingdao Tenglong Reagent Chemical Ltd., and Qingdao Ocean Chemical Factory.

Anhydrous THF, dioxane, toluene, and ether were obtained by refluxing the solvent with sodium. Anhydrous $CH_2Cl_2$ and $CHCl_3$ were obtained by refluxing the solvent with $CaH_2$. EtOAc, PE, hexane, DMAC and DMF were treated with anhydrous $Na_2SO_4$ prior to use.

The reactions set forth below were done generally under a positive pressure of nitrogen or argon or with a drying tube (unless otherwise stated) in anhydrous solvents, and the reaction flasks were typically fitted with rubber septa for the introduction of substrates and reagents via syringe. Glassware was oven dried and/or heat dried. Column chromatography was conducted using a silica gel column. Silica gel (300-400 mesh) was purchased from Qingdao Ocean Chemical Factory. $^1$H NMR spectra were recorded with a Bruker 400 MHz or 600 MHz spectrometer using $CDCl_3$, $d_6$-DMSO, $CD_3OD$ or $d_6$-acetone as solutions (reported in ppm), and using TMS (0 ppm) or chloroform (7.25 ppm) as the reference standard. For multiple peaks, the following abbreviations used: s (singlet), d (doublet), t (triplet), m (multiplet), br (broadened), dd (doublet of doublets), q (quartet), dt (doublet of triplets), tt (triplet of triplets), dddd (doublet of doublet of doublet of doublets), qd (quartet of doublets), ddd (doublet of doublet of doublets), td (triplet of doublets), dq (doublet of quartets), ddt (doublet of doublet of triplets), tdd (triplet of doublet of doublets), dtd (doublet of triplet of doublets). Coupling constants, when given, were reported in Hertz (Hz).

Low-resolution mass spectral (MS) data were determined by an Agilent 6320 Series LC-MS spectrometer equipped with a G1312A binary pump and a G1316A TCC (column was operated at 30° C.). G1329A autosampler and G1315B DAD detector were applied in the analysis, and an ESI source was used in the LC-MS spectrometer.

Low-resolution mass spectral (MS) data were determined by an Agilent 6120 Series LC-MS spectrometer equipped with a G1311A quaternary pump and a G1316A TCC (column was operated at 30° C.). G1329A autosampler and G1315D DAD detector were applied in the analysis, and an ESI source was used on the LC-MS spectrometer.

Both LC-MS spectrometers were equipped with an Agilent Zorbax SB-C18, 2.1×30 mm, 5 µm column. Injection volume was decided by the sample concentration. The flow rate was 0.6 mL/min. The HPLC peaks were recorded by UV-Vis wavelength at 210 nm and 254 nm. The mobile phase was 0.1% formic acid in acetonitrile (phase A) and 0.1% formic acid in ultrapure water (phase B). The gradient elution conditions were showed in Table 1:

TABLE 1

The gradient condition of the mobile phase in Low-resolution mass spectrum analysis

| Time (min) | A ($CH_3CN$, 0.1% HCOOH) | B ($H_2O$, 0.1% HCOOH) |
|---|---|---|
| 0-3 | 5-100 | 95-0 |
| 3-6 | 100 | 0 |
| 6-6.1 | 100-5 | 0-95 |
| 6.1-8 | 5 | 95 |

Purities of compounds were assessed by Agilent 1100 Series high performance liquid chromatography (HPLC) with UV detection at 210 nm and 254 nm (Zorbax SB-C18, 2.1×30 mm, 4 micorn, 10 min, 0.6 mL/min flow rate, 5 to 95% (0.1% formic acid in $CH_3CN$) in (0.1% formic acid in $H_2O$). Column was operated at 40° C.

The following abbreviations are used throughout the specification:

$CDCl_3$ chloroform-d
DMF N,N-dimethylformamide
DMSO dimethylsulfoxide
DMSO-$d_6$ dimethyl sulfoxide-$d_6$
$CD_3OD$ methyl alcohol-$d_4$
$CH_3OH$, MeOH methanol
THF tetrahydrofuran
DCM, $CH_2Cl_2$ dichloromethane
EA, EtOAc ethyl acetate
PE petroleum ether
Pd/C, Pd—C Palladium on activated carbon
g gram
$H_2O$ water
mol mole
mmol millimole
mL milliliter
h hour, hours Synthetic Procedures

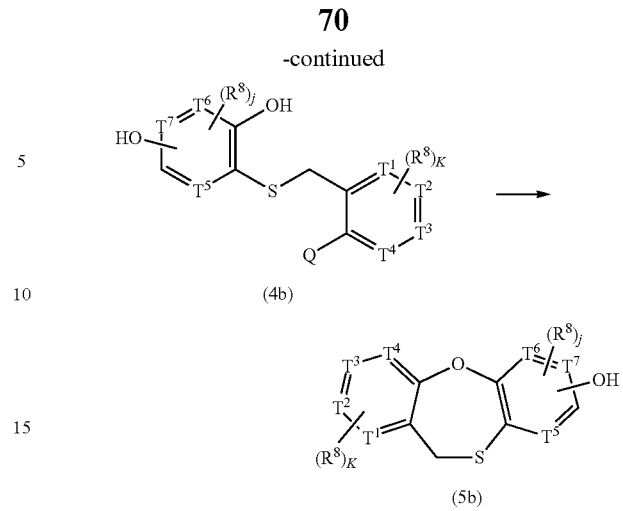

Each of K and j is independently 0, 1, 2, 3 or 4; Q is halogen; $M^1$ is a leaving group; Pg is a protecting group described herein; $R^8$, $T^1$, $T^2$, $T^3$, $T^4$, $T^5$, $T^6$ and $T^7$ are as defined herein.

The substitution reaction of compound (1b) with compound (2b) can afford compound (3b) under an alkaline condition. Leaving groups represented by $M^1$ include, but are not limited to, halogen, methanesulfonyloxy, p-methyl phenylsulfonyloxy, and the like. The bases include, but are not limited to potassium carbonate, and the like. The reaction is carried out in an inert solvent. The solvents include, but are not limited to N,N-dimethylformamide, and the like.

The hydroxy protecting group of compound (3b) can be removed to afford compound (4b), and the method of removal of hydroxy protecting group can refer to "Protective Groups in Organic Synthesis".

By coupling reaction in the presence of a catalyst and a ligand under an alkaline condition, compound (4b) can be converted to compound (5b). The catalysts include, but are not limited to cuprous iodide, and the like. The ligands include, but are not limited to N,N-dimethylglycine, and the like. The bases include, but are not limited to cesium carbonate, and the like. The reaction is carried out in an inert solvent. The solvents include, but are not limited to 1,4-dioxane, and the like.

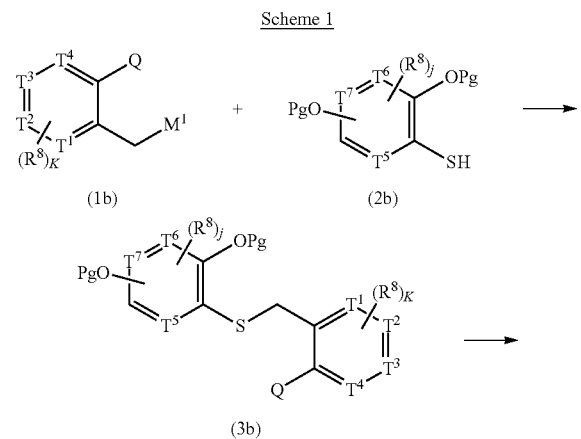

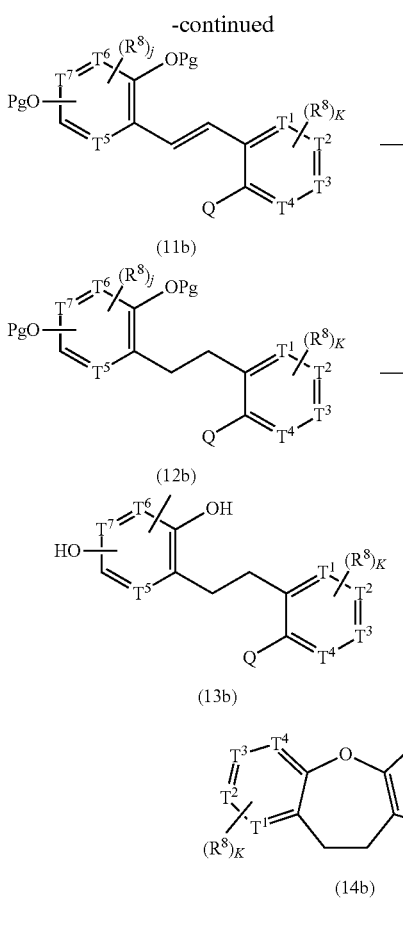

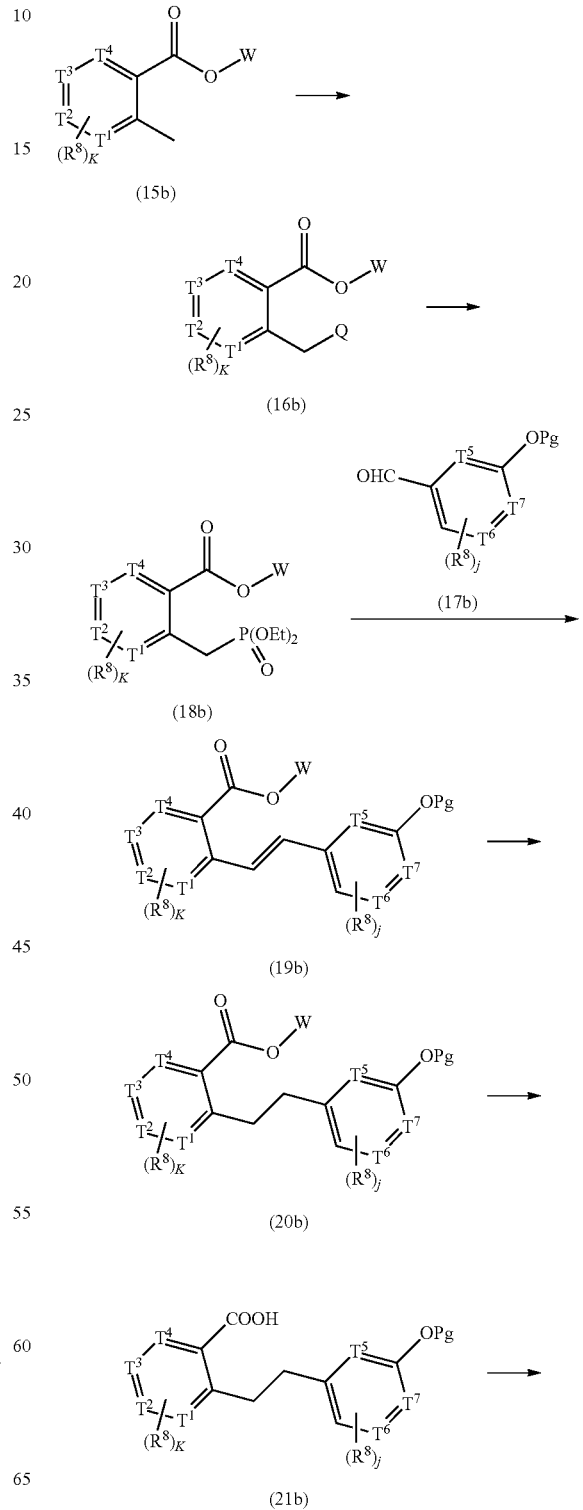

Scheme 3 include, but are not limited to N,N-dimethylglycine, and the like. The bases include, but are not limited to cesium carbonate, and the like. The reaction can be carried out in an inert solvent for the reaction. The solvents include, but are not limited to 1,4-dioxane, and the like.

Q is a halogen; M¹ is a leaving group; each of K and j is independently 0, 1, 2, 3 or 4; Pg is a protecting group; $R^8$, $T^1$, $T^2$, $T^3$, $T^4$, $T^5$, $T^6$ and $T^7$ are as defined herein.

Compound (1b) can react with triethylphosphite to give compound (9b) under a solvent-free condition or in an inert solvent for the reaction.

Horner-Wadsworth-Emmons reaction of compound (9b) with compound (10b) can afford compound (11b). In Horner-Wadsworth-Emmons reaction, the reaction raw materials can be reacted in the presence of a base (base may be, but is not limited to, sodium hydride, potassium t-butoxide, etc.) in a solvent. The reaction is preferably carried out in an inert solvent for the reaction. The solvents include, but are not limited to tetrahydrofuran, and the like.

Compound (11b) can be reduced to afford compound (12b) in the presence of a reducing agent under an alkaline condition. The reducing agents include, but are not limited to p-methyl benzenesulfonohydrazide, and the like. The bases include, but are not limited to sodium acetate, and the like. The reaction can be preferred to carry out in an inert solvent for the reaction. The solvents include, but are not limited to tetrahydrofuran, water or a mixed solvent, and the like.

Compound (12b) can be converted to compound (13b) by removing hydroxy protecting groups, and the method of removal of hydroxy protecting group can refer to "Protective Groups in Organic Synthesis".

By coupling reaction in the presence of a catalyst and a ligand under an alkaline condition, compound (13b) can be converted to compound (14b). The catalysts include, but are not limited to cuprous iodide, and the like. The ligands

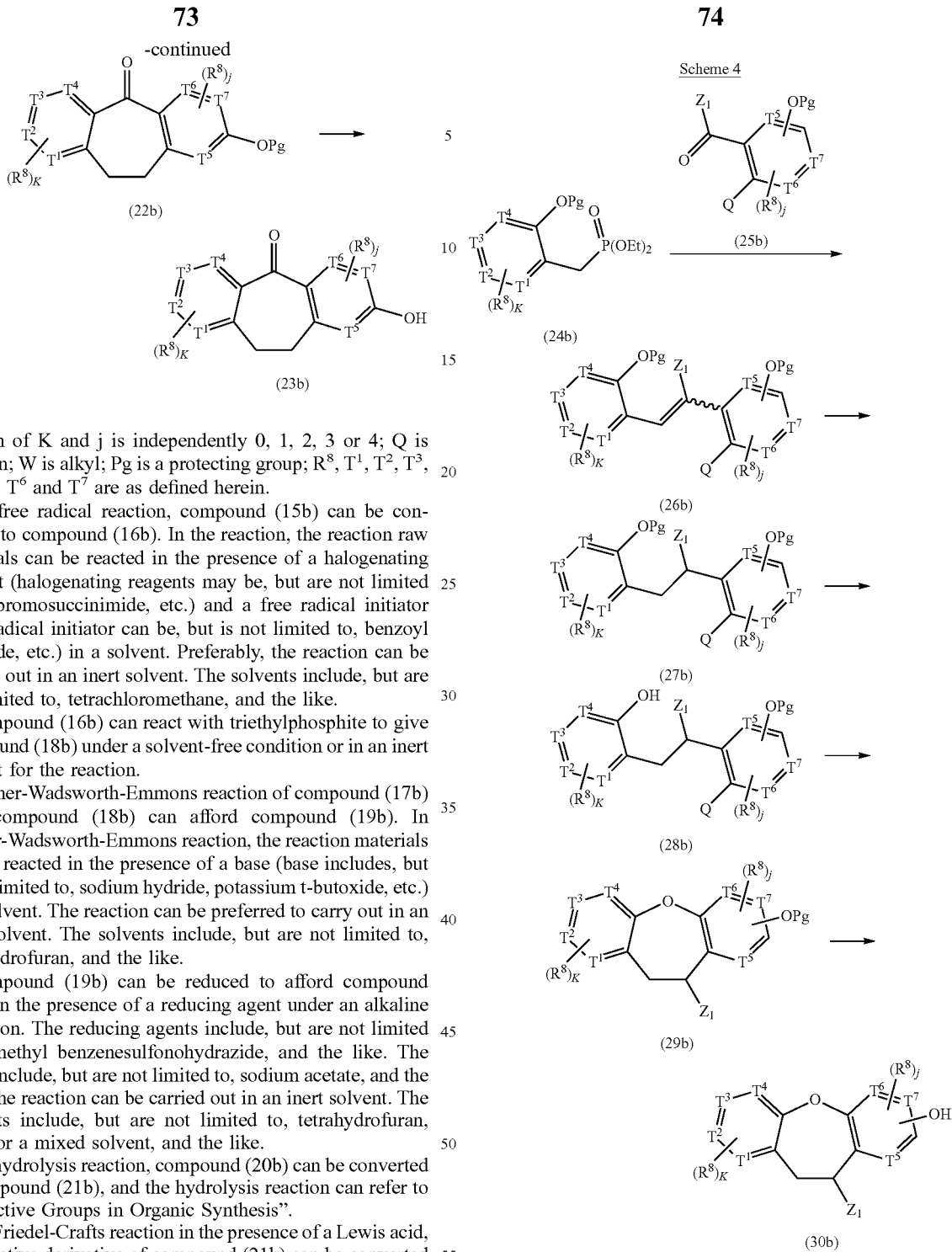

Scheme 4

Each of K and j is independently 0, 1, 2, 3 or 4; Q is halogen; W is alkyl; Pg is a protecting group; $R^8$, $T^1$, $T^2$, $T^3$, $T^4$, $T^5$, $T^6$ and $T^7$ are as defined herein.

By free radical reaction, compound (15b) can be converted to compound (16b). In the reaction, the reaction raw materials can be reacted in the presence of a halogenating reagent (halogenating reagents may be, but are not limited to, N-bromosuccinimide, etc.) and a free radical initiator (free radical initiator can be, but is not limited to, benzoyl peroxide, etc.) in a solvent. Preferably, the reaction can be carried out in an inert solvent. The solvents include, but are not limited to, tetrachloromethane, and the like.

Compound (16b) can react with triethylphosphite to give compound (18b) under a solvent-free condition or in an inert solvent for the reaction.

Horner-Wadsworth-Emmons reaction of compound (17b) with compound (18b) can afford compound (19b). In Horner-Wadsworth-Emmons reaction, the reaction materials can be reacted in the presence of a base (base includes, but is not limited to, sodium hydride, potassium t-butoxide, etc.) in a solvent. The reaction can be preferred to carry out in an inert solvent. The solvents include, but are not limited to, tetrahydrofuran, and the like.

Compound (19b) can be reduced to afford compound (20b) in the presence of a reducing agent under an alkaline condition. The reducing agents include, but are not limited to, p-methyl benzenesulfonohydrazide, and the like. The bases include, but are not limited to, sodium acetate, and the like. The reaction can be carried out in an inert solvent. The solvents include, but are not limited to, tetrahydrofuran, water or a mixed solvent, and the like.

By hydrolysis reaction, compound (20b) can be converted to compound (21b), and the hydrolysis reaction can refer to "Protective Groups in Organic Synthesis".

By Friedel-Crafts reaction in the presence of a Lewis acid, the reactive derivative of compound (21b) can be converted to compound (22b). Reactive derivative can be, but is not limited to: acid halide derived from compound (21b) by reacting with a halogenating agent (including but not limited to oxalyl chloride, etc.), and the like. The Lewis acids include, but are not limited to aluminum chloride, and the like. The reaction is carried out in an inert solvent. The solvents include, but are not limited to, dichloromethane, and the like.

Compound (22b) can be converted to compound (23b) by removing the hydroxy protecting group, and the removal of hydroxy protecting groups can refer to "Protective Groups in Organic Synthesis".

Each of K and j is independently 0, 1, 2, 3 or 4; Q is halogen; $Z^1$ is H or alkyl; Pg is a protecting group; $R^8$, $T^1$, $T^2$, $T^3$, $T^4$, $T^5$, $T^6$ and $T^7$ are as defined herein.

Horner-Wadsworth-Emmons reaction of compound (24b) with compound (25b) can afford compound (26b). In Horner-Wadsworth-Emmons reaction, the reaction starting materials can be reacted in the presence of a base (e.g., sodium hydride, potassium t-butoxide, etc.) in a solvent. The reaction can be preferably carried out in an inert solvent. The solvents include, but are not limited to, tetrahydrofuran, and the like.

Compound (26b) can be reduced to afford compound (27b) in the presence of a reducing agent under an alkaline condition. The reducing agents include, but are not limited to, p-methyl benzenesulfonohydrazide, and the like. The bases include, but are not limited to, sodium acetate, and the like. The reaction can be carried out in an inert solvent. The solvents include, but are not limited to, tetrahydrofuran, water or a mixed solvent, and the like.

The hydroxy protecting group of compound (27b) can be removed to afford compound (28b). The removal of hydroxy protecting group can refer to "Protective Groups in Organic Synthesis".

By coupling reaction in the presence of a catalyst and a ligand under an alkaline condition, compound (28b) can be converted to compound (29b). The catalysts include, but are not limited to, cuprous iodide, and the like. The ligands include, but are not limited to, N,N-dimethylglycine, and the like. The bases include, but are not limited to, cesium carbonate, and the like. The reaction can be carried out in an inert solvent. The solvents include, but are not limited to, 1,4-dioxane, and the like.

The hydroxy protecting group of compound (29b) can be removed to afford compound (30b). The removal of hydroxy protecting group can refer to "Protective Groups in Organic Synthesis".

When M is a leaving group, the substitution reaction of compound (1a) with compound (2a) can afford compound of formula (I) in the presence of a base. Leaving groups represented by M include, but are not limited to, halogen, methanesulfonyloxy, p-methyl phenylsulfonyloxy, and the like. Some non-limiting examples of the base include potassium carbonate, and the like. The reaction can be carried out in an inert solvent. The solvents include, but are not limited to, N,N-dimethylformamide, and the like.

Scheme 6

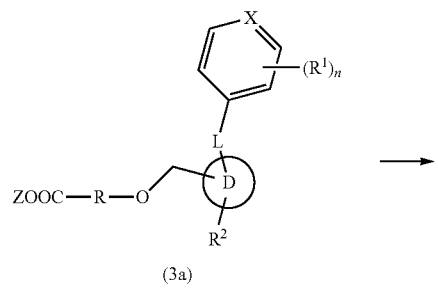

(3a)

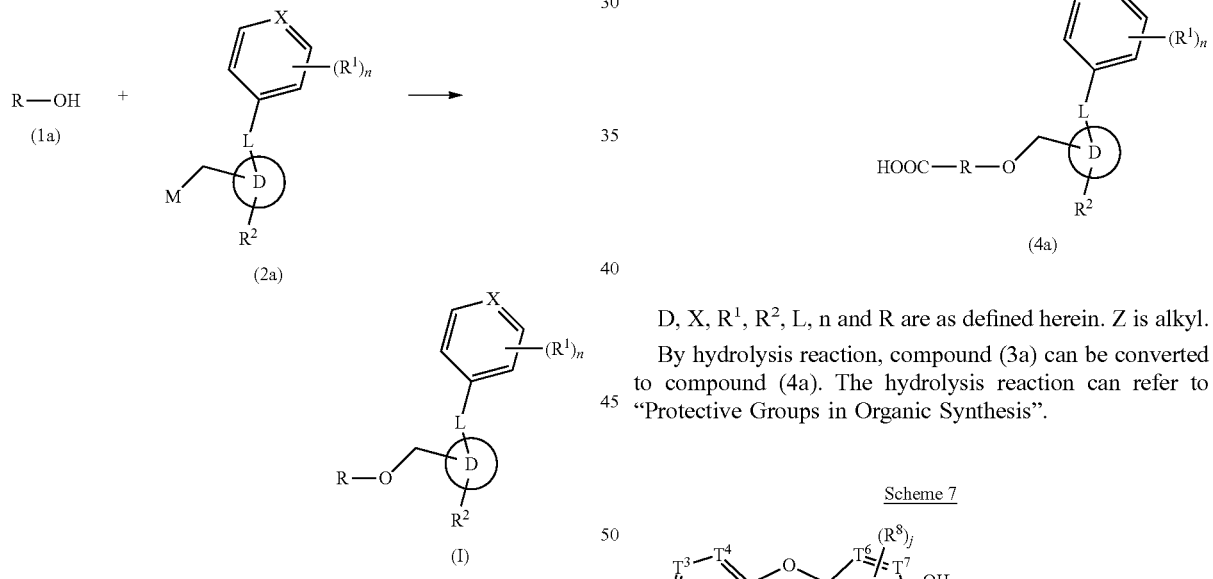

Scheme 5

(1a)

(2a)

(I)

D, X, $R^1$, $R^2$, L, n and R are as defined herein; M is hydroxy or a leaving group.

The synthesis of compound (2a) can refer to Patent WO2011020615 (page 22-111) or Bioorg Med Chem Lett. 2015 Jan. 15; 25 (2): 280-4.

When M is hydroxy, the Mitsunobu reaction of compound (1a) with compound (2a) can afford compound of formula (I). In the Mitsunobu reaction, the reaction raw materials can be reacted in the presence of a azodicarbonyl compound (e.g., diisopropyl azodicarboxylate, 1,1'-(azodicarbonyl) dipiperidine, etc.) and a phosphine (e.g., triphenylphosphine, tributylphosphine) in a solvent. Preferably, the reaction can be carried out in an inert solvent. The solvents include, but are not limited to, toluene, and the like.

(4a)

D, X, $R^1$, $R^2$, L, n and R are as defined herein. Z is alkyl.

By hydrolysis reaction, compound (3a) can be converted to compound (4a). The hydrolysis reaction can refer to "Protective Groups in Organic Synthesis".

Scheme 7

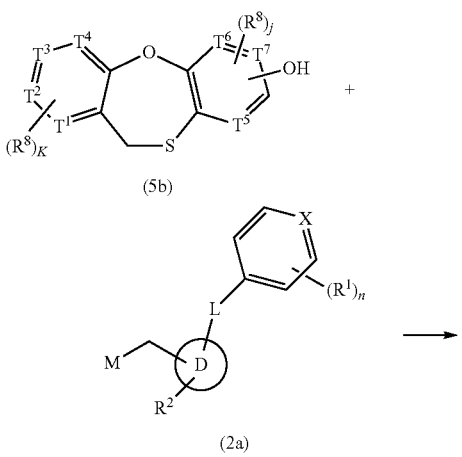

(5b)

(2a)

-continued

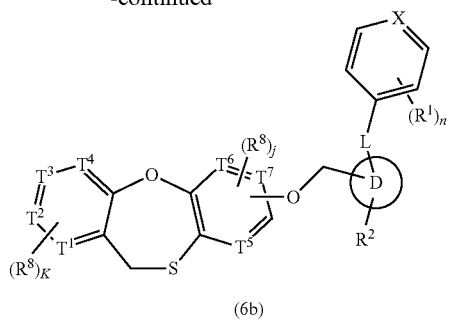

(6b)

Each of K and j is independently 0, 1, 2, 3 or 4; M is hydroxy or a leaving group; D, X, $R^1$, $R^2$, $R^8$, L, n, $T^1$, $T^2$, $T^3$, $T^4$, $T^5$, $T^6$ and $T^7$ are as defined herein.

When M is hydroxy, the Mitsunobu reaction of compound (5b) with compound (2a) can afford compound (6b). In the Mitsunobu reaction, the reaction raw materials can be reacted in the presence of an azodicarbonyl compound (e.g., diisopropyl azodicarboxylate, 1,1'-(azodicarbonyl)dipiperidine) and a phosphine (e.g., triphenylphosphine, tributylphosphine) in a solvent. Preferably, the reaction can be carried out in an inert solvent. The solvents include, but are not limited to, toluene, and the like.

When M is a leaving group, the substitution reaction of compound (5b) with compound (2a) can afford compound (6b) in the presence of a base. Leaving groups represented by M include, but are not limited to, halogen, methanesulfonyloxy, p-methyl phenylsulfonyloxy, and the like. Some non-limiting examples of the base include potassium carbonate, and the like. The reaction can be carried out in an inert solvent. The solvents include, but are not limited to, N,N-dimethylformamide, and the like.

Scheme 8

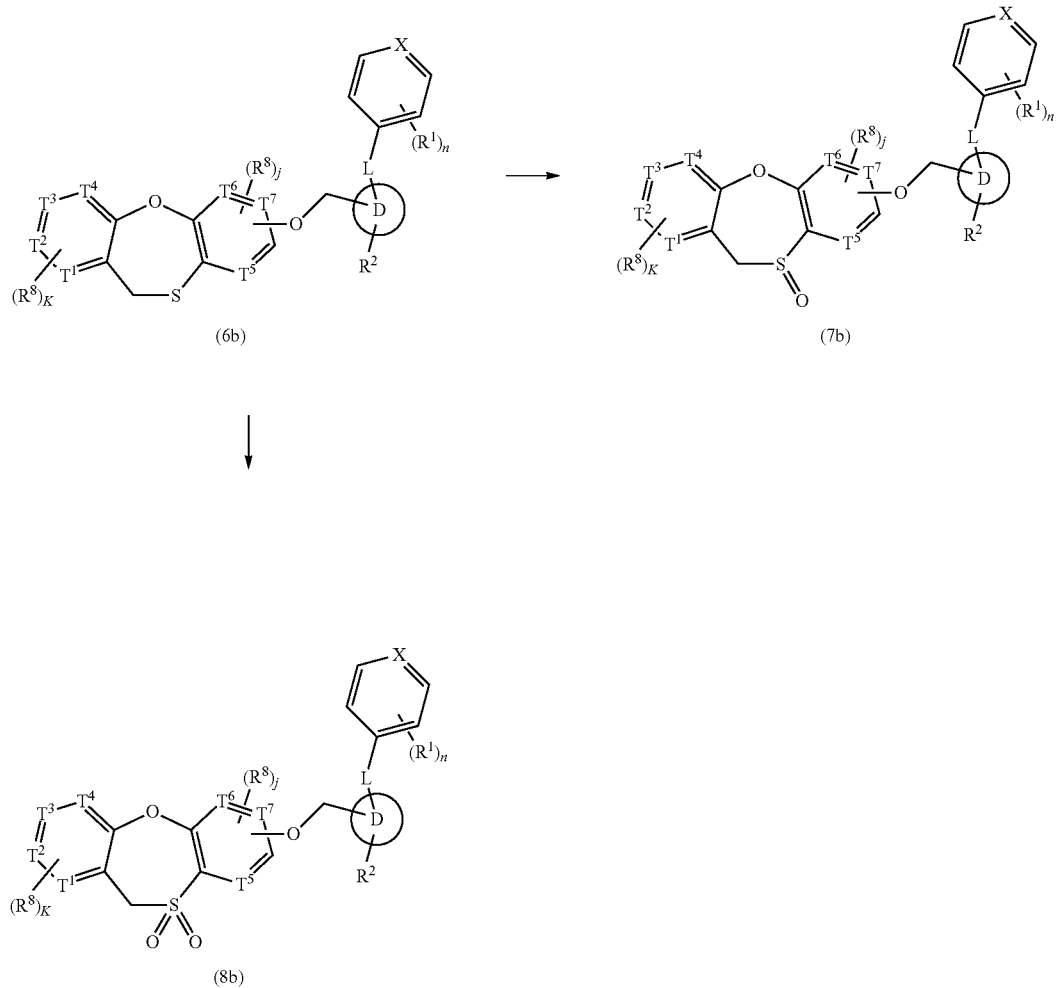

Each of K and j is independently 0, 1, 2, 3 or 4; D, X, $R^1$, $R^2$, $R^8$, L, n, $T^1$, $T^2$, $T^3$, $T^4$, $T^5$, $T^6$ and $T^7$ are as defined herein.

Compound (6b) can be oxidized to give compound (7b) in the presence of an oxidant. The oxidants include, but are not limited to, m-chloroperbenzoic acid, and the like. The reaction can be carried out in an inert solvent. The solvents include, but are not limited to, dichloromethane, and the like.

Compound (6b) can be oxidized to give compound (8b) in the presence of an oxidant. The oxidants include, but are not limited to, m-chloroperbenzoic acid, and the like. The reaction is carried out in an inert solvent. The solvents include, but are not limited to, dichloromethane, and the like.

Scheme 9

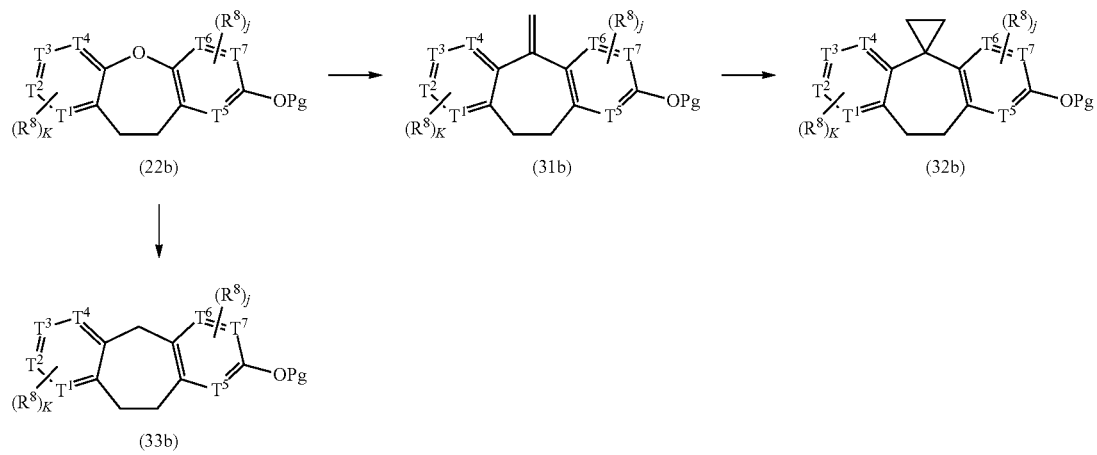

(22b)  (31b)  (32b)

(33b)

Each of K and j is independently 0, 1, 2, 3 or 4; Pg is a protecting group; $R^8$, $T^1$, $T^2$, $T^3$, $T^4$, $T^5$, $T^6$ and $T^7$ are as defined herein.

By the addition-elimination reaction, compound (22b) can be converted to compound (31b). The reaction materials can be reacted in the presence of a methyl Grignard reagent (which may be, but is not limited to, bromide, magnesium, etc.) in the solvent. The reaction can be preferred to carry out in an inert solvent. The solvents include, but are not limited to, tetrahydrofuran, and the like.

By the cycloaddition reaction, compound (31b) can be converted to compound (32b). The reaction materials can be reacted in the presence of diethyl zinc, methylene iodide and acid (acids include, but are not limited to, trifluoroacetic acid, etc.) in the solvent. The reaction can be preferred to carry out in an inert solvent. The solvents include, but are not limited to, dichloromethane, and the like.

Compound (22b) can be reduced to afford compound (33b). The reaction materials can be reacted in the presence of a reducing agent (which may be, but is not limited to, triethylsilane, etc.) in the solvent. The solvents include, but are not limited to, trifluoroacetic acid, and the like.

Scheme 10

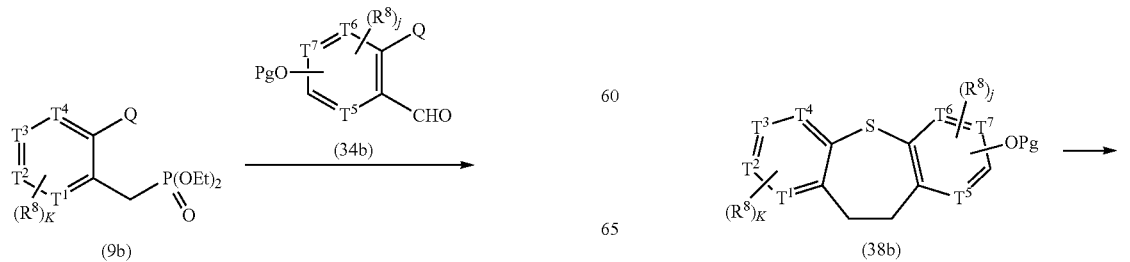

(9b)  (34b)

-continued

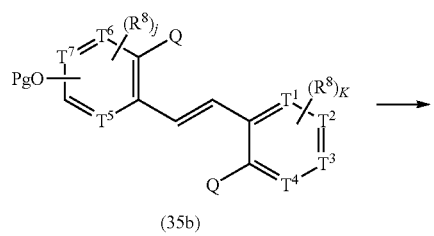

(35b)

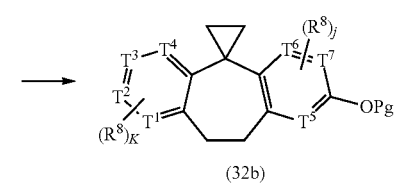

(36b)

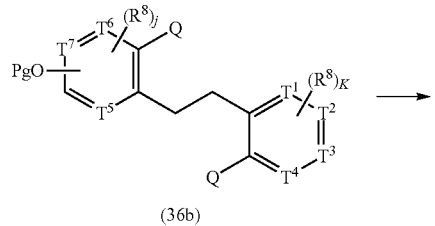

(37b)

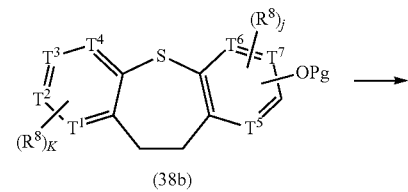

(38b)

-continued

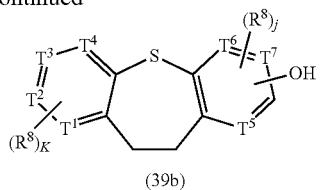

(39b)

each Q is independently halogen; each of K and j is independently 0, 1, 2, 3 or 4; Pg is a protecting group; $R^8$, $T^1$, $T^2$, $T^3$, $T^4$, $T^5$, $T^6$ and $T^7$ are as defined herein.

Horner-Wadsworth-Emmons reaction of compound (9b) with compound (34b) can afford compound (35b). In Horner-Wadsworth-Emmons reaction, the reaction materials can be reacted in the presence of a base (base may be, but is not limited to, sodium hydride, potassium t-butoxide, etc.) in a solvent. The reaction can be preferred to carry out in an inert solvent. The solvents include, but are not limited to, tetrahydrofuran, and the like.

Compound (35b) can be reduced to afford compound (36b) in the presence of a reducing agent under an alkaline condition. The reducing agents include, but are not limited to, p-methyl benzenesulfonohydrazide, and the like. The bases include, but are not limited to, sodium acetate, and the like. The reaction can be carried out in an inert solvent. The solvents include, but are not limited to, tetrahydrofuran, water or a mixed solvent, and the like.

By coupling reaction in the presence of a catalyst under an alkaline condition, compound (36b) can be converted to the linking sulfur intermediate. The linking sulfur intermediate can be reduced to afford compound (37b). The catalysts include, but are not limited to cuprous iodide, and the like. The bases include, but are not limited to potassium carbonate, and the like. The reducing agents include, but are not limited to, sodium borohydride, and the like. The reaction can be carried out in an inert solvent for the reaction. The solvents include, but are not limited to, N,N-dimethylformamide, and the like.

By coupling reaction in the presence of a catalyst and a ligand under an alkaline condition, compound (37b) can be converted to compound (38b). The catalysts include, but are not limited to cuprous iodide, and the like. The ligands include, but are not limited to N,N-dimethylglycine, and the like. The bases include, but are not limited to potassium carbonate, and the like. The reaction can be carried out in an inert solvent for the reaction. The solvents include, but are not limited to N,N-dimethylformamide, and the like.

Compound (38b) can be converted to compound (39b) by removing hydroxy protecting groups, and the removal of hydroxy protecting groups can refer to "Protective Groups in Organic Synthesis".

Scheme 11

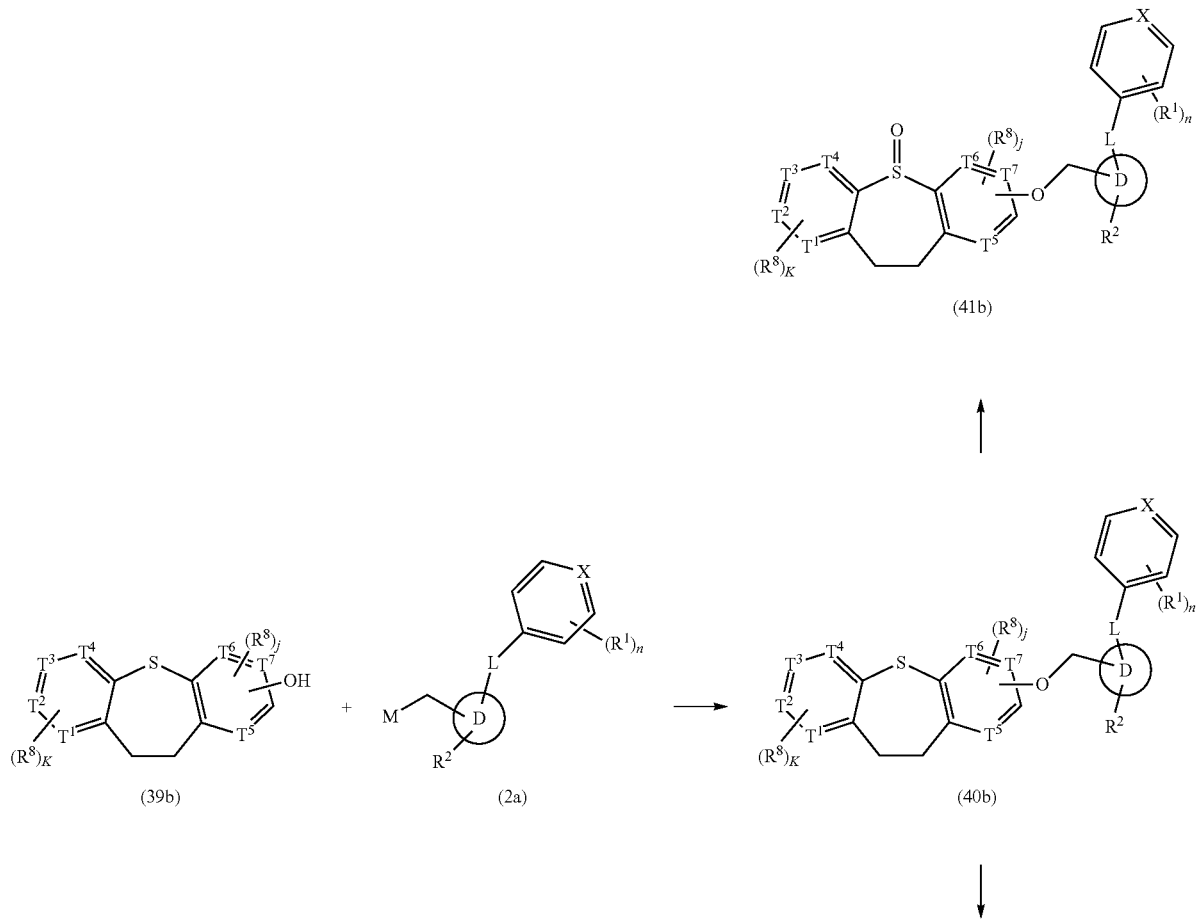

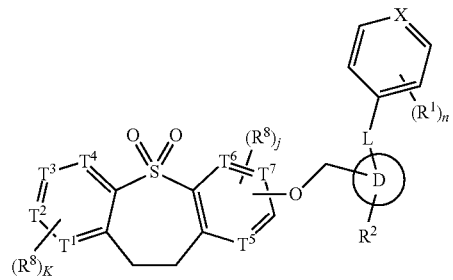

(42b)

Each of K and j is independently 0, 1, 2, 3 or 4; M is hydroxy or a leaving group; D, X, $R^1$, $R^2$, $R^8$, L, n, $T^1$, $T^2$, $T^3$, $T^4$, $T^5$, $T^6$ and $T^7$ are as defined herein.

When M is hydroxy, the Mitsunobu reaction of compound (39b) with compound (2a) can afford compound (40b). In the Mitsunobu reaction, the reaction starting materials can be reacted in the presence of an azodicarbonyl compound (e.g., diisopropyl azodicarboxylate, 1,1'-(azodicarbonyl)dipiperidine) and a phosphine (e.g., triphenylphosphine, tributylphosphine) in a solvent. The reaction is carried out in an inert solvent. The solvents include, but are not limited to, toluene, and the like.

When M is a leaving group, the substitution reaction of compound (39b) with compound (2a) can afford compound (40b) in the presence of a base. Leaving groups represented by M include, but are not limited to, halogen, methanesulfonyloxy, p-methyl phenylsulfonyloxy, and the like. Some non-limiting examples of the base include potassium carbonate, and the like. The reaction can be carried out in an inert solvent. The solvents include, but are not limited to, N,N-dimethylformamide, and the like.

Compound (40b) can be oxidized to give compound (41b) in the presence of an oxidant. The oxidants include, but are not limited to, m-chloroperbenzoic acid, and the like. The reaction can be carried out in an inert solvent. The solvents include, but are not limited to, dichloromethane, and the like.

Compound (40b) can be oxidized to give compound (42b) in the presence of an oxidant. The oxidants include, but are not limited to, m-chloroperbenzoic acid, and the like. The reaction can be carried out in an inert solvent. The solvents include, but are not limited to, dichloromethane, and the like.

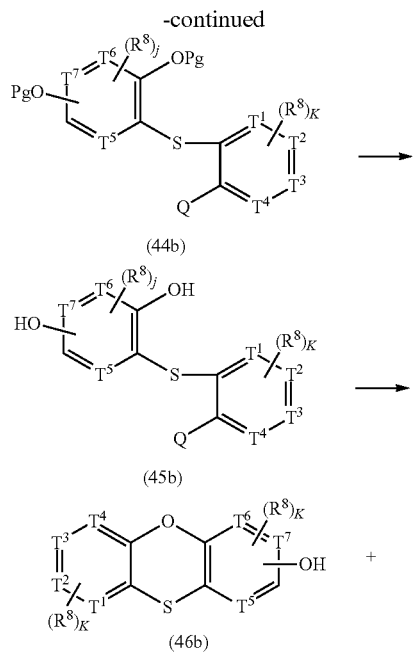

(44b)

(45b)

(46b)

(2a)

Scheme 12

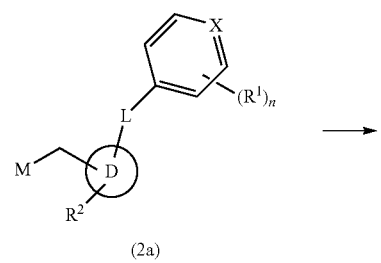

(43b)      (2b)

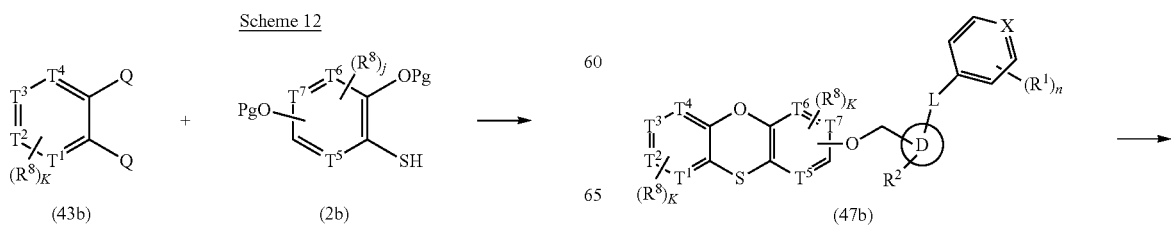

(47b)

-continued

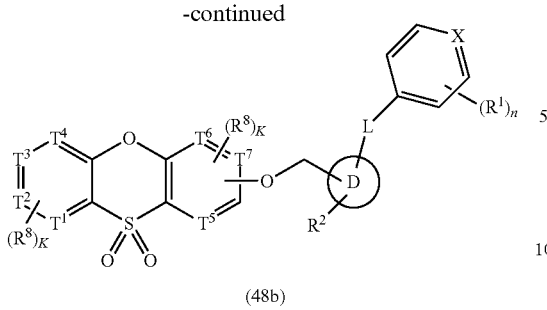

(48b)

Each of K and j is independently 0, 1, 2, 3 or 4; each Q is independently halogen; M is hydroxy or a leaving group; Pg is a protecting group; $R^8$, $R^1$, $R^2$, n, L, D, X, $T^1$, $T^2$, $T^3$, $T^4$, $T^5$, $T^6$ and $T^7$ are as defined herein.

The coupling reaction of compound (43b) with compound (2b) can afford compound (44b) in the presence of a catalyst and a ligand under an alkaline condition. The catalysts include, but are not limited to cuprous iodide, and the like. The ligands include, but are not limited to L-proline, and the like. The bases include, but are not limited to potassium carbonate, and the like. The reaction can be carried out in an inert solvent for the reaction. The solvents include, but are not limited to, ethylene glycol dimethyl ether, and the like.

Compound (44b) can be converted to compound (45b) by removing hydroxy protecting groups, and the removal of hydroxy protecting groups can refer to "Protective Groups in Organic Synthesis".

By coupling reaction in the presence of a catalyst and a ligand under an alkaline condition, compound (45b) can be converted to compound (46b). The catalysts include, but are not limited to, cuprous iodide, and the like. The ligands include, but are not limited to, N,N-dimethylglycine, and the like. The bases include, but are not limited to, cesium carbonate, and the like. The reaction can be carried out in an inert solvent. The solvents include, but are not limited to, 1,4-dioxane, and the like.

When M is hydroxy, the Mitsunobu reaction of compound (46b) with compound (2a) can afford compound (47b). In the Mitsunobu reaction, the reaction starting materials can be reacted in the presence of an azodicarbonyl compound (e.g., diisopropyl azodicarboxylate, 1,1'-(azodicarbonyl) dipiperidine) and a phosphine (e.g., triphenylphosphine, tributylphosphine) in a solvent. The reaction can be preferred to carry out in an inert solvent. The solvents include, but are not limited to, toluene, and the like.

When M is a leaving group, the substitution reaction of compound (46b) with compound (2a) can afford compound (47b) in the presence of a base. Leaving groups represented by M include, but are not limited to, halogen, methanesulfonyloxy, p-methyl phenylsulfonyloxy, and the like. Some non-limiting examples of the base include potassium carbonate, and the like. The reaction can be carried out in an inert solvent. The solvents include, but are not limited to, N,N-dimethylformamide, and the like.

Compound (47b) can be oxidized to give compound (48b) in the presence of an oxidant. The oxidants include, but are not limited to, m-chloroperbenzoic acid, and the like. The reaction can be carried out in an inert solvent. The solvents include, but are not limited to, dichloromethane, and the like.

Scheme 13

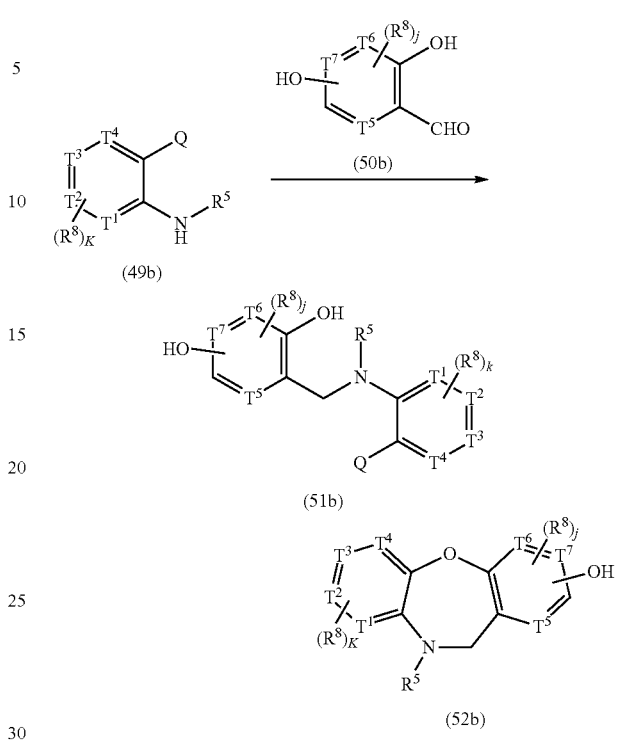

Q is halogen; each of K and j is independently 0, 1, 2, 3 or 4; Pg is a protecting group; $R^5$, $R^8$, $T^1$, $T^2$, $T^3$, $T^4$, $T^5$, $T^6$ and $T^7$ are as defined herein.

The reductive amination of compound (49b) with compound (50b) can afford compound (51b) in the presence of a reducing agent under an acidic or neutral condition. The reducing agents include, but are not limited to, sodium borohydride, and the like. The acids include, but are not limited to, acetic acid, and the like. The solvent include, but are not limited to methanol, and the like.

By coupling reaction in the presence of a catalyst and a ligand under an alkaline condition, compound (51b) can be converted to compound (52b). The catalysts include, but are not limited to, cuprous iodide, and the like. The ligands include, but are not limited to, N,N-dimethylglycine, and the like. The bases include, but are not limited to, cesium carbonate, and the like. The reaction can be carried out in an inert solvent. The solvents include, but are not limited to, 1,4-dioxane, and the like.

Scheme 14

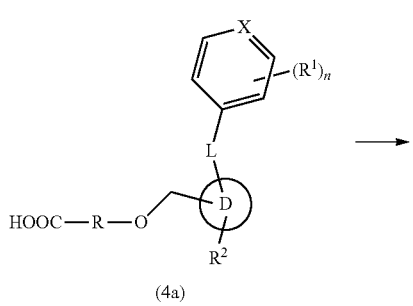

(4a)

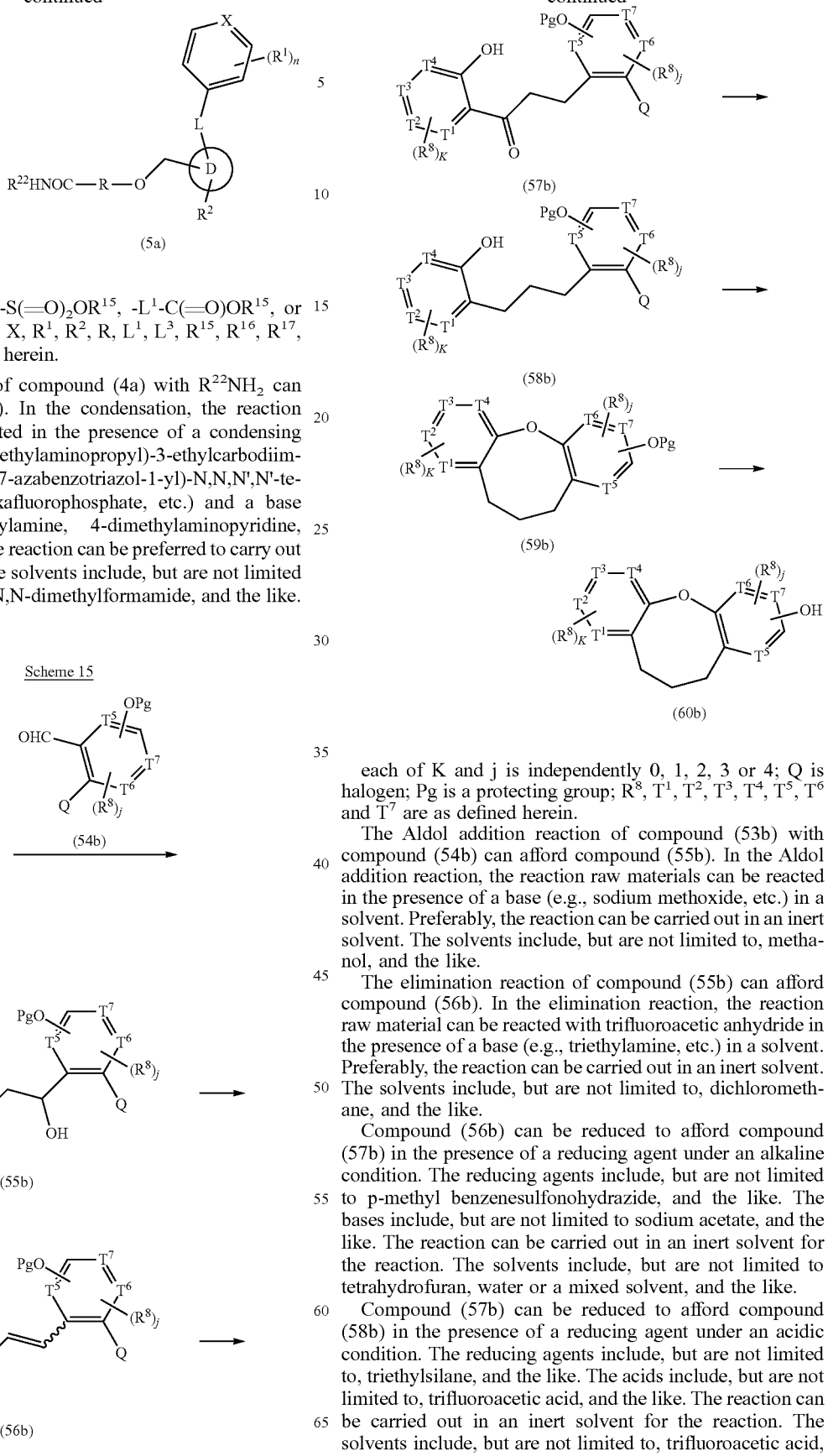

$R^{22}$ is H, $R^{17}$, $-L^3-S(=O)_2OR^{15}$, $-L^1-C(=O)OR^{15}$, or $-L^1-S(=O)_tR^{16}$; D, L, X, $R^1$, $R^2$, R, $L^1$, $L^3$, $R^{15}$, $R^{16}$, $R^{17}$, n and t are as defined herein.

The condensation of compound (4a) with $R^{22}NH_2$ can afford compound (5a). In the condensation, the reaction materials can be reacted in the presence of a condensing agent (e.g., 1-(3-dimethylaminopropyl)-3-ethylcarbodiimide hydrochloride, 2-(7-azabenzotriazol-1-yl)-N,N,N',N'-tetramethyluronium hexafluorophosphate, etc.) and a base (e.g., diisopropylethylamine, 4-dimethylaminopyridine, etc.) in the solvent. The reaction can be preferred to carry out in an inert solvent. The solvents include, but are not limited to, dichloromethane, N,N-dimethylformamide, and the like.

Scheme 15 each of K and j is independently 0, 1, 2, 3 or 4; Q is halogen; Pg is a protecting group; $R^8$, $T^1$, $T^2$, $T^3$, $T^4$, $T^5$, $T^6$ and $T^7$ are as defined herein.

The Aldol addition reaction of compound (53b) with compound (54b) can afford compound (55b). In the Aldol addition reaction, the reaction raw materials can be reacted in the presence of a base (e.g., sodium methoxide, etc.) in a solvent. Preferably, the reaction can be carried out in an inert solvent. The solvents include, but are not limited to, methanol, and the like.

The elimination reaction of compound (55b) can afford compound (56b). In the elimination reaction, the reaction raw material can be reacted with trifluoroacetic anhydride in the presence of a base (e.g., triethylamine, etc.) in a solvent. Preferably, the reaction can be carried out in an inert solvent. The solvents include, but are not limited to, dichloromethane, and the like.

Compound (56b) can be reduced to afford compound (57b) in the presence of a reducing agent under an alkaline condition. The reducing agents include, but are not limited to p-methyl benzenesulfonohydrazide, and the like. The bases include, but are not limited to sodium acetate, and the like. The reaction can be carried out in an inert solvent for the reaction. The solvents include, but are not limited to tetrahydrofuran, water or a mixed solvent, and the like.

Compound (57b) can be reduced to afford compound (58b) in the presence of a reducing agent under an acidic condition. The reducing agents include, but are not limited to, triethylsilane, and the like. The acids include, but are not limited to, trifluoroacetic acid, and the like. The reaction can be carried out in an inert solvent for the reaction. The solvents include, but are not limited to, trifluoroacetic acid, and the like.

By coupling reaction in the presence of a catalyst and a ligand under an alkaline condition, compound (58b) can be converted to compound (59b). The catalysts include, but are not limited to, cuprous iodide, and the like. The ligands include, but are not limited to, N,N-dimethylglycine, and the like. The bases include, but are not limited to, cesium carbonate, and the like. The reaction can be carried out in an inert solvent. The solvents include, but are not limited to, 1,4-dioxane, and the like.

Compound (59b) can be converted to compound (60b) by removing hydroxy protecting groups, and the removal of hydroxy protecting groups can refer to "Protective Groups in Organic Synthesis".

include, but are not limited to, N,N-dimethylglycine, and the like. The bases include, but are not limited to, cesium carbonate, and the like. The reaction can be carried out in an inert solvent. The solvents include, but are not limited to, 1,4-dioxane, and the like.

Compound (62b) can be converted to compound (63b) by removing hydroxy protecting groups, and the removal of hydroxy protecting groups can refer to "Protective Groups in Organic Synthesis".

The cyclization reaction of compound (62b) with a methylating agent can afford compound (64b). The methylating agents include, but are not limited to, trimethyl iodide sulfoxide, and the like. The reaction can be carried out in an Scheme 16

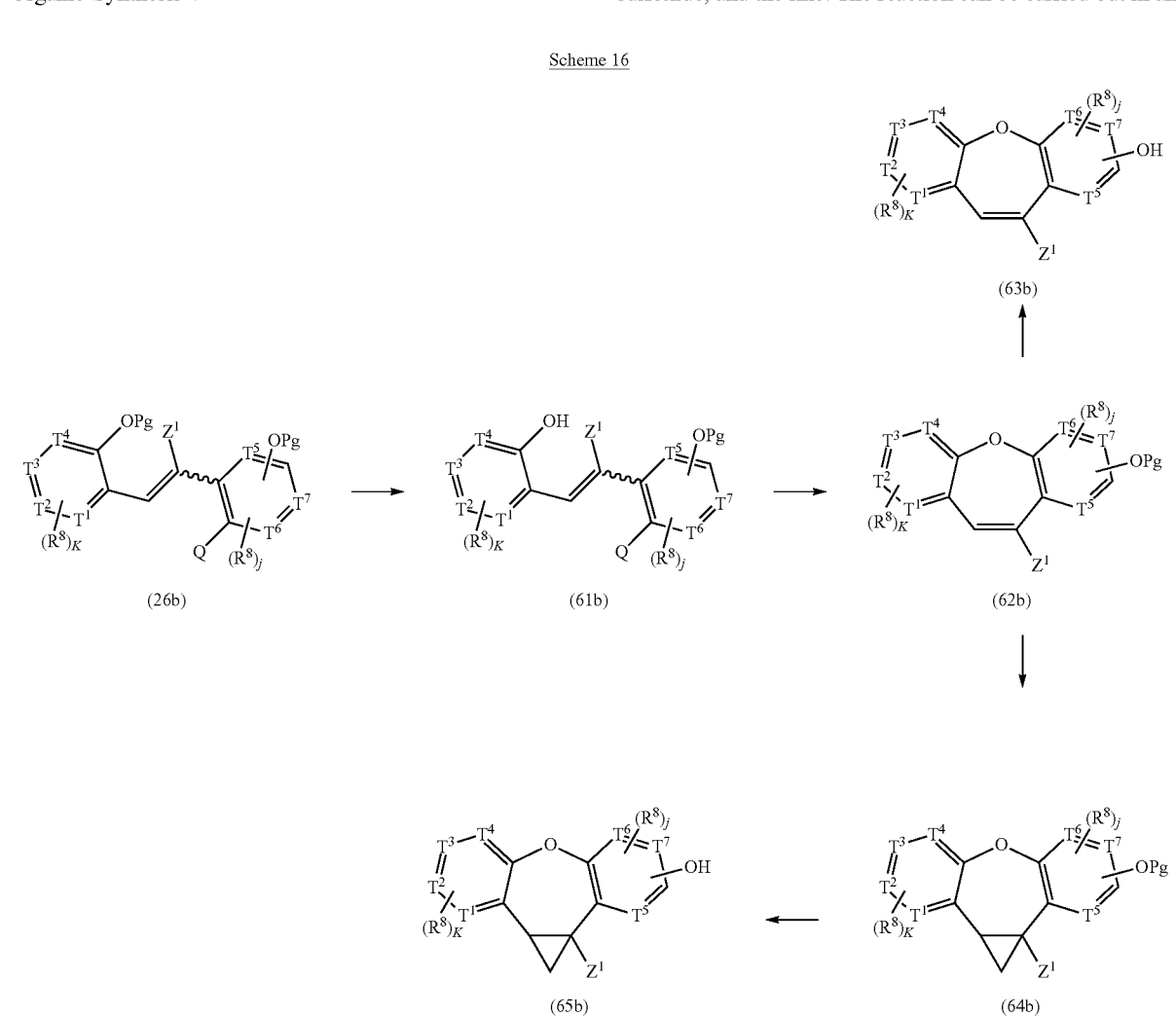

each of K and j is independently 0, 1, 2, 3 or 4; Q is halogen; $Z^1$ is H or alkyl; Pg is a protecting group; $R^8$, $T^1$, $T^2$, $T^3$, $T^4$, $T^5$, $T^6$ and $T^7$ are as defined herein.

Compound (26b) can be converted to compound (61b) by removing hydroxy protecting groups, and the removal of hydroxy protecting groups can refer to "Protective Groups in Organic Synthesis".

By coupling reaction in the presence of a catalyst and a ligand under an alkaline condition, compound (61b) can be converted to compound (62b). The catalysts include, but are not limited to, cuprous iodide, and the like. The ligands inert solvent. The solvents include, but are not limited to, dimethyl sulfoxide, and the like.

Compound (64b) can be converted to compound (65b) by removing hydroxy protecting groups, and the removal of hydroxy protecting groups can refer to "Protective Groups in Organic Synthesis".

The following examples disclosed herein are presented to further describe the invention. However, these examples should not be used to limit the scope of the invention.

DESCRIPTION OF THE PREFERRED EMBODIMENTS

Example

Example 1: 8-((5-cyclopropyl-3-(2,6-dichlorophenyl)isoxazol-4-yl)methoxy)-10,11-dihydrodibenzo[b,f]oxepine-3-carboxylic acid

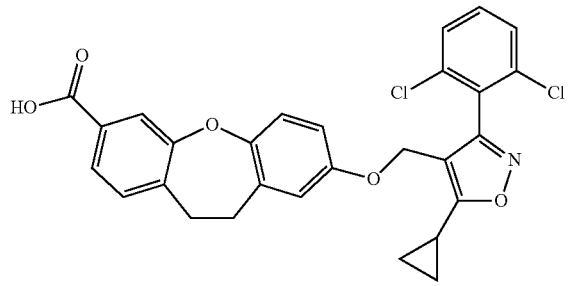 [SMILES: O=C(O)c1ccc2c(c1)Oc1ccc(OCc3c(-c4c(Cl)cccc4Cl)noc3C3CC3)cc1CC2]

Step 1: methyl 3-bromo-4-(bromomethyl)benzoate

To a mixture of methyl 3-bromo-4-methylbenzoate (4.0 g, 17.5 mmol) in carbon tetrachloride (100 mL) were added N-bromosuccinimide (3.7 g, 21.0 mmol) and benzoyl peroxide (420 mg, 1.7 mmol). The mixture was stirred at 70° C. overnight under nitrogen. The reaction mixture was then cooled to room temperature, quenched with 20 mL of saturated aqueous sodium bicarbonate solution, and extracted with dichloromethane (100 mL×2). The combined organic layers were washed with 20 mL of saturated brine, dried over anhydrous sodium sulfate, filtered and concentrated under vacuum. The residue was purified by silica gel column chromatography eluted with (petroleum ether/ethyl acetate (v/v)=30/1), to give the title compound as a yellow oil (4.61 g, 82%).

$^1$H NMR (400 MHz, CDCl$_3$) δ8.25 (d, J=1.4 Hz, 1H), 7.96 (dd, J=8.0, 1.5 Hz, 1H), 7.54 (d, J=8.0 Hz, 1H), 4.61 (s, 2H), 3.94 (s, 3H).

Step 2: methyl 3-bromo-4-((diethoxyphosphoryl)methyl)benzoate

A solution of methyl 3-bromo-4-(bromomethyl)benzoate (4.4 g, 14 mmol) in triethyl phosphite (20 mL) was heated at 150° C. and stirred overnight. The reaction mixture was then cooled to room temperature. The triethyl phosphite was removed by distillation under vacuum to give the title compound as a yellow oil (5.2 g, 100%).

Step 3: methyl 4-(2,5-bis((tert-butyldimethylsilyl)oxy)styryl)-3-bromobenzoate To a mixture of methyl 3-bromo-4-((diethoxyphosphoryl)methyl)benzoate (5.3 g, 15.0 mmol) in tetrahydrofuran (100 mL) was added 60% sodium hydride (700 mg, 27.5 mmol) under an ice bath. After the addition, the reaction solution was stirred for 20 min. A solution of 2,5-bis[[tert-butyl(dimethyl)silyl]oxy]benzaldehyde (5.5 g, 15 mmol) in tetrahydrofuran (10 mL) was then added. The reaction mixture was stirred under an ice bath for 4 h. The reaction mixture was then quenched with 50 mL of saturated ammonium chloride aqueous solution, and extracted with ethyl acetate (200 mL×2). The combined organic layers were washed with 20 mL of saturated brine, dried over anhydrous sodium sulfate, filtered and concentrated under vacuum. The residue was purified by silica gel column chromatography eluted with (petroleum ether/ethyl acetate (v/v)=40/1), to give the title compound as a yellow oil (6.0 g, 69%).

Step 4: methyl 4-(2,5-bis((tert-butyldimethylsilyl)oxy)phenethyl)-3-bromobenzoate Methyl 4-(2,5-bis((tert-butyldimethylsilyl)oxy)styryl)-3-bromobenzoate (6.0 g, 10.4 mmol), sodium acetate (5.1 g, 62.3 mmol) and p-toluenesulfonyl hydrazide (11.6 g, 62.3 mmol) were dissolved in a mixed solvent of tetrahydrofuran (100 mL) and water (50 mL). The reaction mixture was heated to reflux and stirred for 24 h, then cooled to room temperature, diluted with water (50 mL), and extracted with dichloromethane (150 mL×2). The combined organic layers were washed with saturated brine (20 mL), dried over anhydrous sodium sulfate, filtered, and concentrated under vacuum. The residue was purified by column chromatography on silica gel eluted with (petroleum ether/ethyl acetate (v/v)=30/1) to give the title compound as a pale yellow oil (5.0 g, 83%).

$^1$H NMR (600 MHz, CDCl$_3$) δ8.24 (d, J=1.5 Hz, 1H), 7.86 (dd, J=7.9, 1.6 Hz, 1H), 7.18 (d, J=8.0 Hz, 1H), 6.68 (d, J=8.6 Hz, 1H), 6.58 (dd, J=8.6, 3.0 Hz, 1H), 6.54 (d, J=2.9 Hz, 1H), 3.93 (s, 3H), 3.11-3.04 (m, 2H), 2.93-2.85 (m, 2H), 1.04 (s, 9H), 0.97 (s, 9H), 0.25 (s, 6H), 0.13 (s, 6H).

Step 5: methyl 3-bromo-4-(2,5-dihydroxyphenethyl)benzoate

To a solution of 4-(2,5-bis(tert-butyldimethylsilyl)oxy)phenethyl)-3-methyl-bromobenzene (5 g, 8.7 mmol) in tetrahydrofuran (100 mL) was added dropwise a solution of tetrabutylammonium fluoride in tetrahydrofuran (34.6 mL, 34.6 mmoL, 1 M). The reaction mixture was stirred at room temperature for 2 h, followed by dilution with water (50 mL). The resulting mixture was extracted with ethyl acetate (50 mL×2). The combined organic layers were washed with 20 mL of saturated brine, dried over anhydrous sodium sulfate, filtered, and concentrated under vacuum. The residue was purified by column chromatography on silica gel eluted with (petroleum ether/ethyl acetate (v/v)=3/1) to give the title compound as a pale yellow oil (1.7 g, 56%).

$^1$H NMR (600 MHz, DMSO-d$_6$) δ8.64 (s, 1H), 8.54 (s, 1H), 8.08 (d, J=1.5 Hz, 1H), 7.86 (dd, J=7.9, 1.4 Hz, 1H), 7.42 (d, J=7.9 Hz, 1H), 6.60 (d, J=8.5 Hz, 1H), 6.46 (d, J=2.8 Hz, 1H), 6.43 (dd, J=8.5, 2.8 Hz, 1H), 3.86 (s, 3H), 2.98 (dd, J=9.2, 6.7 Hz, 2H), 2.74 (dd, J=9.2, 6.7 Hz, 2H).

Step 6: methyl 8-hydroxy-10,11-dihydrodibenzo[b,f]oxepine-3-carboxylate

Methyl 3-bromo-4-(2,5-dihydroxyphenethyl)benzoate (100 mg, 0.3 mmol), cuprous iodide (6 mg, 0.03 mmol), N,N-dimethylglycine (9 mg, 0.09 mmol) and cesium carbonate (185 mg, 0.6 mmol) were dissolved in anhydrous 1,4-dioxane (3 mL) under nitrogen. The mixture was heated to 90° C. and stirred overnight. After being cooled to room temperature, the mixture was filtered, and the filtrate was concentrated under vacuum. The residue was purified by column chromatography on silica gel eluted with (petroleum ether/ethyl acetate (v/v)=2/1) to give the title compound as a yellow oil (50 mg, 60%).

¹H NMR (400 MHz, CDCl₃) δ7.84 (d, J=1.5 Hz, 1H), 7.70 (dd, J=7.9, 1.6 Hz, 1H), 7.19 (d, J=7.9 Hz, 1H), 7.11-7.02 (m, 1H), 6.68-6.63 (m, 2H), 3.94 (s, 3H), 3.15-3.11 (m, 4H).

Step 7: methyl 8-((5-cyclopropyl-3-(2,6-dichlorophenyl)isoxazol-4-yl)methoxy)-10,11-dihydrodibenzo[b,f]oxepine-3-carboxylate Methyl 8-hydroxy-10,11-dihydrodibenzo[b,f]oxepine-3-carboxylate (300 mg, 1.0 mmol), 4-(chloromethyl)-5-cyclopropyl-3-(2,6-dichlorophenyl)isoxazole (370 mg, 1.2 mmol) (See the synthesis of compound A6e of WO2011020615) and potassium phosphate (353 mg, 1.7 mmol) were dissolved in DMF (10 mL). The reaction mixture was warmed to 60° C. and stirred for 3 h. The reaction mixture was then cooled to room temperature, diluted with water (40 mL) and extracted with ethyl acetate (80 mL×2). The combined organic layers were washed with 20 mL of saturated brine, dried over anhydrous sodium sulfate, filtered and concentrated under vacuum. The residue was purified by column chromatography on silica gel eluted with (petroleum ether/ethyl acetate (v/v)=5/1) to give the title compound as a pale yellow oil (540 mg, 90%).

Step 8: 8-((5-cyclopropyl-3-(2,6-dichlorophenyl)isoxazol-4-yl)methoxy)-10,11-dihydrodibenzo[b,f]oxepine-3-carboxylic acid To a mixture of methyl 8-((5-cyclopropyl-3-(2,6-dichlorophenyl)isoxazol-4-yl)methoxy)-10,11-dihydrodibenzo[b,f]oxepine-3-carboxylate (540 mg, 1.0 mmol) in a mixed solvent of tetrahydrofuran (5 mL) and water (5 mL) was added lithium hydroxide (120 mg, 5.0 mmol), and the mixture was stirred at room temperature overnight. Most of the solvent was removed under vacuum. The residue was diluted with water (20 mL), and then adjusted to acidity with 1 M hydrochloric acid (8 mL). The resulting mixture was extracted with ethyl acetate (30 mL×2). The combined organic layers were washed with 10 mL of saturated brine, dried over anhydrous sodium sulfate, filtered. The filtrate was concentrated under vacuum to give the title compound as a white solid (340 mg, 65%).

MS (ESI, pos. ion) m/z: 522.2 [M+H]⁺; and

¹H NMR (400 MHz, CDCl₃) δ7.87 (d, J=1.4 Hz, 1H), 7.76 (dd, J=7.9, 1.5 Hz, 1H), 7.41-7.39 (m, 2H), 7.33-7.29 (m, 1H), 7.22 (d, J=7.9 Hz, 1H), 7.07 (d, J=8.7 Hz, 1H), 6.63-6.58 (m, 2H), 4.77 (s, 2H), 3.20-3.16 (m, 2H), 3.13-3.04 (m, 2H), 2.15-2.10 (m, 1H), 1.31-1.27 (m, 2H), 1.17-1.10 (m, 2H).

Example 2: 8-((5-cyclopropyl-3-(2,6-dichlorophenyl)isoxazol-4-yl)methoxy)-5-oxo-10,11-dihydro-5H-dibenzo[a,d][7]annulene-3-carboxylic acid

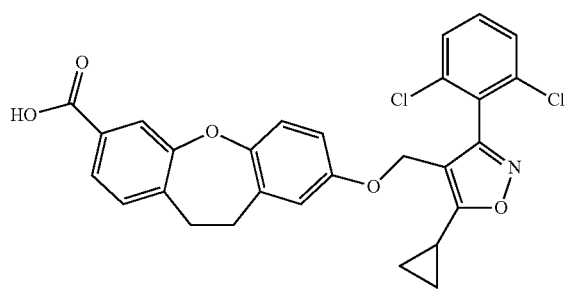 [SMILES: O=C(O)c1ccc2c(c1)Oc1ccc(OCc3c(-c4c(Cl)cccc4Cl)noc3C3CC3)cc1CC2]

Step 1: dimethyl 4-(bromomethyl)isophthalate

To a mixture of dimethyl 4-methylisophthalate (7.6 g, 37 mmol) in carbon tetrachloride (100 mL) were added N-bromosuccinimide (7.2 g, 40.2 mmol) and benzoyl peroxide (400 mg, 1.7 mmol) under nitrogen. The reaction solution was heated to 80° C. and stirred overnight. After being cooled to room temperature, the reaction solution was quenched with 80 mL of saturated aqueous sodium bicarbonate solution, and extracted with dichloromethane (100 mL×2). The combined organic layers were washed with 20 mL of saturated brine, dried over anhydrous sodium sulfate, filtered. The residue was purified by column chromatography on silica gel eluted with (petroleum ether/ethyl acetate (v/v)=20/1) to give the title compound as a yellow solid (3.0 g, 29%).

Step 2: dimethyl 4-((diethoxyphosphoryl)methyl)isophthalate

A solution of dimethyl 4-(bromomethyl)isophthalate (7.0 g, 24.4 mmol) in triethyl phosphite (15 mL) was stirred at 120° C. overnight. The reaction solution was cooled to room temperature. The triethyl phosphite was removed by distillation under vacuum. The resulting residue was purified by column chromatography on silica gel eluted with (CH₂Cl₂/MeOH (v/v)=10/1) to give the title compound as a yellow oil (8.0 g, 95%).

Step 3: dimethyl 4-(3-methoxystyryl)isophthalate

To a mixture of dimethyl 4-((diethoxyphosphoryl)methyl)isophthalate (5.0 g, 14.5 mmol) in tetrahydrofuran (80 mL) was added 60% sodium hydride (600 mg, 25 mmol) under an ice bath. The reaction solution was stirred under an ice bath for 30 min, and a solution of 3-methoxybenzaldehyde (2.0 g, 14.7 mmol) in tetrahydrofuran (10 mL) was added dropwise. The resulting mixture was stirred at room temperature for 30 min. The reaction mixture was then quenched with 50 mL of saturated aqueous ammonium chloride solution, and extracted with ethyl acetate (100 mL×2). The combined organic layers were washed sequentially with 20 mL of saturated brine, dried over anhydrous sodium sulfate, filtered and concentrated under vacuum. The residue was purified by column chromatography on silica gel eluted with (petroleum ether/ethyl acetate (v/v)=40/1) to give the title compound as a yellow oil (1.5 g, 31%).

Step 4: dimethyl 4-(3-methoxyphenethyl)isophthalate

To a mixture of dimethyl dimethyl 4-(3-methoxystyryl)isophthalate (1.5 g, 4.6 mmol) in THF (60 mL) was added 10% Pd/C (200 mg). The mixture was stirred at room temperature overnight under hydrogen. The mixture was filtered. The filtrate was concentrated under vacuum to give the title compound as a yellow oil (1.4 g, 93%).

Step 5: 4-(3-methoxyphenethyl)isophthalic acid

To a solution of dimethyl 4-(3-methoxyphenethyl)isophthalate (1.4 g, 4.3 mmol) in a mixed solvent of tetrahydrofuran (50 mL) and water (50 mL) was added sodium hydroxide (1.7 g, 43 mmol). The reaction mixture was stirred at room temperature overnight. Most of the solvent was removed under vacuum. The resulting residue was diluted with water (10 mL), adjusted to acidity with 2 M hydrochloric acid (40 mL). The resulting mixture was extracted with ethyl acetate (100 mL×2). The combined organic layers were washed with 20 mL of saturated brine, dried over anhydrous sodium sulfate and filtered. The filtrate was concentrated under vacuum to give the title compound as a white solid (1.0 g, 80%).

MS (ESI, neg. ion) m/z: 299.0 [M−H]$^-$.

Step 6: 8-methoxy-5-oxo-10,11-dihydro-5H-dibenzo[a,d][7]annulene 3-carboxylic acid To a mixture of 4-(3-methoxyphenethyl)isophthalic acid (1.0 g, 3.3 mmol) in dichloromethane (80 mL) was added oxalyl chloride (0.84 mL, 9.9 mmol), and the mixture was stirred at room temperature for 1 h. The oxalyl chloride was then removed under vacuum. The resulting residue was dissolved in dichloromethane (100 mL), and aluminum chloride (1.3 g, 9.7 mmol) was added. The resulting mixture was stirred at room temperature overnight. The reaction solution was diluted with water (30 mL), and extracted with dichloromethane (100 mL×2). The combined organic layers were washed with 20 mL of saturated brine, dried over anhydrous sodium sulfate, filtered, and concentrated under vacuum. The residue was purified by column chromatography on silica gel eluted with (petroleum ether/ethyl acetate (v/v)=5/1) to give the title compound as a yellow solid (800 mg, 90%).

Step 7: 8-hydroxy-5-oxo-10,11-dihydro-5H-dibenzo[a,d][7]annulene-3-carboxylic acid 8-Methoxy-5-oxo-10,11-dihydro-5H-dibenzo[a,d][7]annulene-3-carboxylic acid (140 mg, 0.47 mmol) was dissolved in anhydrous dichloromethane (20 mL). The mixture was cooled to −60° C. and a solution of 1 M boron tribromide in methylene chloride (7.5 mL, 7.5 mmol) was added dropwise. The reaction solution was stirred at −60° C. for 0.5 h, then warmed to room temperature and continued to stir for two days. The reaction mixture was quenched with 20 mL of water and extracted with ethyl acetate (40 mL×2). The combined organic layers were washed with 20 mL of saturated brine, dried over anhydrous sodium sulfate, filtered and concentrated under vacuum. The residue was purified by column chromatography on silica gel eluted with (petroleum ether/ethyl acetate (v/v)=3/1) to give the title compound as a yellow solid (110 mg, 87%).

MS (ESI, pos. ion) m/z: 269.1 [M+H]$^+$.

Step 8: methyl 8-hydroxy-5-oxo-10,11-dihydro-5H-dibenzo[a,d][7]annulene-3-carboxylate To a solution of 8-hydroxy-5-oxo-10,11-dihydro-5H-dibenzo[a,d][7]annulene-3-carboxylic acid (110 mg, 0.41 mmol) in methanol (10 mL) was added thionyl chloride (0.05 mL, 7 mmol) under an ice bath. The reaction solution was heated to 80° C. and stirred overnight. The reaction mixture was then cooled to room tempreture and concentrated under vacuum. The residue was purified by column chromatography on silica gel eluted with (petroleum ether/ethyl acetate (v/v)=4/1) to give the title compound as a yellow oil (110 mg, 95%).

Step 9: methyl 8-((5-cyclopropyl-3-(2,6-dichlorophenyl)methoxy)-5-oxo-10,11-dihydro-5H-dibenzo[a,d][7]annulene-3-carboxylate Methyl 8-hydroxy-5-oxo-10,11-dihydro-5H-dibenzo[a,d][7]annulene-3-carboxylate (120 mg, 0.43 mmol), 4-(chloromethyl)-5-cyclopropyl-3-(2,6-dichlorophenyl)isoxazole (150 mg, 0.50 mmol) and potassium phosphate (180 mg, 0.85 mmol) were dissolved in DMF (10 mL). The reaction mixture was stirred at 60° C. for 30 min, then cooled to room temperature and diluted with water (30 mL). The resulting mixture was extracted with ethyl acetate (80 mL×2). The combined organic layers were washed with 20 mL of saturated brine, dried over anhydrous sodium sulfate, filtered and concentrated under vacuum. The residue was purified by column chromatography on silica gel eluted with (petroleum ether/ethyl acetate (v/v)=3/1) to give the title compound as a yellow oil (120 mg, 51%).

MS (ESI, pos. ion) m/z: 547.7 [M+H]$^+$.

Step 10: 8-((5-cyclopropyl-3-(2,6-dichlorophenyl)isoxazol-4-yl)methoxy)-5-oxo-10,11-dihydro-5H-dibenzo[a,d][7]annulene-3-carboxylic acid Methyl 8-((5-cyclopropyl-3-(2,6-dichlorophenyl)isoxazole-4-yl)methoxy)-5-oxo-10,11-dihydro-5H-dibenzo[a,d][7]annulene-3-carboxylate (100 mg, 0.2 mmol) was dissolved in a mixed solvent of tetrahydrofuran (5 mL) and water (5 mL), and lithium hydroxide (55 mg, 2.3 mmol) was added. The reaction mixture was stirred at room temperature overnight. Most of the solvent was removed under vacuum. The residue was diluted with water (20 mL), and adjusted to acidity with 1 M hydrochloric acid (5 mL). The resulting mixture was extracted with ethyl acetate (30 mL×2). The combined organic layers were washed with 10 mL of saturated brine, dried over anhydrous sodium sulfate, filtered, and concentrated under vacuum. The residue was purified by column chromatography on silica gel eluted with (petroleum ether/ethyl acetate (v/v)=3/1) to give the title compound as a white solid (14 mg, 10%).

MS (ESI, pos. ion) m/z: 534.1 [M+H]$^+$; and
$^1$H NMR (400 MHz, DMSO-d$_6$) δ 8.43 (d, J=1.7 Hz, 1H), 8.02 (dd, J=7.9, 1.8 Hz, 1H), 7.94 (d, J=8.5 Hz, 1H), 7.63-7.61 (m, 2H), 7.56-7.52 (m, 1H), 7.47 (d, J=8.0 Hz, 1H), 6.85-6.79 (m, 2H), 4.98 (s, 2H), 3.21-3.14 (m, 2H), 3.14-3.06 (m, 2H), 2.49-2.45 (m, 1H), 1.20-1.14 (m, 4H).

Example 3: 2-((5-cyclopropyl-3-(2,6-dichlorophenyl)isoxazol-4-yl)methoxy)-10,11-dihydrobenzo[6,7]oxepino[3,2-b]pyridine-7-carboxylic acid

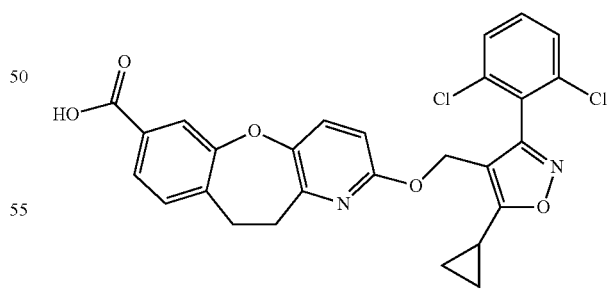

Step 1: methyl 3-acetoxy-4-methylbenzoate

To a mixture of methyl 3-hydroxy-4-methylbenzoate (4.3 g, 26 mmol) and pyridine (3.5 mL, 43 mmol) in dichloromethane (50 mL) was added acetic anhydride (4.0 mL, 43 mmol) under an ice bath, and the mixture was stirred at room temperature for 5 h. The mixture was quenched with 50 mL of water. The resulting mixture was extracted with dichloromethane (50 mL×2). The combined organic layers were washed with 1 M hydrochloric acid, dried over anhydrous sodium sulfate, filtered and concentrated under vacuum. The residue was purified by column chromatography on silica gel eluted with (petroleum ether/ethyl acetate (v/v)=10/1) to give the title compound as a colorless oil (5.3 g, 98%).

Step 2: methyl 3-acetoxy-4-(bromomethyl)benzoate

To a mixture of methyl 3-acetoxy-4-methylbenzoate (5.3 g, 25.5 mmol) and N-bromosuccinimide (4.6 g, 25.7 mmol) in carbon tetrachloride (100 mL) was added azobisisobutyronitrile (210 mg, 1.3 mmol). The mixture was heated to reflux and stirred for 5 h. The mixture was concentrated under vacuum. The residue was purified by column chromatography on silica gel eluted with (petroleum ether/ethyl acetate (v/v)=20/1) to give the title compound as a colorless oil (5.7 g, 77%).

Step 3: methyl 3-acetoxy-4-((diethoxyphosphoryl)methyl)benzoate

A solution of methyl 3-acetoxy-4-(bromomethyl)benzoate (5.6 g, 20 mmol) in triethyl phosphite (10 mL) was heated at 150° C. and stirred overnight. The mixture was cooled to room temperature. The triethyl phosphite was removed by distillation under vacuum. The residue was purified by column chromatography on silica gel eluted with ($CH_2Cl_2$/MeOH (v/v)=10/1) to give the title compound as a colorless oil (6.7 g, 100%).

Step 4: methyl 4-((diethoxyphosphoryl)methyl)-3-hydroxybenzoate

To a mixture of methyl 3-acetoxy-4-((diethoxyphosphoryl)methyl)benzoate (6.5 g, 19 mmol) in methanol (100 mL) was added potassium carbonate aqueous solution (30 mL, 30 mmol, 1.0 M). The resulting mixture was allowed to stir at room temperature for 1 h. Most of the methanol was removed by concentration under vacuum. The residue was diluted with water (20 mL), and extracted with ethyl acetate (50 mL×2). The combined organic layers were washed with 10 mL of saturated brine, dried over anhydrous sodium sulfate, filtered, and concentrated under vacuum. The residue was purified by column chromatography on silica gel eluted with (petroleum ether/ethyl acetate (v/v)=2/1) to give the title compound as a white solid (5.2 g, 91%).

MS (ESI, pos. ion) m/z: 303.2 [M+H]$^+$.

Step 5: methyl 4-((diethoxyphosphoryl)methyl)-3-(methoxymethoxy)benzoate

Methyl 4-((diethoxyphosphoryl)methyl)-3-hydroxybenzoate (5.2 g, 17 mmol) and diisopropylethyl amine (6.0 mL, 34 mmol) were dissolved in dichloromethane (60 mL), and chloromethyl methyl ether (2.3 mL, 30 mmol) was added dropwise under an ice bath. The resulting mixture was stirred at room temperature overnight, quenched with 50 mL of water and extracted with dichloromethane (50 mL×2). The combined organic layers were washed with 10 mL of saturated brine, dried over anhydrous sodium sulfate, filtered, and concentrated under vacuum. The residue was purified by column chromatography on silica gel eluted with (petroleum ether/ethyl acetate (v/v)=4/1) to give the title compound as a colorless oil (3.8 g, 64%).

MS (ESI, pos. ion) m/z: 347.2 [M+H]$^+$.

Step 6: methyl 4-(2-(3-bromo-6-methoxypyridin-2-yl)vinyl)-3-(methoxymethoxy) benzoate To a mixture of methyl 4-(diethoxyphosphorylmethyl)-3-(methoxymethoxy)benzoate (1.8 g, 5.2 mmol) in tetrahydrofuran (30 mL) was added 60% sodium hydride (270 mg, 6.8 mmol) under an ice bath. The miaxture was stirred under an ice bath for 30 min, and 3-bromo-6-methoxypyridine-2-carbaldehyde (1.0 g, 4.6 mmol) was then added (See the synthetic method described in Organic and Biomolecular Chemistry, 2003, (1) 16, 2865-2876). The resulting mixture was warmed to room and continued to stir for 4 h. The reaction mixture was then quenched with 10 mL of saturated aqueous atm onium chloride. The resulting mixture was extracted with ethyl acetate (20 mL×2). The combined organic layers were washed with 20 mL of saturated brine, dried over anhydrous sodium sulfate, filtered, and concentrated under vacuum. The residue was purified by column chromatography on silica gel eluted with (petroleum ether/ethyl acetate (v/v)=5/1) to give the title compound as a yellow solid (980 mg, 51%).

Step 7: methyl 4-(2-(3-bromo-6-methoxypyridin-2-yl)ethyl)-3-(methoxymethoxy) benzoate Methyl 4-(2-(3-bromo-6-methoxypyridin-2-yl)vinyl)-3-(methoxymethoxy)benzoate (850 mg, 2.1 mmol), sodium acetate (1.1 g, 12.8 mmol) and p-toluenesulfonyl hydrazide (2.4 g, 12.6 mmol) were dissolved in a mixed solvent of tetrahydrofuran (30 mL) and water (15 mL). The reaction mixture was heated to reflux and stirred for 24 h. The reaction mixture was then cooled to room temperature, diluted with water (10 mL) and extracted with ethyl acetate (100 mL×2). The combined organic layers were washed with 20 mL of saturated brine, dried over anhydrous sodium sulfate, filtered, and concentrated under vacuum. The residue was purified by column chromatography on silica gel eluted with (petroleum ether/ethyl acetate (v/v)=5/1) to give the title compound as a pale yellow oil (850 mg, 99%).

Step 8: methyl 4-(2-(3-bromo-6-methoxypyridin-2-yl)ethyl)-3-hydroxybenzoate

To a mixture of methyl 4-(2-(3-bromo-6-methoxypyridin-2-yl)ethyl)-3-(methoxymethoxy) benzoate (850 mg, 2.1 mmol) in tetrahydrofuran (5 mL) was added 6 M hydrochloric acid (4 mL, 24 mmol), and the mixture was heated to 50° C. and stirred for 5 h. The mixture was then cooled to room temperature and diluted with water (20 mL). The resulting mixture was adjusted to basicity with solid potassium carbonate, and extracted with ethyl acetate (30 mL×2). The combined organic layers were washed with 10 mL of saturated brine, dried over anhydrous sodium sulfate, filtered, and concentrated under vacuum. The residue was purified by column chromatography on silica gel eluted with (petroleum ether/ethyl acetate (v/v)=3/1) to give the title compound as a white solid (740 mg, 98%).

Step 9: methyl 2-methoxy-10,11-dihydrobenzo[6,7]oxepino[3,2-b]pyridine-7-carboxylate Cuprous iodide (160 mg, 0.84 mmol), N,N-dimethylglycine (90 mg, 0.87 mmol), cesium carbonate (1.42 g, 4.04 mmol) and 4-(2-(3-bromo-6-methoxypyridin-2-yl)ethyl)-3-hydroxybenzoate (740 mg, 2.1 mmol) were dissolved in 1,4-dioxane (10 mL) under nitrogen. The reaction solution was heated to reflux and stirred overnight. The reaction mixture was cooled to room tempreture, filtered and concentrated under vacuum. The residue was purified by column chromatography on silica gel eluted with ($CH_2Cl_2$/ MeOH (v/v)=50/1) to give the product as a white solid (470 mg, 82%).

$^1$H NMR (400 MHz, $CDCl_3$) δ7.82 (d, J=1.5 Hz, 1H), 7.77 (dd, J=7.8, 1.6 Hz, 1H), 7.44 (d, J=8.7 Hz, 1H), 7.30 (s, 1H), 6.56 (d, J=8.7 Hz, 1H), 3.93 (s, 3H), 3.88 (s, 3H), 3.28-3.16 (m, 4H).

Step 10: methyl 2-oxo-1,2,10,11-tetrahydrobenzo[6,7]oxepino[3,2-b]pyridine-7-carboxylate Methyl 2-methoxy-10,11-dihydrobenzo[6,7]-oxepino[3,2-]pyridine-7-carboxylate (470 mg, 1.6 mmol) and sodium iodide (780 mg, 5.2 mmol) were dissolved in acetonitrile (5 mL) and trimethylsilyl chloride (0.43 mL, 5.0 mmol) was added at room tempreture. The reaction mixture was heated to 85° C. and stirred for 3 h. The reaction mixture was cooled to room tempreture, quenched with 50 mL of saturated sodium thiosulfate solution, and extracted with ethyl acetate (50 mL×2). The combined organic layers were washed with 30 mL of saturated brine, dried over anhydrous sodium sulfate, filtered, and concentrated under vacuum. The residue was purified by column chromatography on silica gel eluted with ($CH_2Cl_2$/MeOH (v/v)=50/1) to give the title compound as a white solid (400 mg, 90%).

$^1$H NMR (400 MHz, DMSO-$d_6$) δ10.47 (s, 1H), 7.01-6.84 (m, 2H), 6.69 (dd, J=19.8, 8.7 Hz, 2H), 5.41 (d, J=9.6 Hz, 1H), 3.06 (s, 3H), 2.40-2.35 (m, 2H), 2.19-2.03 (m, 2H).

Step 11: methyl 2-((5-cyclopropyl-3-(2,6-dichlorophenyl)isoxazol-4-yl)methoxy)-10,11-dihydrobenzo[6,7]oxepino[3,2-b]pyridine-7-carboxylate Methyl 2-oxo-1,2,10,11-tetrahydrobenzo[6,7]oxepino[3,2-b]pyridine-7-carboxylate (400 mg, 1.5 mmol), 4-(chloromethyl)-5-cyclopropyl-3-(2,6-dichlorophenyl)isoxazole (490 mg, 1.6 mmol) and potassium phosphate (1.0 g, 5 mmol) were dissolved in DMF (10 mL). The reaction mixture was stirred at 60° C. for 30 min. The reaction mixture was then cooled to room tempreture, diluted with water (30 mL), and extracted with ethyl acetate (40 mL×2). The combined organic layers were washed with 20 mL of saturated brine, dried over anhydrous sodium sulfate, filtered, and concentrated under vacuum. The residue was purified by column chromatography on silica gel eluted with (petroleum ether/ethyl acetate (v/v)=5/1) to give the title compound as a white solid (490 mg, 62%).

Step 12: 2-((5-cyclopropyl-3-(2,6-dichlorophenyl)isoxazol-4-yl)methoxy)-10,11-dihydrobenzo[6,7]oxepino[3,2-b]pyridine-7-carboxylic acid To a solution of methyl 2-((5-cyclopropyl-3-(2,6-dichlorophenyl)isoxazol-4-yl)methoxy)-10,11-dihydrobenzo[6,7]oxepino[3,2-b]pyridine-7-carboxylate (490 mg, 0.92 mmol) in a mixed solvent of tetrahydrofuran (5 mL) and water (5 mL) was added lithium hydroxide (360 mg, 9 mmol). The reaction solution was heated to 80° C. and stirred overnight. The reaction solution was then cooled to room temperature. Most of the solvent was removed under vacuum. The residue was diluted with water (10 mL), and adjusted to acidity with 2 M hydrochloric acid (8 mL). The resulting mixture was extracted with ethyl acetate (30 mL×2). The combined organic layers were washed with 10 mL of saturated brine, dried over anhydrous sodium sulfate, filtered, and concentrated under vacuum. The residue was purified by column chromatography on silica gel eluted with (petroleum ether/ ethyl acetate (v/v)=1/1) to give the title compound as a white solid (370 mg, 78%).

MS (ESI, pos. ion) m/z: 522.7 [M+H]$^+$; and $^1$H NMR (400 MHz, $CDCl_3$) δ7.93-7.77 (m, 2H), 7.37-7.33 (m, 4H), 7.26-7.22 (m, 1H), 6.42 (d, J=8.7 Hz, 1H), 5.13 (s, 2H), 3.24-3.21 (m, 2H), 3.13-3.10 (m, 2H), 2.36-2.29 (m, 1H), 1.30-1.24 (m, 2H), 1.16-1.12 (m, 2H).

Example 4: 3-((5-cyclopropyl-3-(2,6-dichlorophenyl)isoxazol-4-yl)methoxy)-5,6-dihydrobenzo[6,7]oxepino[2,3-c]pyridine-9-carboxylic acid

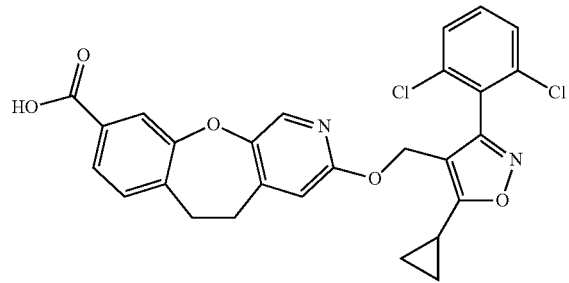

Step 1: 2-methoxy-5-(methoxymethoxy)pyridine

To a mixture of 2-methoxy-5-hydroxypyridine (3.3 g, 26.0 mmol) in DMF (60 mL) was added 60% sodium hydride (2.2 g, 55 mmol) under an ice bath. The reaction mixture was stirred under an ice bath for 1 h. Chloromethyl methyl ether (3.0 mL, 39 mmol) was then added. The resulting mixture was warmed to room temperature and stirred for additional 3 h. The mixture was quenched with 50 mL of water. The resulting mixture was extracted with dichloromethane (50 mL×2). The combined organic layers were washed with 20 mL of saturated brine, dried over anhydrous sodium sulfate, filtered and concentrated under vacuum. The residue was purified by column chromatography on silica gel eluted with (petroleum ether/ethyl acetate (v/v)=10/1) to give the compound as a colorless oil (2.0 g, 46%).

$^1$H NMR (400 MHz, $CDCl_3$) δ7.97 (d, J=2.9 Hz, 1H), 7.35 (dd, J=8.9, 3.0 Hz, 1H), 6.70 (d, J=8.9 Hz, 1H), 5.12 (s, 2H), 3.91 (s, 3H), 3.51 (s, 3H).

Step 2: 2-methoxy-5-(methoxymethoxy)pyridine-4-carboxaldehyde

2-Methoxy-5-(methoxymethoxy)pyridine (2.0 g, 12 mmol) and diisopropylamine (0.03 mL, 0.3 mmol) were dissolved in tetrahydrofuran (40 mL). The reaction mixture was cooled to −40° C., and a solution of methyllithium in diethyl ether (13.3 mL, 21 mmol, 1.6 M) was added. The reaction mixture was then warmed to 0° C. and stirred for 3 h. The mixture was allowed to cool to −40° C. again and DMF (1.7 mL, 22 mmol) was added. The reaction mixture continued to stir at −40° C. for 1 h. The reaction mixture was then quenched with cincentrated hydrochloric acid (8 mL) and tetrahydrofuran (19 mL), followed by dilution with water (20 mL). The resulting mixture was adjusted to basicity with solid potassium carbonate, and extracted with ethyl acetate (100 mL×2). The combined organic layers were washed with 20 mL of saturated brine, dried over anhydrous sodium sulfate, filtered and concentrated under vacuum. The residue was purified by column chromatography on silica gel eluted with (petroleum ether/ethyl acetate (v/v)=10/1) to give the compound as a yellow solid (1.4 g, 60%).

$^1$H NMR (400 MHz, CDCl$_3$) δ10.45 (s, 1H), 8.26 (s, 1H), 7.10 (s, 1H), 5.27 (s, 2H), 3.94 (s, 3H), 3.56 (s, 3H).

Step 3: methyl 3-bromo-4-(2-(2-methoxy-5-(methoxymethoxy)pyridin-4-yl)vinyl) benzoate To a mixture of methyl 3-bromo-4-(diethoxyphosphorylmethyl)benzoate (3.9 g, 11 mmol) in tetrahydrofuran (20 mL) was added 60% sodium hydride (450 mg, 11 mmol) under an ice bath. The reaction solution was stirred under an ice bath for 20 min, and a solution of 2-methoxy-5-(methoxymethoxy)pyridine-4-carbaldehyde (1.4 g, 7.1 mmol) in tetrahydrofuran (5 mL) was added dropwise. The resulting mixture was warmed to room temperature and continued to stir for 3 h. The mixture was quenched with 50 mL of water and extracted with ethyl acetate (50 mL×2). The combined organic layers were washed with 20 mL of saturated brine, dried over anhydrous sodium sulfate, filtered and concentrated under vacuum. The residue was purified by column chromatography on silica gel eluted with (petroleum ether/ethyl acetate (v/v)=5/1) to give the title compound as a yellow solid (1.4 g, 48%).

$^1$H NMR (400 MHz, CDCl$_3$) δ8.29 (d, J=1.5 Hz, 1H), 8.07 (s, 1H), 8.00 (d, J=8.2 Hz, 1H), 7.78 (d, J=8.2 Hz, 1H), 7.68 (d, J=16.4 Hz, 1H), 7.35 (d, J=16.4 Hz, 1H), 6.99 (s, 1H), 5.22 (s, 2H), 3.96 (s, 3H), 3.95 (s, 3H), 3.55 (s, 3H).

Step 4: methyl 3-bromo-4-(2-(2-methoxy-5-(methoxymethoxy)pyridin-4-yl)ethyl) benzoate Methyl 3-bromo-4-(2-(2-methoxy-5-(methoxymethoxy)pyridin-4-yl)vinyl)benzoate (1.4 g, 3.4 mmol), sodium acetate (1.7 g, 21 mmol) and p-toluenesulfonyl hydrazide (3.8 g, 20 mmol) were dissolved in a mixed solvent of tetrahydrofuran (20 mL) and water (10 mL). The reaction mixture was heated to reflux and stirred for 24 h. The reaction mixture was then cooled to room tempreture, diluted with water (50 ml) and extracted with ethyl acetate (50 mL×2). The combined organic layers were washed with 10 mL of saturated brine, dried over anhydrous sodium sulfate, filtered and concentrated under vacuum. The residue was purified by column chromatography on silica gel eluted with (petroleum ether/ethyl acetate (v/v)=5/1) to give the title compound as pale yellow oil (1.0 g, 72%).

$^1$H NMR (600 MHz, CDCl$_3$) δ8.24 (s, 1H), 7.96 (s, 1H), 7.89 (d, J=7.9 Hz, 1H), 7.23 (d, J =7.9 Hz, 1H), 6.55 (s, 1H), 5.13 (s, 2H), 3.93 (s, 3H), 3.89 (s, 3H), 3.51 (s, 3H), 3.13-3.03 (m, 2H), 2.96-2.90 (m, 2H).

Step 5: methyl 3-bromo-4-(2-(5-hydroxy-2-methoxypyridin-4-yl)ethyl)benzoate

To a mixture of methyl 3-bromo-4-(2-(2-methoxy-5-(methoxymethoxy)pyridin-4-yl)ethyl) benzoate (1.0 g, 2.4 mmol) in tetrahydrofuran (5 mL) was added hydrochloric acid (4 mL, 12 mmol, 3 M), and the reaction mixture was heated to 50° C. and stirred for 1 h. The mixture was then cooled to room temperature, and diluted with water (10 mL). The resulting mixture was adjusted to neutral with solid potassium carbonate, and extracted with ethyl acetate (50 mL×2). The combined organic layers were washed with 10 mL of saturated brine, dried over anhydrous sodium sulfate, filtered and concentrated under vacuum. The residue was purified by column chromatography on silica gel eluted with (petroleum ether/ethyl acetate (v/v)=3/1) to give product as a yellow solid (680 mg, 76%).

Step 6: methyl 3-methoxy-5,6-dihydrobenzo[6,7]oxepino[2,3-c]pyridine-9-carboxylate Cuprous iodide (140 mg, 0.74 mmol), N,N-dimethylglycine (380 mg, 3.68 mmol), cesium carbonate (1.30 g, 3.68 mmol) and methyl 3-bromo-4-(2-(5-hydroxy-2-methoxypyridin-4-yl) ethyl)benzoate (670 mg, 1.83 mmol) were dissolved in 1,4-dioxane (10 mL) under nitrogen. The reaction solution was heated to reflux and stirred overnight. The reaction mixture was then cooled to room tempreture and filtered. The filtrate was concentrated under vacuum. The residue was purified by column chromatography on silica gel eluted with (petroleum ether/ethyl acetate (v/v)=5/1) to give product as a colorless oil (500 mg, 96%).

$^1$H NMR (400 MHz, CDCl$_3$) δ8.08 (d, J=3.1 Hz, 1H), 7.86 (d, J=1.6 Hz, 1H), 7.74 (dd, J =7.9, 1.7 Hz, 1H), 7.22 (d, J=7.9 Hz, 1H), 6.53 (s, 1H), 3.93 (s, 3H), 3.90 (s, 3H), 3.23-3.15 (m, 2H), 3.15-3.06 (m, 2H).

Step 7: methyl 3-oxo-2,3,5,6-tetrahydrobenzo[6,7]oxepino[2,3-c]pyridine-9-carboxylate To a mixture of methyl 3-methoxy-5,6-dihydrobenzo[6,7]oxepino[2,3-c]pyridine-9-carboxylate (490 mg, 1.7 mmol) and sodium iodide (1.4 g, 9.3 mmol) in acetonitrile (8 mL) were added trimethylsilyl chloride (1.1 mL, 13 mmol). The mixture was heated to 85° C. and stirred for 5 h. The mixture was then allowed to cool to room temperature, quenched with 50 mL of saturated aqueous sodium thiosulfate, and extracted with ethyl acetate (40 mL×2). The combined organic layers were washed with 10 mL of saturated brine, dried over anhydrous sodium sulfate, filtered and and concentrated under vacuum. The residue was purified by column chromatography on silica gel eluted with (CH$_2$Cl$_2$/MeOH (v/v)=50/1) to give the product as a brown oil (330 mg, 75%).

Step 8: methyl 3-((5-cyclopropyl-3-(2,6-dichlorophenyl)isoxazol-4-yl)methoxy)-5,6-dihydrobenzo[6,7]oxepino[2,3-c]pyridine-9-carboxylate Methyl 3-oxo-2,3,5,6-tetrahydrobenzo[6,7]oxepino[2,3-c]pyridine-9-carboxylate (158 mg, 0.6 mmol), 4-(chloromethyl)-5-propyl-3-(2,6-dichlorophenyl)isoxazole (414 mg, 1.4 mmol) and potassium phosphate (396 mg, 1.9 mmol) were dissolved in DMF (5 mL). The reaction mixture was heated to 60° C. and stirred for 2 h. The mixture was then cooled to room tempreture, diluted with water (30 mL), and extracted with ethyl acetate (40 mL×2). The combined organic layers were washed with 20 mL of saturated brine, dried over anhydrous sodium sulfate, filtered and concentrated under vacuum. The residue was purified by column chromatography on silica gel eluted with (petroleum ether/ethyl acetate (v/v)=5/1) to give the title compound as a yellow solid (130 mg, 42%).

Step 9: 3-((5-cyclopropyl-3-(2,6-dichlorophenyl)isoxazol-4-yl)methoxy)-5,6-dihydrobenzo[6,7]oxepino[2,3-c]pyridine-9-carboxylic acid Methyl 3-((5-cyclopropyl-3-(2,6-dichlorophenyl)isoxazol-4-yl)methoxy)-5,6-dihydrobenzo[6,7]oxepino[2,3-c]

pyridine-9-carboxylate (148 mg, 0.27 mmol) was dissolved in a mixed solvent of tetrahydrofuran (2 mL) and water (2 mL), and lithium hydroxide (120 mg, 2.9 mmol) was added. The reaction solution was heated to 80° C. and stirred for 3 h. Most of the solvent was removed under vacuum. The residue was diluted with water (10 mL), and adjusted to acidity with 2 M hydrochloric acid (5 mL). The resulting mixture was extracted with ethyl acetate (30 mL×2). The combined organic layers were washed with 10 mL of saturated brine, dried over anhydrous sodium sulfate, filtered and concentrated under vacuum to give the title compound as a white solid (120 mg, 83%).

MS (ESI, pos. ion) m/z: 523.2 [M+H]$^+$; and $^1$H NMR (600 MHz, DMSO-d$_6$) δ7.93 (s, 1H), 7.69 (d, J=1.2 Hz, 1H), 7.66-7.65 (m, 1H), 7.56-7.55 (m, 2H), 7.51-7.44 (m, 1H), 7.36 (d, J=7.9 Hz, 1H), 6.48 (s, 1H), 5.10 (s, 2H), 3.13-3.11 (m, 2H), 3.04-3.02 (m, 2H), 2.49-2.43 (m, 1H), 1.19-1.17 (m, 2H), 1.12-1.10 (m, 2H).

Example 5: 8-((5-cyclopropyl-3-(2,6-dichlorophenyl)isoxazol-4-yl)methoxy)-11H-dibenzo[b,f][1,4]oxathiepine-3-carboxylic acid-10,10-dioxide

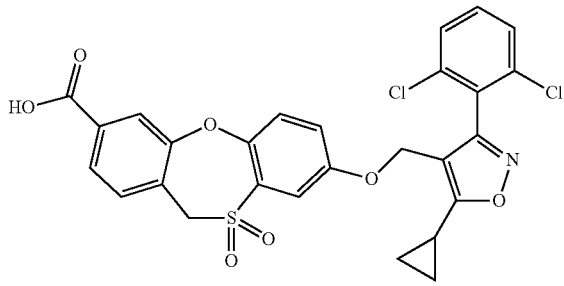 [SMILES: O=C(O)c1ccc2c(c1)Oc1ccc(OCc3c(-c4c(Cl)cccc4Cl)noc3C3CC3)cc1S(=O)(=O)C2]

Step 1: methyl 3-bromo-4-(((2,5-dimethoxyphenyl)thio)methyl)benzoate

To a mixture of methyl 3-bromo-4-(bromomethyl)benzoate (1.7 g, 5.5 mmol) in N,N-dimethylformamide (30 mL) were added potassium carbonate (1.5 g, 11 mmol) and 2,5-dimethylbenzene thiol (0.83 mL, 6.1 mmol) under an ice bath. The mixture was stirred under an ice bath for 2 h. The reaction mixture was then diluted with water (20 ml), and extracted with ethyl acetate (30 mL×2). The combined organic layers were washed with 20 mL of saturated brine, dried over anhydrous sodium sulfate, filtered and concentrated under vacuum. The residue was purified by column chromatography on silica gel eluted with (petroleum ether/ethyl acetate (v/v)=20/1) to give the title compound as a yellow oil (2.0 g, 89%).

$^1$H NMR (600 MHz, CDCl$_3$) δ8.23 (d, J=1.7 Hz, 1H), 7.84 (dd, J=8.0, 1.7 Hz, 1H), 7.32 (d, J=8.0 Hz, 1H), 6.80 (s, 1H), 6.76 (dd, J=4.7, 2.2 Hz, 2H), 4.24 (s, 2H), 3.92 (s, 3H), 3.86 (s, 3H), 3.70 (s, 3H).

Step 2: methyl 3-bromo-4-(((2,5-dihydroxyphenyl)thio)methyl)benzoate

Methyl 3-bromo-4-(((2,5-dimethoxyphenyl)thio)methyl)benzoate (100 mg, 0.25 mmol) was dissolved in dry dichloromethane (30 mL) under nitrogen. The mixture was cooled to −78° C., and a solution of boron tribromide in methylene chloride (2.5 mL, 2.5 mmol, 1 M) was added dropwise. The resulting mixture was allowed to warm to room temperature and stirred overnight. The reaction mixture was quenched with 5 mL of methanol, diluted with water (20 mL), and extracted with dichloromethane (40 mL×2). The combined organic layers were washed with 20 mL of saturated brine, dried over anhydrous sodium sulfate, filtered and concentrated under vacuum. The residue was purified by column chromatography on silica gel eluted with (petroleum ether/ethyl acetate (v/v)=4/1) to give the title compound as a yellow solid (53 mg, 57%).

MS (ESI, pos. ion) m/z: 369.0 [M+H]$^+$.

Step 3: methyl 8-hydroxy-11H-dibenzo[b,f][1,4]oxathiepine-3-carboxylate

Methyl 3-bromo-4-((2,5-dihydroxyphenyl)thio)methyl)benzoate (400 mg, 1.1 mmol), cuprous iodide (20 mg, 0.11 mmol), N,N-dimethylglycine (33 mg, 0.32 mmol) and cesium carbonate (710 mg, 2.2 mmol) were dissolved in dioxane (10 mL) under nitrogen. The reaction mixture was heated to 90° C. and stirred overnight. After being cooled to room tempreture, the mixture was filtered. The filter cake was washed with ethyl acetate (10 mL). The combined filtrates were concentrated under vacuum. The residue was purified by column chromatography on silica gel eluted with (petroleum ether/ethyl acetate (v/v)=4/1) to give the title compound as a yellow oil (60 mg, 20%).

$^1$H NMR (600 MHz, CDCl$_3$) δ7.86-7.84 (m, 2H), 7.35 (d, J=8.4 Hz, 1H), 7.12 (d, J=8.6 Hz, 1H), 6.56-6.49 (m, 2H), 5.03 (s, 1H), 4.33 (s, 2H), 3.93 (s, 3H).

Step 4: methyl 8-((5-cyclopropyl-3-(2,6-dichlorophenyl)isoxazol-4-yl)methoxy)-11H-dibenzo[b,f][1,4]oxathiepine-3-carboxylate 4-(Chloromethyl)-5-cyclopropyl-3-(2,6-dichlorophenyl)isoxazole (100 mg, 0.33 mmol), methyl 8-hydroxy-11H-dibenzo[b,f][1,4]oxathiepine-3-carboxylate (60 mg, 0.21 mmol) and potassium phosphate (66 mg, 0.31 mmol) were dissolved in N,N-dimethylformamide (10 mL). The reaction mixture was heated to 60° C. and stirred overnight. The reaction mixture was then cooled to room tempreture, diluted with water (10 mL) and extracted with ethyl acetate (20 mL×2). The combined organic layers were washed with 20 mL of saturated brine, dried over anhydrous sodium sulfate, filtered and concentrated under vacuum. The residue was purified by column chromatography on silica gel eluted with (petroleum ether/ethyl acetate (v/v)=10/1) to give the title compound as a yellow oil (50 mg, 43%).

Step 5: methyl 8-((5-cyclopropyl-3-(2,6-dichlorophenyl)isoxazol-4-yl)methoxy)-11H-dibenzo[b,f][1,4]oxathiepine-3-carboxylate-10,10-dioxide To a mixture of methyl 8-((5-cyclopropyl-3-(2,6-dichlorophenyl)isoxazol-4-yl)methoxy)-11H-dibenzo[b,f][1,4]oxathiepine-3-carboxylate (200 mg, 0.36 mmol) in dichloromethane (10 mL) was added m-chloroperbenzoic acid (300 mg, 1.48 mmol). The reaction mixture was stirred at room temperature overnight. Saturated sodium carbonate aqueous solution (30 mL) was added. The resulting mixture was stirred for 30 min, and extracted with dichloromethane (30 mL×2). The combined organic layers were washed with 20 mL of saturated brine, dried over anhydrous sodium sulfate, filtered and concentrated under vacuum. The residue was purified by column chromatography on silica gel eluted with (petroleum ether/ethyl acetate (v/v)=4/1) to give the title compound as a yellow solid (200 mg, 95%).

Step 6: 8-((5-cyclopropyl-3-(2,6-dichlorophenyl) isoxazol-4-yl)methoxy)-11H-dibenzo [b,f][1,4]oxathiepine-3-carboxylic acid-10,10-dioxide Methyl 8-((5-cyclopropyl-3-(2,6-dichlorophenyl)isoxazol-4-yl)methoxy)-11H-dibenzo [b,f][1,4]oxathia-3-carboxylate-10,10-dioxide (200 mg, 0.34 mmol) was dissolved in a mixed solvent of tetrahydrofuran (4 mL) and water (4 mL), and lithium hydroxide (150 mg, 3.57 mmol) was added. The reaction mixture was heated to 40° C. and stirred overnight. The reaction mixture was then cooled to room tempreture. Most of the solvent was removed under vacuum. The residue was diluted with water (10 mL). The resulting mixture was adjusted to acidity with 2 M hydrochloric acid (5 mL), and extracted with ethyl acetate (20 mL×2). The combined organic layers were washed with 10 mL of saturated brine, dried over anhydrous sodium sulfate, filtered. The filtrate was concentrated under vacuum to give the title compound as a white solid (120 mg, 61%).

MS (ESI, pos. ion) m/z: 572.1 [M+H]⁺; and
$^1$H NMR (400 MHz, CDCl$_3$) δ8.02-7.96 (m, 2H), 7.55 (d, J=7.9 Hz, 1H), 7.40-7.38 (m, 2H), 7.30-7.24 (m, 3H), 6.96 (dd, J=9.0, 2.9 Hz, 1H), 4.83 (s, 2H), 4.81 (s, 2H), 2.17-2.10 (m, 1H), 1.30-1.26 (m, 2H), 1.19-1.14 (m, 2H).

Example 6: 8-((5-cyclopropyl-3-(2,6-dichlorophenyl)isoxazol-4-yl)methoxy)-11H-dibenzo [b,f][1,4] oxathiepine-3-carboxylic acid

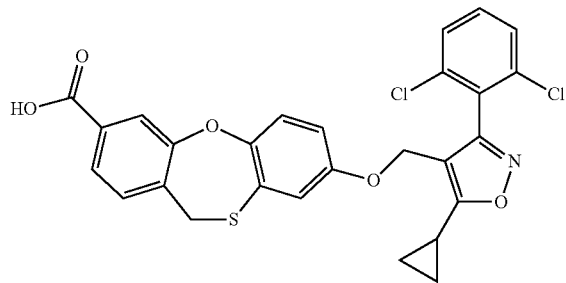 [SMILES: O=C(O)c1ccc2c(c1)Oc1ccc(OCc3c(-c4c(Cl)cccc4Cl)noc3C3CC3)cc1SC2]

Step 1: 8-((5-cyclopropyl-3-(2,6-dichlorophenyl) isoxazol-4-yl)methoxy)-11H-dibenzo [b,f][1,4]oxathiepine-3-carboxylic acid Methyl 8-((5-cyclopropyl-3-(2,6-dichlorophenyl)isoxazol-4-yl)methoxy)-11H-dibenzo [b,f][1,4]oxathiepine-3-carboxylate (50 mg, 0.1 mmol) was dissolved in a mixed solvent of tetrahydrofuran (2 mL) and water (2 mL), and lithium hydroxide (40 mg, 1.0 mmol) was added. The reaction mixture was heated to 40° C. and stirred overnight. The reaction mixture was then cooled to room tempreture. Most of the solvent was removed under vacuum. The residue was diluted with water (10 mL), adjusted to acidity with 2 M hydrochloric acid (3 mL). The resulting mixture was extracted with ethyl acetate (20 mL×2). The combined organic layers were washed with 10 mL of saturated brine, dried over anhydrous sodium sulfate, filtered and concentrated under vacuum. The residue was purified by column chromatography on silica gel eluted with (petroleum ether/ethyl acetate (v/v)=1/1) to give the title compound as a white solid (35 mg, 72%).

MS (ESI, pos. ion) m/z: 540.1 [M+H]⁺; and
$^1$H NMR (600 MHz, CDCl$_3$) δ7.92-7.88 (m, 2H), 7.39-7.37 (m, 3H), 7.31-7.28 (m, 1H), 7.11 (d, J=8.9 Hz, 1H), 6.51 (dd, J=8.9, 2.9 Hz, 1H), 6.45 (d, J=2.8 Hz, 1H), 4.72 (s, 2H), 4.32 (s, 2H), 2.15-2.10 (m, 1H), 1.30-1.26 (m, 2H), 1.15-1.12 (m, 2H).

Example 7: 8-((5-cyclopropyl-3-(2,6-dichlorophenyl)isoxazol-4-yl)methoxy)-11H-dibenzo [b,f][1,4] oxathiepine-3-carboxylic acid-10-oxide

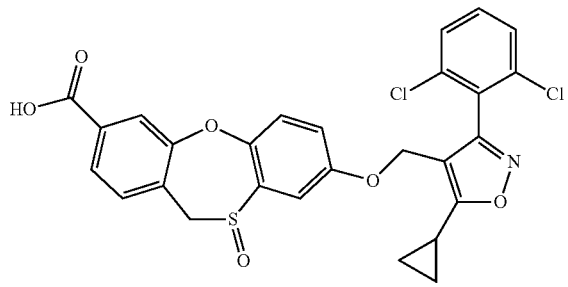 [SMILES: O=C(O)c1ccc2c(c1)Oc1ccc(OCc3c(-c4c(Cl)cccc4Cl)noc3C3CC3)cc1S(=O)C2]

Step 1: methyl 8-((5-cyclopropyl-3-(2,6-dichlorophenyl)isoxazol-4-yl)methoxy)-11H-dibenzo[b,f][1,4]oxathiepine-3-carboxylate-10-oxide Methyl 8-((5-cyclopropyl-3-(2,6-dichlorophenyl)isoxazol-4-yl)methoxy)-11H-dibenzo [b,f][1,4]oxathiepine-3-carboxylate (200 mg, 0.36 mmol) was dissolved in dichloromethane (10 mL), and 3-chlorobenzoperoxoic acid (69 mg, 0.34 mmol) was added portionwise under an ice bath. The reaction solution was stirred overnight under an ice bath. Saturated sodium carbonate aqueous solution (30 mL) was then added. The resulting solution was stirred for 30 min, and extracted with dichloromethane (30 mL×2). The combined organic layers were washed with 20 mL of saturated brine, dried over anhydrous sodium sulfate, filtered and concentrated under vacuum. The residue was purified by column chromatography on silica gel eluted with (petroleum ether/ethyl acetate (v/v)=4/1) to give the title compound as a white solid (154 mg, 75%).

Step 2: 8-((5-cyclopropyl-3-(2,6-dichlorophenyl) isoxazol-4-yl)methoxy)-11H-dibenzo [b,f][1,4]oxathiepine-3-carboxylic acid-10-oxide Methyl 8-((5-cyclopropyl-3-(2,6-dichlorophenyl)isoxazol-4-yl)methoxy)-11H-dibenzo [b,f][1,4]oxathiepine-3-carboxylate-10-oxide (154 mg, 0.27 mmol) was dissolved in a mixed solvent of tetrahydrofuran (3 mL) and water (3 mL), and lithium hydroxide (120 mg, 2.8 mmol) was added. The reaction mixture was heated to 40° C. and stirred overnight. The reaction mixture was then cooled to room tempreture. Most of the solvent was removed under vacuum. The resulting mixture was diluted with water (10 mL), and adjusted to acidity with 2 M hydrochloric acid (4 mL). The resulting mixture was extracted with ethyl acetate (20 mL×2). The combined organic layers were washed with 10 mL of saturated brine, dried over anhydrous sodium sulfate, filtered and concentrated under vacuum to give the title compound as a white solid (134 mg, 89%).

MS (ESI, pos. ion) m/z: 556.1 [M+H]+; and

1H NMR (400 MHz, DMSO-d6) δ13.23 (s, 1H), 7.80-7.77 (m, 2H), 7.61-7.49 (m, 4H), 7.40 (d, J=8.9 Hz, 1H), 7.12 (d, J=2.5 Hz, 1H), 6.97 (dd, J=8.8, 2.6 Hz, 1H), 4.94 (q, J=12.3 Hz, 2H), 4.86 (d, J=13.6 Hz, 1H), 4.56 (d, J=13.6 Hz, 1H), 2.46-2.42 (m, 1H), 1.28-1.12 (m, 4H).

Example 8: 8-((5-cyclopropyl-3-(2,6-dichlorophenyl)isoxazol-4-yl)methoxy phenoxathiine-3-carboxylic acid-10,10-dioxide

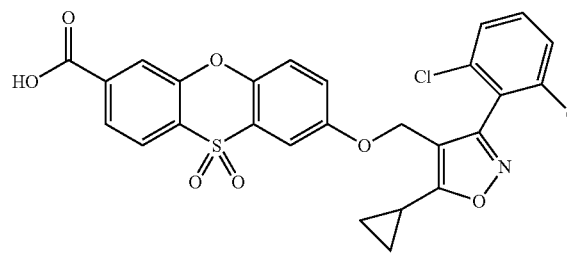

Step 1: methyl 3-bromo-4-iodobenzoate

To a solution of methyl 4-amino-3-bromobenzoate (5.0 g, 21.7 mmol) in tetrahydrofuran (10 mL) was added hydrochloric acid (40 mL, 120 mmol, 3 M) under an ice bath, then a solution of sodium nitrite (1.65 g, 23.9 mmol) in water (20 mL) was slowly added dropwise, and the mixture was stirred for 1 h under an ice bath. A solution of potassium iodide (7.2 g, 43 mmol) in water (20 mL) was added, and the resulting mixture was warmed to room temperature and stirred for 2 h. The mixture was quenched with 20 mL of saturated aqueous sodium bisulfate. The resulting mixture was extracted with ethyl acetate (30 mL×2). The combined organic layers were washed with 10 mL of saturated brine, dried over anhydrous sodium sulfate, filtered and concentrated under vacuum. The residue was purified by column chromatography on silica gel eluted with (petroleum ether/ethyl acetate (v/v)=20/1) to give the compound as a yellow oil (5.8 g, 78%).

Step 2: methyl 3-bromo-4-((2,5-dimethoxyphenyl)thio)benzoate

Methyl 3-bromo-4-iodobenzoate (500 mg, 1.0 mmol), 2,5-dimethoxythiophenol (0.22 mL, 1.5 mol), L-proline (33 mg, 0.29 mmol), cuprous iodide (28 mg, 0.15 mmol) and potassium carbonate (405 mg, 2.9 mmol) were dissolved in ethylene glycol dimethyl ether (5 mL), and the mixture was heated to 80° C. and stirred overnight. The mixture was then cooled to room tempreture, and quenched with 10 mL of water. The resulting mixture was extracted with ethyl acetate (30 mL×2). The combined organic layers were washed with 10 mL of saturated brine, dried over anhydrous sodium sulfate, filtered and concentrated under vacuum. The residue was purified by column chromatography on silica gel eluted with (petroleum ether/ethyl acetate (v/v)=4/1) to give the title compound as a yellow oil (530 mg, 90%).

1H NMR (400 MHz, CDCl3) δ8.20 (d, J=1.6 Hz, 1H), 7.74 (dd, J=8.4, 1.6 Hz, 1H), 7.10 (d, J=3.0 Hz, 1H), 7.04 (dd, J=9.0, 3.0 Hz, 1H), 6.98 (d, J=9.0 Hz, 1H), 6.72 (d, J=3.3 Hz, 1H), 3.90 (s, 3H), 3.80 (s, 3H), 3.79 (s, 3H).

Step 3: methyl 3-bromo-4-((2,5-dihydroxyphenyl)thio)benzoate

Methyl 3-bromo-4-((2,5-dimethoxyphenyl)thio)benzoate (625 mg, 1.6 mmol) was dissolved in dry dichloromethane (30 mL) under nitrogen, the mixture was cooled to −78° C., and a solution of boron tribromide in methylene chloride (8.1 mL, 8.1 mmol, 1.0 M) was added dropwise. The resulting mixture was then allowed to warm to room temperature and stirred overnight. The mixture was quenched with 5 mL of methanol, and diluted with water (20 mL). The resulting mixture was extracted with dichloromethane (30 mL×2). The combined organic layers were washed with 20 mL of saturated brine, dried over anhydrous sodium sulfate, filtered and concentrated under vacuum. The residue was purified by column chromatography on silica gel eluted with (petroleum ether/ethyl acetate (v/v)=4/1) to give the title compound as a yellow oil (241 mg, 42%).

MS (ESI, neg. ion) m/z: 353.0 [M−H]−.

Step 4: methyl 8-hydroxyphenoxathiine-3-carboxylate

Methyl 3-bromo-4-((2,5-dihydroxyphenyl)thio)benzoate (241 mg, 0.68 mmol), N,N-dimethylglycine (20 mg, 0.19 mmol), cuprous iodide (12 mg, 0.06 mmol), and cesium carbonate (440 mg, 1.32 mmol) were dissolved in 1,4-dioxane (10 mL), and the reaction mixture was heated to 90° C. and stirred overnight. The reaction mixture was then cooled to room tempreture, diluted with water (10 mL) and extracted with ethyl acetate (30 mL×2). The combined organic layers were washed with 20 mL of saturated brine, dried over anhydrous sodium sulfate, filtered and concentrated under vacuum. The residue was purified by column chromatography on silica gel eluted with (petroleum ether/ethyl acetate (v/v)=4/1) to give the compound as a yellow oil (50 mg, 27%).

MS (ESI, pos. ion) m/z: 275.0 [M+H]+.

Step 5: methyl 8-((5-cyclopropyl-3-(2,6-dichlorophenyl)isoxazol-4-yl)methoxy) phenoxathiine-3-carboxylate 4-(Chloromethyl)-5-cyclopropyl-3-(2,6-dichlorophenyl)isoxazole (80 mg, 0.26 mmol), methyl 8-hydroxyphenoxathiine-3-carboxylate (50 mg, 0.18 mmol) and potassium phosphate (60 mg, 0.28 mmol) were dissolved in DMF (10 mL), and the mixture was heated to 60° C. and stirred overnight. The mixture was then cooled to room tempreture, diluted with water (10 mL) and extracted with ethyl acetate (20 mL×2). The combined organic layers were washed with 10 mL of saturated brine, dried over anhydrous sodium sulfate, filtered and concentrated under vacuum. The residue was purified by column chromatography on silica gel eluted with (petroleum ether/ethyl acetate (v/v)=10/1) to give the compound as a yellow solid (56 mg, 57%).

Step 6: methyl 8-((5-cyclopropyl-3-(2,6-dichlorophenyl)isoxazol-4-yl)methoxy) phenoxathiine-3-carboxylate-10,10-dioxide To a solution of methyl 8-((5-cyclopropyl-3-(2,6-dichlorophenyl)isoxazol-4-yl)methoxy)phenoxathiine-3-carboxylate (56 mg, 0.1 mmol) in dichloromethane (10 mL) was added m-chloroperbenzoic acid (100 mg, 0.5 mmol), and the reaction mixture was stirred at room temperature overnight. Saturated sodium carbonate aqueous solution (30 mL) was added. The resulting mixture was stirred for 30 min, and extracted with dichloromethane (30 mL×2). The combined organic layers were washed with 20 mL of saturated brine, dried over anhydrous sodium sulfate, filtered and concentrated under vacuum. The residue was purified by column chromatography on silica gel eluted with (petroleum ether/ethyl acetate (v/v)=4/1) to give the title compound as a white solid (56 mg, 94%).

Step 7: 8-((5-cyclopropyl-3-(2,6-dichlorophenyl)isoxazol-4-yl)methoxy)phenoxathiine-3-carboxylic acid-10,10-dioxide Methyl 8-((5-cyclopropyl-3-(2,6-dichlorophenyl)isoxazol-4-yl)methoxy)phenoxathiine-3-carboxylate-10,10-dioxide (60 mg, 0.1 mmol) was dissolved in a mixed solvent of tetrahydrofuran (2 mL) and water (2 mL), and lithium hydroxide (44 mg, 1.1 mmol) was added. The mixture was heated to 40° C. and stirred overnight. The mixture was then cooled to room temperature, and most of the solvent was removed under vacuum. The residue was diluted with water (10 mL). The resulting mixture was adjusted to acidity with hydrochloric acid (2 mL, 2 M). The resulting mixture was extracted with ethyl acetate (20 mL×2). The combined organic layers were washed with 10 mL of saturated brine, dried over anhydrous sodium sulfate and filtered. The filtrate was concentrated under vacuum to give the title compound as a white solid (35 mg, 60%).

LC-MS (ES-API, neg. ion) m/z: 556.0 [M–H]$^-$; and
$^1$H NMR (400 MHz, DMSO-d$_6$) δ13.56 (s, 1H), 8.20-8.18 (m, 1H), 8.00-7.90 (m, 2H), 7.62-7.48 (m, 5H), 7.22-7.20 (m, 1H), 5.07 (s, 2H), 2.18-1.99 (m, 1H), 1.35-1.14 (m, 4H).

Example 9: 2'-((5-cyclopropyl-3-(2,6-dichlorophenyl)isoxazol-4-yl)methoxy)-10',11'-dihydrospiro[cyclopropane-1,5'-dibenzo[a,d][7]annulene]-7'-carboxylic acid

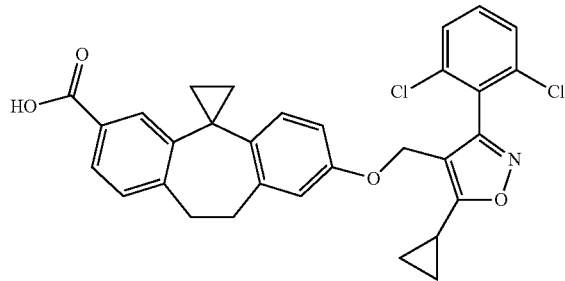 [SMILES: O=C(O)c1ccc2c(c1)C1(CC1)c1ccc(OCc3c(-c4c(Cl)cccc4Cl)noc3C3CC3)cc1CC2]

Step 1: 8-methoxy-5-methylene-10,11-dihydro-5H-dibenzo[a,d][7]annulene-3-carboxylic acid To a mixture of methyl 8-methoxy-5-oxo-10,11-dihydro-5H-dibenzo[a,d][7]annulene-3-carboxylic acid (510 mg, 1.8 mmol) in anhydrous tetrahydrofuran (20 mL) was added dropwise a solution of magnesium bromide in tetrahydrofuran (1.8 mL, 5.4 mmol, 3.0 M) under an ice bath. After the addition, the mixture was stirred under an ice bath for 30 min, then warmed to room temperature and stirred for 1h, and finally warmed to reflux and stirred overnight. The mixture was then allowed to cool to room temperature, and quenched with 20 mL of saturated ammonium chloride aqueous solution. The resulting mixture was extracted with ethyl acetate (30 mL×3). The combined organic layers were washed with 20 mL of saturated brine, dried over anhydrous sodium sulfate, filtered and concentrated under vacuum. The residue was purified by silica gel column chromatography eluted with (CH$_2$Cl$_2$/MeOH (v/v)=50/1) to give the title compound as a pale yellow solid (262 mg, 52%).

MS (ESI, pos. ion) m/z: 281.3 [M+H]$^+$; and
$^1$H NMR (400 MHz, DMSO-d$_6$) δ12.81 (br.s, 1H), 7.85 (d, J=1.5 Hz, 1H), 7.79 (dd, J=7.8, 1.6 Hz, 1H), 7.34-7.23 (m, 2H), 6.81-6.71 (m, 2H), 5.39 (d, J=15.3 Hz, 2H), 3.73 (s, 3H), 3.13-3.01 (m, 4H).

Step 2: methyl 8 methoxy-5-methylene-10,11-dihydro-5H-dibenzo[a,d][7]annulene-3-carboxylate Methyl 8-methoxy-5-methylene-10,11-dihydro-5H-dibenzo[a,d][7]annulene-3-carboxylic acid (250 mg, 0.89 mmol), anhydrous methanol (50 mg, 1.56 mmol) and triphenylphosphine (350 mg, 1.33 mmol) were dissolved in anhydrous tetrahydrofuran (15 mL). The mixture was cooled to 0° C., and diethyl azodicarboxylate (0.22 mL, 1.4 mmol) was slowly added dropwise. The resulting mixture was then warmed to room temperature and stirred for 1 h. The mixture was quenched with 20 mL of water, and the resulting mixture was extracted with dichloromethane (30 mL×2). The combined organic layers were washed with 20 mL of saturated brine, dried over anhydrous sodium sulfate, filtered and concentrated under vacuum. The residue was purified by column chromatography on silica gel eluted with (petroleum ether/ethyl acetate (v/v)=10/1) to give the title compound as a white solid (220 mg, 84%).

MS (ESI, pos. ion) m/z: 295.2 [M+H]$^+$.

Step 3: methyl 2'-methoxy-10',11'-dihydrospiro[cyclopropane-1,5'-dibenzo[a,d][7]annulene]-7'-carboxylate Anhydrous dichloromethane (30 mL) and a solution of diethyl zinc in n-hexane (3.4 mL, 3.4 mmol, 1.0 M) were placed in a reaction flask, the mixture was cooled to −20° C., and then trifluoroacetic acid (0.25 mL, 3.4 mmol) was added dropwise. The resulting mixture was continued to stir at −20° C. for 1 h. The fixture was then warmed to 0° C., and diiodomethane (0.27 mL, 3.3 mmol) was added dropwise. The resulting mixture was stirred at 0° C. for 40 min, and a solution of methyl 8-methoxy-5-methylene-10,11-dihydro-5H-dibenzo[a,d][7]annulene-3-carboxylate (330 mg, 1.1 mmol) in dichloromethane (10 mL) was added dropwise. The resulting mixture was warmed to room temperature and stirred for 3 h. The mixture was quenched with 20 mL of saturated ammonium chloride aqueous solution, and the resulting mixture was extracted with dichloromethane (30 mL×2). The combined organic layers were washed with 20 mL of saturated brine, dried over anhydrous sodium sulfate, filtered and concentrated under vacuum. The residue was purified by column chromatography on silica gel eluted with (petroleum ether/ethyl acetate (v/v)=10/1) to give the title compound as a pale yellow solid (300 mg, 87%).

MS (ESI, pos. ion) m/z: 309.2 [M+H]$^+$.

Step 4: methyl 2'-hydroxy-10',11'-dihydrospiro[cyclopropane-1,5'-dibenzo[a,d][7]annulene]-7'-carboxylate Methyl 2'-hydroxy-10',11'-dihydrospiro[cyclopropane-1,5'-dibenzo[a,d][7]annulene]-7'-carboxylate (200 mg, 0.65 mmol) was dissolved in anhydrous dichloromethane (20 mL) under nitrogen. The mixture was cooled to −78° C., and a solution of boron tribromide in methylene chloride (1.4 mL, 1.4 mmol, 1.0 M) was added dropwise. The resulting mixture was warmed to room temperature and stirred overnight. The mixture was quenched with 5 mL of methanol, diluted with water (20 mL), and extracted with dichloromethane (30 mL×2). The combined organic layers were washed with 20 mL of saturated brine, dried over anhydrous sodium sulfate, filtered and concentrated under vacuum. The residue was purified by column chromatography on silica gel eluted with (petroleum ether/ethyl acetate (v/v)=5/1) to give the title compound as a yellow oil (80 mg, 41%).

MS (ESI, pos. ion) m/z: 295.2 [M+H]⁺.

Step 5: methyl 2'-((5-cyclopropyl-3-(2,6-dichlorophenyl)isoxazol-4-yl)methoxy)-10',11'-dihydrospiro[cyclopropane-1,5'-dibenzo[a,d][7]annulene]-7'-carboxylate 4-(Chloromethyl)-5-cyclopropyl-3-(2,6-dichlorophenyl)isoxazole (53 mg, 0.17 mmol), methyl 2'-hydroxy-10',11'-dihydrospiro[cyclopropane-1,5'-[a,d][7]annulene]-7'-carboxylate (40 mg, 0.14 mmol) and potassium phosphate (58 mg, 0.27 mmol) were dissolved in DMF (8 mL), and the mixture was warmed to 60° C. and stirred overnight. The mixture was then cooled to room temperature, diluted with water (10 mL), and extracted with ethyl acetate (20 mL×2). The combined organic layers were washed with 10 mL of saturated brine, dried over anhydrous sodium sulfate, filtered and concentrated under vacuum. The residue was purified by column chromatography on silica gel eluted with (petroleum ether/ethyl acetate (v/v)=5/1) to give the title compound as a pale yellow soild (50 mg, 66%).

Step 6: 2'-((5-cyclopropyl-3-(2,6-dichlorophenyl)isoxazol-4-yl)methoxy)-10',11'-dihydrospiro[cyclopropane-1,5'-dibenzo[a,d][7]annulene]-7'-carboxylic acid Methyl 2'-((5-cyclopropyl-3-(2,6-dichlorophenyl)isoxazol-4-yl)methoxy)-10',11'-dihydrospiro[cyclopropane-1,5'-dibenzo[a,d][7]annulene]-7'-carboxylate (55 mg, 0.1 mmol) was dissolved in a mixed solvent of tetrahydrofuran (2 mL) and water (2 mL), lithium hydroxide (44 mg, 1.0 mmol) was added, and the mixture was heated to 80° C. and stirred for 3 h. The reaction mixture was then cooled to room temperature, and most of the solvent was removed under vacuum. The residue was diluted with water (10 mL). The resulting mixture was adjusted to acidity with hydrochloric acid (2 mL, 2 M). The resulting mixture was extracted with ethyl acetate (20 mL×2). The combined organic layers were washed with 10 mL of saturated brine, dried over anhydrous sodium sulfate and filtered. The filtrate was concentrated under vacuum to give the title compound as a white solid (42 mg, 80%).

MS (ESI, pos. ion) m/z: 546.2 [M+H]⁺; and

¹H NMR (400 MHz, CDCl₃) δ7.95 (d, J=1.5 Hz, 1H), 7.83 (dd, J=7.8, 1.6 Hz, 1H), 7.39-7.34 (m, 2H), 7.30 (s, 1H), 7.20 (d, J=7.9 Hz, 1H), 7.13 (d, J=8.4 Hz, 1H), 6.59 (d, J=2.5 Hz, 1H), 6.55 (dd, J=8.5, 2.6 Hz, 1H), 4.73 (s, 2H), 3.42-3.26 (m, 4H), 2.19-2.09 (m, 1H), 1.36-1.28 (m, 4H), 1.14-1.08 (m, 2H), 0.93-0.86 (m, 2H).

Example 10: 8-((5-cyclopropyl-3-(2,6-dichlorophenyl)isoxazol-4-yl)methoxy)-10,11-dihydrodibenzo[b,f]thiepine-3-carboxylic acid-5-oxide

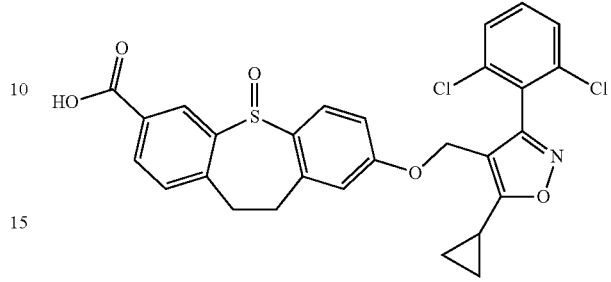

Step 1: methyl 4-(bromomethyl)-3-iodobenzoate

To a mixture of methyl 3-iodo-4-methylbenzoate (4.8 g, 17.5 mmol) in carbon tetrachloride (100 mL) were added N-bromosuccinimide (3.7 g, 21.0 mmol) and benzoyl peroxide (0.4 g, 1.7 mmol) under nitrogen, and the mixture was warmed to 70° C. and stirred overnight. After being cooled to room tempreture, the mixture was quenched with 20 mL of saturated aqueous sodium bicarbonate solution. The resulting mixture was extracted with dichloromethane (100 mL×2). The combined organic layers were washed with 20 mL of saturated brine, dried over anhydrous sodium sulfate, filtered and concentrated under vacuum. The residue was purified by column chromatography on silica gel eluted with (petroleum ether/ethyl acetate (v/v)=30/1) to give the title compound as a yellow oil (5.0 g, 80%).

Step 2: methyl 4-((diethoxyphosphoryl)methyl)-3-iodobenzoate

A solution of methyl 4-(bromomethyl)-3-iodobenzoate (5.0 g, 14.0 mmol) in triethyl phosphite (20 mL) was heated to 150° C. and stirred overnight. The solution was cooled to room tempreture, and the triethyl phosphite was removed by distillation under vacuum to give the title compound as a yellow oil (5.7 g, 100%).

Step 3: methyl 4-(2-bromo-5-(methoxymethoxy)styryl)-3-iodobenzoate

To a mixture of methyl 4-((diethoxyphosphoryl)methyl)-3-iodobenzoate (5.7 g, 14.0 mmol) in tetrahydrofuran (100 mL) was added 60% sodium hydride (660 mg, 27.5 mmol) under an ice bath. The reaction solution was stirred under an ice bath for 20 min, and a solution of 2-bromo-5-(methoxymethoxy)benzaldehyde (3.7 g, 15 mmol) in tetrahydrofuran (10 mL) was added dropwise. The resulting mixture was continued to stir under an ice bath for 4 h. The reaction mixture was then quenched with 20 mL of saturated ammonium chloride aqueous solution. The resulting mixture was extracted with ethyl acetate (200 mL×2). The combined organic layers were washed with 20 mL of saturated brine, dried over anhydrous sodium sulfate, filtered and concentrated under vacuum. The residue was purified by silica gel column chromatography eluted with (petroleum ether/ethyl acetate (v/v)=40/1), to give the title compound as a yellow oil (5.6 g, 80%).

Step 4: methyl 4-(2-bronco-5-(methoxyethoxy) phenethyl)-3-iodobenzoate

Methyl 4-(2-bronco-5-(methoxymethoxy)styryl)-3-iodobenzoate (5.2 g, 10.4 mmol), sodium acetate (5.1 g, 62.3 mmol) and p-toluenesulfonyl hydrazide (11.6 g, 62.3 mmol) were dissolved in a mixed solvent of tetrahydrofuran (100 mL) and water (50 mL), and the mixture was heated to reflux and stirred for 24 h. The reaction mixture was then cooled to room temperature, and diluted with water (50 mL). The resulting mixture was extracted with dichloromethane (150 mL×2). The combined organic layers were washed with 20 mL of saturated brine, dried over anhydrous sodium sulfate, filtered, and concentrated under vacuum. The residue was purified by column chromatography on silica gel eluted with (petroleum ether/ethyl acetate (v/v)=30/1) to give the title compound as a pale yellow oil (4.5 g, 85%).

Step 5: methyl 4-(2-bromo-5-(methoxymethoxy) phenethyl)-3-mercaptobenzoate

Methyl 4-(2-bromo-5-(methoxymethoxy)phenethyl)-3-iodobenzoate (500 mg, 1.0 mmol), sublimed sulfur (95 mg, 3.0 mmol), cuprous iodide (18 mg, 0.1 mmol) and potassium carbonate (273 mg, 2.0 mmol) were dissolved in DMF (5 mL), and the mixture was heated to 90° C. and stirred overnight. The reaction mixture was cooled to 0° C., followed by the addition of sodium borohydride (113 mg, 3.0 mmol) in portions. The resulting mixture was warmed to 40° C. and stirred for 5 h, then cooled to room temperature, and quenched with 20 mL of water. The resulting mixture was extracted with ethyl acetate (30 mL×2). The combined organic layers were washed with 10 mL of saturated brine, dried over anhydrous sodium sulfate, filtered and concentrated under vacuum. The residue was purified by column chromatography on silica gel eluted with (petroleum ether/ethyl acetate (v/v)=8/1) to give the title compound as a white solid (170 mg, 42%).

LC-MS (ES-API, neg. ion) m/z: 409.1 [M−H]$^-$.

Step 6: methyl 8-(methoxymethoxy)-10,11-dihydrodibenzo[b,f]thiepine-3-carboxylate Methyl 4-(2-bromo-5-(triethoxymethoxy)phenethyl)-3-mercapto benzoate (170 mg, 0.4 mmol), cuprous iodide (15 mg, 0.08 mmol), N,N-dimethylglycine (8 mg, 0.07 mmol) and potassium carbonate (263 mg, 1.24 mmol) were dissolved in anhydrous DMF (10 mL) under nitrogen, and the mixture was heated to 125° C. and stirred overnight. The mixture was then cooled to room temperature, and quenched with 20 mL of water. The resulting mixture was extracted with ethyl acetate (40 mL×2). The combined organic layers were washed with 20 mL of saturated brine, dried over anhydrous sodium sulfate, filtered and concentrated under vacuum. The residue was purified by column chromatography on silica gel eluted with (petroleum ether/ethyl acetate (v/v)=10/1) to give the title compound as a white solid (90 mg, 66%).

$^1$H NMR (400 MHz, CDCl$_3$) δ8.13 (d, J=1.6 Hz, 1H), 7.80 (dd, J=8.0, 1.7 Hz, 1H), 7.42 (d, J=8.5 Hz, 1H), 7.20 (d, J=8.0 Hz, 1H), 6.90 (d, J=2.6 Hz, 1H), 6.82 (dd, J=8.5, 2.7 Hz, 1H), 5.16 (s, 2H), 3.91 (s, 3H), 3.47 (s, 3H), 3.37 (s, 4H).

Step 7: methyl 8-hydroxy-10,11-dihydrodibenzo[b,f]thiepine-3-carboxylate

To a mixture of methyl 8-(methoxymethoxy)-10,11-dihydrodibenzo[b,f]thiepine-3-carboxylate (370 mg, 1.12 mmol) in tetrahydrofuran (10 mL) was added hydrochloric acid (20 mL, 60 mmol, 3 M), and the mixture was heated to 50° C. and stirred overnight. The mixture was then cooled to room temperature, and diluted with water (20 mL). The resulting mixture was adjusted to neutral with solid potassium carbonate, and the resulting mixture was extracted with ethyl acetate (50 mL×2). The combined organic layers were washed with 10 mL of saturated brine, dried over anhydrous sodium sulfate, filtered and concentrated under vacuum. The residue was purified by column chromatography on silica gel eluted with (petroleum ether/ethyl acetate (v/v)=4/1) to give product as a white solid (310 mg, 97%).

Step 8: methyl 8-((5-cyclopropyl-3-(2,6-dichlorophenyl)isoxazol-4-yl)methoxy)-10,11-dihydrodibenzo[b,f]thiepine-3-carboxylate A solution of methyl 8-hydroxy-10,11-dihydrodibenzo[b,f]thiepine-3-carboxylate (310 mg, 1.1 mmol), 4-(chloromethyl)-5-cyclopropyl-3-(2,6-dichlorophenyl)isoxazole (500 mg, 1.6 mmol) and potassium phosphate (340 g, 1.6 mmol) in DMF (10 mL) was heated to 60° C. and stirred for 3 h. The mixture was then cooled to room temperature, and diluted with water, and the resulting mixture was extracted with ethyl acetate (50 mL×2). The combined organic layers were washed with 10 mL of saturated brine, dried over anhydrous sodium sulfate, filtered and concentrated under vacuum. The residue was purified by column chromatography on silica gel eluted with (petroleum ether/ethyl acetate (v/v)=10/1) to give the title compound as white solid (340 mg, 57%).

Step 9: methyl 8-((5-cyclopropyl-3-(2,6-dichlorophenyl)isoxazol-4-yl 10,11-dihydrodibenzo[b,f]thiepine-3-carboxylate-5-oxide To a solution of methyl 8-((5-cyclopropyl-3-(2,6-dichlorophenyl)isoxazol-4-yl)methoxy)-10,11-dihydrodibenzo[b,f]thiepine-3-carboxylate (130 mg, 0.24 mmol) in dichloromethane (10 mL) was added m-chloroperbenzoic acid (45 mg, 0.22 mmol) in portions under an ice bath, and the mixture was stirred under an ice bath overnight. Then saturated sodium carbonate aqueous solution (30 mL) was added. The resulting mixture was stirred for 30 min, and extracted with dichloromethane (30 mL×2). The combined organic layers were washed with 20 mL of saturated brine, dried over anhydrous sodium sulfate, filtered and concentrated under vacuum. The residue was purified by column chromatography on silica gel eluted with (petroleum ether/ethyl acetate (v/v)=4/1) to give the title compound as a white solid (70 mg, 52%).

Step 10: 8-((5-cyclopropyl-3-(2,6-dichlorophenyl)isoxazol-4-yl)methoxy)-10,11-dihydrodibenzo[b,f]-thiepine-3-carboxylic acid-5-oxide Methyl 8-((5-cyclopropyl-3-(2,6-dichlorophenyl)isoxazol-4-yl)methoxy)-10,11-dihydrodibenzo[b,f]thiepine-3-carboxylate-5-oxide (70 mg, 0.12 mmol) was dissolved in a mixed solvent of tetrahydrofuran (2 mL) and water (2 mL), followed by the addition of hydroxide (50 mg, 1.2 mmol), and the mixture was heated to 40° C. and stirred overnight. The mixture was then cooled to room temperature, and most of the solvent was removed under vacuum. The residue was diluted with water (10 mL). The resulting mixture was adjusted to acidity with hydrochloric acid (2 mL, 2 M). The resulting mixture was extracted with ethyl acetate (20 mL×2). The combined organic layers were washed with 10 mL of saturated brine, dried over anhydrous sodium sulfate and filtered. The filtrate was concentrated under vacuum to give the title compound as a white solid (54 mg, 79%).

MS (ESI, pos. ion) m/z: 553.7 [M+H]$^+$; and $^1$H NMR (400 MHz, DMSO-d$_6$) δ8.18 (s, 1H), 7.92 (dd, J=7.8, 1.4 Hz, 1H), 7.55-7.42 (m, 2H), 7.51-7.40 (m, 3H), 6.86-6.79 (m, 1H), 6.79 (s, 1H), 4.87 (s, 2H), 3.49-3.43 (m, 4H), 2.44-2.37 (m, 1H), 1.17-1.09 (m, 4H).

Example 11: 8-((5-cyclopropyl-3-(2,6-dichlorophenyl)isoxazol-4-yl)methoxy)-10,11-dihydrodibenzo[b,f]thiepine-3-carboxylic acid-5,5-dioxide

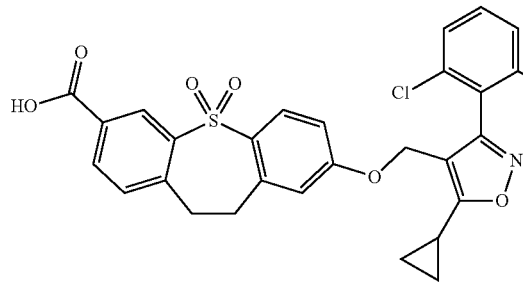

Step 1: methyl 8-((5-cyclopropyl-3-(2,6-dichlorophenyl)isoxazol-4-yl)methoxy)-10,11-dihydrodibenzo[b,f]thiepine-3-carboxylate-5,5-dioxide To a solution of methyl 8-((5-cyclopropyl-3-(2,6-dichlorophenyl)isoxazol-4-yl)methoxy)-10,11-dihydrodibenzo[b,f]thiepine-3-carboxylate (120 mg, 0.22 mmol) in dichloromethane (10 mL) was added m-chloroperbenzoic acid (220 mg, 1.1 mmol), the mixture was stirred at room temperature overnight. Saturated sodium carbonate aqueous solution (50 mL) was added. The resulting mixture was stirred for 30 min, and extracted with dichloromethane (30 mL×2). The combined organic layers were washed with 20 mL of saturated brine, dried over anhydrous sodium sulfate, filtered and concentrated under vacuum. The residue was purified by column chromatography on silica gel eluted with (petroleum ether/ethyl acetate (v/v)=5/1) to give the title compound as a white solid (67 mg, 53%).

Step 2: 8-((5-cyclopropyl-3-(2,6-dichlorophenyl)isoxazol-4-yl)methoxy)-10,11-dihydrodibenzo[b,f]thiepine-3-carboxylic acid-5,5-dioxide Methyl 8-((5-cyclopropyl-3-(2,6-dichlorophenyl)isoxazol-4-yl)methoxy)-10,11-dihydrodibenzo[b,f]thiepine-3-carboxylate-5,5-dioxide (70 mg, 0.12 mmol) was dissolved in a mixed solvent of tetrahydrofuran (2 mL) and water (2 mL), followed by the addition of lithium hydroxide (50 mg, 1.2 mmol), and the mixture was heated to 40° C. and stirred overnight. The mixture was and then cooled to room temperature, and most of the solvent was removed under vacuum. The residue was diluted with water (10 mL). The resulting mixture was adjusted to acidity with hydrochloric acid (2 mL, 2 M). The resulting mixture was extracted with ethyl acetate (20 mL×2). The combined organic layers were washed with 10 mL of saturated brine, dried over anhydrous sodium sulfate and filtered. The filtrate was concentrated under vacuum to give the title compound as a white solid (45 mg, 66%).

MS (ESI, pos. ion) m/z: 570.0 [M+H]$^+$; and $^1$H NMR (400 MHz, DMSO-d$_6$) δ8.48 (s, 1H), 8.16-8.08 (m, 1H), 7.85-7.83 (m, 1H), 7.64-7.45 (m, 4H), 7.01-6.85 (m, 2H), 4.97 (s, 2H), 3.50-3.45 (m, 4H), 2.47-2.42 (m, 1H), 1.19-1.12 (m, 4H).

Example 12: 2-((5-cyclopropyl-3-(2,6-dichlorophenyl)isoxazol-4-yl)methoxy)-10-methyl-10,11-dihydrodibenzo[b,f][1,4]oxazepine-7-carboxylic acid

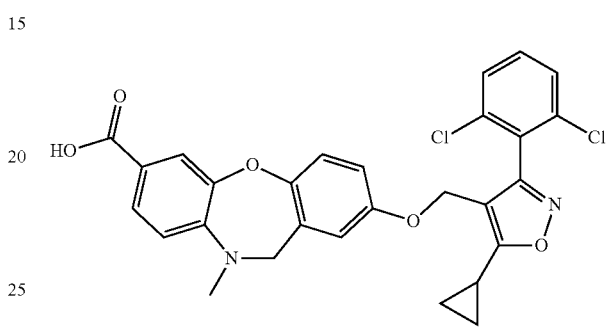

Step 1: methyl 3-bromo-4-((2,5-dihydroxyphenyl)amino)benzoate

A mixture of methyl 4-amino-3-bromobenzoate (5.0 g, 21.7 mol) and 2,5-hydroxybenzaldehyde (4.5 g, 33 mmol) in methanol (50 mL) was warmed to 40° C. and stirred overnight. The mixture was cooled to 0° C., followed by the addition of sodium borohydride (1.65 g, 43.4 mmol) in portions. The resulting mixture was warmed to room temperature and stirred for 6 h. Most of the solvent was removed under vacuum. The residue was diluted with water (50 mL). The resulting mixture was extracted with ethyl acetate (80 mL×2). The combined organic layers were washed with 20 mL of saturated brine, dried over anhydrous sodium sulfate and filtered. The residue was purified by column chromatography on silica gel eluted with (petroleum ether/ethyl acetate (v/v)=4/1) to give the title compound as a brown solid (3.6 g, 47%).

Step 2: methyl 3-bromo-4-(6-hydroxy-2H-benzo[e][1,3]oxazin-3(4H)-yl)benzoate To a mixture of methyl 3-bromo-4-((2,5-dihydroxyphenyl)amino)benzoate (3.0 g, 8.5 mmol) in dichloromethane (100 mL) was added formaldehyde (2.4 mmol) and acetic acid (0.2 mL), and the mixture was stirred at room temperature for 4 h. The mixture was quenched with 30 mL of saturated ammonium chloride aqueous solution. The resulting mixture was extracted with dichloromethane (100 mL×2). The combined organic layers were washed with 20 mL of saturated brine, dried over anhydrous sodium sulfate, filtered and concentrated under vacuum. The residue was purified by silica gel column chromatography eluted with (petroleum ether/ethyl acetate (v/v)=4/1) to give the title compound as a yellow solid (2.5 g, 81%).

$^1$H NMR (600 MHz, CDCl$_3$) δ8.26 (d, J=2.0 Hz, 1H), 7.87 (dd, J=8.4, 2.0 Hz, 1H), 7.42 (d, J=8.4 Hz, 1H), 6.76 (d,

J=8.8 Hz, 1H), 6.67 (dd, J=8.8, 3.0 Hz, 1H), 6.52 (d, J=2.9 Hz, 1H), 5.27 (s, 2H), 5.05 (s, 1H), 4.57 (s, 2H), 3.90 (s, 3H).

Step 3: methyl 3-bromo-4-((2,5-dihydroxybenzyl)(methyl)amino)benzoate

Methyl 3-bromo-4-(6-hydroxy-2H-benzo[e][1,3]oxazin-3(4H)-yl)benzoate (2.5 g, 6.9 mmol) was dissolved in tetrahydrofuran (10 mL), sodium borohydride (1.3 g, 34 mmol) was added portionwise under an ice bath, then acetic acid (20 mL) was slowly added dropwise, and the mixture was warmed to room temperature and stirred overnight. The mixture was quenched with 50 mL of saturated aqueous sodium bicarbonate solution. The resulting mixture was extracted with ethyl acetate (100 mL×2). The combined organic layers were washed with 20 mL of saturated brine, dried over anhydrous sodium sulfate, filtered and concentrated under vacuum. The residue was purified by silica gel column chromatography eluted with ($CH_2Cl_2$/MeOH (v/v)=30/1) to give the title compound as a white solid (1.6 g, 65%).
$^1$H NMR (400 MHz, $CDCl_3$) δ8.78 (s, 1H), 8.29 (d, J=1.9 Hz, 1H), 8.01 (dd, J=8.4, 1.9 Hz, 1H), 7.31 (d, J=8.4 Hz, 1H), 6.77 (d, J=8.6 Hz, 1H), 6.71 (dd, J=8.6, 2.9 Hz, 1H), 6.65 (d, J=2.8 Hz, 1H), 5.14 (s, 1H), 4.24 (s, 2H), 3.93 (s, 3H), 2.75 (s, 3H).

Step 4: methyl 2-hydroxy-10-methyl-10,11-dihydrodibenzo[b,f][1,4]oxazepine-7-carboxylate Methyl 3-bromo-4-((2,5-dihydroxybenzyl)(methy)amino)benzoate (1.6 g, 4.4 mmol), cuprous iodide (83 mg, 0.44 mmol), N,N-dimethylglycine (140 mg, 1.36 mmol) and cesium carbonate (2.8 g, 8.6 mmol) were dissolved in dioxane (50 mL) under nitrogen, and the mixture was heated to 90° C. and stirred overnight. After being cooled to room temperature, the mixture was filtered. The filter cake was washed with ethyl acetate (10 mL). The combined filtrates were concentrated under vacuum. The residue was purified by column chromatography on silica gel eluted with (petroleum ether/ethyl acetate (v/v)=4/1) to give the title compound as a yellow solid (680 mg, 55%).
MS (ESI, pos. ion) m/z: 286.2 $[M+H]^+$.

Step 5: methyl 2-((5-cyclopropyl-3-(2,6-dichlorophenyl)isoxazol-4-yl)methoxy)-10-methyl-10,11-dihydrodibenzo[b,f][1,4]oxazepine-7-carboxylate Methyl 2-hydroxy-10-methyl-10,11-dihydrodibenzo[b,f][1,4]oxazepine-7-carboxylate (680 mg, 2.4 mmol), 4-(chloromethyl)-5-cyclopropyl-3-(2,6-dichlorophenyl)isoxazole (1.0 g, 3.3 mmol) and potassium phosphate (760 mg, 3.6 mmol) were dissolved in DMF (20 mL), and the mixture was stirred at 60° C. for 3 h. The mixture was then cooled to room temperature, diluted with water (20 mL), and extracted with ethyl acetate (50 mL×2). The combined organic layers were washed with 10 mL of saturated brine, dried over anhydrous sodium sulfate, filtered and concentrated under vacuum. The residue was purified by column chromatography on silica gel eluted with (petroleum ether/ethyl acetate (v/v)=4/1) to give the title compound as a yellow oil (750 mg, 57%).

Step 6: methyl 2-((5-cyclopropyl-3-(2,6-dichlorophenyl)isoxazol-4-yl)methoxy)-10-methyl-10,11-dihydrodibenzo[b,f][1,4]oxazepine-7-carboxylic acid Methyl 2-((5-cyclopropyl-3-(2,6-dichlorophenyl)isoxazol-4-yl)methoxy)-10-methyl-10,11-dihydrodibenzo[b,f][1,4]oxazepine-7-carboxylate (750 mg, 1.4 mmol) was dissolved in a mixed solvent of tetrahydrofuran (15 mL) and water (15 mL), followed by the addition of lithium hydroxide (570 mg, 14 mmol), and the mixture was heated to 50° C. and stirred for 4 days. The mixture was then cooled to room temperature. Most of the solvent was removed under vacuum. The residue was diluted with water (20 mL). The resulting mixture was adjusted to acidity with hydrochloric acid (10 mL, 2 M). The resulting mixture was extracted with ethyl acetate (20 mL×2). The combined organic layers were washed with 10 mL of saturated brine, dried over anhydrous sodium sulfate and filtered. The filtrate was concentrated under vacuum to give the title compound as a white solid (530 mg, 73%).
MS (ESI, pos. ion) m/z: 537.3 $[M+H]^+$; and
$^1$H NMR (400 MHz, DMSO-$d_6$) δ7.60-7.46 (m, 5H), 7.09 (d, J=8.7 Hz, 1H), 6.86 (d, J=2.5 Hz, 1H), 6.73-6.68 (m, 2H), 4.83 (s, 2H), 4.51 (s, 2H), 3.01 (s, 3H), 2.44-2.34 (m, 1H), 1.19-1.06 (m, 4H).

Example 13: 8-((5-cyclopropyl-3-(2,6-dichlorophenyl)isoxazol-4-yl)methoxy)-9-fluoro-10,11-dihydrodibenzo[b,f]oxepine-3-carboxylic acid

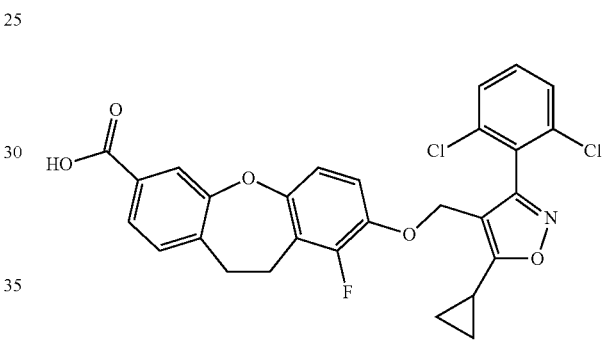

Step 1: 2-fluoro-3,6-dimethoxybenzaldehyde

A solution of 2-fluoro-1,4-dimethoxybenzene (1.0 g, 6.4 mmol) in anhydrous tetrahydrofuran (20 mL) was cooled to −78° C., and a solution of n-butyllithium in n-hexane (2.9 mL, 7.0 mmol, 2.4 M) was slowly added dropwise. The mixture was stirred at −78° C. for 1 h, and anhydrous DMF (0.54 mL, 7.0 mmol) was added dropwise. The resulting mixture was continued to stir at −78° C. for 3 h. Acetic acid (5 mL) was added dropwise to quench the reaction, and the resulting mixture was diluted with water (50 mL), and extracted with ethyl acetate (80 mL×2). The combined organic layers were washed with 20 mL of saturated brine, dried over anhydrous sodium sulfate, filtered and concentrated under vacuum. The residue was purified by column chromatography on silica gel eluted with (petroleum ether/ethyl acetate (v/v)=10/1) to give the title compound as a brown solid (800 mg, 68%).
MS (ESI, pos. ion) m/z: 185.1 $[M+H]^+$; and
$^1$H NMR (400 MHz, $CDCl_3$) δ10.44 (s, 1H), 7.20-7.15 (m, 1H), 6.71-6.68 (m, 1H), 3.90 (s, 3H), 3.89 (s, 3H).

Step 2: methyl 3-bromo-4-(2-fluoro-3,6-dimethoxystyryl)benzoate

Using 2-fluoro-3,6-dimethoxybenzaldehyde (2.0 g, 10.9 mmol) and menthyl 3-bromo-4-((diethoxyphosphoryl)methyl)benzoate (6.0 g, 16.4 mmol) as starting materials, the title compound was prepared according to the procedure described in step 3 of example 1 as a yellow oil (2.7 g, 65%).

Step 3: methyl 3-bromo-4-(2-fluoro-3,6-dimethoxyphenethyl)benzoate

Using methyl 3-bromo-4-(2-fluoro-3,6-dimethoxystyryl)benzoate (2.5 g, 6.3 mmol) as a starting material, the title compound was prepared according to the procedure described in step 4 of example 1 as a yellow solid (1.9 g, 77%).

Step 4: methyl 3-bromo-4-(2-fluoro-3,6-dihydroxyphenethyl)benzoate

Methyl 3-bromo-4-(2-fluoro-3,6-dimethoxyphenethyl)benzoate (1.9 g, 4.6 mmol) was dissolved in dry dichloromethane (50 mL) under nitrogen. The mixture was cooled to −78° C., and a solution of boron tribromide in methylene chloride (18.6 mL, 18.6 mmol, 1 M)) was added dropwise. The resulting mixture was allowed to warm to room temperature and stirred overnight. The mixture was quenched with 5 mL of methanol, and diluted with dichloromethane (30 mL). The organic layer was washed equentially with 10 mL of water and 10 mL of saturated brine, dried over anhydrous sodium sulfate, filtered, and concentrated under vacuum to give the title compound as a yellow solid (1.8 g, 100%).

Step 5: methyl 9-fluoro-8-hydroxy-10,11-dihydrodibenzo[b,f]oxepine-3-carboxylate Using methyl 3-bromo-4-(2-fluoro-3,6-dihydroxyphenethyl)benzoate (1.9 g, 5.1 mmol) as a starting material, the title compound vas prepared according to the procedure described in step 6 of example 1 as a yellow solid (100 mg, 7%).
$^1$H NMR (400 MHz, CDCl$_3$) δ7.82 (s, 1H), 7.76 (dd, J=7.8, 1.6 Hz, 1H), 7.26 (d, J=7.9 Hz, 1H), 6.94 (dd, J=8.9, 1.8 Hz, 1H), 6.84-6.79 (m, 1H), 4.96 (d, J=3.8 Hz, 1H), 3.93 (s, 3H), 3.25-3.21 (m, 2H), 3.17-3.09 (m, 2H).

Step 6: methyl 8-((5-cyclopropyl-3-(2,6-dichlorophenyl)isoxazol-4-yl)methoxy)-9-fluoro-10,11-dihydrodibenzo[b,f]oxepine-3-carboxylate Using methyl 9-fluoro-8-hydroxy-10,11-dihydrodibenzo[b,f]oxepine-3-carboxylate (100 mg, 0.35 mmol) and 4-(chloromethyl)-5-cyclopropyl-3-(2,6-dichlorophenyl)isoxazole (150 mg, 0.49 mmol) as starting materials, the title compound was prepared according to the procedure described in step 7 of example 1 as a yellow solid (150 mg, 78%).

Step 7: 8-((5-cyclopropyl-3-(2,6-dichlorophenyl)isoxazol-4-yl)methoxy)-9-fluoro-10,11-dihydrodibenzo[b,f]oxepine-3-carboxylic acid Using methyl 8-((5-cyclopropyl-3-(2,6-dichlorophenyl)isoxazol-4-yl)methoxy)-9-fluoro-10,11-dihydrodibenzo[b,f]oxepine-3-carboxylate (150 mg, 0.27 mmol) as a starting material, the title compound was prepared according to the procedure described in step 8 of example 1 as a yellow solid (120 mg, 83%).
MS (ESI, pos. ion) m/z: 539.7 [M+H]$^+$; and
$^1$H NMR (400 MHz, DMSO-d$_6$) δ12.90 (s, 1H), 7.68-7.67 (m, 2H), 7.59-7.44 (m, 3H), 7.38-7.36 (m, 1H), 6.97-6.88 (m, 2H), 4.90 (s, 2H), 3.15-3.13 (m, 2H), 2.95-2.94 (m, 2H), 2.43-2.41 (m, 1H), 1.18-1.07 (m, 4H).

Example 14: 2-((5-cyclopropyl-3-(2,6-dichlorophenyl)isoxazol-4-yl)methoxy)-10,11-dihydrobenzo[6,7]oxepino[3,2-d]pyrimidine-7-carboxylic acid

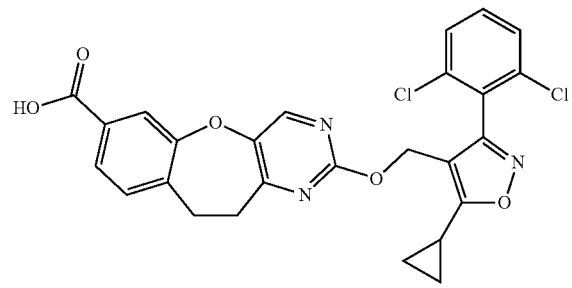 [SMILES: O=C(O)c1ccc2c(c1)Oc1cnc(OCc3c(-c4c(Cl)cccc4Cl)noc3C3CC3)nc1CC2]

Step 1: 2-chloro-5-methoxy-4-methylpyrimidin 2,4-Dichloro-5-methoxypyrimidine (5.0 g, 28 mmol), trimethylboroxine (9 mL, 32 mmol), trans-dichlorobis(triphenyl-phosphine)palladium(II) (2.0 g, 2.8 mmol) and potassium phosphoric acid (11.8 g, 55.8 mmol) were dissolved in tetrahydrofuran (50 mL), and the mixture was heated to reflux and stirred overnight. The mixture was cooled to room temperature, diluted with ethyl acetate (30 mL) and filtered. The filter cake was washed with ethyl acetate (30 mL). The organic layer was washed with saturated brine (30 mL), dried over anhydrous sodium sulfate, filtered, and concentrated under vacuum. The residue was purified by column chromatography on silica gel eluted with (petroleum ether/ethyl acetate (v/v)=10/1) to give the title compound as a yellow solid (3.8 g, 87%).
MS (ESI, pos. ion) m/z: 159.0 [M+H]$^+$.

Step 2: 2-chloro-5-methoxypyrimidine-4-carbaldehyde

A solution of 2-chloro-5-methoxy-4-methylpyrimidine (3.8 g, 24 mmol) and selenium dioxide (11 g, 97 mmol) in 1,4-dioxane (100 mL) was heated to reflux and stirred overnight. The reaction solution was cooled to room temperature and filtered. The filter cake washed with ethyl acetate (20 mL), and the filtrate was concentrated under vacuum. The residue was purified by column chromatography on silica gel eluted with (petroleum ether/ethyl acetate (v/v)=3/1) to give the title compound as a yellow solid (2.2 g, 52%).
$^1$H NMR (400 MHz, CDCl$_3$) δ: 10.19 (s, 1H), 8.64 (s, 1H), 4.11 (s, 3H).

Step 3: methyl 3-bromo-4-(2-(2-chloro-5-methoxypyrimidin-4-yl)vinyl)benzoate

Using 2-chloro-5-methoxypyrimidin-4-carbaldehyde (3.2 g, 19 mmol) and methyl 3-bromo-4-((diethoxyphosphoryl)methyl)benzoate (10.0 g, 27 mmol) as starting materials, the title compound was prepared according to the procedure described in step 3 of example 1 as a yellow solid (7.0 g, 98%).

Step 4: methyl 3-bromo-4-(2-(2-chloro-5-methoxy-pyrimidin-4-yl)ethyl)benzoate Using methyl 3-bromo-4-(2-(2-chloro-5-methoxypyrimidin-4-yl)vinyl)benzoate (7.0 g, 18.3 mmol) as a starting material, the title compound was prepared according to the procedure described in step 4 of example 1 as a pale yellow solid (3.0 g, 43%).

Step 5: methyl 3-bromo-4-(2-(2-chloro-5-hydroxy-pyrimidin-4-yl)ethyl)benzoate Using methyl 3-bromo-4-(2-(2-chloro-5-methoxypyrimidin-4-yl)ethyl)benzoate (3.0 g, 7.8 mmol) as a starting material, the title compound was prepared according to the procedure described in step 4 of example 13 as a pale yellow solid (2.7 g, 93%).

Step 6: methyl 2-chloro-10,11-dihydrobenzo[6,7]oxepino[3,2-d]pyrimidine-7-carboxylate Using methyl 3-bromo-4-(2-(2-chloro-5-hydroxypyrimidin-4-yl)ethyl)benzoate (1.4 g, 3.8 mmol) as a starting material, the title compound was prepared according to the procedure described in step 6 of example 1 as a pale yellow solid (510 mg, 47%).
MS (ESI, pos. ion) m/z: 291.1 [M+H]$^+$.

Step 7: 2-methoxy-10,11-dihydrobenzo[6,7]oxepino[3,2-d]pyrimidine-7-carboxylic acid Methyl 2-chloro-10,11-dihydrobenzo[6,7]oxepino[3,2-d]pyrimidine-7-carboxylate (500 mg, 1.7 mmol) and sodium methoxide (371 mg, 6.9 mmol) were dissolved in anhydrous methanol (50 mL), and the mixture was heated to reflux and stirred overnight. The mixture was then cooled to room temperature, and the solvent was removed under vacuum. The residue was diluted with water (50 mL). The resulting mixture was adjusted to acidity with hydrochloric acid (5 mL, 2 M). The resulting mixture was extracted with ethyl acetate (50 mL×3). The combined organic layers were washed with 10 mL of saturated brine, dried over anhydrous sodium sulfate and filtered. The residue was purified by column chromatography on silica gel eluted with (petroleum ether/ethyl acetate (v/v)=2/1) to give the title compound as a white solid (400 mg, 85%).

Step 8: 2-hydroxy-10,11-dihydrobenzo[6,7]oxepino[3,2-d]pyrimidine-7-carboxylic acid A mixture of 2-methoxy-10,11-dihydrobenzo[6,7]oxepino[3,2-d]pyrimidine-7-carboxylic acid (46 mg, 0.17 mmol) in concentrated hydrochloric acid (5 mL) was heated to reflux and stirred overnight. After being cooled to room temperature, the mixture was filtered. The filter cake was washed with water (10 mL), and dried in vacuum to give the title compound as a yellow-brown solid (30 mg, 66%).
MS (ESI, pos. ion) m/z: 259.0 [M+H]$^+$.

Step 9: methyl 2-hydroxy-10,11-dihydrobenzo[6,7]oxepino[3,2-d]pyrimidine-7-carboxylate To a solution of methyl 2-hydroxy-10,11-dihydrobenzo[6,7]oxepino[3,2-]pyrimidine-7-carboxylic acid in methanol (5 mL) was slowly added dropwise thionyl chloride (0.012 mL, 0.17 mmol) in an ice bath, and the mixture was warmed to reflux and stirred for 4 h. The mixture was cooled to room temperature, and concentrated in vacuum. The residue was purified by column chromatography on silica gel eluted with (CH$_2$Cl$_2$/MeOH (v/v)=10/1) to give the title compound as a yellow solid (20 mg, 63%).

Step 10: methyl 2-((5-cyclopropyl-3-(2,6-dichlorophenyl)isoxazol-4-yl)methoxy)-10,11-dihydrobenzo[6,7]oxepino[3,2-d]pyrimidine-7-carboxylate Using methyl 2-hydroxy-10,11-dihydrobenzo[6,7]oxepino[3,2-d]pyrimidine-7-carboxylate (20 mg, 0.073 mmol) and 4-(chloromethyl)-5-cyclopropyl-3-(2,6-dichlorophenyl)isoxazole (33 mg, 0.11 mmol) as starting materials, the title compound was prepared according to the procedure described in step 7 of example 1 as a yellow solid (11 mg, 28%).
MS (ESI, pos. ion) m/z: 538.3 [M+H]$^+$.

Step 11: 2-((5-cyclopropyl-3-(2,6-dichlorophenyl)isoxazol-4-yl)methoxy)-10,11-dihydrobenzo[6,7]oxepino[3,2-d]pyrimidine-7-carboxylic acid Using methyl 2-((5-cyclopropyl-3-(2,6-dichlorophenyl)isoxazol-4-yl)methoxy)-10,11-dihydrobenzo[6,7]oxepino[3,2-d]pyrimidine-7-carboxylate (80 mg, 0.15 mmol) as a starting material, the title compound was prepared according to the procedure described in step 8 of example 1 as a yellow solid (46 mg, 59%).
MS (ESI, pos. ion) m/z: 524.3 [M+H]$^+$; and
$^1$H NMR (600 MHz, CDCl$_3$) δ8.31 (s, 1H), 7.89 (d, J=0.9 Hz, 1H), 7.88 (d, J=7.8 Hz, 1H), 7.41-7.23 (m, 4H), 5.18 (s, 2H), 3.27-3.22 (m, 2H), 3.16-3.12 (m, 2H), 2.39-2.35 (m, 1H), 1.30-1.29 (m, 2H), 1.17-1.15 (m, 2H).

Example 15: 7-((5-cyclopropyl-3-(2,6-dichlorophenyl)isoxazol-4-yl)methoxy)-10,11-dihydrodibenzo[b,f]oxepine-2-carboxylic acid

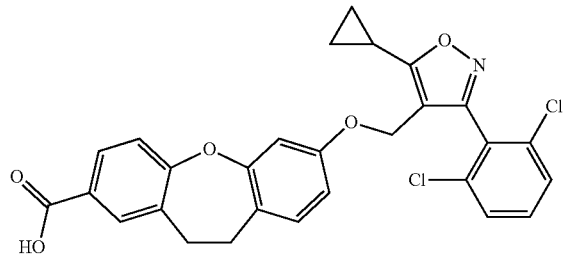 [SMILES: O=C(O)c1ccc2c(c1)CCc1ccc(OCc3c(-c4c(Cl)cccc4Cl)noc3C3CC3)cc1O2]

Step 1: methyl 4-bromo-3-(bromomethyl)benzoate

Using methyl 4-bromo-3-methylbenzoate (16.6 g, 72.5 mmol) as a starting material, the title compound was prepared according to the procedure described in step 1 of example 1 as a white solid (21.0 g, 91%).
$^1$H NMR (400 MHz, CDCl$_3$) δ8.14 (d, J=1.8 Hz, 1H), 7.84 (dd, J=8.3, 1.9 Hz, 1H), 7.69 (d, J=8.3 Hz, 1H), 4.64 (s, 2H), 3.95 (s, 3H).

Step 2: methyl 4-bromo-3-((diethoxyphosphoryl)methyl)benzoate

Using methyl 4-bromo-3-(bromomethyl)benzoate (6.8 g, 22 mmol) as a starting material, the title compound was prepared according to the procedure described in step 2 of example 1 as a pale yellow oil (8.0 g, 99%).

Step 3: methyl 3-(2,4-bis((tert-butyldimethylsilyl)oxy)styryl)-4-bromobenzoate

Using methyl 4-bromo-3-((diethoxyphosphoryl)methyl)benzoate (10 g, 27 mmol) and 2,4-bis((tert-butyl(dimethyl)silyl)oxy)benzaldehyde (9.3 g, 25 mmol) as starting materials, the title compound was prepared according to the procedure described in step 3 of example 1 as a yellow oil (8.1 g, 55%).
$^1$H NMR (400 MHz, CDCl$_3$) δ8.36 (d, J=1.9 Hz, 1H), 7.73 (dd, J=8.3, 2.0 Hz, 1H), 7.66 (d, J=8.3 Hz, 1H), 7.57 (d, J=8.5 Hz, 1H), 7.52 (d, J=16.4 Hz, 1H), 7.30 (d, J=10.7 Hz, 1H), 6.55 (dd, J=8.5, 2.3 Hz, 1H), 6.38 (d, J=2.3 Hz, 1H), 3.95 (s, 3H), 1.10 (s, 9H), 1.02 (s, 9H), 0.28 (s, 6H), 0.25 (s, 6H).

Step 4: methyl 3-(2,4-bis((tert-butyldimethylsilyl)oxy)phenethyl)-4-bromobenzoate Using methyl 3-(2,4-bis((tert-butyldimethylsilyl)oxy)styryl)-4-bromobenzoate (8.1 g, 14 mmol) as a starting material, the title compound was prepared according to the procedure described in step 4 of example 1 as a pale yellow solid (7.5 g, 92%).
$^1$H NMR (400 MHz, CDCl$_3$) δ7.86-7.80 (m, 2H), 7.74-7.69 (m, 1H), 7.64-7.59 (m, 1H), 6.90 (d, J=8.1 Hz, 1H), 6.37-6.34 (m, 1H), 3.91 (s, 3H), 3.06-2.98 (m, 2H), 2.88-2.81 (m, 2H), 1.05 (s, 9H), 1.00 (s, 9H), 0.28 (s, 6H), 0.20 (s, 6H).

Step 5: methyl 4-bromo-3-(2,4-dihydroxyphenethyl)benzoate

Using methyl 3-(2,4-bis((tert-butyldimethylsilyl)oxy)phenethyl)-4-bromobenzoate (8.0 g, 13.8 mmol) as a starting material, the title compound was prepared according to the procedure described in step 5 of example 1 as a yellow oil (4.0 g, 82%).
MS (ESI, pos. ion) m/z: 351.0 [M+H]$^+$.

Step 6: methyl 7-hydroxy-10,11-dihydrodibenzo[b,f]oxepine-2-carboxylate

Using methyl 4-bromo-3-(2,4-dihydroxyphenethyl)benzoate (2.0 g, 5.7 mmol) as a starting material, the title compound was prepared according to the procedure described in step 6 of example 1 as a yellow oil (680 mg, 44%).
$^1$H NMR (400 MHz, DMSO-d$_6$) δ9.50 (s, 1H), 7.81 (d, J=2.0 Hz, 1H), 7.77 (dd, J=8.4, 2.1 Hz, 1H), 7.24 (d, J=8.4 Hz, 1H), 6.99 (d, J=8.3 Hz, 1H), 6.59 (d, J=2.4 Hz, 1H), 6.51 (dd, J=8.2, 2.4 Hz, 1H), 3.82 (s, 3H), 3.11-3.05 (m, 2H), 2.99-2.93 (m, 2H).

Step 7: methyl 7-((5-cyclopropyl-3-(2,6-dichlorophenyl)isoxazol-4-yl)methoxy)-10,11-dihydrodibenzo[b,f]oxepine-2-carboxylate Using methyl 7-hydroxy-10,11-dihydrodibenzo[b,f]oxepine-2-carboxylate (680 mg, 2.5 mmol) and 4-(chloromethyl)-5-cyclopropyl-3-(2,6-dichlorophenyl)isoxazole (840 mg, 2.8 mmol) as starting materials, the title compound was prepared according to the procedure described in step 7 of example 1 as a yellow oil (1.1 g, 82%).

Step 8: 7-((5-cyclopropyl-3-(2,6-dichlorophenyl)isoxazol-4-yl)methoxy)-10,11-dihydrodibenzo[b,f]oxepine-2-carboxylic acid Using methyl 7-((5-cyclopropyl-3-(2,6-dichlorophenyl)isoxazol-4-yl)methoxy)-10,11-dihydrodibenzo[b,f]oxepine-2-carboxylate (1.1 g, 2.1 mmol) as a starting material, the title compound was prepared according to the procedure described in step 8 of example 1 as a white solid (400 mg, 40%).
MS (ESI, neg. ion) m/z: 520.2 [M−H]$^-$; and
$^1$H NMR (400 MHz, DMSO-d$_6$) δ7.83-7.73 (m, 2H), 7.62-7.56 (m, 2H), 7.55-7.48 (m, 1H), 7.21 (d, J=8.3 Hz, 1H), 7.05 (d, J=8.4 Hz, 1H), 6.65 (d, J=2.5 Hz, 1H), 6.53 (dd, J=8.4, 2.5 Hz, 1H), 4.86 (s, 2H), 3.10-3.03 (m, 2H), 3.01-2.94 (m, 2H), 2.47-2.40 (m, 1H), 1.21-1.08 (m, 4H).

Example 16: 3-((5-cyclopropyl-3-(2,6-dichlorophenyl)isoxazol-4-yl)methoxy)-5,6-dihydrobenzo[6,7]oxepino[2,3-b]pyridine-9-carboxylic acid

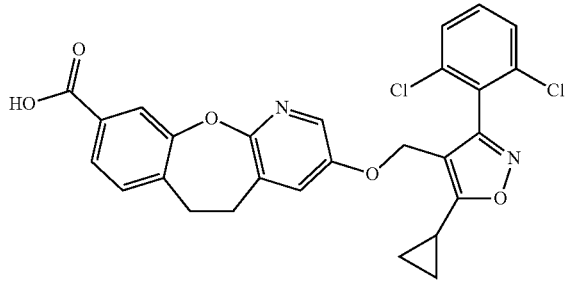 [SMILES: O=C(O)c1ccc2c(c1)Oc1ncc(OCc3c(-c4c(Cl)cccc4Cl)noc3C3CC3)cc1CC2]

Step 1: methyl 4-(2-(5-bromo-2-chloropyridin-3-yl)vinyl)-3-(methoxymethoxy) benzoate Using methyl 4-(diethoxyphosphorylmethyl)-3-(methoxymethoxy)benzoate (2.0 g, 5.78 mmol) and 5-bromo-2-chloropyridine-3-carbaldehyde (1.53 g, 6.94 mmol) (See the synthesis of intermediate 110 of step 2 on page 180 of WO2011103202) as starting materials, the title compound was prepared according to the procedure described in step 6 of example 3 as a yellow oil (2.1 g, 88%).

Step 2: methyl 4-(2-(5-bromo-6-chloropyridin-3-yl)ethyl)-3-(methoxymethoxy) benzoate Using methyl 4-(2-(5-bromo-2-chloropyridin-3-yl)vinyl)-3-(methoxymethoxy)benzoate (400 mg, 0.97 mmol) as a starting material, the title compound was prepared according to the procedure described in step 7 of example 3 as a colorless oil (320 mg, 80%).

Step 3: methyl 4-(2-(5-bromo-6-chloropyridin-3-yl)ethyl)-3-hydroxybenzoate

Using methyl 4-(2-(5-bromo-6-chloropyridin-3-yl)ethyl)-3-(methoxymethoxy)benzoate (450 mg, 1.1 mmol) as a starting material, the title compound was prepared according to the procedure described in step 8 of example 3 as a pale yellow solid (300 mg, 75%).

Step 4: methyl 3-bromo-5,6-dihydrobenzo[6,7]ox-epino[2,3-b]pyridine-9-carboxylate Cuprous chloride (26 mg, 0.26 mmol), 2,2,6,6-tetramethyl-3,5-heptane dione (10 mg, 0.05 mmol), cesium carbonate (351 mg, 1.1 mmol) and methyl 4-(2-(5-bromo-6-chloropyridin-3-yl) ethyl)-3-(methoxymethoxy)benzoate (200 mg, 0.54 mmol) were dissolved in N-methylpyrrolidone (5 mL) under nitrogen. The mixture was heated to 120° C. and stirred overnight. The mixture was cooled to room temperature, and diluted with water (20 mL). The resulting mixture was extracted with ethyl acetate (30 mL×2). The combined organic layers were washed with 20 mL of saturated brine, dried over anhydrous sodium sulfate, filtered and concentrated under vacuum. The residue was purified by column chromatography on silica gel eluted with (petroleum ether/ethyl acetate (v/v)=2/1) to give the title compound as a pale yellow solid (100 mg, 55%).

Step 5: methyl 3-hydroxy-5,6-dihydrobenzo[6,7]oxepino[2,3-b]pyridine-9-carboxylate Cuprous iodide (6 mg, 0.03 mmol), N,N-dimethylglycine (14 mg, 0.16 mmol), potassium phosphate (70 mg, 0.33 mmol) and methyl 3-bromo-5,6-dihydrobenzo[6,7]oxepino[2,3-b]pyridine-9-carboxylate (100 mg, 0.3 mmol) were dissolved in water (5 mL) under nitrogen. The reaction mixture was heated to 180° C. and irradiated in the microwave for 30 min. The reaction mixture was then cooled to room temperature and diluted with 1 M hydrochloric acid (10 mL). The resulting mixture was extracted with ethyl acetate (30 mL×3). The combined organic layers were washed with 10 mL of saturated brine, dried over anhydrous sodium sulfate and filtered. The residue was purified by column chromatography on silica gel eluted with (petroleum ether/ethyl acetate (v/v)=5/1) to give the title compound as a pale yellow solid (56 mg, 69%).

MS (ESI, pos. ion) m/z: 272.1 [M+H]$^+$.

Step 6: methyl 3-((5-cyclopropyl-3-(2,6-dichlorophenyl)isoxazol-4-yl)methoxy)-5,6-dihydrobenzo[6,7]oxepino[2,3-b]pyridine-9-carboxylate Using methyl 3-hydroxy-5,6-dihydrobenzo[6,7]oxepino[2,3-b]pyridine-9-carboxylate (65 mg, 0.24 mmol) and 4-(chloromethyl)-5-cyclopropyl-3-(2,6-dichlorophenyl)isoxazole (102 mg, 0.33 mmol) as starting materials, the title compound was prepared according to the procedure described in step 11 of example 3 as a pale yellow solid (70 mg, 54%).

MS (ESI, pos. ion) m/z: 537.0 [M+H]$^+$.

Step 7: 3-((5-cyclopropyl-3-(2,6-dichlorophenyl)isoxazol-4-yl)methoxy)-5,6-dihydrobenzo[6,7]oxepino[2,3-b]pyridine-9-carboxylic acid Using methyl 3-((5-cyclopropyl-3-(2,6-dichlorophenyl)isoxazol-4-yl)methoxy)-5,6-dihydrobenzo[6,7]oxepino[2,3-b]pyridine-9-carboxylate (70 mg, 0.13 mmol) as a starting material, the title compound was prepared according to the procedure described in step 12 of example 3 as a white solid (45 mg, 66%).

MS (ESI, pos. ion) m/z: 523.2 [M+H]$^+$; and $^1$H NMR (400 MHz, DMSO-d$_6$) δ7.72-7.57 (m, 5H), 7.56-7.48 (m, 1H), 7.35 (d, J=7.8 Hz, 1H), 7.25 (d, J=2.8 Hz, 1H), 4.93 (s, 2H), 3.17-3.10 (m, 2H), 3.01-2.98 (m, 2H), 2.47-2.41 (m, 1H), 1.18-1.15 (m, 2H), 1.14-1.12 (m, 2H).

Example 17: 2-((1-(2,6-dichlorophenyl)-4-isopropyl-1H-pyrazol-5-yl)methoxy)-10,11-dihydrobenzo[6,7]oxepino[3,2-b]pyridine-7-carboxylic acid

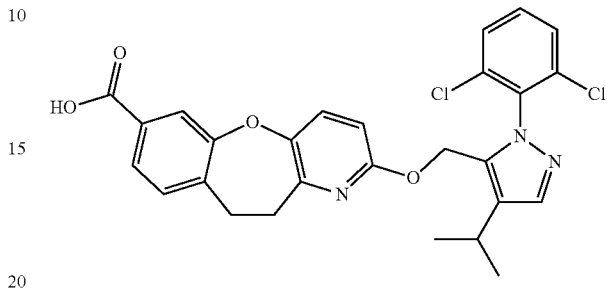

Step 1: 5-(chloromethyl)-1-(2,6-dichlorophenyl)-4-isopropyl-1H-pyrazole

To a mixture of 1H-benzotriazole (350 mg, 3.0 mmol) in dichloromethane (10 mL) was slowly added dropwise thionyl chloride (0.21 mL, 3.0 mmol) in an ice bath, and the mixture was warmed to room temperature and stirred for 1 h. The mixture above was added dropwise into a solution of (1-(2,6-dichlorophenyl)-4-isopropyl-1H-pyrazol-5-yl)methanol (560 mg, 2.0 mmol) (See the synthetic method described in *Bioorg. Med. Chem. Lett.*, 2015, 25(2), 280-284) in dichloromethane (10 mL). The resulting mixture was stirred at room temperature overnight. The mixture was diluted with water (20 mL), and the resulting mixture was extracted with dichlormethane (30 mL×2). The combined organic layers were washed with 20 mL of saturated brine, dried over anhydrous sodium sulfate, filtered and concentrated under vacuum. The residue was purified by column chromatography on silica gel eluted with (petroleum ether/ethyl acetate (v/v)=20/1) to give the title compound as a yellow solid (530 mg, 89%).

Step 2: methyl 2-((1-(2,6-dichlorophenyl)-4-isopropyl-1H-pyrazol-5-yl)methoxy)-10,11-dihydrobenzo[6,7]oxepino[3,2-b]pyridine-7-carboxylate Using methyl 2-oxo-1,2,10,11-tetrahydrobenzo[6,7]oxepino[3,2-b]pyridine-7-carboxylate (200 mg, 0.73 mmol) and 5-(chloromethyl)-1-(2,6-dichlorophenyl)-4-isopropyl-1H-pyrazole (150 mg, 0.49 mmol) as starting materials, the title compound was prepared according to the procedure described in step 11 of example 3 as a yellow solid (250 mg, 94%).

MS (ESI, pos. ion) m/z: 538.1 [M+H]$^+$.

Step 3: 2-((1-(2,6-dichlorophenyl)-4-isopropyl-1H-pyrazol-5-yl)methoxy)-10,11-dihydrobenzo[6,7]oxepino[3,2-b]pyridine-7-carboxylic acid Using methyl 2-((1-(2,6-dichlorophenyl)-4-isopropyl-1H-pyrazol-5-yl)methoxy)-10,11-dihydrobenzo[6,7]oxepino[3,2-b]pyridine-7-carboxylate (250 mg, 0.46 mmol) as a starting material, the title compound was prepared according to the procedure described in step 12 of example 3 as a white solid (160 mg, 66%).

MS (ESI, pos. ion) m/z: 524.4 [M+H]+; and

¹H NMR (400 MHz, DMSO-d₆) δ13.02 (s, 1H), 7.71-7.67 (m, 3H), 7.56-7.53 (m, 3H), 7.43-7.37 (m, 2H), 6.41 (d, J=8.7 Hz, 1H), 5.19 (s, 2H), 3.16-3.10 (m, 3H), 2.99-2.93 (m, 2H), 1.23 (d, J=6.9 Hz, 6H).

Example 18: 8-((5-cyclopropyl-3-(2,6-dichlorophenyl)isoxazol-4-yl)methoxy)-10,11-dihydro-5H-dibenzo[a,d][7]annulene-3-carboxylic acid

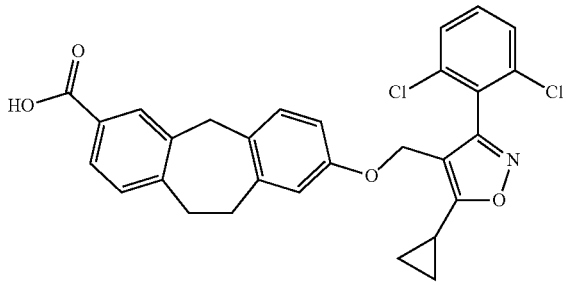 [SMILES: O=C(O)c1ccc2c(c1)Cc1ccc(OCc3c(-c4c(Cl)cccc4Cl)noc3C3CC3)cc1CC2]

Step 1: 8-methoxy-10,11-dihydro-5H-dibenzo[a,d][7]annulene-3-carboxylic acid To a mixture of 8-methoxy-5-oxo-10,11-dihydro-5H-dibenzo[a,d][7]annulene-3-carboxylic acid (300 mg, 1.1 mmol) in trifluoroactic acid (8 mL) was added dropwise triethyisilane (0.85 mL, 5.3 mmol), and the mixture was stirred at room temperature overnight. The mixture was diluted with water (20 mL). The resulting mixture was extracted with dichloromethane (30 mL×2). The combined organic layers were washed with 20 mL of saturated brine, dried over anhydrous sodium sulfate, filtered and concentrated under vacuum. The residue was purified by column chromatography on silica gel eluted with (CH₂Cl₂/MeOH (v/v)=50/1) to give the title compound as a white solid (200 mg, 70%).

MS (ESI, pos. ion) m/z: 269.2 [M+H]+.

Step 2: 8-hydroxy-10,11-dihydro-5H-dibenzo[a,d][7]annulene-3-carboxylic acid Using 8-methoxy-10,11-dihydro-5H-dibenzo[a,d][7]annulene-3-carboxylic acid (200 mg, 0.74 mmol) as a starting material, the title compound was prepared according to the procedure described in step 4 of example 9 as a pale yellow solid (170 mg, 90%).

MS (ESI, pos. ion) m/z: 255.1 [M+H]+.

Step 3: methyl 8-hydroxy-10,11-dihydro-5H-dibenzo[a,d][7]annulene-3-carboxylate To a mixture of 8-hydroxy-10,11-dihydro-5H-dibenzo[a,d][7]annulene-3-carboxylic acid (190 mg, 0.75 mmol) in methanol (20 mL) was added dropwise thionyl chloride (0.1 mL, 1.0 mol), and the mixture was heated to 80° C. and stirred for 4 h. After being cooled to room temperature, the mixture was quenched with 20 mL of water, and the resulting mixture was extracted with ethyl acetate (30 mL×2). The combined organic layers were washed with 20 mL of saturated brine, dried over anhydrous sodium sulfate, filtered and concentrated under vacuum to give the title compound as a pale yellow solid (190 mg, 95%).

MS (ESI, pos. ion) m/z: 269.2 [M+H]+.

Step 4: methyl 8-((5-cyclopropyl-3-(2,6-dichlorophenyl)isoxazol-4-yl)methoxy)-10,11-dihydro-5H-dibenzo[a,d][7]annulene-3-carboxylate Using methyl 8-hydroxy-10,11-dihydro-5H-dibenzo[a,d][7]annulene-3-carboxylate (65 mg, 0.24 mmol) and 4-(chloromethyl)-5-cyclopropyl-3-(2,6-dichlorophenyl)isoxazole (102 mg, 0.34 mmol) as starting materials, the title compound was prepared according to the procedure described in step 5 of example 9 as a pale yellow solid (110 mg, 85%).

Step 5: 8-((5-cyclopropyl-3-(2,6-dichlorophenyl)isoxazol-4-yl)methoxy)-10,11-dihydro-5H-dibenzo[a,d][7]annulene-3-carboxylic acid Using methyl 8-((5-cyclopropyl-3-(2,6-dichlorophenyl)isoxazol-4-yl)methoxy)-10,11-dihydro-5H-dibenzo[a,d][7]annulene-3-carboxylate (110 mg, 0.21 mmol) as a starting material, the title compound was prepared according to the procedure described in step 6 of example 9 a white solid (90 mg, 84%).

MS (ESI, neg. ion) m/z: 518.2 [M−H]−; and

¹H NMR (600 MHz, CDCl₃) δ7.91 (s, 1H), 7.86 (d, J=7.8 Hz, 1H), 7.39-7.37 (m, 2H), 7.32-7.29 (m, 1H), 7.21 (d, J=7.9 Hz, 1H), 7.06 (d, J=7.9 Hz, 1H), 6.60-6.58 (m, 2H), 4.75 (s, 2H), 4.10 (s, 2H), 3.23-3.21 (m, 2H), 3.13-3.11 (m, 2H), 2.19-2.14 (m, 1H), 1.15-1.10 (m, 2H), 0.94-0.83 (m, 2H).

Example 19: 2-((5-cyclopropyl-3-(2,6-dichlorophenyl)isoxazol-4-yl)methoxy)-N-(methylsulfonyl)-10,11-dihydrobenzo[6,7]oxepino[3,2-b]pyridine-7-carboxamide

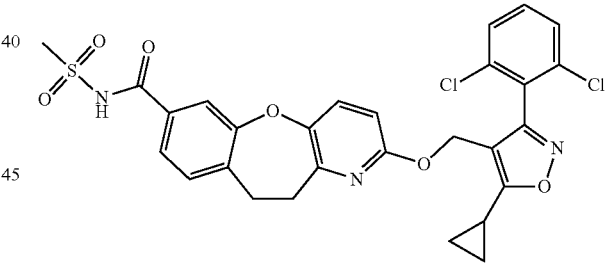

Step 1: 2-((5-cyclopropyl-3-(2,6-dichlorophenyl)isoxazol-4-yl)methoxy)-N-(methylsulfonyl)-10,11-dihydrobenzo[6,7]oxepino[3,2-b]pyridine-7-carboxamide 2-((5-Cyclopropyl-3-(2,6-dichlorophenyl)isoxazol-4-yl)methoxy)-10,11-dihydrobenzo[6,7]oxepino[3,2-b]pyridine-7-carboxylic acid (750 mg, 1.4 mmol), methanesulfonamide (170 mg, 1.8 mmol), 4-dimethylaminopyridine (230 mg, 1.9 mmol) and 1-(3-dimethylaminopropyl)-3-ethylcarbodiimide hydrochloride (360 mg, 1.9 mmol) were dissolved in dichloromethane (30 mL), and the reaction mixture was stirred at room temperature overnight. The solvent was removed under vacuum. The residue was purified by column chromatography on silica gel eluted with (CH₂Cl₂/MeOH (v/v)=30/1) to give the title compound as a white solid (120 mg, 14%).

MS (ESI, pos. ion) m/z: 599.8 [M+H]⁺; and

¹H NMR (600 MHz, CDCl₃) δ7.66 (d, J=1.4 Hz, 1H), 7.58 (dd, J=7.9, 1.5 Hz, 1H), 7.36-7.24 (m, 5H), 6.42 (d, J=8.7 Hz, 1H), 5.13 (s, 2H), 4.80 (s, 1H), 3.43 (s, 3H), 3.22-3.17 (m, 2H), 3.13-3.07 (m, 2H), 2.35-2.31 (m, 1H), 1.28-1.25 (m, 2H), 1.17-1.12 (m, 2H).

Example 20: 8-((5-cyclopropyl-3-(2,6-dichlorophenyl)isoxazol-4-yl)methoxy)-10,11-dihydrodibenzo[b,f]oxepine-2-carboxylic acid

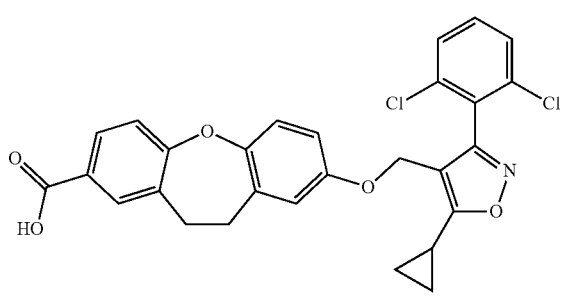 [SMILES: O=C(O)c1ccc2c(c1)CCc1cc(OCc3c(-c4c(Cl)cccc4Cl)noc3C3CC3)ccc1O2]

Using methyl 4-bromo-3-methylbenzoate as a starting material, the title compound was prepared according to the procedures described in example 1 as a white solid (25 mg).

MS (ESI, pos. ion) m/z: 521.7 [M+H]⁺; and

¹H NMR (400 MHz, DMSO-d₆) δ7.79-7.72 (m, 2H), 7.64-7.57 (m, 2H), 7.55-7.49 (m, 1H), 7.20 (d, J=8.3 Hz, 1H), 7.03 (d, J=8.7 Hz, 1H), 6.68 (s, 1H), 6.65-6.58 (m, 1H), 4.82 (s, 2H), 3.11-3.05 (m, 2H), 3.02-2.97 (m, 2H), 2.44-2.38 (m, 1H), 1.27-1.21 (m, 4H).

Example 21: 8-((5-cyclopropyl-3-(2,6-dichlorophenyl)isoxazol-4-yl)methoxy)-5-oxo-10,11-dihydro-5H-dibenzo[a,d][7]annulene-2-carboxylic acid

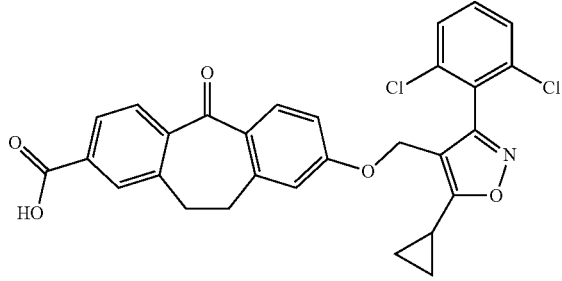 [SMILES: O=C(O)c1ccc2c(c1)CCc1cc(OCc3c(-c4c(Cl)cccc4Cl)noc3C3CC3)ccc1C2=O]

Using dimethyl 2-methylterephthalate as a starting material, the title compound was prepared according to the procedures described in example 2 as a white solid (180 mg).

MS (ESI, pos. ion) m/z: 534.3 [M+H]⁺; and

¹H NMR (400 MHz, DMSO-d₆) δ7.95-7.85 (m, 4H), 7.63-7.57 (m, 2H), 7.55-7.49 (m, 1H), 6.84-6.76 (m, 2H), 4.98 (s, 2H), 3.18-3.13 (m, 2H), 3.12-3.07 (m, 2H), 2.49-2.43 (m, 1H), 1.19-1.12 (m, 4H).

Example 22: 8-((5-cyclopropyl-3-(2,6-dichlorophenyl)isoxazol-4-yl)methoxy)-11H-dibenzo[b,f][1,4]oxathiepine-2-carboxylic acid-10,10-dioxide

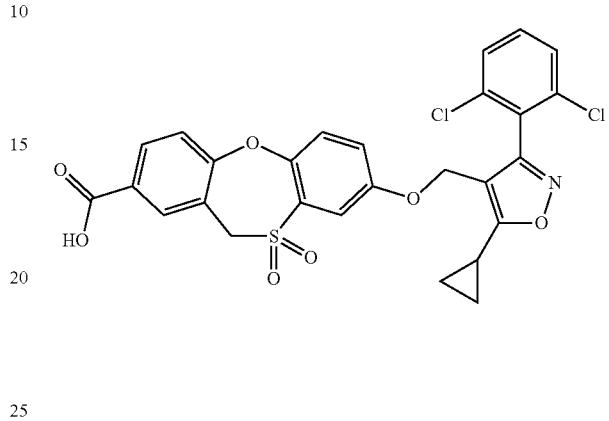

Using methyl 4-bromo-3-(bromoethyl)benzoate as a starting material, the title compound was prepared according to the procedures described in example 5 as a white solid (140 mg).

MS (ESI, pos. ion) m/z: 572.0 [M+H]⁺; and

¹H NMR (400 MHz, CDCl₃) δ8.19-8.13 (m, 2H), 7.38-7.27 (m, 6H), 6.70-6.96 (m, 1H), 4.81 (s, 4H), 2.13-2.07 (m, 1H), 1.28-1.17 (m, 4H).

Example 23: 2-((5-cyclopropyl-3-(2,6-dichlorophenyl)isoxazol-4-yl)methoxy)-10,11-dihydrobenzo[6,7]oxepino[3,2-b]pyridine-8-carboxylic acid

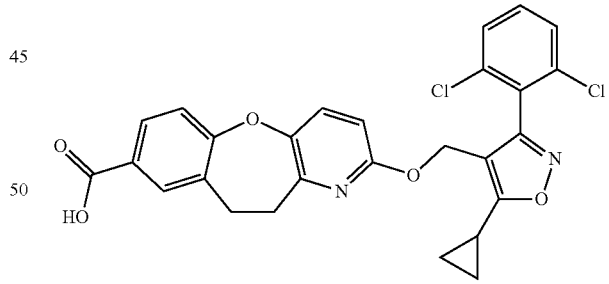

Using methyl 4-hydroxy-3-methylbenzoate as a starting material, the title compound was prepared according to the procedures described in example 3 as a white solid (180 mg).

MS (ESI, pos. ion) m/z: 523.3 [M+H]⁺; and

¹H NMR (400 MHz, DMSO-d₆) δ12.89 (s, 1H), 7.89 (d, J=1.9 Hz, 1H), 7.80 (dd, J=8.3, 2.0 Hz, 1H), 7.54-7.49 (m, 3H), 7.44-7.40 (m, 1H), 7.25 (d, J=8.4 Hz, 1H), 6.44 (d, J=8.7 Hz, 1H), 5.15 (s, 2H), 3.16-3.09 (m, 2H), 3.01-2.94 (m, 2H), 2.56-2.52 (m, 1H), 1.20-1.16 (m, 2H), 1.14-1.09 (m, 2H).

Example 24: 8-((5-cyclopropyl-3-(2,6-dichlorophenyl)isoxazol-4-yl)methoxy)-1-methyl-1,4-dihydrochromeno[4,3-c]pyrazole-3-carboxylic acid

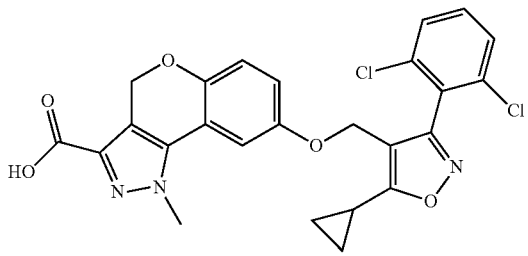 [SMILES: Cn1nc(C(=O)O)c2c1-c1cc(OCc3c(-c4c(Cl)cccc4Cl)noc3C3CC3)ccc1OC2]

Step 1: ethyl 2-(6-methoxy-4-oxochroman-3-yl)-2-oxoacetate

A mixture of 6-methoxychroman-4-one (2.0 g, 11 mmol) in tetrahydrofuran (50 mL) was cooled to −78° C., and a solution of bis(trimethylsilyl) sodium amide in tetrahydrofuran (6.0 mL, 12 mmol, 2.0 M) was slowly added dropwise. The reaction mixture was stirred at −78° C. for 30 min. and diethyl oxalate (2.3 mL, 17 mmol) was slowly added dropwise. The resulting mixture was allowed to warm to room temperature and stirred overnight. The mixture was diluted with water (50 mL), and adjusted to acidity with hydrochloric acid (30 mL, 1 M), and the resulting mixture was extracted with ethyl acetate (80 mL×2). The combined organic layers were washed with 20 mL of saturated brine, dried over anhydrous sodium sulfate and filtered. The residue vas purified by column chromatography on silica gel eluted with (petroleum ether/ethyl acetate (v/v)=5/1) to give the title compound as a yellow solid (3.0 g, 96%).

MS (ESI, pos. ion) m/z: 279.3 [M+H]$^+$.

Step 2: ethyl 8-methoxy-1-methyl-1,4-dihydrochromeno[4,3-c]pyrazole-3-carboxylate Ethyl 2-(6-methoxy-4-oxochroman-3-yl)-2-oxoacetate (4.0 g, 14 mmol) was dissolved in hot ethanol (50 mL), followed by the addition of methyl hydrazine (5.2 mL, 16 mmol), and the reaction mixture was stirred at room temperature overnight. The solvent was removed under vacuum. The residue was purified by column chromatography on silica gel eluted with (petroleum ether/ethyl acetate (v/v)=10/1) to give the title compound as a yellow solid (230 mg, 6%).

MS (ESI, pos. ion) m/z: 289.2 [M+H]$^+$; and
$^1$H NMR (400 MHz, CDCl$_3$) δ7.27 (d, J=3.0 Hz, 1H), 6.89 (d, J=8.9 Hz, 1H), 6.79 (dd, J =8.9, 3.0 Hz, 1H), 5.38 (s, 2H), 4.38 (q, J=7.1 Hz, 2H), 4.23 (s, 3H), 3.84 (s, 3H), 1.41 (t, J=7.1 Hz, 3H).

Step 3: ethyl 8-hydroxy-1-methyl-1,4-dihydrochromeno[4,3-c]pyrazole-3-carboxylate Using ethyl 8-methoxy-1-methyl-1,4-dihydrochromeno[4,3-c]pyrazole-3-carboxylate (230 mg, 0.8 mmol) as a starting material, the title compound was prepared according to the procedure described in step 4 of example 9 as a yellow solid (210 mg, 96%).

Step 4: ethyl 8-((5-cyclopropyl-3-(2,6-dichlorophenyl)isoxazol-4-yl)methoxy)-1-methyl-1,4-dihydrochromeno[4,3-c]pyrazole-3-carboxylate Using ethyl 8-hydroxy-1-methyl-1,4-dihydrochromeno[4,3-c]pyrazole-3-carboxylate (220 mg, 0.8 mmol) and 4-(chloromethyl)-5-cyclopropyl-3-(2,6-dichlorophenyl)isoxazole (364 mg, 1.2 mmol) as starting materials, the title compound was prepared according to the procedure described in step 5 of example 9 as a yellow solid (120 mg, 28%).

MS (ESI, pos. ion) m/z: 540.5 [M+H]$^+$.

Step 5: 8-((5-cyclopropyl-3-(2,6-dichlorophenyl)isoxazol-4-yl)methoxy)-1-methyl-1,4-dihydrochromeno[4,3-c]pyrazole-3-carboxylic acid Ethyl 8-((5-cyclopropyl-3-(2,6-dichlorophenyl)isoxazol-4-yl)methoxy)-1-methyl-1,4-dihydrochromeno[4,3-c]pyrazole-3-carboxylate (100 mg, 0.19 mmol) was dissolved in a mixed solvent of tetrahydrofuran (12 mL) and water (3 mL), followed by the addition of sodium hydroxide (14 mg, 0.35 mmol), and the mixture was heated to 60° C. and stirred overnight. Most of the solvent was removed under vacuum. The residue was diluted with water (20 mL). The resulting mixture was adjusted to acidity with hydrochloric acid (3 mL, 1 M). The resulting mixture was extracted with ethyl acetate (20 mL×2). The combined organic layers were washed with 10 mL of saturated brine, dried over anhydrous sodium sulfate and filtered. The filtrate was concentrated under vacuum to give the title compound as a white solid (93 mg, 98%).

MS (ESI, pos. ion) m/z: 512.4 [M+H]$^+$; and
$^1$H NMR (600 MHz, DMSO-d$_6$) δ7.63-7.61 (m, 2H), 7.55-7.52 (m, 1H), 7.04 (d, J=2.0 Hz, 1H), 6.80 (d, J=8.7 Hz, 1H), 6.64-6.62 (m, 1H), 5.30 (s, 2H), 4.87 (s, 2H), 4.12 (s, 3H), 2.50-2.45 (m, 1H), 1.22-1.11 (m, 4H).

Example 25: 2-((5-cyclopropyl-3-(2,6-dichlorophenyl)isoxazol-4-yl)methoxy)-5-oxo-10,11-dihydro-5H-benzo[4,5]cyclohepta[1,2-b]pyridine-7-carboxylic acid

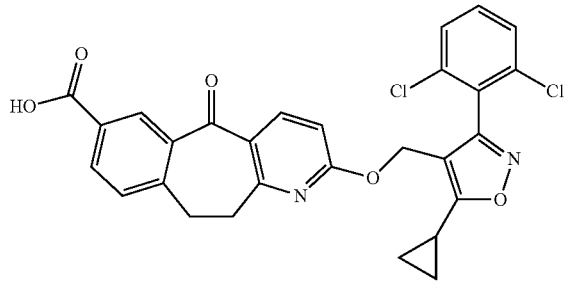 [SMILES: O=C(O)c1ccc2c(c1)C(=O)c1ccc(OCc3c(-c4c(Cl)cccc4Cl)noc3C3CC3)nc1CC2]

Step 1: methyl 2-((diethoxyphosphoryl)methyl)nicotinate

A mixture of methyl 2-(chloromethyl)nicotinate (10.0 g, 53 mmol) (See the synthetic method described in step 2 of example 10 on page 51 of WO2010011375) in triethyl phosphite (26 mL, 156 mmol) was heated at 120° C. and stirred for 3 h. The reaction solution was then cooled to room temperature. The triethyl phosphite was removed by distillation under vacuum. The resulting residue was purified by column chromatography on silica gel eluted with (petroleum ether/ethyl acetate (v/v)=10/1) to give the title compound as a yellow oil (15.0 g, 96%).

Step 2: methyl 2-(4-bromostyryl)nicotinate

Using methyl 2-((diethoxyphosphoryl)methyl)nicotinate (15.0 g, 52 mmol) and 4-bromobenzaldehyde (9.7 g, 52 mmol) as starting materials, the title compound was prepared according to the procedure described in step 3 of example 2 as a yellow oil (11.0 g, 66%).

Step 3: methyl 2-(4-bromophenethyl)nicotinate

Using methyl 2-(4-bromostyryl)nicotinate (11.0 g, 34 mmol) as a starting material, the title compound was prepared according to the procedure described in step 4 of example 2 as a yellow oil (11.0 g, 99%).

Step 4: 2-(4-bromophenyl)-3-(methoxycarbonyl)pyridine-1-oxide

To a mixture of methyl 2-(4-bromophenethyl)nicotinate (11.0 g, 34 mmol) in chloroform (100 mL) was added m-chloroperbenzoic acid (8.4 g, 41 mmol), and the mixture was heated to reflux and stirred for 3 h. The mixture was cooled to room temperature, followed by the addition of solid sodium carbonate (5.0 g). The resulting mixture was continued to stir at room temperature for 30 min. The mixture was filtered, and the filtrate was concentrated under vacuum. The residue was purified by column chromatography on silica gel eluted with ($CH_2Cl_2$/MeOH (v/v)=20/1) to give the title compound as a yellow oil (11.0 g, 95%).

Step 5: methyl 2-(4-bromophenethyl)-6-chloronicotinate 2-(4-Bromophenyl)-3-(methoxycarbonyl)pyridine-1-oxide (13.0 g, 38 mmol) was dissolved in phosphorus oxychloride (35 mL) under an ice bath. The reaction mixture was stirred under an ice bath for 30 min, then warmed to reflux and stirred for 4 h. The reaction mixture was cooled to room temperature, and ice water (700 mL) was slowly added to quench the reaction. The resulting mixture was adjusted to basicity with solid sodium carbonate (22 g). The resulting mixture was extracted with ethyl acetate (500 mL×2). The combined organic layers were washed with 50 mL of saturated brine, dried over anhydrous sodium sulfate, filtered and concentrated under vacuum. The residue was purified by column chromatography on silica gel eluted with (petroleum ether/ethyl acetate (v/v)=20/1) to give the title compound as a yellow oil (5.1 g, 37%).

Step 6: methyl 2-(4-bromophenethyl)-6-methoxynicotinate

Methyl 2-(4-bromophenethyl)-6-chloronicotinate (5.4 g, 15 mmol) was dissolved in methanol (100 mL), a solution of sodium methylate in methanol (15 mL, 75 mmol, 5.0 M) was slowly added dropwise, and the mixture was stirred at 80° C. for 2 h. The mixture was then cooled to room temperature, and quenched with 400 mL of saturated aqueous ammonium chloride. The resulting mixture was extracted with ethyl acetate (500 mL×2). The combined organic layers were washed with 50 mL of saturated brine, dried over anhydrous sodium sulfate and filtered. The filtrate was concentrated under vacuum to give the title compound as a yellow oil (5.0 g, 94%).

Step 7: 2-(4-bromophenethyl)-6-methoxynicotinic acid

Methyl 2-(4-bromophenethyl)-6-methoxynicotinate (5.0 g, 14 mmol) was dissolved in a mixed solvent of tetrahydrofuran (100 mL) and water (50 mL), followed by the addition of sodium hydroxide (5.6 g, 140 mmol), and the mixture was heated to 50° C. and stirred overnight. The mixture was cooled to room temperature, and most of the solvent was removed under vacuum. The residue was diluted with water (200 mL). The resulting mixture was adjusted to acidity with hydrochloric acid (80 mL, 2 M). The resulting mixture was extracted with ethyl acetate (200 mL×2). The combined organic layers were washed with 10 mL of saturated brine, dried over anhydrous sodium sulfate, filtered and concentrated under vacuum. The residue vas purified by column chromatography on silica gel eluted with (petroleum ether/ethyl acetate (v/v)=5/1) to give the title compound as a yellow solid (4.8 g, 100%).

Step 8: 7-bromo-2-methoxy-10,11-dihydro-5H-benzo[4,5]cyclohepta[1,2-b]pyridin-5-one Using 2-(4-bromophenethyl)-6-methoxynicotinic acid (5.4 g, 16 mmol) as a starting material, the title compound was prepared according to the procedure described in step 6 of example 2 as a white solid (800 mg, 20%).

Step 9: methyl 2-methoxy-5-oxo-10,11-dihydro-5H-benzo[4,5]cyclohepta [1,2-b]pyridine-7-carboxylate 7-Bromo-2-methoxy-10,11-dihydro-5H-benzo[4,5]cyclohepta[1,2-b]pyridin-5-one (1.8 g, 5.7 mmol), triethylamine (1.56 mL, 11 mmol) and [1,1'-bis(diphenylphosphino)ferrocene]dichloropalladium (460 mg, 0.63 mmol) were dissolved in methanol (100 mL), and the reaction mixture was placed in an autoclave, heated to 100° C. and stirred for 2 days under carbon monoxide (3.0 MPa). The mixture was cooled to room temperature, and the solvent was removed under vacuum. The residue was purified by column chromatography on silica gel eluted with (petroleum ether/ethyl acetate (v/v)=30/1) to give the title compound as a white solid (280 mg, 17%).

Step 10: methyl 2,5-dioxo-2,5,10,11-tetrahydro-1H-benzo[4,5]cyclohepta[1,2-b]pyridine-7-carboxylate Using methyl 2-methoxy-5-oxo-10,11-dihydro-5H-benzo[4,5]cyclohepta[1,2-b]pyridine-7-carboxylate (280 mg, 0.94 mmol) as a starting material, the title compound was prepared according to the procedure described in step 10 of example 3 as a white solid (210 mg, 79%).

$^1$H NMR (400 MHz, DMSO-$d_6$) δ12.03 (s, 1H), 8.36 (d, J=1.6 Hz, 1H), 8.14 (d, J=9.8 Hz, 1H), 8.04 (dd, J=7.9, 1.7 Hz, 1H), 7.50 (d, J=7.9 Hz, 1H), 6.35 (d, J=9.8 Hz, 1H), 3.87 (s, 3H), 3.24-3.17 (m, 2H), 3.13-3.07 (m, 2H).

Step 11: methyl 2-((5-cyclopropyl-3-(2,6-dichlorophenyl)isoxazol-4-yl)methoxy)-5-oxo-10,11-dihydro-5H-benzo[4,5]cyclohepta [1,2-b]pyridine-7-carboxylate 4-(Chloromethyl)-5-cyclopropyl-3-(2,6-dichlorophenyl)isoxazole (260 mg, 0.86 mmol), methyl 2,5-dioxo-2,5,10, 11-tetrahydro-1H-benzo[4,5]cyclohepta[1,2-b]pyridine-7-carboxylate (200 mg, 0.7 mmol) and potassium phosphate (212 mg, 1.0 mmol)) were dissolved in DMF (10 mL), and the mixture was stirred at 40° C. for 3 h. The mixture was then cooled to room temperature and diluted with water (20 mL). The resulting mixture was extracted with ethyl acetate (40 mL×2). The combined organic layers were washed with 10 mL of saturated brine, dried over anhydrous sodium sulfate, filtered and concentrated under vacuum. The residue was purified by column chromatography on silica gel eluted with (petroleum ether/ethyl acetate (v/v)=10/1) to give the title compound as a yellow solid (220 mg, 60%).

$^1$H NMR (400 MHz, CDCl$_3$) δ8.55 (s, 1H), 8.37 (d, J=8.7 Hz, 1H), 8.12 (d, J=7.6 Hz, 1H), 7.39-7.28 (m, 4H), 6.59 (d, J=8.7 Hz, 1H), 5.29 (s, 2H), 3.94 (s, 3H), 3.24-3.20 (m, 4H), 2.36-2.32 (m, 1H), 1.33-1.28 (m, 2H), 1.20-1.14 (m, 2H).

Step 12: 2-((5-cyclopropyl-3-(2,6-dichlorophenyl)isoxazol-4-yl)methoxy)-5-oxo-10,11-dihydro-5H-benzo[4,5]cyclohepta[1,2-b]pyridine-7-carboxylic acid Methyl 2-((5-cyclopropyl-3-(2,6-dichlorophenyl)isoxazol-4-yl)methoxy)-5-oxo-10,11-dihydro-5H-benzo[4,5]cyclohepta[1,2-b]pyridine-7-carboxylate (220 mg, 0.4 mmol) was dissolved in a mixed solvent of tetrahydrofuran (6 mL) and water (6 mL), followed by the addition of sodium hydroxide (80 mg, 2.0 mmol), and the reaction mixture was stirred at room temperature for 3 h. Most of the solvent was removed under vacuum. The residue was diluted with water (20 mL). The resulting mixture was adjusted to acidity with hydrochloric acid (5 mL, 1 M). The resulting mixture was extracted with ethyl acetate (20 mL×2). The combined organic layers were washed with 10 mL of saturated brine, dried over anhydrous sodium sulfate, filtered and concentrated under vacuum. The residue was purified by column chromatography on silica gel eluted with (petroleum ether/ethyl acetate (v/v)=3/1) to give the title compound as a white solid (100 mg, 50%).

MS (ESI, neg. ion) m/z: 533.2 [M−H]$^-$; and $^1$H NMR (600 MHz, CDCl$_3$) δ8.62 (s, 1H), 8.38 (d, J=8.7 Hz, 1H), 8.18 (d, J=7.7 Hz, 1H), 7.40-7.36 (m, 3H), 7.32-7.28 (m, 1H), 6.60 (d, J=8.7 Hz, 1H), 5.29 (s, 2H), 3.26-3.22 (m, 4H), 2.38-2.30 (m, 1H), 1.33-1.30 (m, 2H), 1.21-1.15 (m, 2H).

Example 26: 2-((4-cyclopropyl-1-(2,6-dichlorophenyl)-1H-pyrazol-5-yl)methoxy)-10,11-dihydrobenzo[6,7]oxepino[3,2-b]pyridine-7-carboxylic acid

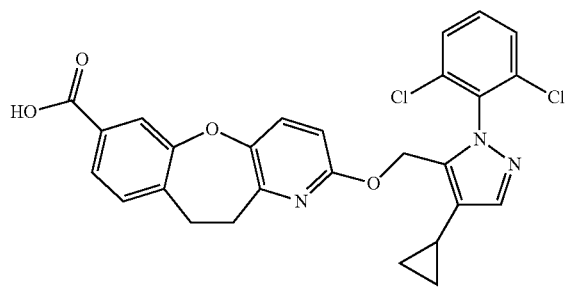 [SMILES: O=C(O)c1ccc2c(c1)Oc1ccc(OCc3c(C4CC4)cnn3-c3c(Cl)cccc3Cl)nc1CC2]

Using (4-cyclopropyl-1-(2,6-dichlorophenyl)-1H-pyrazol-5-yl)methanol (See the synthesis of intermediate 16 on page 24 of WO200912125) as a starting material, the title compound was prepared according to the procedures described in example 17 as a pale yellow solid (124 mg).

MS (ESI, pos. ion) m/z: 522.0 [M+H]$^+$; and $^1$H NMR (400 MHz, CDCl$_3$) δ7.85-7.80 (m, 2H), 7.47 (s, 1H), 7.37-7.35 (m, 3H), 7.31-7.28 (m, 1H), 7.23-7.17 (m, 1H), 6.40 (d, J=8.7 Hz, 1H), 5.30 (s, 2H), 3.23-3.17 (m, 2H), 3.14-3.06 (m, 2H), 1.95-1.87 (m, 1H), 0.98-0.92 (m, 2H), 0.74-0.66 (m, 2H).

Example 27: 8-((1-(2,6-dichlorophenyl)-4-isopropyl-1H-1,2,3-triazol-5-yl)methoxy)-5-oxo-10,11-dihydro-5H-dibenzo[a,d][7]annulene-3-carboxylic acid

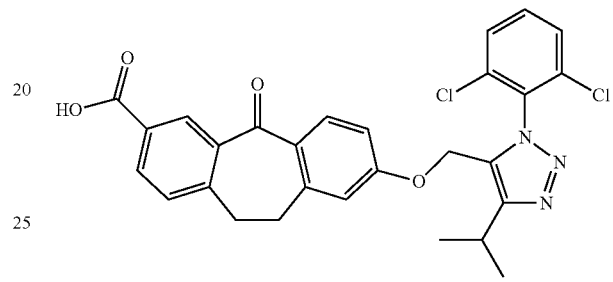

Step 1: 2-azido-1,3-dichlorobenzene

To a mixture of 2,6-dichloroaniline (5.0 g, 31 mmol) in ethyl acetate (100 mL) was added concentrated hydrochloric acid (30 mL) under an ice bath, and then a solution of sodium nitrite (6.4 g, 93 mmol) in water (15 mL) was slowly added dropwise. The mixture was stirred under an ice bath for 30 min. A solution of sodium azide (6.1 g, 93 mmol) in water (10 mL) was slowly added dropwise to the reaction mixture. The resulting mixture was continued to stir for 1 h, and diluted with water (50 mL). The resulting mixture was extracted with ethyl acetate (100 mL×2). The combined organic layers were washed with 10 mL of saturated brine, dried over anhydrous sodium sulfate, filtered and concentrated under vacuum. The residue was purified by column chromatography on silica gel eluted with (petroleum ether) to give the title compound as a yellow oil (5.5 g, 95%).

Step 2: methyl 4-methylpent-2-ynoate

A solution of 3-methylbut-1-yne (10.0 g, 147 mmol) in anhydrous tetrahydrofuran (50 mL) was cooled to −78° C., and a solution of n-butyllithium in n-hexane (67 mL, 160 mmol, 2.4 M) was added dropwise. The resulting mixture was stirred at −78° C. for 2 h, and methylchloroformate (11.6 mL, 150 mmol) was added dropwise. The resulting mixture was continued to stir at −78° C. for 5 h. The mixture was then allowed to warm to room temperature, and quenched with 50 mL of saturated aqueous ammonium chloride solution. The resulting mixture was extracted with ethyl acetate (100 mL×2). The combined organic layers were washed with 20 mL of saturated brine, dried over anhydrous sodium sulfate, filtered and concentrated under vacuum. The residue was purified by column chromatography on silica gel eluted with (petroleum ether) to give the title compound as a yellow oil (3.4 g, 18%).

$^1$H NMR (400 MHz, CDCl$_3$) δ3.74 (s, 3H), 2.68 (s, 1H), 1.23 (d, J=6.9 Hz, 6H).

Step 3: methyl 1-(2,6-dichlorophenyl)-4-isopropyl-1H-1,2,3-triazole-5-carboxylate 2-Azido-1,3-dichlorobenzene (3.9 g, 21 mmol) and methyl methyl 4-methylpent-2-ynoate (2.1 g, 17 mmol) were dissolved in toluene (100 mL) under nitrogen, and the mixture was heated to reflux and stirred overnight. The reaction mixture was then cooled to room temperature, and diluted with water (50 mL). The resulting mixture was extracted with ethyl acetate (100 mL×2). The combined organic layers were washed with 20 mL of saturated brine, dried over anhydrous sodium sulfate, filtered and concentrated under vacuum. The residue was purified by column chromatography on silica gel eluted with (petroleum ether/ethyl acetate (v/v)=20/1) to give the title compound as a red oil (1.1 g, 21%).

MS (ESI, pos. ion) m/z: 314.1 [M+H]$^+$.

Step 4: (1-(2,6-dichlorophenyl)-4-isopropyl-1H-1,2,3-triazole-5-yl)methanol

To a mixture of lithium aluminum hydride (160 mg, 4.2 mmol) in anhydrous tetrahydrofuran (20 mL) was added dropwise a solution of methyl 1-(2,6-dichlorophenyl)-4-isopropyl-1H-1,2,3-triazole-5-carboxylate (1.1 g, 3.5 mmol) in tetrahydrofuran (5 mL) in an ice bath, and the mixture was stirred in an ice bath for 2 h. The reaction was then quenched with 5 mL of methanol. The resulting mixture was filtered. The filter cake was washed with ethyl acetate (50 mL×2). The combined organic layers were concentrated under vacuum. The residue was purified by column chromatography on silica gel eluted with (petroleum ether/ethyl acetate (v/v)=8/1) to give the title compound as a pale yellow oil (630 mg, 63%)).

MS (ESI, pos. ion) m/z: 286.0 [M+H]$^+$.

Step 5: 5-(chloromethyl)-1-(2,6-dichlorophenyl)-4-isopropyl-1H-1,2,3-triazole To a mixture of (1-(2,6-dichlorophenyl)-4-isopropyl-1H-1,2,3-triazole-5-yl)methanol (60 mg, 0.2 mmol) in methylene chloride (10 mL) were added carbon tetrachloride (2 mL) and triphenylphosphine (110 mg, 0.4 mmol), and the mixture was stirred at room temperature overnight. The mixture was diluted with water (20 mL), and the resulting mixture was extracted with ethyl acetate (30 mL×2). The combined organic layers were washed with 20 mL of saturated brine, dried over anhydrous sodium sulfate, filtered and concentrated under vacuum. The residue was purified by column chromatography on silica gel eluted with (petroleum ether/ethyl acetate (v/v)=20/1) to give the title compound as a colorless oil (60 mg, 94%).

MS (ESI, pos. ion) m/z: 304.0 [M+H]$^+$.

Step 6: methyl 8-((1-(2,6-dichlorophenyl)-4-isopropyl-1H-1,2,3-triazol-5-yl)methoxy)-5-oxo-10,11-dihydro-5H-dibenzo[a,d][7]annulene-3-carboxylate Using methyl 8-hydroxy-5-oxo-10,11-dihydro-5H-dibenzo[a,d][7]annulene-3-carboxylate (150 mg, 0.53 mmol) and 5-(chloromethyl)-1-(2,6-dichlorophenyl)-4-isopropyl-1H-1,2,3-triazole (200 mg, 0.65 mmol) as starting materials, the title compound was prepared according to the procedure described in step 9 of example 2 as a pale yellow oil (276 mg, 94%).

MS (ESI, pos. ion) m/z: 550.3 [M+H]$^+$.

Step 7: 8-((1-(2,6-dichlorophenyl)-4-isopropyl-1H-1,2,3-triazol-5-yl)methoxy)-5-oxo-10,11-dihydro-5H-dibenzo[a,d][7]annulene-3-carboxylic acid Using methyl 8-((1-(2,6-dichlorophenyl)-4-isopropyl-1H-1,2,3-triazol-5-yl)methoxy)-5-oxo-10,11-dihydro-5H-dibenzo[a,d][7]annulene-3-carboxylate (260 mg, 0.47 mmol) as a starting material, the title compound was prepared according to the procedure described in step 10 of example 2 as a pale yellow solid (230 mg, 91%).

MS (ESI, pos. ion) m/z: 536.2 [M+H]$^+$; and
$^1$H NMR (400 MHz, DMSO-d$_6$) δ11.69 (s, 1H), 8.42 (d, J=1.6 Hz, 1H), 8.02 (dd, J=7.9, 1.7 Hz, 1H), 7.93 (d, J=9.1 Hz, 1H), 7.77-7.75 (m, 2H), 7.67-7.62 (m, 1H), 7.47 (d, J=7.9 Hz, 1H), 6.83-6.81 (m, 2H), 5.16 (s, 2H), 3.32-3.26 (m, 1H), 3.18-3.09 (m, 4H), 1.34 (d, J=6.9 Hz, 6H).

Example 28: 4-((4-cyclopropyl-1-(2,6-dichlorophenyl)-1H-1,2,3-triazol-5-yl)methoxy)-5-oxo-10,11-dihydro-5H-dibenzo[a,d][7]annulene-3-carboxylic acid

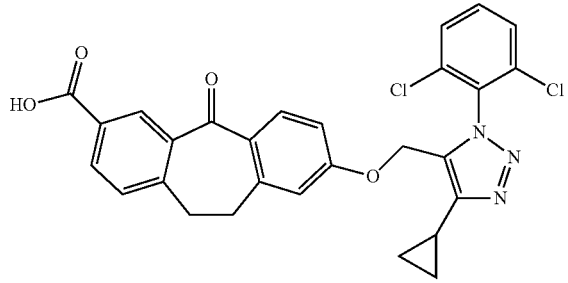 [SMILES: O=C(O)c1ccc2c(c1)C(=O)c1ccc(OCc3c(C4CC4)nnn3-c3c(Cl)cccc3Cl)cc1CC2]

Using cyproterone acetylene as a starting material, the title compound was prepared according to the procedures described in example 27 as a pale yellow solid (160 mg).

MS (ESI, pos. ion) m/z: 534.3 [M+H]$^+$; and
$^1$H NMR (400 MHz, CDCl$_3$) δ8.72 (s, 1H), 8.19-8.07 (m, 2H), 7.56-7.47 (m, 2H), 7.42 (dd, J=9.2, 6.9 Hz, 1H), 7.35 (d, J=8.0 Hz, 1H), 6.78 (dd, J=8.8, 2.4 Hz, 1H), 6.64 (d, J=2.1 Hz, 1H), 5.09 (s, 2H), 3.24-3.16 (m, 4H), 2.02-1.96 (m, 1H), 1.25-1.18 (m, 2H), 1.14-1.04 (m, 2H).

Example 29: 2-(2-((5-cyclopropyl-3-(2,6-dichlorophenyl)isoxazol-4-yl)methoxy)-10,11-dihydrobenzo[6,7]oxepino[3,2-b]pyridine-7-carboxamido)ethanesulfonic acid

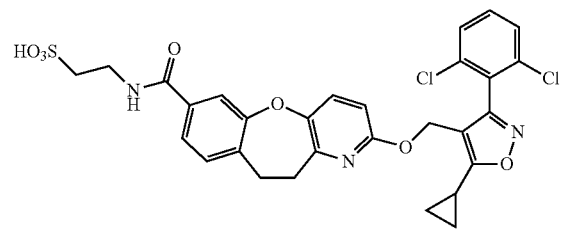 [SMILES: O=C(NCCS(=O)(=O)O)c1ccc2c(c1)Oc1ccc(OCc3c(-c4c(Cl)cccc4Cl)noc3C3CC3)nc1CC2]

Step 1: 2-(2-((5-cyclopropyl-3-(2,6-dichlorophenyl)isoxazol-4-yl)methoxy)-10,11-dihydrobenzo[6,7]oxepino[3,2-b]pyridine-7-carboxamido)ethanesulfonic acid To a mixture of 2-((5-cyclopropyl-3-(2,6-dichlorophenyl)isoxazol-4-yl)methoxy)-10,11-dihydrobenzo[6,7]oxepino[3,2-b]pyridine-7-carboxylic acid (0.5 g, 1.0 mmol) and 2-(7-azabenzotriazol-1-yl)-N,N,N',N'-tetramethyluronium hexafluorophosphate (0.52 g, 1.4 mmol) in N,N-dimethylformamide (15 mL) were added sequentially taurine (0.2 g, 2.0 mmol) and diisopropylethylamine (0.3 g, 0.4 mmol) in an ice bath, and the mixture was warmed to room temperature and stirred overnight. The mixture was concentrated under vacuum. The residue was purified by column chromatography on silica gel eluted with (CH$_2$Cl$_2$/MeOH (v/v) =15/1) to give the title compound as a pale yellow solid (310 mg, 50%).

MS (ESI, pos. ion) m/z: 629.7 [M+H]$^+$; and
$^1$H NMR (400 MHz, DMSO-d$_6$) δ8.51 (t, J=5.2 Hz, 1H), 7.59-7.48 (m, 5H), 7.42-7.36 (m, 2H), 6.42 (d, J=8.7 Hz, 1H), 5.14 (s, 2H), 3.68-3.56 (m, 2H), 3.56-3.46 (m, 2H), 3.14 (s, 1H), 3.13-3.10 (m, 2H), 2.99-2.91 (m, 2H), 2.55-2.52 (m, 1H), 1.19-1.16 (m, 2H), 1.14-1.09 (m, 2H).

Example 30: 2-((5-cyclopropyl-3-(2,6-dichlorophenyl)isoxazol-4-yl)methoxy)benzo[6,7]oxepino[3,2-b]pyridine-7-carboxylic acid

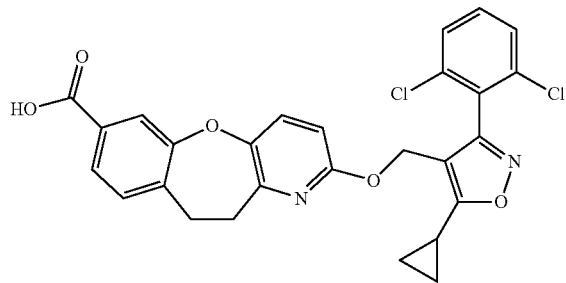 [SMILES: O=C(O)c1ccc2c(c1)Oc1ccc(OCc3c(-c4c(Cl)cccc4Cl)noc3C3CC3)nc1CC2]

Step 1: methyl 4-(2-(3-bromo-6-methoxypyridin-2-yl)vinyl)-3-hydroxybenzoate

Using methyl 4-(2-(3-bromo-6-methoxypyridin-2-yl)vinyl)-3-(methoxymethoxy) benzoate (450 mg, 1.1 mmol) as a starting material, the title compound was prepared according to the procedure described in step 8 of example 3 as a pale yellow solid (300 mg, 75%).
MS (ESI, pos. ion) m/z: 365.1 [M+2]$^+$.

Step 2: methyl 2-methoxybenzo[6,7]oxepino[3,2-b]pyridine-7-carboxylate

Under nitrogen, the complex of copper(II) trifluoromethanesulfonate and toluene (60 mg, 0.12 mmol), cesium carbonate (540 mg, 1.66 mmol) and methyl 4-(2-(3-bromo-6-methoxypyridin-2-yl)vinyl)-3-hydroxybenzoate (400 mg, 1.1 mmol) were dissolved in pyridine (30 mL), and the mixture was warmed to reflux and stirred overnight. After being cooled to room temperature, the mixture was diluted with water (50 mL), and extracted with ethyl acetate (100 mL×2). The organic layers were combined, and the combined organic layers were washed with saturated brine (20 mL), dried over anhydrous sodium sulfate, filtered, and concentrated under vacuum. The residue was purified by column chromatography on silica gel eluted with (petroleum ether/ethyl acetate (v/v)=2/1) to give the title compound as a yellow solid (96 mg, 31%).
MS (ESI, pos. ion) m/z: 284.1 [M+H]$^+$.

Step 3: methyl 2-oxo-1,2-dihydrobenzo[6,7]oxepino[3,2-b]pyridine-7-carboxylate

Using methyl 2-methoxybenzo[6,7]oxepino[3,2-b]pyridine-7-carboxylate (50 mg, 0.18 mmol) as a starting material, the title compound was prepared according to the procedure described in step 10 of example 3 as a pale yellow solid (31 mg, 55%).
MS (ESI, pos. ion) m/z: 270.1 [M+H]$^+$.

Step 4: methyl 2-((5-cyclopropyl-3-(2,6-dichlorophenyl)isoxazol-4-yl)methoxy)benzo[6,7]oxepino[3,2-b]pyridine-7-carboxylate Using methyl 2-oxo-1,2-dihydrobenzo[6,7]oxepino[3,2-b]pyridine-7-carboxylate (31 mg, 0.12 mmol) and 4-(chloromethyl)-5-cyclopropyl-3-(2,6-dichlorophenyl)isoxazole (53 mg, 0.18 mmol) as astarting materials, the title compound was prepared according to the procedure described in step 11 of example 3 as a pale yellow solid (42 mg, 66%).
MS (ESI, pos. ion) m/z: 535.1 [M+H]$^+$.

Step 5: 2-((5-cyclopropyl-3-(2,6-dichlorophenyl)isoxazol-4-yl)methoxy)benzo [6,7]oxepino [3,2-b]pyridine-7-carboxylic acid Using methyl methyl 2-((5-cyclopropyl-3-(2,6-dichlorophenyl)isoxazol-4-yl)methoxy) benzo[6,7]oxepino[3,2-b]pyridine-7-carboxylate (42 mg, 0.08 mmol) as a starting material, the title compound was prepared according to the procedure described in step 12 of example 3 as a pale yellow solid (32 mg, 80%).
MS (ESI, pos. ion) m/z: 521.3 [M+H]$^+$; and
$^1$H NMR (600 MHz, CDCl$_3$) δ7.92-7.83 (m, 2H), 7.38 (d, J=8.7 Hz, 1H), 7.35 (d, J=8.1 Hz, 2H), 7.30 (d, J=8.1 Hz, 1H), 7.26-7.21 (m, 1H), 6.90 (d, J=11.6 Hz, 1H), 6.76 (d, J=11.6 Hz, 1H), 6.58 (d, J=8.7 Hz, 1H), 5.17 (s, 2H), 2.36-2.29 (m, 1H), 1.18-1.11 (m, 2H), 0.95-0.84 (m, 2H).

Example 31: 3-((5-cyclopropyl-3-(2,6-dichlorophenyl)isoxazol-4-yl)methoxy)-6,7-dihydro-5H-benzo[7,8]oxocino[3,2-b]pyridine-10-carboxylic acid

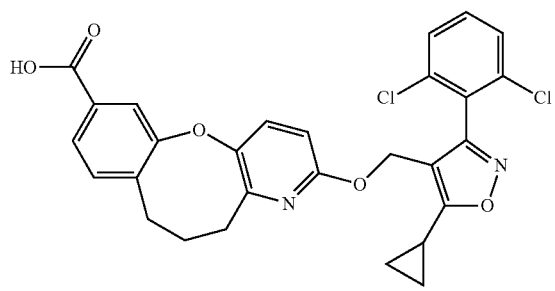 [SMILES: O=C(O)c1ccc2c(c1)Oc1ccc(OCc3c(-c4c(Cl)cccc4Cl)noc3C3CC3)nc1CCC2]

Step 1: methyl 4-acetyl-3-hydroxybenzoate

To a solution of 4-bromo-2-hydroxyacetophenone (8.0 g, 37.2 mmol) in methanol (80 were added [1,1'-bis(diphenylphosphino)ferrocene]dichloropalladium (II) (0.6 g, 0.8 mmol) and triethylamine (7.6 g, 75 mmol) at room temperature. The mixture was placed in an autoclave, and stirred at 100° C. for 24 h under carbon monoxide (4.0 MPa). The mixture was cooled to room temperature, and concentrated under vacuum. The residue was purified by column chromatography on silica gel eluted with (petroleum ether/ethyl acetate (v/v)=10/1) to give the title compound as a white solid (7.2 g, 100%).

$^1$H NMR (600 MHz, CDCl$_3$) δ12.17 (s, 1H), 7.82 (d, J=8.3 Hz, 1H), 7.65 (d, J=1.5 Hz, 1H), 7.56 (dd, J=8.3, 1.5 Hz, 1H), 3.96 (s, 3H), 2.70 (s, 3H).

Step 2: methyl 4-(3-(3-bromo-6-methoxypyridin-2-yl)-3-hydroxypropanoyl)-3-hydroxybenzoate To a mixture of methyl 4-acetyl-3-hydroxybenzoate (3.0 g, 15.5 mmol) and 3-bromo-6-methoxy-2-carbaldehyde (3.3 g, 15.0 mmol) in methanol (90 mL) was added slowly a solution of sodium methoxide in methanol (6.3 mL, 32 mmol, 5 M) at room temperature, and the mxiture was stirred at room temperature overnight. The reaction mixture was quenched with 500 mL of saturated ammonium chloride aqueous solution. The resulting solution was extracted with with ethyl acetate (200 mL×2). The organic layers were combined. The combined organic layers were washed with 50 mL of saturated brine, dried over anhydrous sodium sulfate, filtered, and concentrated under vacuum. The residue was purified by column chromatography on silica gel eluted with (petroleum ether/ethyl acetate (v/v)=10/1) to give the title compound as a yellow solid (1.6 g, 25%).

Step 3: methyl 4-(3-(3-bromo-6-methoxypyridin-2-yl)acryloyl)-3-hydroxybenzoate To a solution of methyl 4-(3-(3-bromo-6-methoxypyridin-2-yl)-3-hydroxypropanoyl)-3-hydroxybenzoate (1.6 g, 3.9 mmol) in dichloromethane (40 mL) were added sequentially 4-dimethylaminopyridine (24 mg, 0.2 mmol), triethylamine (510 mg, 5.1 mmol) and trifluoroacetic anhydride (1.1 g, 5.1 mmol) under an ice bath. The mixture was stirred for 3 h under an ice bath, and then warmed to room temperature and stirred overnight. The organic layers were combined. The combined organic layers were washed with 20 mL of saturated brine, dried over anhydrous sodium sulfate, filtered, and concentrated under vacuum. The residue was purified by column chromatography on silica gel eluted with (petroleum ether/ethyl acetate (v/v)=10/1) to give the title compound as a yellow solid (1.5 g, 98%).

Step 4: methyl 4-(3-(3-bromo-6-methoxypyridin-2-yl)propanoyl)-3-hydroxybenzoate Methyl 4-(3-(3-bromo-6-methoxypyridin-2-yl)acryloyl)-3-hydroxybenzoate (4.0 g, 10.2 mmol), sodium acetate (4.2 g, 51 mmol) and p-toluenesulfonyl hydrazide (9.5 g, 51 mmol) were dissolved in a mixture of tetrahydrofuran (80 mL) and water (40 mL), and the reaction mixture was warmed to reflux and stirred for 2 h. The reaction mixture was cooled to room temperature, and diluted with water (100 mL). The resulting mixture was extracted with ethyl acetate (150 mL×2). The organic layers were combined. The combined organic layers were washed with 20 mL of saturated brine, dried over anhydrous sodium sulfate, filtered, and concentrated under vacuum. The residue was purified by column chromatography on silica gel eluted with (petroleum ether/ethyl acetate (v/v)=20/1) to give the title compound as a pale yellow oil (1.8 g, 45%).

Step 5: methyl 4-(3-(3-bromo-6-methoxypyridin-2-yl)propyl)-3-hydroxybenzoate To a solution of methyl 4-(3-(3-bromo-6-methoxypyridin-2-yl)propanoyl)-3-hydroxybenzoate (1.8 g, 4.6 mmol) in trifluoroacetic acid (6 mL) was added triethylsilane (2.6 g, 23 mmol) at room temperature, and the reaction mixture was stirred at room temperature for 2 days. The reaction mixture was quenched with 50 mL of saturated sodium bicarbonate aqueous solution, and extracted with ethyl acetate (100 mL×2). The organic layers were washed with 20 mL of saturated brine, dried over anhydrous sodium sulfate, filtered, and concentrated under vacuum. The residue was purified by column chromatography on silica gel eluted with (petroleum ether/ethyl acetate (v/v)=30/1) to give the title compound as a yellow solid (1.3 g, 75%).

Step 6: methyl 3-methoxy-6,7-dihydro-5H-benzo[7,8]oxocino[3,2-b]pyridine-10-carboxylate Using methyl 4-(3-(3-bromo-6-methoxypyridin-2-yl)propyl)-3-hydroxybenzoate (600 mg, 0.6 mmol) as a starting material, the title compound was prepared according to the procedure described in step 6 of example 4 as a yellow solid (15 mg, 3%).

MS (ESI, pos. ion) m/z: 300.0 [M+H]$^+$.

Step 7: methyl 3-oxo-4,5,6,7-tetrahydro-3H-benzo[7,8]oxocino[3,2-b]pyridine-10-carboxylate Using methyl 3-methoxy-6,7-dihydro-5H-benzo[7,8]oxocino[3,2-b]pyridine-10-carboxylate (45 mg, 0.15 mmol) as a starting material, the title compound was prepared according to the procedure described in step 7 of example 4 as a yellow solid (34 mg, 79%).

Step 8: methyl 3-((5-cyclopropyl-3-(2,6-dichlorophenyl)isoxazol-4-yl)methoxy)-6,7-dihydro-5H-benzo[7,8]oxocino[3,2-b]pyridine-10-carboxylate Using methyl 3-oxo-4,5,6,7-tetrahydro-3H-benzo[7,8]oxocino[3,2-b]pyridine-10-carboxylate (50 mg, 0.18 mmol) and 4-(chloromethyl)-5-cyclopropyl-3-(2,6-dichlorophenyl)isoxazole (50 mg, 0.17 mmol) as starting materials, the title compound was prepared according to the procedure described in step 8 of example 4 as a colorless oil (34 mg, 52%).

MS (ESI, pos. ion) m/z: 551.2 [M+H]$^+$.

Step 9: 3-((5-cyclopropyl-3-(2,6-dichlorophenyl)isoxazol-4-yl)methoxy)-6,7-dihydro-5H-benzo[7,8]oxocino[3,2-b]pyridine-10-carboxylic acid Using methyl 3-((5-cyclopropyl-3-(2,6-dichlorophenyl)isoxazol-4-yl)methoxy)-6,7-dihydro-5H-benzo[7,8]oxocino[3,2-b]pyridine-10-carboxylate (34 mg, 0.06 mmol) as a starting material, the title compound was prepared according to the procedure described in step 9 of example 4 as a white solid (13 mg, 39%).

MS (ESI, pos. ion) m/z: 537.2 [M+H]$^+$; and
$^1$H NMR (400 MHz, CDCl$_3$) δ7.89 (s, 1H), 7.83-7.76 (m, 1H), 7.75-7.53 (m, 1H), 7.46-7.34 (m, 3H), 7.23-7.17 (m, 1H), 6.44 (d, J=8.6 Hz, 1H), 5.16 (s, 2H), 2.89-2.79 (m, 4H), 2.98-2.73 (m, 4H), 2.39-2.30 (m, 1H), 1.97-1.84 (m, 2H), 1.19-1.10 (m, 2H), 0.93-0.82 (m, 2H).

Example 32: 2-((5-cyclopropyl-3-(2,6-dichlorophenyl)isoxazol-4-yl)methoxy)-7-(methylsulfonyl)-10,11-dihydrobenzo[6,7]oxepino[3,2-b]pyridine

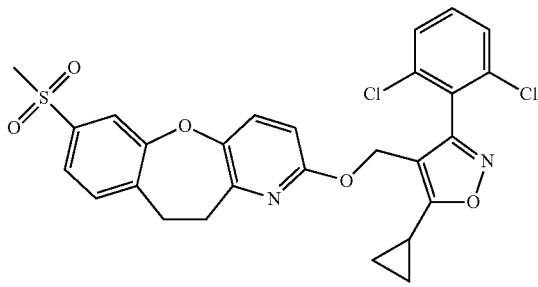 [SMILES: CS(=O)(=O)c1ccc2c(c1)Oc1ccc(OCc3c(-c4c(Cl)cccc4Cl)noc3C3CC3)nc1CC2]

Step 1:
3-bromo-2-(bromomethyl)-6-methoxypyridine

To a solution of (3-bromo-6-methoxypyridin-2-yl)methanol (2.4 g, 11 mmol) (See the synthetic method described in Organic and Biomolecular Chemistry, 2003, (1)16, 2865-2876) in dichloromethane (150 mL) were added sequentially triphenylphosphine (3.3 g, 12.7 mmol) and N-bromosuccinimide (1.78 g, 12.6 mmol) under an ice bath, and the mixture was stirred for 3 h under the ice bath. The reaction mixture was quenched with 50 mL of saturated sodium bicarbonate aqueous solution, and the resulting solution was extracted with dichloromethane (150 mL×2). The organic layers were combined, and the combined organic layers were washed with 20 mL of saturated brine, dried over anhydrous sodium sulfate, filtered, and concentrated under vacuum. The residue was purified by column chromatography on silica gel eluted with (petroleum ether/ethyl acetate (v/v)=30/1) to give the title compound as a colorless oil (2.8 g, 91%).

Step 2: diethyl ((3-bromo-6-methoxypyridin-2-yl)methyl)phosphonate

Using 3-bromo-2-(bromomethyl)-6-methoxypyridine (2.8 g, 10 mmol) as a starting material, the title compound was prepared according to the procedure described in step 3 of example 3 as a yellow oil (3.4 g, 100%).

Step 3: 4-bromo-2-(methoxymethoxy)benzaldehyde

Using 4-bromosalicylaldehyde (5.0 g, 25 mmol) as a starting material, the title compound was prepared according to the procedure described in step 5 of example 3 as a white solid (6.0 g, 98%).

Step 4: 3-bromo-2-(4-bromo-2-(methoxymethoxy)styryl)-6-methoxypyridine

Using diethyl ((3-bromo-6-methoxypyridin-2-yl)methyl)phosphonate (3.4 g, 10 mmol) and 4-bromo-2-(methoxymethoxy)benzaldehyde (3.0 g, 12 mmol) as starting materials, the title compound was prepared according to the procedure described in step 6 of example 3 as a yellow oil (3.8 g, 88%).

$^1$H NMR (400 MHz, CDCl$_3$) δ8.05 (d, J=15.7 Hz, 1H), 7.69 (d, J=8.6 Hz, 1H), 7.60 (d, J=15.7 Hz, 1H), 7.53 (d, J=8.3 Hz, 1H), 7.34 (s, 1H), 7.20 (d, J=8.3 Hz, 1H), 6.55 (d, J=8.6 Hz, 1H), 5.29 (s, 2H), 4.02 (s, 3H), 3.56 (s, 3H).

Step 5: 3-bromo-2-(4-bromo-2-(methoxymethoxy)phenethyl)-6-methoxypyridine

Using 3-bromo-2-(4-bromo-2-(methoxymethoxy)styryl)-6-methoxypyridine (3.8 g, 8.9 mmol) as a starting material, the title compound was prepared according to the procedure described in step 7 of example 3 as a white solid (3.0 g, 79%).

Step 6: 5-bromo-2-(2-(3-bromo-6-methoxypyridin-2-yl)ethyl)phenol

Using 3-bromo-2-(4-bromo-2-(methoxymethoxy)phenethyl)-6-methoxypyridine (3.0 g, 7.0 mmol) as a starting material, the title compound was prepared according to the procedure described in step 8 of example 3 as a white solid (2.5 g, 93%).

$^1$H NMR (400 MHz, CDCl$_3$) δ8.47 (s, 1H), 7.73 (d, J=8.7 Hz, 1H), 7.05 (d, J=1.7 Hz, 1H), 7.02 (s, 1H), 6.99 (d, J=1.7 Hz, 1H), 6.56 (d, J=8.7 Hz, 1H), 3.99 (s, 3H), 3.21 (t, J=6.4 Hz, 2H), 3.06 (t, J=6.5 Hz, 2H).

Step 7: 7-bromo-2-methoxy-10,11-dihydrobenzo[6,7]oxepino[3,2-b]pyridine

Using 5-bromo-2-(2-(3-bromo-6-methoxypyridin-2-yl)ethyl)phenol (200 mg, 0.5 mmol) as a starting material, the title compound was prepared according to the procedure described in step 8 of example 3 as a yellow solid (80 mg, 50%).

Step 8: 2-methoxy-7-(methylsulfonyl)-10,11-dihydrobenzo[6,7]oxepino[3,2-b]pyridine Under nitrogen, 7-bromo-2-methoxy-10,11-dihydrobenzo[6,7]oxepino[3,2-b]pyridine (100 mg, 0.3 mmol), iodide copper (6 mg, 0.03 mmol), L-proline, sodium (9 mg, 0.07 mmol) and sodium methylsulfinyl (40 mg, 0.4 mmol) were dissolved in dimethyl sulfoxide (10 mL), and the mixture was warmed to 95° C. and stirred for 36 h. The reaction mixture was cooled to room temperature, diluted with water (30 mL), and extracted with ethyl acetate (40 mL×2). The organic layers were combined. The combined organic layers were washed with 20 mL of saturated brine, dried over anhydrous sodium sulfate, filtered, and concentrated under vacuum. The residue was purified by column chromatography on silica gel eluted with (petroleum ether/ethyl acetate (v/v)=5/1) to give the title compound as a yellow solid (30 mg, 30%).

MS (ESI, pos. ion) m/z: 306.1 [M+H]$^+$.

Step 9: 7-(methylsulfonyl)-10,11-dihydrobenzo[6,7]oxepino[3,2-b]pyridin-2(1H)-one Using 2-methoxy-7-(methylsulfonyl)-10,11-dihydrobenzo[6,7]oxepino[3,2-b]pyridine (200 mg, 0.7 mmol) as a starting material, the title compound was prepared according to the procedure described in step 10 of example 3 as a yellow solid (190 mg, 100%).

MS (ESI, pos. ion) m/z: 392.0 [M+H]$^+$.

Step 10: 2-((5-cyclopropyl-3-(2,6-dichlorophenyl)isoxazol-4-yl)methoxy)-7-(methylsulfonyl)-10,11-dihydrobenzo[6,7]oxepino[3,2-b]pyridine Using 7-(methylsulfonyl)-10,11-dihydrobenzo[6,7]oxepino[3,2-b]pyridin-2(1H)-one (190 mg, 0.65 mmol) and 4-(chloromethyl)-5-cyclopropyl-3-(2,6-dichlorophenyl)isoxazole (240 mg, 0.8 mmol) as starting materials, the title compound was prepared according to the procedure described in step 11 of example 3 as a yellow solid (200 mg, 60%).

MS (ESI, pos. ion) m/z: 557.0 [M+H]$^+$; and
$^1$H NMR (400 MHz, CDCl$_3$) δ7.75-7.70 (m, 1H), 7.69-7.63 (m, 1H), 7.45-7.40 (m, 1H), 7.39-7.34 (m, 3H), 7.31-7.29 (m, 1H), 6.44 (d, J=8.7 Hz, 1H), 5.13 (s, 2H), 3.27-3.20 (m, 2H), 3.16-3.09 (m, 2H), 3.06 (s, 3H), 2.38-2.29 (m, 1H), 1.29-1.27 (m, 2H), 1.19-1.11 (m, 2H).

Example 33: 8-((5-cyclopropyl-3-(2,6-dichlorophenyl)isoxazol-4-yl)methoxy)-10,11-dihydrooxepino[3,2-b:7,6-c']dipyridine-3-carboxylic acid

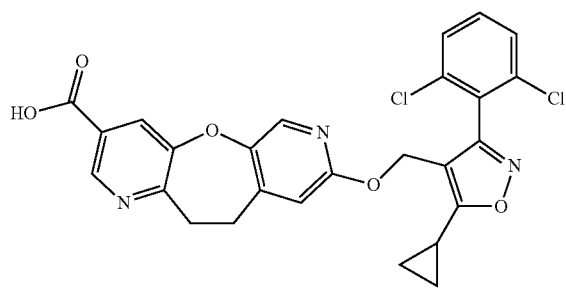 [SMILES: O=C(O)c1cnc2c(c1)Oc1cnc(OCc3c(-c4c(Cl)cccc4Cl)noc3C3CC3)cc1CC2]

Step 1: methyl 5-bromo-6-iodonicotinate

To a mixture of methyl 5-bromo-6-chloronicotinate (8.0 g, 32 mmol) in acetonitrile (120 mL) were added sequentially sodium iodide (14 g, 93 mmol) and trimethylsilyl iodide (7.0 g, 35 mmol) at room temperature, and the mxiture was stirred at room temperature overnight. The organic layers were combined, and the combined organic layers were washed with 20 mL of saturated brine, dried over anhydrous sodium sulfate, filtered, and concentrated under vacuum. The residue was purified by column chromatography on silica gel eluted with (petroleum ether/ethyl acetate (v/v)=20/1) to give the title compound as a white solid (8.1 g, 74%).

Step 2: dimethyl 3-bromopyridine-2,5-dicarboxylate

To a mixture of methyl 5-bromo-6-iodonicotinate (5.0 g, 14.6 mmol) in a mixture of acetonitrile (60 mL) and methanol (20 mL) were added trans-dichlorobis(triphenyl-phosphine)Palladium(II) (0.3 g, 0.44 mmol) and triethylamine (2.2 g, 21 mmol). The mixture was placed in an autoclave and stirred at 50° C. for 5 h under carbon monoxide (4.0 MPa). The reaction mixture was cooled to room temperature, and concentrated under vacuum. The residue was purified by column chromatography on silica gel eluted with (petroleum ether/ethyl acetate (v/v)=10/1) to give the title compound as a yellow solid (3.3 g, 82%).

MS (ESI, pos. ion) m/z: 273.9 [M+H]$^+$; and
$^1$H NMR (400 MHz, CDCl$_3$) δ9.16 (s, 1H), 8.60 (s, 1H), 4.05 (s, 3H), 4.01 (s, 3H).

Step 3: methyl 5-bromo-6-(hydroxymethyl)nicotinate

To a mixture of dimethyl 3-bromopyridine-2,5-dicarboxylate (3.3 g, 12 mmol) in a mixture tetrahydrofuran (25 mL) and methanol (50 mL) were added sequentially calcium chloride (5.4 g, 48 mmol) and sodium borohydride (1.1 g, 71 mmol) under an ice bath, and the mixture was stirred for 2 h under the ice bath. The reaction mixture was quenched with 50 mL of water. The resulting solution was extracted with ethyl acetate (100 mL×2). The organic layers were combined, and the combined organic layers were washed with 20 mL of saturated brine, dried over anhydrous sodium sulfate, filtered, and concentrated under vacuum. The residue was purified by column chromatography on silica gel eluted with (petroleum ether/ethyl acetate (v/v)=10/1) to give the title compound as a white solid (1.0 g, 34%).

$^1$H NMR (400 MHz, CDCl$_3$) δ9.13 (s, 1H), 8.48 (s, 1H), 4.83 (d, J=4.6 Hz, 2H), 4.00 (s, 3H).

Step 4: methyl 5-bromo-6-(bromomethyl)nicotinate

To a mixture of methyl 5-bromo-6-(hydroxymethyl)nicotinate (3.3 g, 12 mmol) in dichloromethane (150 mL) were added sequentially triphenylphosphine (1.2 g, 4.6 mmol) and N-bromosuccinimide (0.7 g, 3.8 mmol) under an ice bath, and the mixture was stirred for 3 h under the ice bath. The reaction mixture was quenched with 20 mL of saturated sodium bicarbonate aqueous solution. The resulting solution was extracted with dichloromethane (150 mL×2). The organic layers were combined, and the combined organic layers were washed with 20 mL of saturated brine, dried over anhydrous sodium sulfate, filtered, and concentrated under vacuum. The residue was purified by column chromatography on silica gel eluted with (petroleum ether/ethyl acetate (v/v)=30/1) to give the title compound as a white solid (900 mg, 70%).

Step 5: methyl 5-bromo-6-((diethoxyphosphoryl)methyl)nicotinate

A solution of methyl 5-bromo-6-(bromomethyl)nicotinate (0.9 g, 3 mmol) in triethyl phosphite (35 mL) was heated to 130° C. and stirred for 2.5 h. The reaction solution was cooled to room temperature, and triethyl phosphite was removed by evaporation under vacuum to give the title compound as a yellow oil (1.0 g, 90%).

Step 6: methyl 5-bromo-6-(2-(2-methoxy-5-(methoxymethoxy)pyridin-4-yl)vinyl) nicotinate Using methyl 5-bromo-6-((diethoxyphosphoryl)methyl) nicotinate (1.0 g, 2.7 mmol) and 2-methoxy-5-(methoxymethoxy)pyridine-4-carbaldehyde (0.64 g, 3.2 mmol) as starting materials, the title compound was prepared according to the procedure described in step 3 of example 4 as a yellow solid (800 mg, 70%).

$^1$H NMR (400 MHz, CDCl$_3$) δ9.17-9.11 (m, 1H), 8.51-8.46 (m, 1H), 8.14 (d, J=15.8 Hz, 1H), 8.10 (s, 1H), 7.86 (d, J=15.8 Hz, 1H), 7.02 (s, 1H), 5.24 (s, 2H), 3.99 (s, 3H), 3.95 (s, 3H), 3.56 (s, 3H).

Step 7: methyl 5-bromo-6-(2-(2-methoxy-5-(methoxymethoxy)pyridin-4-yl)ethyl) nicotinate Using methyl 5-bromo-6-(2-(2-methoxy-5-(methoxymethoxy)pyridin-4-yl)vinyl) nicotinate (0.8 g, 2.0 mmol) as a starting material, the title compound was prepared according to the procedure described in step 4 of example 4 as a yellow solid (600 mg, 70%).

Step 8: methyl 5-bromo-6-(2-(5-hydroxy-2-methoxypyridin-4-yl)ethyl)nicotinate Using methyl 5-bromo-6-(2-(2-methoxy-5-(methoxymethoxy)pyridin-4-yl)ethyl) nicotinate (0.6 g, 1.4 mmol) as a starting material, the title compound was prepared according to the procedure described in step 5 of example 4 as a yellow solid (460 mg, 90%).

Step 9: methyl 8-methoxy-10,11-dihydrooxepino[3,2-b:7,6-c']dipyridine-3-carboxylate Using methyl 5-bromo-6-(2-(5-hydroxy-2-methoxypyridin-4-yl)ethyl)nicotinate (50 mg, 0.13 mmol) as a starting material, the title compound was prepared according to the procedure described in step 6 of example 4 as a yellow solid (20 mg, 50%).

MS (ESI, pos. ion) m/z: 287.0 [M+H]$^+$.

Step 10: methyl 8-oxo-7,8,10,11-tetrahydrooxepino[3,2-b:7,6-c']dipyridine-3-carboxylate Using methyl 8-methoxy-10,11-dihydrooxepino[3,2-b:7,6-c']dipyridine-3-carboxylate (130 mg, 0.45 mmol) as a starting material, the title compound was prepared according to the procedure described in step 7 of example 4 as a yellow solid (120 mg, 97%).

MS (ESI, pos. ion) m/z: 273.0 [M+H]$^+$.

Step 11: methyl 8-((5-cyclopropyl-3-(2,6-dichlorophenyl)isoxazol-4-yl)methoxy)-10,11-dihydrooxepino[3,2-b:7,6-c']dipyridine-3-carboxylate Using methyl 8-oxo-7,8,10,11-tetrahydrooxepino[3,2-b:7,6-c']dipyridine-3-carboxylate (120 mg, 0.44 mmol) and 4-(chloromethyl)-5-cyclopropyl-3-(2,6-dichlorophenyl)isoxazole (160 mg, 0.53 mmol) as starting materials, the title compound was prepared according to the procedure described in step 8 of example 4 as a yellow oil (40 mg, 20%).

MS (ESI, pos. ion) m/z: 538.0 [M+H]$^+$.

Step 12: 8-((5-cyclopropyl-3-(2,6-dichlorophenyl)isoxazol-4-yl)methoxy)-10,11-dihydrooxepino[3,2-b:7,6-c']dipyridine-3-carboxylic acid Using methyl 8-((5-cyclopropyl-3-(2,6-dichlorophenyl)isoxazol-4-yl)methoxy)-10,11-dihydrooxepino[3,2-b:7,6-c']dipyridine-3-carboxylate (40 mg, 0.07 mmol) as a starting material, the title compound was prepared according to the procedure described in step 9 of example 4 as a white solid (10 mg, 26%).

MS (ESI, pos. ion) m/z: 524.0 [M+H]$^+$; and
$^1$H NMR (400 MHz, CDCl$_3$) δ8.95 (s, 1H), 8.13 (s, 1H), 7.94 (s, 1H), 7.45-7.36 (m, 2H), 7.34-7.29 (m, 1H), 6.48 (s, 1H), 5.13 (s, 2H), 3.46-3.33 (m, 2H), 3.25-3.08 (m, 2H), 2.36-2.29 (m, 1H), 1.20-1.12 (m, 2H), 0.96-0.88 (m, 2H).

Example 34: methyl 3-((5-cyclopropyl-3-(2,6-dichlorophenyl)isoxazol-4-yl)methoxy)-1a,10b-dihydro-1H-benzo[6,7]cyclopropa[4,5]oxepino[3,2-b]pyridine-8-carboxylate

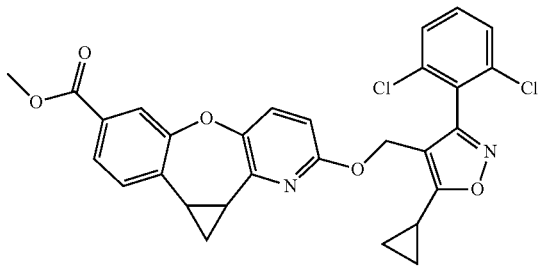 [SMILES: COC(=O)c1ccc2c(c1)Oc1ccc(OCc3c(-c4c(Cl)cccc4Cl)noc3C3CC3)nc1C1CC21]

Step 1: methyl 3-methoxy-1a,10b-dihydro-1H-benzo[6,7]cyclopropa[4,5]oxepino[3,2-b]pyridine-8-carboxylate Under nitrogen, trimethyl iodide sulfoxide (1.77 g, 8.0 mmol) was dissolved in dimethyl sulfoxide (12 mL), sodium hydride (300 mg, 2.8 mmol) was added slowly at room temperature, and the mixture was stirred at room temperature for 30 min. To the mixture was added a solution of methyl 2-methoxybenzo[6,7]oxepino[3,2-b]pyridine-7-carboxylate (450 mg, 1.5 mmol) in dimethyl sulfoxide (2 mL), and the mxiture was warmed to 80° C. and stirred overnight. After being cooled to room temperature, the mixture was quenched with saturated ammonium chloride aqueous solution (50 mL), and extracted with ethyl acetate (100 mL×2). The organic layers were combined, and the combined organic layers were washed with 20 mL of saturated brine, dried over anhydrous sodium sulfate, filtered, and concentrated under vacuum. The residue was purified by column chromatography on silica gel eluted with (petroleum ether/ethyl acetate (v/v)=10/1) to give the title compound as a pale yellow solid (45 mg, 9.5%).

MS (ESI, pos. ion) m/z: 298.1 [M+H]$^+$.

Step 2: methyl 3-oxo-1a,2,3,10b-tetrahydro-1H-benzo[6,7]cyclopropa[4,5]oxepino [3,2-b]pyridine-8-carboxylate Using methyl 3-methoxy-1a,10b-dihydro-1H-benzo[6,7]cyclopropa[4,5]oxepino [3,2-b]pyridine-8-carboxylate (45 mg, 0.15 mmol) as a starting material, the title compound was prepared according to the procedure described in step 10 of example 3 as a pale yellow solid (36 mg, 85%).

MS (ESI, pos. ion) m/z: 284.0 [M+H]$^+$.

Step 3: methyl 3-((5-cyclopropyl-3-(2,6-dichlorophenyl)isoxazol-4-yl)methoxy)-1a,10b-dihydro-1H-benzo[6,7]cyclopropa[4,5]oxepino[3,2-b]pyridine-8-carboxylate Using methyl 3-oxo-1a,2,3,10b-tetrahydro-1H-benzo[6,7]cyclopropa[4,5]oxepino [3,2-b]pyridine-8-carboxylate (36 mg, 0.13 mmol) and 4-(chloromethyl)-5-cyclopropyl-3-(2,6-dichlorophenyl)isoxazole (53 mg, 0.18 mmol) as starting materials, the title compound was prepared according to the procedure described in step 11 of example 3 as a pale yellow solid (42 mg, 60%).

MS (ESI, pos. ion) m/z: 549.0 [M+H]$^+$.

Example 35: 7-carboxy-2-((5-cyclopropyl-3-(2,6-dichlorophenyl)isoxazol-4-yl)methoxy)-10,11-dihydrobenzo[6,7]oxepino[3,2-b]pyridine-1-oxide

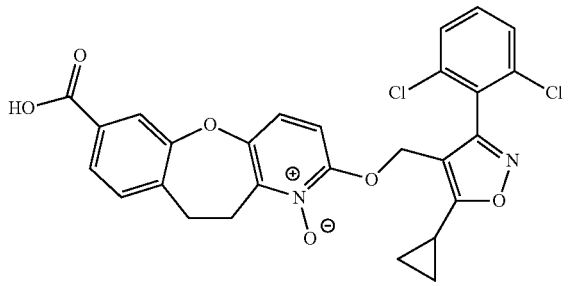 [SMILES: O=C(O)c1ccc2c(c1)Oc1ccc(OCc3c(-c4c(Cl)cccc4Cl)noc3C3CC3)[n+]([O-])c1CC2]

Step 1: 2-((5-cyclopropyl-3-(2,6-dichlorophenyl)isoxazol-4-yl)methoxy)-7-(methoxycarbonyl)-10,11-dihydrobenzo[6,7]oxepino[3,2-b]pyridine-1-oxide To a solution of methyl 2-((5-cyclopropyl-3-(2,6-dichlorophenyl)isoxazol-4-yl)methoxy)-10,11-dihydrobenzo[6,7]oxepino[3,2-b]pyridine-7-carboxylate (190 mg, 0.35 mmol) in chloroform (10 mL) was added m-chloroperbenzoic acid (130 mg, 0.7 mmol) in portions at room temperature, and the mixture was stirred for 6 h at room temperature, then heated to 60° C. and stirred for 10 h. The mixture was quenched with saturated sodium bicarbonate aqueous solution (50 mL), and extracted with dichloromethane (150 mL×2). The organic layers were combined, and the combined organic layers were washed with 20 mL of saturated brine, dried over anhydrous sodium sulfate, filtered, and concentrated under vacuum. The residue was purified by column chromatography on silica gel eluted with (dichloromethane/ethyl acetate (v/v)=5/1) to give the title compound as a white solid (40 mg, 20%).

MS (ESI, pos. ion) m/z: 553.1 [M+H]$^+$.

Step 2: 7-carboxy-2-((5-cyclopropyl-3-(2,6-dichlorophenyl)isoxazol-4-yl)methoxy)-10,11-dihydrobenzo[6,7]oxepino[3,2-b]pyridine-1-oxide 2-((5-Cyclopropyl-3-(2,6-dichlorophenyl)isoxazol-4-yl)methoxy)-7-(methoxycarbonyl)-10,11-dihydrobenzo[6,7]oxepino[3,2-b]pyridine-1-oxide (40 mg, 0.07 mmol) was dissolved in a mixed solvent of tetrahydrofuran (5 mL) and water (5 mL), and sodium hydroxide (17 mg, 0.42 mmol) was added. The reaction mixture was stirred at room temperature overnight. Most of the solvent was removed under vacuum. The residue was diluted with water (10 mL), and adjusted to acidity with 1 M hydrochloric acid (2 mL). The resulting mixture was extracted with ethyl acetate (20 mL×2). The organic layers were combined, and the combined organic layers were washed with 10 mL of saturated brine, dried over anhydrous sodium sulfate, filtered, and concentrated under vacuum. The residue was purified by column chromatography on silica gel eluted with (dichloromethane/methanol (v/v)=10/1) to give the title compound as a white solid (20 mg, 53%).

MS (ESI, pos. ion) m/z: 539.1 [M+H]+; and
1H NMR (400 MHz, CDCl$_3$) δ7.89 (d, J=7.8 Hz, 1H), 7.84 (s, 1H), 7.42-7.34 (m, 3H), 7.34-7.29 (m, 1H), 7.12 (d, J=9.0 Hz, 1H), 6.64 (d, J=9.0 Hz, 1H), 5.29 (s, 2H), 3.28-3.23 (m, 4H), 2.31-2.23 (m, 1H), 1.23-1.17 (m, 2H), 1.06-0.98 (m, 2H).

Example 36: TR-FRET Farnesoid X Receptor Coactivator Assay

1. Test Method
Purchasing invitrogen PV4833 kits.
First, the required amount of the compound was weighed and dissolved in 100% DMSO at the maximum concentration of 3000 μM. The solution at the maximum concentration was diluted by 3-fold serial dilution in DMSO to get 10 concentrations;

Second, the above prepared solutions of different concentrations were diluted to 100-fold with a buffer supplied with the kit, followed by mixing and then 10 μL of the diluted solution was added to a 384 well plate;

Third, nuclear receptor FXR recombinant protein was diluted with a buffer to give a concentration of 4×, and 5 μL of the diluent was added to the 384 well plate of second step;

Fourth, Fluorescein-SRC2-2 and Tb anti-GST antibody were diluted with a buffer to give a concentration of 4× respectively. Then two reagents were mixed together, and 10 μL of the mixture was added to the 384 well plate of third step;

Finally, the solution of the 384 well above was mixed uniformly by centrifuging, and then incubated at room temperature for 1 h. Then the TR-FRET Endpoint was used for measuring the solution at wavelengths of 520 nm, 495 nm and 337 nm. EC50 values were calculated according to the measured value of ER=520 nm/495 nm.

2. Test Results: See Table 2

TABLE 2

Test results of TR-FRET farnesoid X receptor protein coactivator activity

| Compound No | EC$_{50}$ (nM) | Compound No. | EC$_{50}$ (nM) |
| --- | --- | --- | --- |
| Example 1 | 18 | Example 15 | 35 |
| Example 2 | 4 | Example 17 | 23 |
| Example 3 | 37 | Example 19 | 6 |
| Example 4 | 46 | Example 27 | 12 |
| Example 5 | 6 | Example 29 | 11 |
| Example 6 | 55 | Example 30 | 27 |
| Example 7 | 15 | Example 31 | 56 |
| Example 9 | 38 | Example 32 | 54 |
| Example 11 | 56 | Example 33 | 18 |

3. Conclusion:
EC50 values in Table 2 indicated that the compounds of the present invention showed good activity, and played a good role in the regulation of farnesoid X receptor protein.

Example 37: Pharmacokinetics Test

1. Test Method
Experimental animals: six healthy adult male SD rats (purchased from Hunan Slack King of Laboratory Animal Co. Ltd.) were divided into two groups, three rats in each group, and the two grops were given intravenous injection and oral administration respectively.

Drug preparation: a quantity of a compound of the present invention was weighed, and 5% DMSO, 10% Kolliphor HS15 and 85% saline (0.9%) were added to give target concentrations of the compound solution.

Administration and sample collection: animals were fasting for 12 h until administered, eating 3 h after the administration. Hind legs of SD rats of one group were given intravenous injection (IV, 1 mg/kg) and SD rats of the other group were given oral administration (PO, 5 mg/kg) respectively. Then blood was collected in the rat tail vein at the time point 0, 0.083, 0.25, 0.5, 1, 2, 4, 6, 8, 24 h respectively, and the blood volume was about 200-400 μL/time points. After the collection of whole blood at each time point, the colleted blood was set in K2EDTA anticoagulant tube, and the tube was placed in the incubator with ice packs. All samples were centrifuged for 5 min at 4° C. at 4600 r/min within 15 min. Plasma was separated and colleted. The concentrations of different compounds in the plasma of the rats after adminstration were measured using LC/MS/MS method, and the pharmacokinetic parameters were calculated according to the curve of the drug concentration-time.

Pharmacokinetic properties of the compounds of the present invention were tested by the experiment above, and the pharmacokinetic parameters were shown in Table 3.

2. Test Results

TABLE 3

Pharmacokinetic activity of the compound of the invention

| Compound No | Route of administration | Dose (mg/kg) | F (%) | $AUC_{INF}$ (h*ng/ml) | $AUC_{last}$ (h*ng/ml) | Cl (ml/min/kg) | $C_{max}$ (ng/ml) | $MRT_{INF}$ (h) | $T_{1/2}$ (h) | $T_{max}$ (h) | $V_{ss}$ (l/kg) |
|---|---|---|---|---|---|---|---|---|---|---|---|
| Example 2 | iv | 1 | 189.7 | 1210 | 1180 | 14 | 2560 | 1.05 | 1.82 | 0.08 | 0.86 |
| | po | 5 | | 11300 | 11200 | / | 9970 | 2.35 | 4.16 | 0.33 | / |
| Example 4 | iv | 1 | 44.7 | 878 | 877 | 19 | 1900 | 0.4 | 0.5 | 0.08 | 0.45 |
| | po | 5 | | 1980 | 1960 | / | 1800 | 1.37 | 4.9 | 0.33 | / |
| Example 5 | iv | 1 | 62.6 | 941 | 926 | 18 | 2420 | 0.76 | 1.56 | 0.08 | 0.82 |
| | po | 5 | | 3350 | 2900 | / | 1300 | 8.57 | 11.7 | 0.33 | / |
| Example 17 | iv | 1 | 67.7 | 1840 | 1840 | 50 | 4280 | 0.32 | 0.43 | 0.08 | 0.89 |
| | po | 5 | | 6240 | 6230 | / | 5960 | 0.84 | 0.79 | 0.33 | / |

Conclusions: Table 3 indicated that blood concentration and exposure levels of the rats were high after oral administration of the compounds of the present invention, clear rate of the compound was low, and bioavailability of the compound was high. So the compounds of the present invention had good pharmacokinetic characteristics Finally, it should be noted that there are other ways to practice the invention. Accordingly, embodiments of the present invention is to be described as examples, but the present invention is not limited to the contents described, further modifications may be made within the scope of the present invention or the equivalents added in the claims. All publications or patents cited herein are incorporated by reference in this invention.

What is claimed is:

1. A compound of Formula (I) or a stereoisomer, a geometric isomer, a tautomer, an N-oxide, a hydrate, a solvate, a pharmaceutically acceptable salt or a prodrug thereof,

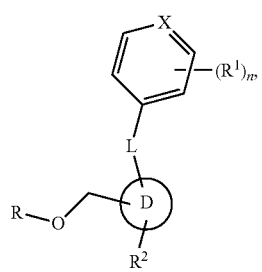

(I)

wherein:

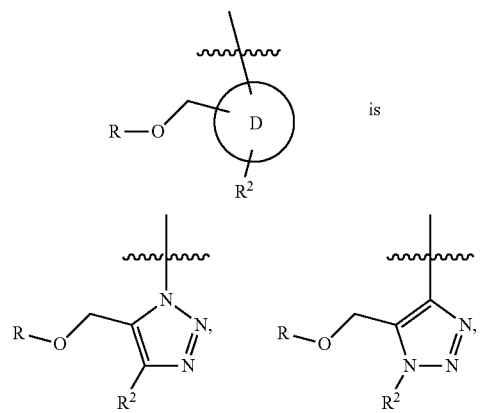

is

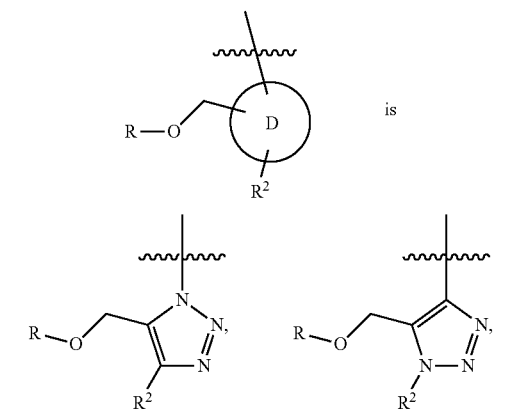

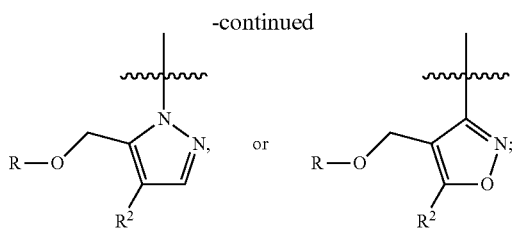

X is N or CH;
L is a bond;
R is:

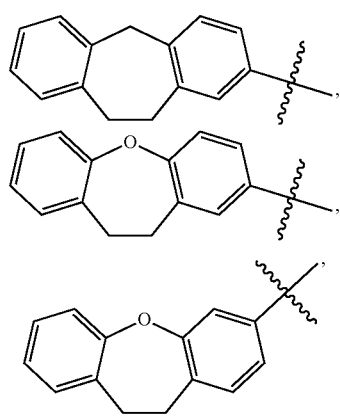

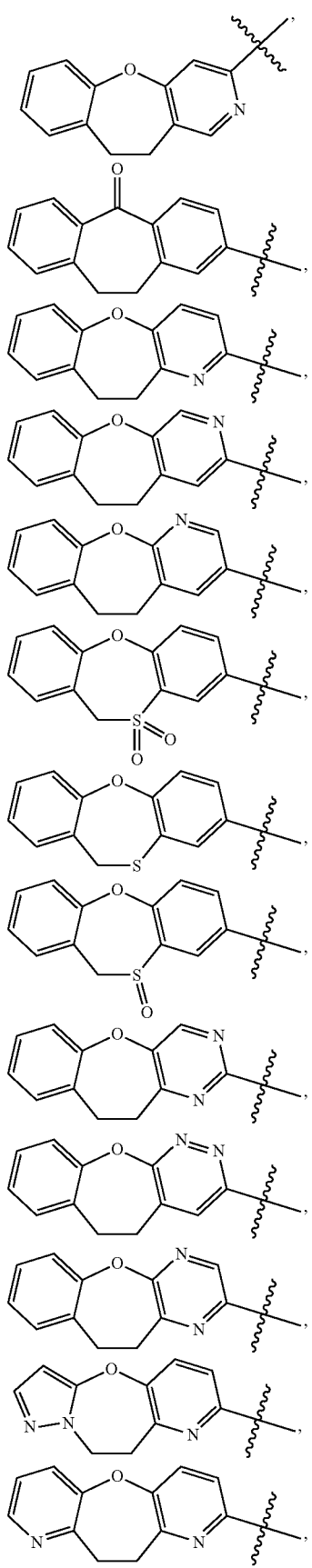
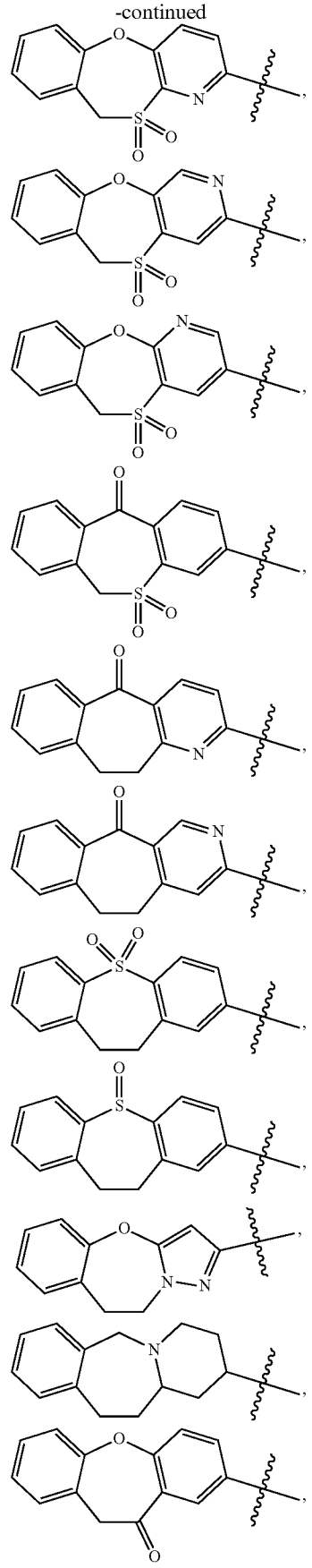

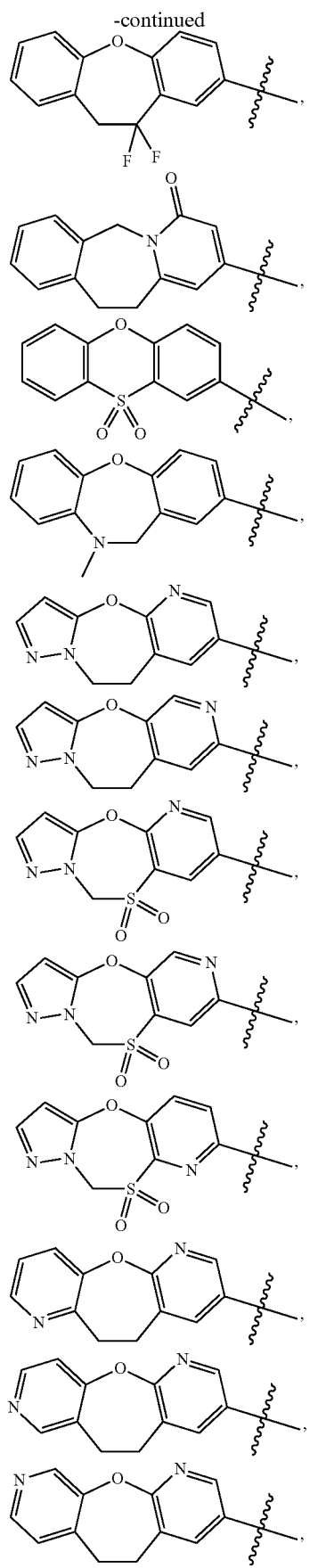
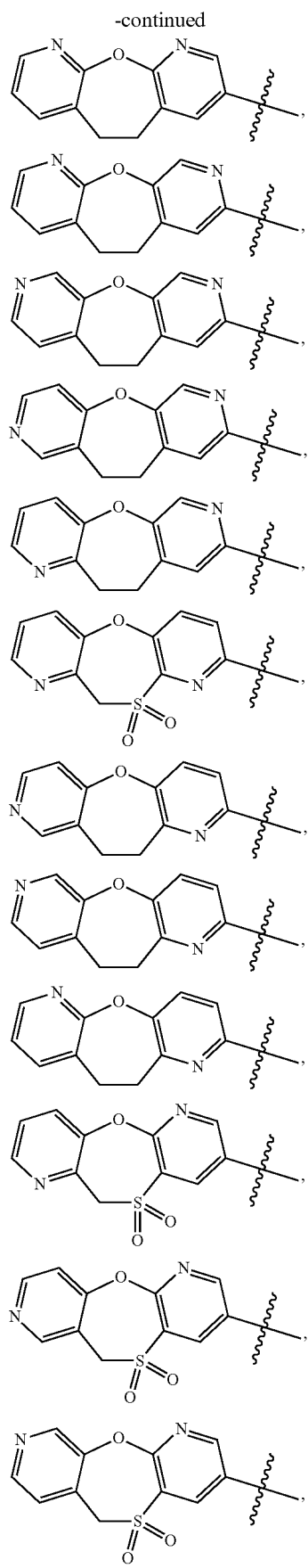

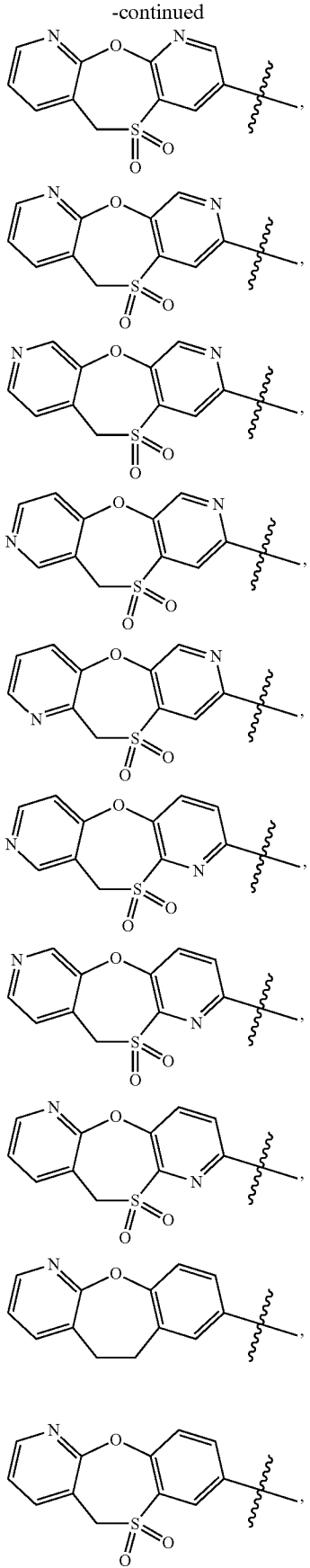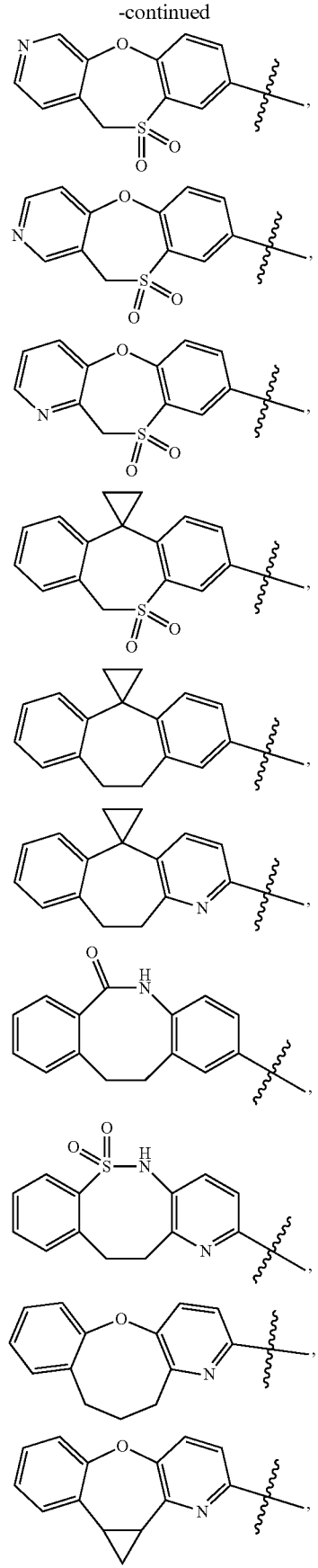

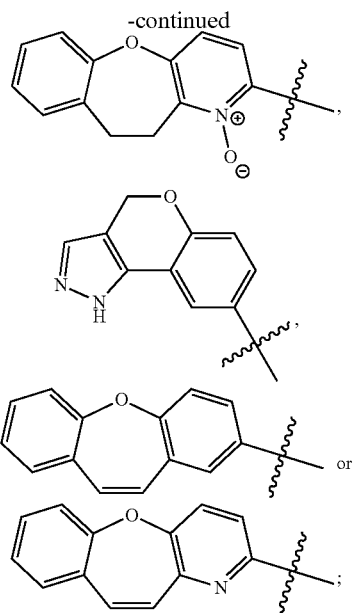

wherein each moiety represented by R is independently and optionally substituted with one, two, three, four or five $R^8$;

each $R^1$ is independently H, deuterium, F, Cl, Br, I, hydroxy, amino, nitro, cyano, alkyl, haloalkyl, haloalkoxy, cycloalkyl, heterocyclyl, alkenyl, alkynyl, alkylamino, alkoxy, aryl or heteroaryl;

$R^2$ is H, deuterium, F, Cl, Br, I, hydroxy, amino, nitro, cyano, alkyl, haloalkyl, haloalkoxy, alkoxyalkyl, cycloalkyl, hydroxyalkyl, heterocyclyl, alkylamino or alkoxy;

each $R^8$ is independently H, deuterium, F, Cl, Br, I, hydroxy, nitro, amino, aminoalkyl, alkylamino, alkyl, hydroxyalkyl, alkoxy, haloalkyl, haloalkoxy, cycloalkyl, cycloalkoxy, alkenyl, alkynyl, aryl, halo-substituted aryl, arylalkyl, oxo (=O), -$L^1$-C(=O)OR$^{15}$, -$L^1$-S(=O)$_t$R$^{16}$, —O-$L^2$-C(=O)OR$^{15}$, —O-$L^2$-S(=O)$_t$R$^{16}$, —C(=O)NR$^{17}$R$^{18}$, —C(=O)N(R$^{17}$)S(=O)$_2$R$^{16}$, —C(=NR$^{17}$)NR$^{17}$R$^{18}$, —C(=O)N(R$^{17}$)-$L^3$-S(=O)$_2$OR$^{15}$, —C(=O)N(R$^{17}$)C(=O)OR$^{15}$, —C(=O)N(R$^{17}$)-$L^3$-C(=O)OR$^{15}$, cyano, heterocyclyl or heteroaryl; or two $R^8$, together with the same C atom to which they are attached, independently and optionally form cycloalkyl or heterocyclyl; or two $R^8$, together with the adjacent C atoms to which they are attached, independently and optionally form cycloalkyl, heterocyclyl, aryl or heteroaryl; wherein $R^8$ is independently and optionally substituted with one or more $R^{19}$;

each $R^{15}$ is independently H, deuterium, alkyl, aminoalkyl, alkenyl, alkynyl, haloalkyl, cycloalkyl, heterocyclyl or aryl;

each $R^{16}$ is independently H, deuterium, hydroxy, amino, alkyl, aminoalkyl, alkenyl, alkynyl, haloalkyl, cycloalkyl, heterocyclyl, aryl or —NR$^{17}$R$^{18}$;

each of $R^{17}$ and $R^{18}$ is independently H, deuterium, alkyl, aminoalkyl, alkenyl, alkynyl, haloalkyl, cycloalkyl, heterocyclyl or aryl;

each $L^1$ is independently a bond, —C(=O)—, $C_{1-6}$ alkylene, $C_{2-6}$ alkenylene or $C_{2-6}$ alkynylene;

each $L^2$ is independently $C_{1-6}$ alkylene, $C_{2-6}$ alkenylene or $C_{2-6}$ alkynylene;

each $L^3$ is independently a bond or $C_{1-4}$ alkylene;

n is 0, 1, 2, 3 or 4;

each f is independently 0, 1 or 2;

each t is independently 0, 1, or 2; and $R^{19}$ is H, deuterium, F, Cl, Br, I, cyano, oxo (=O), hydroxy, alkyl, alkylamino, amino, aryl, heterocyclyl, heteroaryl, alkenyl, alkynyl, cycloalkyl, alkoxy or haloalkyl.

2. The compound of claim 1, wherein each $R^1$ is independently H, deuterium, F, Cl, Br, I, hydroxy, amino, nitro, cyano, $C_{1-6}$ alkyl, $C_{1-6}$ haloalkyl, $C_{1-6}$ haloalkoxy, $C_{3-6}$ cycloalkyl, $C_{2-9}$ heterocyclyl, $C_{2-6}$ alkenyl, $C_{2-6}$ alkynyl, $C_{1-6}$ alkylamino, $C_{1-6}$ alkoxy, $C_{6-10}$ aryl or $C_{1-9}$ heteroaryl; and $R^2$ is H, deuterium, F, Cl, Br, I, hydroxy, amino, nitro, cyano, $C_{1-6}$ alkyl, $C_{1-6}$ haloalkyl, $C_{1-6}$ haloalkoxy, $C_{1-6}$ alkoxy-$C_{1-6}$-alkyl, $C_{3-6}$ cycloalkyl, $C_{1-6}$ hydroxyalkyl, $C_{2-9}$ heterocyclyl, $C_{1-6}$ alkylamino or $C_{1-6}$ alkoxy; or wherein each $R^1$ is independently H, deuterium, F, Cl, Br, I, hydroxy, amino, nitro, cyano, $C_{1-3}$ alkyl, $C_{1-3}$ haloalkyl, $C_{1-3}$ haloalkoxy, $C_{3-6}$ cycloalkyl, $C_{2-9}$ heterocyclyl, $C_{2-4}$ alkenyl, $C_{2-4}$ alkynyl, $C_{1-3}$ alkylamino, $C_{1-3}$ alkoxy, $C_{6-10}$ aryl or $C_{1-9}$ heteroaryl; and $R^2$ is H, deuterium, F, Cl, Br, I, hydroxy, amino, nitro, cyano, $C_{1-3}$ alkyl, $C_{1-3}$ haloalkyl, $C_{1-3}$ haloalkoxy, $C_{1-3}$ alkoxy-$C_{1-3}$-alkyl, $C_{3-6}$ cycloalkyl, $C_{1-3}$ hydroxyalkyl, $C_{2-9}$ heterocyclyl, $C_{1-3}$ alkylamino or $C_{1-3}$ alkoxy.

3. The compound of claim 1, wherein each $R^8$ is independently H, deuterium, F, Cl, Br, I, hydroxy, nitro, amino, $C_{1-6}$ aminoalkyl, $C_{1-6}$ alkylamino, $C_{1-6}$ alkyl, $C_{1-4}$ hydroxyalkyl, $C_{1-6}$ alkoxy, $C_{1-6}$ haloalkyl, $C_{1-6}$ haloalkoxy, $C_{3-6}$ cycloalkyl, $C_{3-6}$ cycloalkoxy, $C_{2-6}$ alkenyl, $C_{2-6}$ alkynyl, $C_{6-10}$ aryl, halo-substituted $C_{6-10}$ aryl, $C_{6-10}$ aryl-$C_{1-6}$-alkyl, oxo (=O), -$L^1$-C(=O)OR$^{15}$, -$L^1$-S(=O)$_t$R$^{16}$, —O-$L^2$-C(=O)OR$^{15}$, —O-$L^2$-S(=O)$_t$R$^{16}$, —C(=O)NR$^{17}$R$^{18}$, —C(=O)N(R$^{17}$)S(=O)$_2$R$^{16}$, —C(=NR$^{17}$)NR$^{17}$R$^{18}$, —C(=O)N(R$^{17}$)-$L^3$-S(=O)$_2$OR$^{15}$, —C(=O)N(R$^{17}$)C(=O)OR$^{15}$, —C(=O)N(R$^{17}$)-$L^3$-C(=O)OR$^{15}$, cyano, $C_{2-9}$ heterocyclyl or $C_{1-9}$ heteroaryl; or two $R^8$, together with the same C atom to which they are attached, independently and optionally form $C_{3-6}$ cycloalkyl or $C_{2-9}$ heterocyclyl; or two $R^8$, together with the adjacent C atoms to which they are attached, independently and optionally form $C_{3-6}$ cycloalkyl, $C_{2-9}$ heterocyclyl, $C_{6-10}$ aryl or $C_{1-9}$ heteroaryl;

each $R^{15}$ is independently H, deuterium, $C_{1-6}$ alkyl, $C_{1-6}$ aminoalkyl, $C_{2-6}$ alkenyl, $C_{2-6}$ alkynyl, $C_{1-6}$ haloalkyl, $C_{3-6}$ cycloalkyl, $C_{2-9}$ heterocyclyl or $C_{6-10}$ aryl;

each $R^{16}$ is independently H, deuterium, hydroxy, amino, $C_{1-6}$ alkyl, $C_{1-6}$ aminoalkyl, $C_{2-6}$ alkenyl, $C_{2-6}$ alkynyl, $C_{1-6}$ haloalkyl, $C_{3-6}$ cycloalkyl, $C_{2-9}$ heterocyclyl, $C_{6-10}$ aryl or —NR$^{17}$R$^{18}$; and each of $R^{17}$ and $R^{18}$ is independently H, deuterium, $C_{1-6}$ alkyl, $C_{1-6}$ aminoalkyl, $C_{2-6}$ alkenyl, $C_{2-6}$ alkynyl, $C_{1-6}$ haloalkyl, $C_{3-6}$ cycloalkyl, $C_{2-9}$ heterocyclyl or $C_{6-10}$ aryl.

4. The compound of claim 1 of Formula (II) or Formula (V) or a stereoisomer, a geometric isomer, a tautomer, an N-oxide, a hydrate, a solvate, a pharmaceutically acceptable salt or a prodrug thereof,

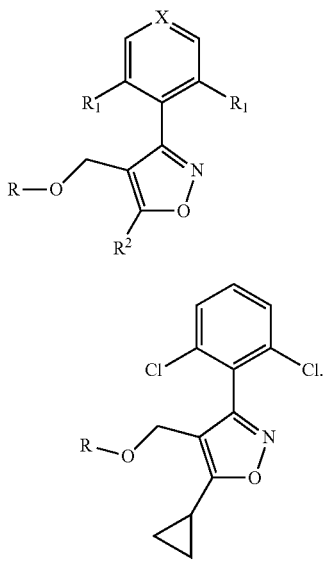

(II)

(V)

5. The compound of claim 1, wherein
each $R^5$ is independently H, deuterium, $C_{1-6}$ alkyl, $C_{1-6}$ aminoalkyl, $C_{1-6}$ haloalkyl, $C_{3-6}$ cycloalkyl, $C_{2-9}$ heterocyclyl, $C_{6-10}$ aryl, halo-substituted $C_{6-10}$ aryl or $C_{6-10}$ aryl-$C_{1-6}$-alkyl; and
each of $R^6$ and $R^7$ is independently H, deuterium, F, Cl, Br, I, cyano, hydroxy, $C_{1-6}$ hydroxyalkyl, $C_{1-6}$ alkyl, $C_{1-6}$ alkylamino, $C_{1-6}$ aminoalkyl, $C_{2-6}$ alkenyl, $C_{2-6}$ alkynyl, $C_{3-6}$ cycloalkyl, $C_{1-6}$ haloalkyl, $C_{6-10}$ aryl, halo-substituted $C_{6-10}$ aryl or $C_{6-10}$ aryl-$C_{1-6}$-alkyl; or $R^6$ and $R^7$, together with the C atom to which they are attached, independently and optionally form $C_{3-6}$ cycloalkyl or $C_{2-9}$ heterocyclyl; or
each $R^5$ is independently H, deuterium, $C_{1-3}$ alkyl, $C_{1-3}$ aminoalkyl, $C_{1-3}$ haloalkyl, $C_{3-6}$ cycloalkyl, $C_{2-6}$ heterocyclyl, phenyl or benzyl; and
each of $R^6$ and $R^7$ is independently H, deuterium, F, Cl, Br, I, cyano, hydroxy, $C_{1-3}$ alkyl, $C_{1-4}$ hydroxyalkyl, $C_{1-3}$ alkylamino, $C_{1-3}$ aminoalkyl, $C_{2-4}$ alkenyl, $C_{2-4}$ alkynyl, $C_{3-6}$ cycloalkyl, $C_{1-3}$ haloalkyl, phenyl or benzyl; or $R^6$ and $R^7$, together with the C atom to which they are attached, independently and optionally form $C_{3-6}$ cycloalkyl or $C_{2-6}$ heterocyclyl.

6. The compound of claim 1, wherein
each $R^8$ is independently H, deuterium, F, Cl, Br, I, hydroxy, nitro, amino, $C_{1-3}$ aminoalkyl, $C_{1-3}$ alkylamino, $C_{1-3}$ alkyl, $C_{1-4}$ hydroxyalkyl, $C_{1-3}$ alkoxy, $C_{1-3}$ haloalkyl, $C_{1-3}$ haloalkoxy, $C_{3-6}$ cycloalkyl, $C_{3-6}$ cycloalkyloxy, $C_{2-4}$ alkenyl, $C_{2-4}$ alkynyl, $C_{6-10}$ aryl, halo-substituted $C_{6-10}$ aryl, $C_{6-10}$ aryl-$C_{1-4}$-alkyl, oxo (=O), —C(=O)OR$^{15}$, —S(=O)$_t$R$^{16}$, —C(=O)NR$^{17}$R$^{18}$, —C(=O)N(R$^{17}$)S(=O)$_2$R$^{16}$, —C(=O)NH—C$_{1-4}$ alkylene —S(=O)$_2$OR$^{15}$, —C(=O)NH—C$_{1-4}$ alkylene —C(=O)OR$^{15}$, cyano, triazolyl or tetrazolyl; or two $R^8$, together with the same C atom to which they are attached, independently and optionally form $C_{3-6}$ cycloalkyl or $C_{2-9}$ heterocyclyl; or two $R^8$, together with the adjacent C atoms to which they are attached, independently and optionally form $C_{3-6}$ cycloalkyl, $C_{2-9}$ heterocyclyl, $C_{6-10}$ aryl or $C_{1-9}$ heteroaryl;

each $R^{15}$ is H, deuterium, $C_{1-4}$ alkyl, $C_{1-4}$ aminoalkyl, $C_{2-4}$ alkenyl, $C_{2-4}$ alkynyl, $C_{1-4}$ haloalkyl, $C_{3-6}$ cycloalkyl, $C_{1-6}$ heterocyclyl or $C_{6-10}$ aryl;
each $R^{16}$ is H, deuterium, hydroxy, amino, $C_{1-4}$ alkyl, $C_{1-4}$ aminoalkyl, $C_{2-4}$ alkenyl, $C_{2-4}$ alkynyl, $C_{1-4}$ haloalkyl, $C_{3-6}$ cycloalkyl, $C_{2-6}$ heterocyclyl, $C_{6-10}$ aryl or —NR$^{17}$R$^{18}$; and
each of $R^{17}$ and $R^{18}$ is independently H, deuterium, $C_{1-4}$ alkyl, $C_{1-4}$ aminoalkyl, $C_{2-4}$ alkenyl, $C_{2-4}$ alkynyl, $C_{1-3}$ haloalkyl, $C_{3-6}$ cycloalkyl, $C_{2-6}$ heterocyclyl or $C_{6-10}$ aryl.

7. The compound of claim 1, wherein
each $R^1$ is independently H, deuterium, F, Cl, Br, I, hydroxy, amino, nitro, cyano, methyl, ethyl, n-propyl, isopropyl, t-butyl, dimethylamino, difluoromethyl, trifluoromethyl, tert-butyloxy, difluoromethyloxy, trifluoromethyloxy, cyclopropyl, oxiranyl, phenyl, naphthyl, oxazolyl, pyrazolyl or thiazolyl; and
each $R^2$ is independently H, deuterium, F, Cl, Br, I, hydroxy, amino, nitro, cyano, methyl, ethyl, n-propyl, isopropyl, t-butyl, dimethylamino, difluoromethyl, trifluoromethyl, tert-butyloxy, difluoromethyloxy, trifluoromethyloxy, methoxymethyl, isopropoxymethyl, tert-butoxymethyl, cyclopropyl, cycobutyl, oxiranyl or pyrrolidinyl.

8. The compound of claim 1, wherein
each $R^8$ is independently H, deuterium, F, Cl, Br, I, hydroxy, nitro, amino, oxo (=O), $C_{1-3}$ alkyl, $C_{1-3}$ haloalkyl, —COOH, —C(=O)O—C$_{1-4}$ alkyl, —C(=O)NHS(=O)$_2$—C$_{1-4}$ alkyl, —C(=O)NHS(=O)$_2$-phenyl, —C(=O)NH—C$_{1-4}$ alkylene —S(=O)$_2$OH, —C(=O)NH—C$_{1-4}$ alkylene —C(=O)OH, —S(=O)$_2$NH$_2$, —S(=O)$_2$OH, —S(=O)$_2$—C$_{1-2}$ alkyl, —C(=O)NH$_2$, —C(=O)N(CH$_3$)$_2$, cyano, triazolyl or tetrazolyl.

9. The compound of claim 1 having one of the following structures or a stereoisomer, a geometric isomer, a tautomer, an N-oxide, a hydrate, a solvate, a pharmaceutically acceptable salt or a prodrug thereof:

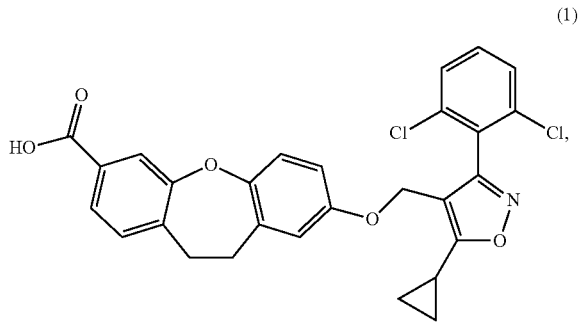

(1)

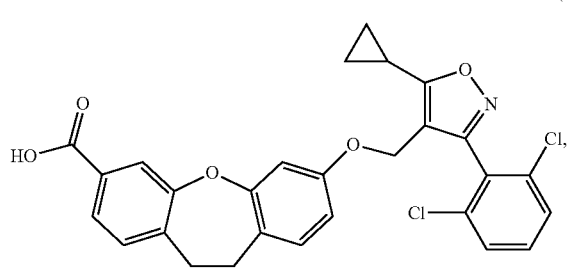

(2)

(3)
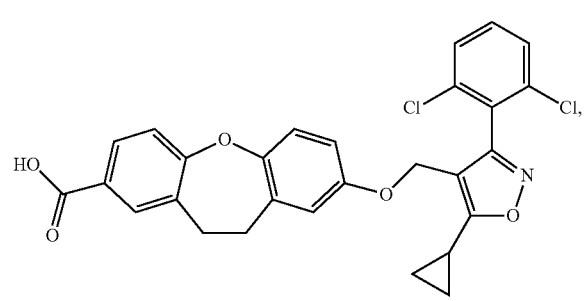
(4)
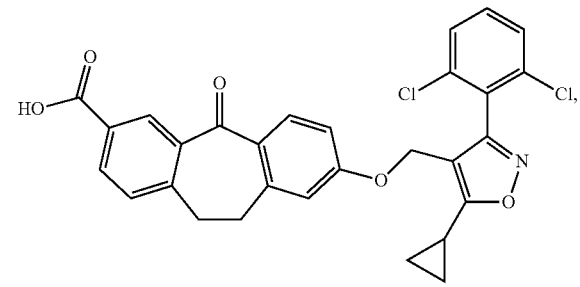
(5)
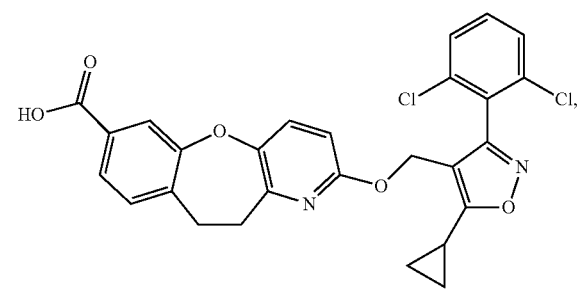
(6)
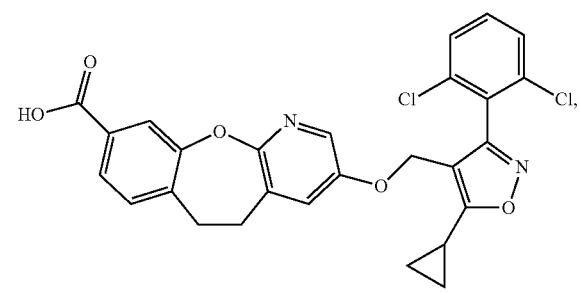
(7)
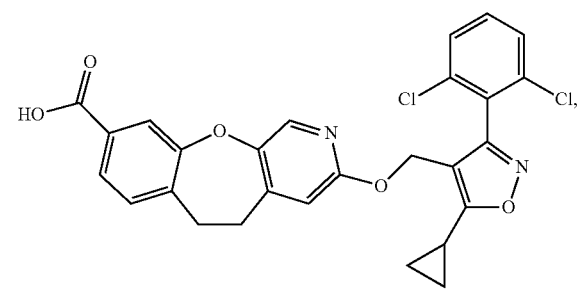
(8)
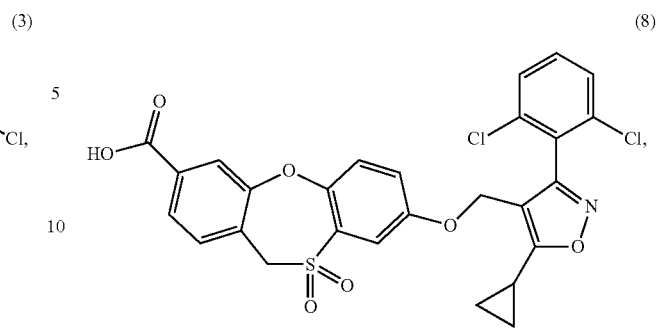
(9)
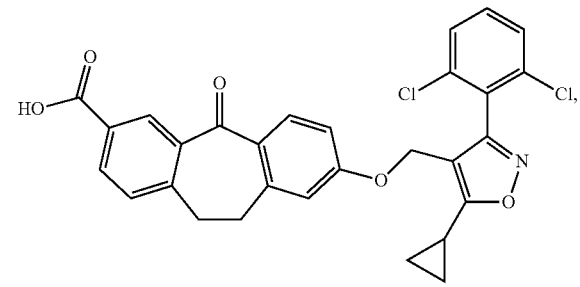
(10)
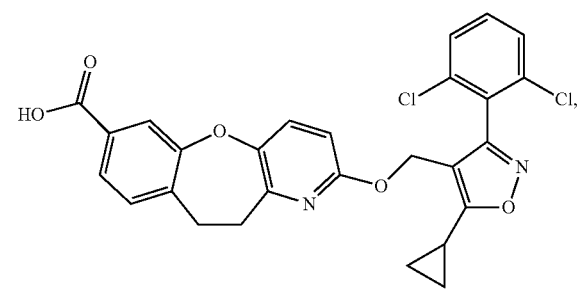
(11)
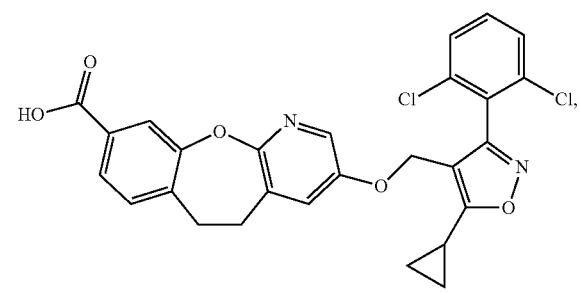
(12)
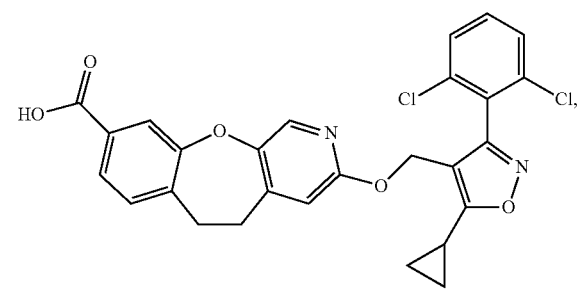

(13) 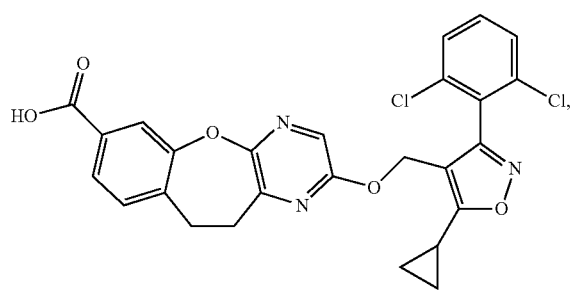
(14) 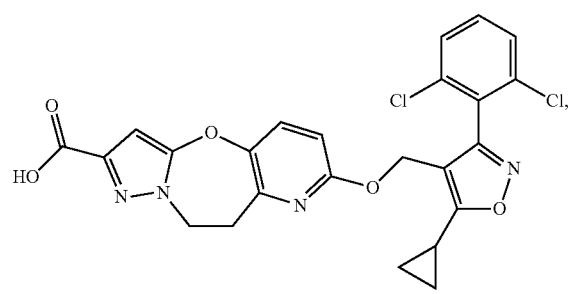
(15) 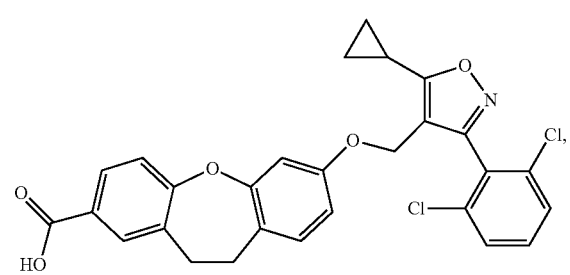
(16) 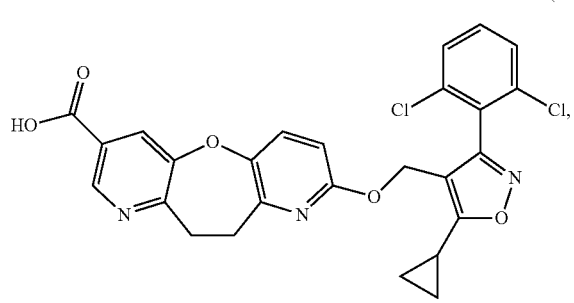
(17) 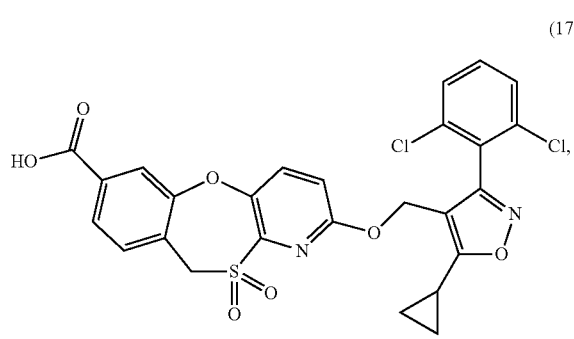
(18) 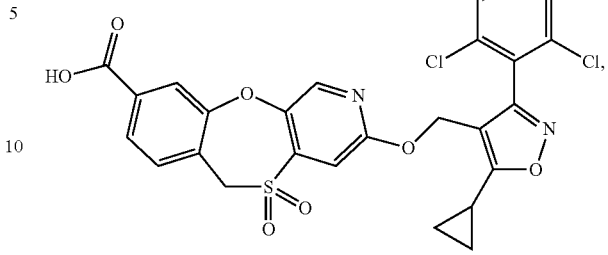
(19) 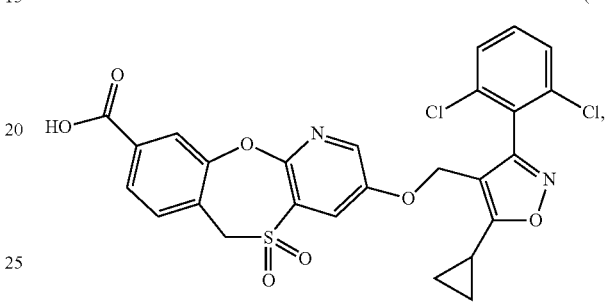
(20) 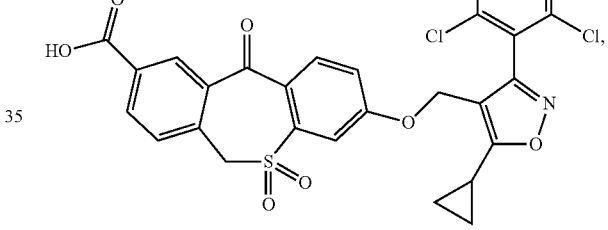
(21) 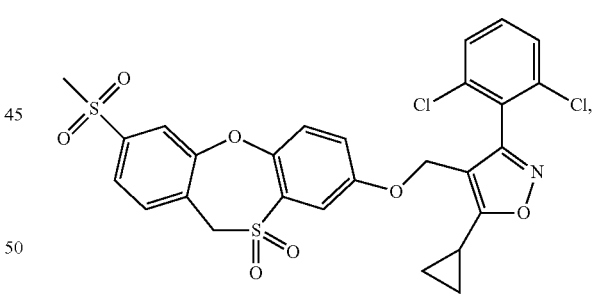
(22) 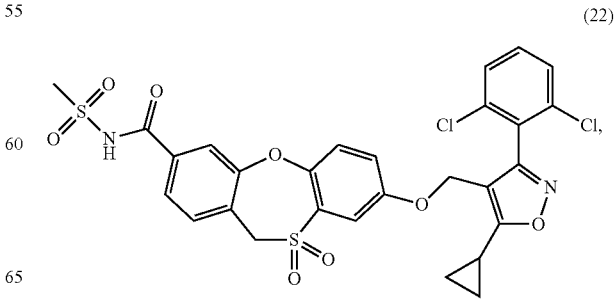

(23)
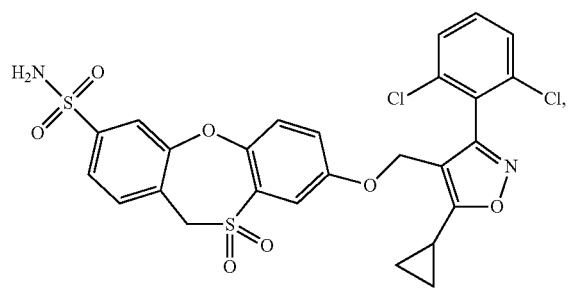
(24)
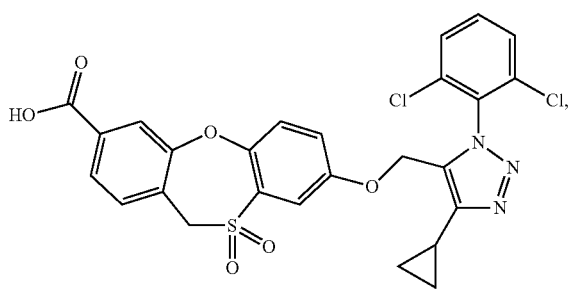
(25)
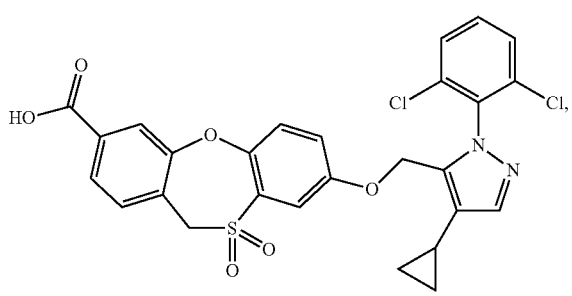
(26)
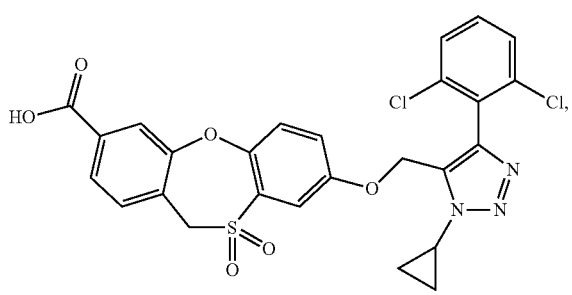
(27)
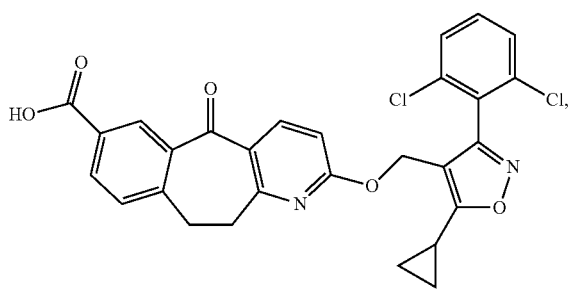
(28)
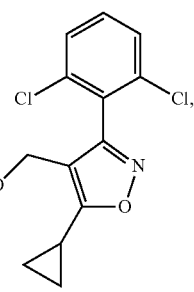
(29)
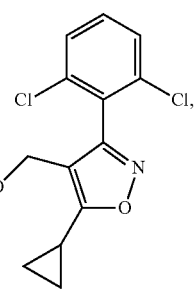
(30)
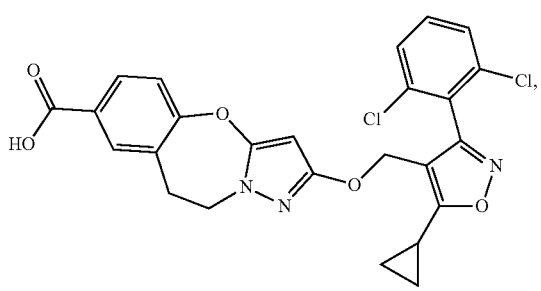
(31)
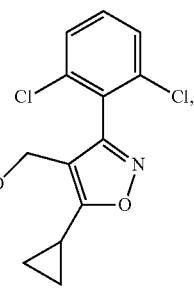
(32)
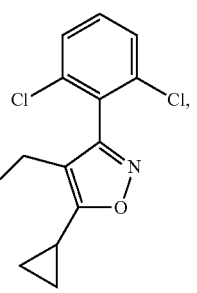

(33)
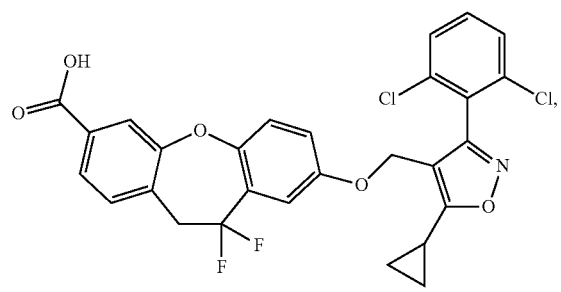
(34)
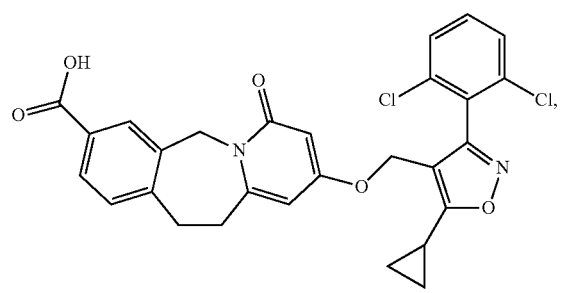
(35)
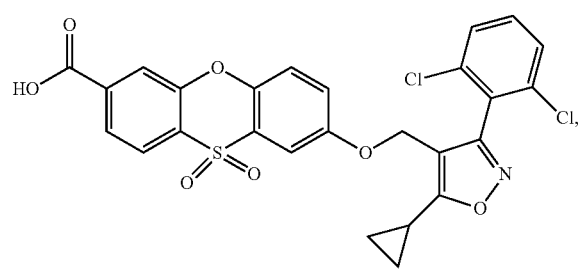
(36)
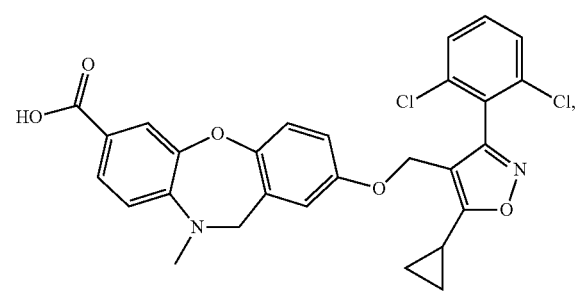
(37)
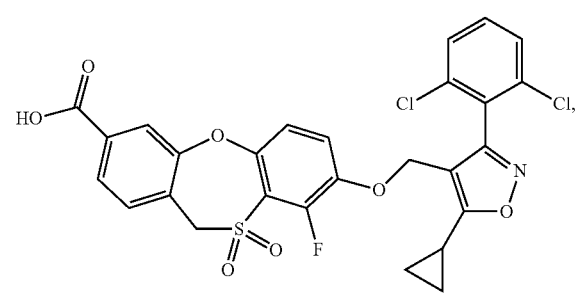
(38)
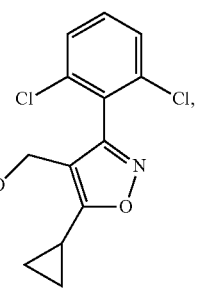
(39)
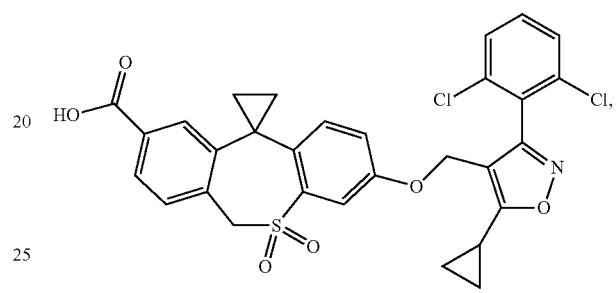
(40)
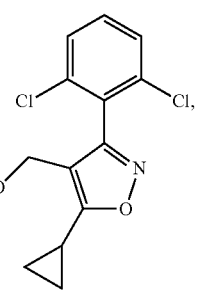
(41)
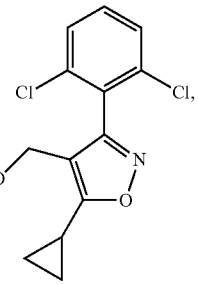
(42)
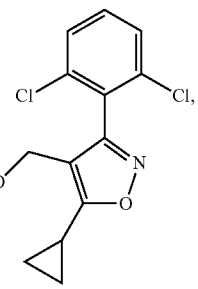

(43)
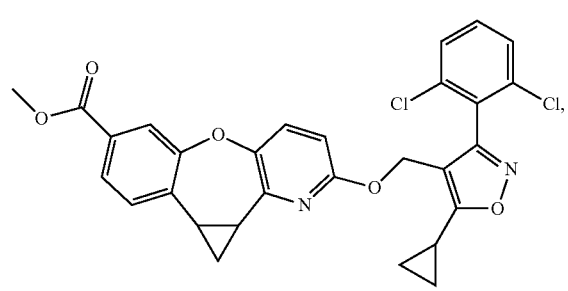
(44)
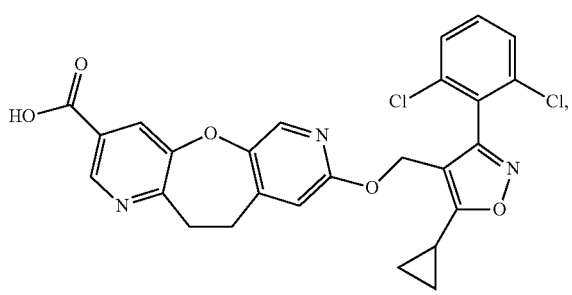
(45)
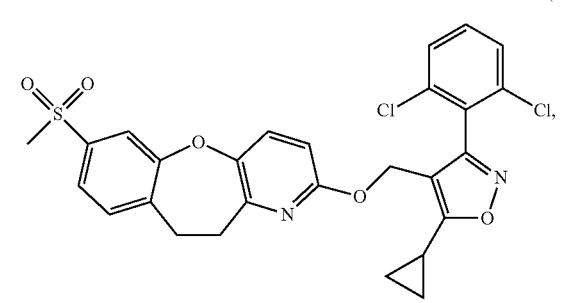
(46)
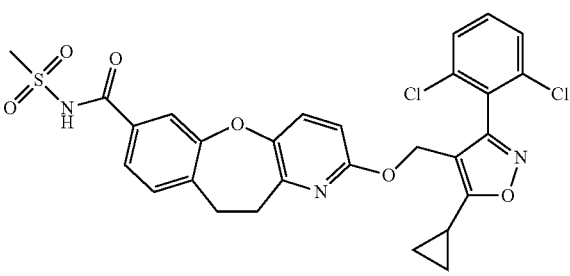
(47)
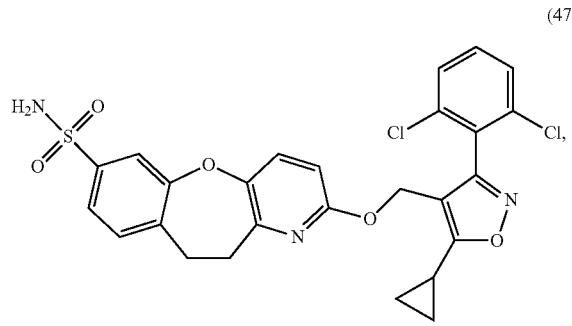
(48)
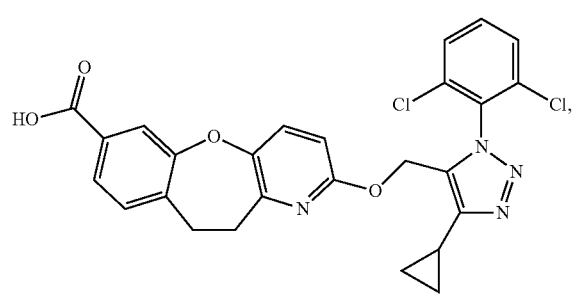
(49)
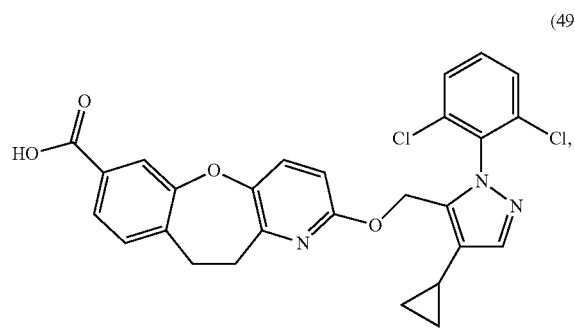
(50)
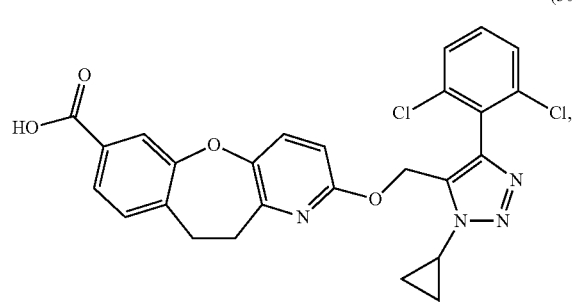
(51)
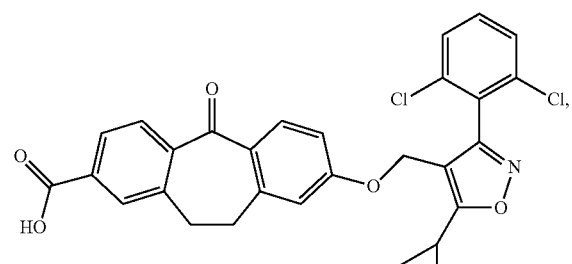
(52)
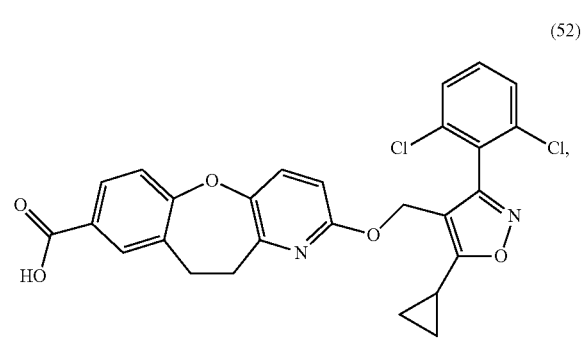

-continued
(53)
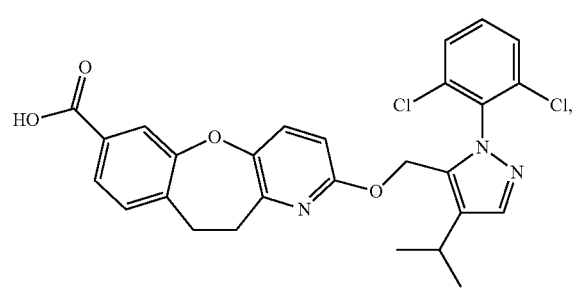
(54)
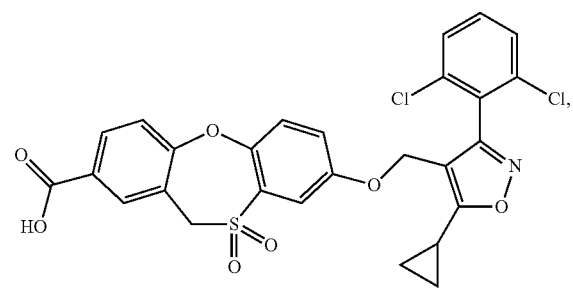
(55)
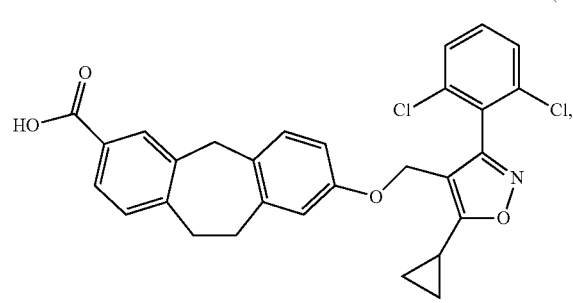
(56)
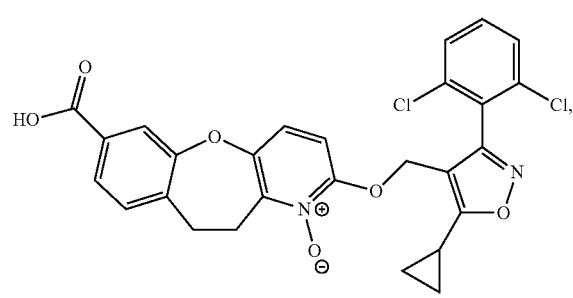
(57)
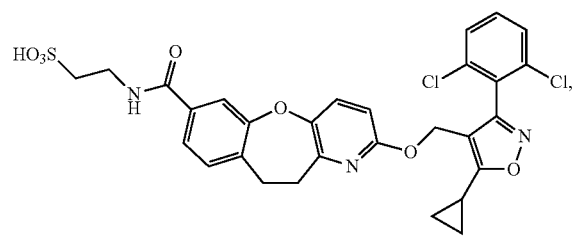
-continued
(58)
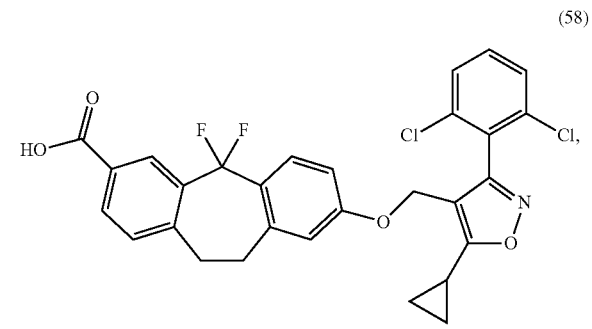
(59)
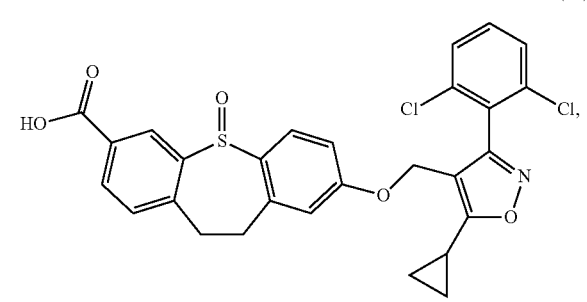
(60)
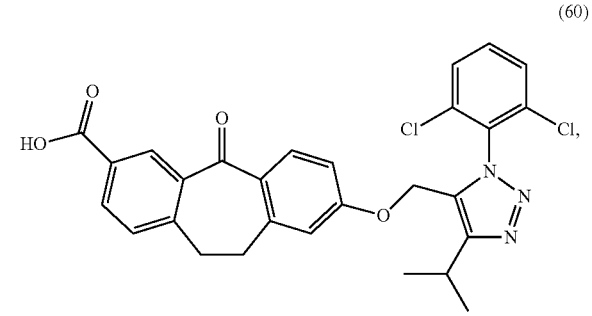
(61)
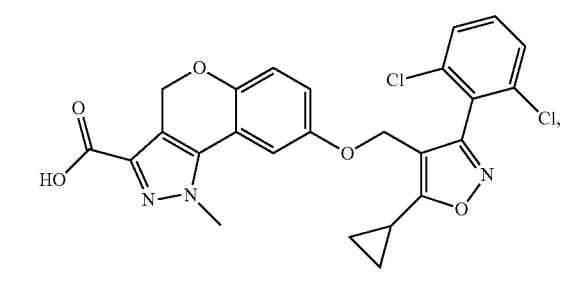
(62)
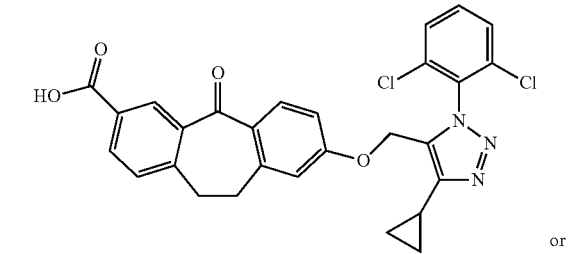
or -continued (63)

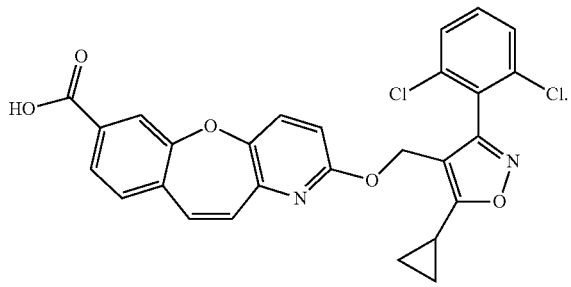

10. A pharmaceutical composition comprising the compound of claim 1, and a pharmaceutically acceptable carrier, excipient, diluent, adjuvant, vehicle, or a combination thereof.

11. A method of managing, treating or lessening a disease mediated by FXR in a patient comprising administering to the patient a therapeutic effective amount of the compound of claim 1, wherein the disease mediated by FXR is obesity, metabolic syndrome, insulin resistance, hyperglycemia, hyperinsulinemia, elevated blood level of fatty acid or glycerol, hyperlipidemia, hypertriglyceridemia, hypercholesterolemia, X syndrome, atherosclerosis, hypertension, acute anemia, neutropenia, dyslipidemia, type II diabetes, diabetic nephropathy, diabetic retinopathy, acute myocardial infarction, veno-occlusive disease, heart failure, peripheral aterial occlusive diseases, sexual dysfunction, stroke or thrombosis.

12. A method of managing, treating or lessening a disease mediated by FXR in a patient comprising administering to the patient a therapeutic effective amount of the pharmaceutical composition of claim 10, wherein the disease mediated by FXR is obesity, metabolic syndrome, insulin resistance, hyperglycemia, hyperinsulinemia, elevated blood level of fatty acid or glycerol, hyperlipidemia, hypertriglyceridemia, hypercholesterolemia, X syndrome, atherosclerosis, hypertension, acute anemia, neutropenia, dyslipidemia, type II diabetes, diabetic nephropathy, diabetic retinopathy, acute myocardial infarction, veno-occlusive disease, heart failure, peripheral aterial occlusive diseases, sexual dysfunction, stroke or thrombosis.

* * * * *